(12) United States Patent
Cheesman et al.

(10) Patent No.: US 6,818,201 B2
(45) Date of Patent: Nov. 16, 2004

(54) VITRONECTIN RECEPTOR ANTAGONIST PHARMACEUTICALS

(75) Inventors: Edward H. Cheesman, Lunenberg, MA (US); Michael Sworin, Tyngsboro, MA (US); Milind Rajopadhye, Westford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/306,244

(22) Filed: Nov. 26, 2002

(65) Prior Publication Data

US 2003/0143235 A1 Jul. 31, 2003

Related U.S. Application Data

(62) Division of application No. 09/466,582, filed on Dec. 17, 1999, now Pat. No. 6,558,649.
(60) Provisional application No. 60/112,831, filed on Dec. 18, 1998.

(51) Int. Cl.[7] .............................................. A61K 49/00
(52) U.S. Cl. ...................... 424/9.1; 424/1.11; 424/1.65; 424/1.69; 534/14
(58) Field of Search ........................... 514/2; 424/1.11, 424/1.65, 1.69, 9.1, 9.2, 9.3, 9.4, 9.5, 9.6, 9.7, 9.8; 534/10–16; 530/300

(56) References Cited

U.S. PATENT DOCUMENTS

| | | | |
|---|---|---|---|
| 4,248,802 A | 2/1981 | Kuntz | |
| 4,472,509 A | 9/1984 | Gansow et al. | |
| 4,536,387 A | 8/1985 | Sakamoto et al. | |
| 4,859,777 A | 8/1989 | Toner | |
| 4,988,827 A | 1/1991 | Bergstein et al. | |
| 5,021,236 A | 6/1991 | Gries et al. | |
| 5,064,956 A | 11/1991 | Kruper, Jr. | |
| 5,087,440 A | 2/1992 | Cacheris et al. | |
| 5,155,215 A | 10/1992 | Ranney | |
| 5,281,704 A | 1/1994 | Love et al. | |
| 5,342,757 A | 8/1994 | Garin-Chesa et al. | |
| 5,350,837 A | 9/1994 | Bridger et al. | |
| 5,376,356 A | 12/1994 | Morgan, Jr. et al. | |
| 5,382,654 A | 1/1995 | Lyle et al. | |
| 5,395,609 A | 3/1995 | Stuttle | |
| 5,403,713 A | 4/1995 | Bevilacqua et al. | |
| 5,412,148 A | 5/1995 | Keana | |
| 5,417,959 A | 5/1995 | Wallace | |
| 5,520,904 A | 5/1996 | Nosco et al. | |
| 5,556,939 A | 9/1996 | Flanagan et al. | |
| 5,567,411 A | 10/1996 | Keana et al. | |
| 5,650,134 A | 7/1997 | Albert et al. | |
| 5,659,013 A | 8/1997 | Senger et al. | |
| 5,659,041 A | 8/1997 | Pollak et al. | |
| 5,660,827 A | 8/1997 | Thorpe et al. | |
| 5,679,810 A | 10/1997 | Love et al. | |
| 5,739,789 A | 4/1998 | Kronhamn .................. 342/465 |
| 5,750,088 A | 5/1998 | Sworin et al. ............. 424/1.69 |
| 5,760,191 A | 6/1998 | Snow et al. | |
| 5,766,591 A | 6/1998 | Brooks et al. | |
| 5,776,427 A | 7/1998 | Thorpe et al. | |
| 5,801,228 A | 9/1998 | Hollister et al. | |
| 5,804,161 A | 9/1998 | Long et al. | |
| 5,855,866 A | 1/1999 | Thorpe et al. | |
| 5,863,538 A | 1/1999 | Thorpe et al. | |
| 5,879,659 A | 3/1999 | Edwards et al. ........... 424/1.69 |
| 6,010,679 A | 1/2000 | Edwards et al. ........... 424/1.69 |
| 6,040,311 A | 3/2000 | Duggan et al. | |
| 6,051,207 A | 4/2000 | Klaveness et al. | |
| 6,051,230 A | 4/2000 | Thorpe et al. | |
| 6,056,973 A | 5/2000 | Allen et al. | |
| 6,143,274 A | 11/2000 | Tweedle et al. | |
| 6,232,308 B1 | 5/2001 | Askew | |
| 6,254,852 B1 | 7/2001 | Glajch et al. .............. 424/9.52 |

FOREIGN PATENT DOCUMENTS

| | | |
|---|---|---|
| AU | 5 314 694 | 7/1994 |
| CA | 2 113 245 | 6/1988 |
| CA | 2 039 259 | 10/1991 |
| CA | 2 156 620 | 10/1994 |
| CA | 2 232 315 | 4/1997 |
| DE | 4 311 023 | 10/1994 |
| DE | 19 536 781 | 3/1997 |
| DE | 19 536 785 | 3/1997 |
| DE | 19 725 368 | 12/1998 |

(List continued on next page.)

OTHER PUBLICATIONS

Baker, et al., *Life Sci.*, 1991, 49, 1583–1591.
Krenning, et al., *Eur. J. Nucl. Med.*, 1993, 20, 716–731.
Krenning, et al., *Digestion*, 1996, 57, 57–61.
Folkman, *J. Nature Medicine,*, 1995, 1, 27–31.
O'Reilly, et al., *Cell*, 1994, 79, 315–328.
O'Reilly, et al., *Cell*, 1997, 88, 277–285.
Burrows, et al., *Proc. Nat. Acad. Sci., USA*, 1993, 90, 8996–9000.

(List continued on next page.)

*Primary Examiner*—Dameron L. Jones
(74) *Attorney, Agent, or Firm*—Warren K. Volles; Woodcock Washburn LLP

(57) ABSTRACT

The present invention describes novel compounds of the formula:

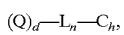

$(Q)_d\text{—}L_n\text{—}C_h,$ useful for the diagnosis and treatment of cancer, methods of imaging tumors in a patient, and methods of treating cancer in a patient. The present invention also provides novel compounds useful for monitoring therapeutic angiogenesis treatment and destruction of new angiogenic vasculature. The present invention further provides novel compounds useful for imaging atherosclerosis, restenosis, cardiac ischemia and myocardial reperfusion injury. The present invention still further provides novel compounds useful for the treatment of rheumatoid arthritis. The pharmaceuticals are comprised of a targeting moiety that binds to a receptor that is upregulated during angiogenesis, an optional linking group, and a therapeutically effective radioisotope or diagnostically effective imageable moiety. The imageable moiety is a gamma ray or positron emitting radioisotope, a magnetic resonance imaging contrast agent, an X-ray contrast agent, or an ultrasound contrast agent.

55 Claims, No Drawings

FOREIGN PATENT DOCUMENTS

| | | |
|---|---|---|
| EP | 0 107 734 | 7/1987 |
| EP | 0 359 347 | 3/1990 |
| EP | 0 436 005 | 10/1991 |
| EP | 0 606 683 | 7/1994 |
| EP | 0 727 225 | 8/1996 |
| WO | WO 81/01145 | 4/1981 |
| WO | WO 90/03801 | 4/1990 |
| WO | WO 90/05539 | 5/1990 |
| WO | WO 90/12585 | 11/1990 |
| WO | WO 90/13300 | 11/1990 |
| WO | WO 91/01144 | 2/1991 |
| WO | WO 91/14460 | 10/1991 |
| WO | WO 91/15244 | 10/1991 |
| WO | WO 92/12729 | 8/1992 |
| WO | WO 92/17215 | 10/1992 |
| WO | WO 92/19646 | 11/1992 |
| WO | WO 93/08174 | 4/1993 |
| WO | WO 93/08210 | 4/1993 |
| WO | WO 93/17715 | 9/1993 |
| WO | WO 94/05328 | 4/1994 |
| WO | WO 94/11499 | 5/1994 |
| WO | WO 94/22496 | 10/1994 |
| WO | WO 94/22497 | 10/1994 |
| WO | WO 95/18619 | 7/1995 |
| WO | WO 95/25543 | 9/1995 |
| WO | WO 96/00574 | 1/1996 |
| WO | WO 96/00730 | 1/1996 |
| WO | WO 96/01653 | 1/1996 |
| WO | WO 96/31243 | 10/1996 |
| WO | WO 96/41803 | 12/1996 |
| WO | WO 97/08145 | 3/1997 |
| WO | WO 97/16474 | 5/1997 |
| WO | WO 97/18207 | 5/1997 |
| WO | WO 97/23480 | 7/1997 |
| WO | WO 93/23074 | 9/1997 |
| WO | WO 98/16256 | 2/1998 |
| WO | WO 98/14220 | 4/1998 |
| WO | WO 95/18619 | 7/1998 |
| WO | WO 98/47541 | 10/1998 |
| WO | WO 99/06049 | 2/1999 |
| WO | WO 99/13329 | 3/1999 |
| WO | WO 99/40947 | 8/1999 |

OTHER PUBLICATIONS

*Clin. Can. Res.*, 1995, 1,1623–1634.
Takeshita, S., et al., *J. Clin. Invest.*, 1994, 93, 663–670.
Henry, T., et al., *J. Amer. College Cardiology*, 1998, 31, 65A.
Remington's Pharmaceutical Sciences, $17^{th\ Ed.}$, Mack Publishing Company, Easton, PA, 1985, p. 1418.
Cheresh, et al., *Science*, 1995, 270, 1500–1502.
Senger, et al., *Proc. Natl. Acad. Sci. USA*, 1997, 94, 13612–13617.
Brinkley, M., *Bioconjugate Chemistry*, 1992, 3(1).
Margerstadt, et al., *Magn. Reason. Med.*, 1986, 3, 808.
Brechbiel, M., et al., *J. Chem. Soc. Perkin Trans.*, 1992, 1, 1175.
Brechbiel, M., et al., *Bioconjugate Chem.*, 1991, 2, 187.
Deshpande, S., et al., *J. Nucl. Med.*, 1990, 31, 473.
Runge, et al., *Radiology*, 1988, 166, 835.
Bousquet, et al., *Radiology*, 1988, 166, 693.
DeGrado, et al., *J. Org. Chem.*, 1980, 45, 1295.
*Bioconj. Chem.*, 1997, 8, 611.
Kirk, K.L., *J. Org. Chem.*, 1978, 43, 4381.
Denekamp, J., et al., *Br. J. Cancer*, 1982, 45, 136–139.
Denekamp, et al., *Br. J. Cancer*, 1982, 46, 711–720.
Ghose, et al., *Meth. Enzymology*, 1983, 93, 280–333.
Denekamp, J., *Acta Radiologica Oncology*, 1984, 23 Fasc. 4, 217–225.
Hagemeier, et al., *Int. J. Cancer*, 1986, 38, 481–488.
Bevilacqua, et al., *Proc. Natl. Acad Sci.*, 1987, 84, 9238–9242.
Knowles, et al., *Analytical Biochemistry*, 1987, 160, 440–443.
DiZio, et al., *Bioconjugate Chem.*, 1991, 2, 353–366.
Wellicome, et al., *J. Immunol.*, 1990, 144(7), 2558–2565.
Juliana Denekamp, *Cancer Meta. Rev.*, 1990, 9, 267–282.
Clauss, et al., *J. Biological Chemistry*, 1990, 265(12), 7078–7083.
Dvorak, et al., *Cancer Cells*, 1991, 3, 77–85.
Orlando, et al., *J. Biological Chemistry*, Oct. 1991, 266(29), 19543–19550.
Burrows, F.J., et al., *Cancer Research*, 1992, 52, 5954–5962.
Mueller, et al., *Proc. Natl. Acad. Sci. USA*, 1992, 89, 11832–11836.
Burrows, et al., *J. Controlled Release*, Jan. 1994, 28(1), 195–202.
Hu, et al., *Oncology Research*, 1994, 6(7), 321–327.
Thorpe, et al., *Breast Cancer Research & Treatment*, 1995, 36(2), 237–251.
Abstract, *Nucl. Med., Proceeding of the $42^{nd}$ Annual Meeting*, May 1995, 36(5), No. 287, p. 71.
Horton, et al., *Int. J. Biochem. Cell. Biol.*, May 1997, 29(5), 721–725.
Haubner, *V313 Nuclear–Medizine*, Mar. 1997.
Srivatsa, et al., *Cardiovascular Res.*, 1997, 36, 408–428.
Olson, et al., *Int. J. Cancer*, 1997, 73, 865–870.
Sipkins, et al., *Nature Medicine*, May 1998, 4(5), 623–626.
Molema, et al., *Biochemical Pharmacology*, 1998, 55, 1939–1945.
Kennel, et al., *Nuclear Medicine & Biology*, 1998, 25, 241–246.
Kerr, et al., *Anticancer Research*, Mar.–Apr. 1999, 19(2A), 958–968.
Liu, et al., *Inorg. Chem.*, 1999, 38(6), 1326–1335.
Sellke, et al., *Drugs*, 1999, 58(3), 391–396.
DeNardo, et al., *Cancer Biotherapy & Radiopharm*, Feb. 2000, 15(1), 71–79.
Van Waes, et al., *International J. Oncology*, 2000, 16, 1189–1195.
Batt, et al., *J. Med. Chem.*, 2000, 43, 41–58.
Coker, M.I., et al., "Myocardial matrix metalloproteinase activity and abundance with congestive heart failure," *Am. J. Physiol.*, 1998, 274, H1516–H5123.
McDowell, R.S., et al., "From peptide to non–peptide. 2. The de novo design of potent, non–peptidal inhibitors of platelet aggregation based on a benzodiazepinedione scaffold," *J. Amer. Chem. Soc.*,1994, 116, 5077–5083.
McNulty, et al., "McNulty, P.H., et al., Glycogen depletion contributes to ischemic preconditioning in the rat heart in vivo," *Am. Physiol.*, 1996, H2283–H2289.
Mousa, S.A., "Recent advances in cell adhesion molecules and extracellular matrix proteins: potential clinical implications," *DDT*, May 1997, 2(5), 187–199.
Samanen, J., et al., "Vascular indications for integrin αv antagonists," *Current Pharm. Design*, 1997, 3, 545–584.
Sinusas, A.J., "Experimental evaluatrion of radiotracers: role of intact biological models," *J. Nucl. Cardiol.*, Mar./Apr. 1998, 5, 167–183.
Srivatsa, S.S., et al., "Selective αvβ integrin blockade potently limits neointimal hyperplasia and lumen stenosis following deep coronary arterial stent injury: Evidence for the functional importance of integrin αβ and osteopontin expression during neointima formation," *Cardiovascular Res.*, 1997, 36, 408–428.
Youker, K.A., et al., "Time–dependent neutrophil β1 and β3 integrin expression in the reperfused myocardium: role in tissue migration," Circulation, 1999, 1433, p. I–275.

VITRONECTIN RECEPTOR ANTAGONIST PHARMACEUTICALS

This application is a divisional application of U.S. Ser. No. 09/466,582, filed Dec. 17, 1999, now U.S. Pat. No. 6,558,649, which claims the benefit of U.S. Ser. No. 60/112,831, filed Dec. 18, 1998.

FIELD OF THE INVENTION

The present invention provides novel pharmaceuticals useful for the diagnosis and treatment of cancer, methods of imaging tumors in a patient, and methods of treating cancer in a patient. The pharmaceuticals are comprised of a targeting moiety that binds to the vitronectin receptor that is expressed in tumor vasculature, an optional linking group, and a therapeutically effective radioisotope or diagnostically effective imageable moiety. The therapeutically effective radioisotope emits a gamma ray or alpha particle sufficient to be cytotoxic. The imageable moiety is a gamma ray or positron emitting radioisotope, a magnetic resonance imaging contrast agent, an X-ray contrast agent, or an ultrasound contrast agent.

BACKGROUND OF THE INVENTION

Cancer is a major public health concern in the United States and around the world. It is estimated that over 1 million new cases of invasive cancer will be diagnosed in the United States in 1998. The most prevalent forms of the disease are solid tumors of the lung, breast, prostate, colon and rectum. Cancer is typically diagnosed by a combination of in vitro tests and imaging procedures. The imaging procedures include X-ray computed tomography, magnetic resonance imaging, ultrasound imaging and radionuclide scintigraphy. Frequently, a contrast agent is administered to the patient to enhance the image obtained by X-ray CT, MRI and ultrasound, and the administration of a radiopharmaceutical that localizes in tumors is required for radionuclide scintigraphy.

Treatment of cancer typically involves the use of external beam radiation therapy and chemotherapy, either alone or in combination, depending on the type and extent of the disease. A number of chemotherapeutic agents are available, but generally they all suffer from a lack of specificity for tumors versus normal tissues, resulting in considerable side-effects. The effectiveness of these treatment modalities is also limited, as evidenced by the high mortality rates for a number of cancer types, especially the more prevalent solid tumor diseases. More effective and specific treatment means continue to be needed.

Despite the variety of imaging procedures available for the diagnosis of cancer, there remains a need for improved methods. In particular, methods that can better differentiate between cancer and other pathologic conditions or benign physiologic abnormalities are needed. One means of achieving this desired improvement would be to administer to the patient a metallopharmaceutical that localizes specifically in the tumor by binding to a receptor expressed only in tumors or expressed to a significantly greater extent in tumors than in other tissue. The location of the metallopharmaceutical could then be detected externally either by its imageable emission in the case of certain radiopharmaceuticals or by its effect on the relaxation rate of water in the immediate vicinity in the case of magnetic resonance imaging contrast agents.

This tumor specific metallopharmaceutical approach can also be used for the treatment of cancer when the metallopharmaceutical is comprised of a particle emitting radioisotope. The radioactive decay of the isotope at the site of the tumor results in sufficient ionizing radiation to be toxic to the tumor cells. The specificity of this approach for tumors minimizes the amount of normal tissue that is exposed to the cytotoxic agent and thus may provide more effective treatment with fewer side-effects.

Previous efforts to achieve these desired improvements in cancer imaging and treatment have centered on the use of radionuclide labeled monoclonal antibodies, antibody fragments and other proteins or polypeptides that bind to tumor cell surface receptors. The specificity of these radiopharmaceuticals is frequently very high, but they suffer from several disadvantages. First, because of their high molecular weight, they are generally cleared from the blood stream very slowly, resulting in a prolonged blood background in the images. Also, due to their molecular weight they do not extravasate readily at the site of the tumor and then only slowly diffuse through the extravascular space to the tumor cell surface. This results in a very limited amount of the radiopharmaceutical reaching the receptors and thus very low signal intensity in imaging and insufficient cytotoxic effect for treatment.

Alternative approaches to cancer imaging and therapy have involved the use of small molecules, such as peptides, that bind to tumor cell surface receptors. An In-111 labeled somatostatin receptor binding peptide, In-111-DTPA-D-Phe$^1$-octeotide, is in clinical use in many countries for imaging tumors that express the somatostatin receptor (Baker, et al. Life Sci., 1991, 49, 1583–91 and Krenning, et al., Eur. J. Nucl. Med., 1993, 20, 716–31). Higher doses of this radiopharmaceutical have been investigated for potential treatment of these types of cancer (Krenning, et al., Digestion, 1996, 57, 57–61). Several groups are investigating the use of Tc-99m labeled analogs of In-111-DTPA-D-Phe$^1$-octeotide for imaging and Re-186 labeled analogs for therapy (Flanagan, et al., U.S. Pat. No. 5,556,939, Lyle, et al., U.S. Pat. No. 5,382,654, and Albert et al.,U.S. Pat. No. 5,650,134).

Angiogenesis is the process by which new blood vessels are formed from pre-existing capillaries or post capillary venules; it is an important component of a variety of physiological processes including ovulation, embryonic development, wound repair, and collateral vascular generation in the myocardium. It is also central to a number of pathological conditions such as tumor growth and metastasis, diabetic retinopathy, and macular degeneration. The process begins with the activation of existing vascular endothelial cells in response to a variety of cytokines and growth factors. Tumor released cytokines or angiogenic factors stimulate vascular endothelial cells by interacting with specific cell surface receptors for the factors. The activated endothelial cells secrete enzymes that degrade the basement membrane of the vessels. The endothelial cells then proliferate and invade into the tumor tissue. The endothelial cells differentiate to form lumens, making new vessel offshoots of pre-existing vessels. The new blood vessels then provide nutrients to the tumor permitting further growth and a route for metastasis.

Under normal conditions, endothelial cell proliferation is a very slow process, but it increases for a short period of time during embryogenesis, ovulation and wound healing. This temporary increase in cell turnover is governed by a combination of a number of growth stimulatory factors and growth suppressing factors. In pathological angiogenesis, this normal balance is disrupted resulting in continued increased endothelial cell proliferation. Some of the proangiogenic factors that have been identified include basic fibroblast growth factor (bFGF), angiogenin, TGF-alpha, TGF-beta, and vascular endothelium growth factor (VEGF). While interferon-alpha, interferon-beta and thrombospondin are examples of angiogenesis suppressors.

The proliferation and migration of endothelial cells in the extracellular matrix is mediated by interaction with a variety of cell adhesion molecules (Folkman, J., Nature Medicine, 1995, 1, 27–31). Integrins are a diverse family of heterodimeric cell surface receptors by which endothelial cells attach to the extracellular matrix, each other and other cells. The integrin $\alpha_v\beta_3$ is a receptor for a wide variety for a wide variety of extracellular matrix proteins with an exposed tripeptide Arg-Gly-Asp moiety and mediates cellular adhesion to its ligand: vitronectin, fibronectin, and fibrinogen, among others. The integrin $\alpha_v\beta_3$ is minimally expressed on normal blood vessels, but is significantly upregulated on vascular cells within a variety of human tumors. The role of the $\alpha_v\beta_3$ receptors is to mediate the interaction of the endothelial cells and the extracellular matrix and facilitate the migration of the cells in the direction of the angiogenic signal, the tumor cell population. Angiogenesis induced by bFGF or TNF-alpha depend on the agency of the integrin $\alpha_v\beta_3$, while angiogenesis induced by VEGF depends on the integrin $\alpha_v\beta_3$ (Cheresh et. al., Science, 1955, 270, 1500–2). Induction of expression of the integrins $\alpha_1\beta_1$ and $\alpha_2\beta_1$ on the endothelial cell surface is another important mechanism by which VEGF promotes angiogenesis (Senger, et. al., Proc. Natl. Acad, Sci USA, 1997, 84, 13612–7).

Angiogenic factors interact with endothelial cell surface receptors such as the receptor tyrosine kinases EGFR, FGFR, PDGFR, Flk-1/KDR, Flt-1, Tek, tie, neuropilin-1, endoglin, endosialin, and Axl. The receptors Flk-1/KDR, neuropilin-1, and Flt-1 recognize VEGF and these interactions play key roles in VEGF-induced angiogenesis. The Tie subfamily of receptor tyrosine kinases are also expressed prominently during blood vessel formation.

Because of the importance of angiogenesis to tumor growth and metastasis, a number of chemotherapeutic approaches are being developed to interfere with or prevent this process. One of these approaches, involves the use of anti-angiogenic proteins such as angiostatin and endostatin. Angiostatin is a 38 kDa fragment of plasminogen that has been shown in animal models to be a potent inhibitor of endothelial cell proliferation. (O'Reilly et. al., Cell, 1994, 79, 315–328) Endostatin is a 20 kDa C-terminal fragment of collagen XVIII that has also been shown to be a potent inhibitor. (O'Reilly et. al., Cell, 1997, 88, 277–285) Systemic therapy with endostatin has been shown to result in strong anti-tumor activity in animal models. However, human clinical trials of these two chemotherapeutic agents of biological origin have been hampered by lack of availability.

Another approach to anti-angiogenic therapy is to use targeting moieties that interact with endothelial cell surface receptors expressed in the angiogenic vasculature to which are attached chemotherapeutic agents. Burrows and Thorpe (Proc. Nat. Acad. Sci, USA, 1993, 90, 8996–9000) described the use of an antibody-immunotoxin conjugate to eradicate tumors in a mouse model by destroying the tumor vasculature. The antibody was raised against an endothelial cell class II antigen of the major histocompatibility complex and was then conjugated with the cytotoxic agent, deglycosylated ricin A chain. The same group (Clin. Can. Res., 1995, 1, 1623–1634) investigated the use of antibodies raised against the endothelial cell surface receptor, endoglin, conjugated to deglycosylated ricin A chain. Both of these conjugates exhibited potent anti-tumor activity in mouse models. However, both still suffer drawbacks to routine human use. As with most antibodies or other large, foreign proteins, there is considerable risk of immunologic toxicity which could limit or preclude administration to humans. Also, while the vasculature targeting may improve the local concentration of the attached chemotherapeutic agents, the agents still must be cleaved from the antibody carrier and be transported or diffuse into the cells to be cytotoxic.

Thus, it is desirable to provide anti-angiogenic pharmaceuticals and tumor or new vasculature imaging agents which do not suffer from poor diffusion or transportation, possible immunologic toxicity, limited availability, and/or a lack of specificity.

Another application of anti-angiogenic therapy is in treating rheumatoid arthritis (RA). In RA, the ingrowth of a highly vascularized pannus is caused by the excessive production of angiogenic factors by the infiltrating macrophages, immune cells, or inflammatory cells. Therefore, it is desirable to have new pharmaceuticals to destroy the highly vascularized pannus that results and thus treat the disease.

There is also a growing interest in therapeutic angiogenesis to improve blood flow in regions of the body that have become ischemic or poorly perfused. Several investigators are using growth factors administered locally to cause new vasculature to form either in the limbs or the heart. The growth factors VEGF and bFGF are the most common for this application. Recent publications include: Takeshita, S., et. al., J. Clin. Invest., 1994, 93, 662–670; and Schaper, W. and Schaper, J., Collateral Circulation:Heart, Brain, Kidney, Limbs, Kluwer Academic Publishers, Boston, 1993. The main applications that are under investigation in a number of laboratories are for improving cardiac blood flow and in improving peripheral vessal blood flow in the limbs. For example, Henry, T. et. al. (J. Amer. College Cardiology, 1998, 31, 65A) describe the use of recombinant human VEGF in patients for improving myocardial perfusion by therapeutic angiogenesis. Patients received infusions of rhVEGF and were monitored by nuclear perfusion imaging 30 and 60 days post treatment to determine improvement in myocardial perfusion. About 50% of patients showed improvement by nuclear perfusion imaging whereas 5/7 showed new collatoralization by angiography. Thus, it is desirable to discover a method of monitoring improved cardiac blood flow which is targeted to new collateral vessels themselves and not, as in nuclear perfusion imaging, a regional consequence of new collateral vessels.

The detection, imaging and diagnosis of a number of cardiovascular diseases need to be improved, including restenosis, atherosclerosis, myocardial reperfusion injury, and myocardial ischemia, stunning or infarction. It has recently been determined that in all of these disease conditions, the integrin receptor $\alpha_v\beta_3$ plays an important role.

For example, in the restenosis complication that occurs in ~30–50% of patients having undergone angioplasty or stent placement, neointimal hyperplasia and ultimate reocclusion is caused by aggressively proliferating vascular smooth muscle cells that express $\alpha_v\beta_3$. (Cardiovascular Res., 1997, 36, 408–428; DDT, 1997, 2, 187–199; Current Pharm. Design, 1997, 3, 545–584)

Atherosclerosis proceeds from an intial endothelial damage that results in the recruitment and subintimal migration of monocytes at the site of the injury. Growth factors are released which induce medial smooth muscle cells to proliferate and migrate to the intimal layer. The migrating smooth muscle cells express $\alpha_v\beta_3$.

In reperfusion injury, neutrophil transmigration is integrin dependent and the integrins moderate initial infiltration into the viable border zone. The induction of $\alpha_5\beta_1$, $\alpha_4\beta_1$ and $\alpha_v\beta_5$ in infiltrating neutrophils occurs within 3 to 5 hours after reperfusion as neutrophils move from the border zone to the area of necrosis. (Circulation, 1999, 100, I-275)

Acute or chronic occlusion of a coronary artery is known to result in angiogenesis in the heart as native collateral vessels are recruited to attempt to relieve the ischemia. However, even a gradual occlusion usually results in areas of infarction as the resulting angiogenesis is not sufficient to prevent damage. Cardiac angiogenesis has been associated with increased expression of the growth factors VEGF and FGF and the upregulation of the growth factor receptors flt-1 and flk-1/KDR. (Drugs, 1999, 58, 391–396)

SUMMARY OF THE INVENTION

It is one object of the present invention to provide improved anti-angiogenic pharmaceuticals, comprised of a targeting moiety that binds to the vitronectin receptor that is expressed in tumor neovasculature, an optional linking group, and a radioisotope. The vitronectin receptor binding compounds target the radioisotope to the tumor neovasculature. The beta or alpha-particle emitting radioisotope emits a cytotoxic amount of ionizing radiation which results in cell death. The penetrating ability of radiation obviates the requirement that the cytotoxic agent diffuse or be transported into the cell to be cytotoxic.

It is another object of the present invention to provide pharmaceuticals to treat rheumatoid arthritis. These pharmaceuticals comprise a targeting moiety that binds to a receptor that is upregulated during angiogenesis, an optional linking group, and a radioisotope that emits cytotoxic radiation (i.e., beta particles, alpha particles and Auger or Coster-Kronig electrons). In rheumatoid arthritis, the ingrowth of a highly vascularized pannus is caused by the excessive production of angiogenic factors by the infiltrating macrophages, immune cells, or inflammatory cells. Therefore, the radiopharmaceuticals of the present invention that emit cytotoxic radiation could be used to destroy the new angiogenic vasculature that results and thus treat the disease.

It is another object of the present invention to provide imaging agents, comprised of vitronectin receptor binding compounds conjugated to an imageable moiety, such as a gamma ray or positron emitting radioisotope, a magnetic resonance imaging contrast agent, an X-ray contrast agent, or an ultrasound contrast agent. These imaging agents are useful for imaging tumor neovasculature, therapeutic angiogenesis interventions in the heart, natural angiogenic processes in response to acute or chronic coronary vessel occlusion, restenosis post-angioplasty, atherosclerosis and plaque formation, and reperfusion injury.

It is another object of the present invention to provide compounds useful for preparing the pharmaceuticals of the present invention. These compounds are comprised of a non-peptide benzodiazepine, benzodiazepinedione, or dibenzotrihydroannulene containing targeting moiety that binds to a receptor that is upregulated during angiogenesis or during cardiovascular diseases, Q, an optional linking group, $L_n$, and a metal chelator or bonding moiety, $C_h$. The compounds may have one or more protecting groups attached to the metal chelator or bonding moiety. The protecting groups provide improved stability to the reagents for long-term storage and are removed either immediately prior to or concurrent with the synthesis of the radiopharmaceuticals. Alternatively, the compounds of the present invention are comprised of a peptide or peptidomimetic targeting moiety that binds to a receptor that is upregulated during angiogenesis or during cardiovascular diseases, Q, an optional linking group, $L_n$, and a surfactant, $S_f$.

The pharmaceuticals of the present invention may be used for diagnostic and/or therapeutic purposes. Diagnostic radiopharmaceuticals of the present invention are pharmaceuticals comprised of a diagnostically useful radionuclide (i.e., a radioactive metal ion that has imageable gamma ray or positron emissions). Therapeutic radiopharmaceuticals of the present invention are pharmaceuticals comprised of a therapeutically useful radionuclide, a radioactive metal ion that emits ionizing radiation such as beta particles, alpha particles and Auger or Coster-Kronig electrons.

The pharmaceuticals comprising a gamma ray or positron emitting radioactive metal ion are useful for imaging tumors and by gamma scintigraphy or positron emission tomography. The pharmaceuticals comprising a gamma ray or positron emitting radioactive metal ion are also useful for imaging therapeutic angiogenesis, natural angiogenic processes in response to acute or chronic coronary vessel occlusion, restenosis post-angioplasty, atherosclerosis and plaque formation, and reperfusion injury by gamma scintigraphy or positron emission tomography. The pharmaceuticals comprising a particle emitting radioactive metal ion are useful for treating cancer by delivering a cytotoxic dose of radiation to the tumors. The pharmaceuticals comprising a particle emitting radioactive metal ion are also useful for treating rheumatoid arthritis by destroying the formation of angiogenic vasculature. The pharmaceuticals comprising a paramagnetic metal ion are useful as magnetic resonance imaging contrast agents. The pharmaceuticals comprising one or more X-ray absorbing or "heavy" atoms of atomic number 20 or greater are useful as X-ray contrast agents. The pharmaceuticals comprising a microbubble of a biocompatible gas, a liquid carrier, and a surfactant microsphere, are useful as ultrasound contrast agents.

DETAILED DESCRIPTION OF THE INVENTION

Thus, in a first embodiment, the present invention provides a novel compound, comprising: a targeting moiety and a chelator, wherein the targeting moiety is bound to the chelator, is a benzodiazepine, benzodiazepinedione, or dibenzotrihydroannulene nonpeptide, and binds to a receptor that is upregulated during angiogenesis and the compound has 0–1 linking groups between the targeting moiety and chelator.

In a preferred embodiment, the receptor is the integrin $\alpha_v\beta_3$ or $\alpha_v\beta_5$ and the compound is of the formula:

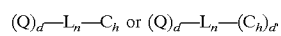

wherein, Q is a compound of Formulae (Ia), (Ib) or (Ic):

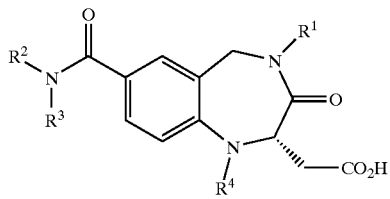
(Ia)

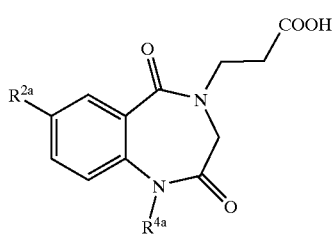
(Ib)

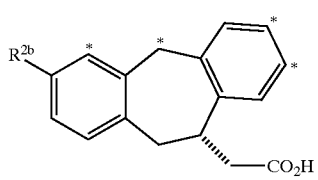
(Ic)

wherein:
- $R^1$ and $R^3$ are independently selected from the group: $C_1$–$C_6$ alkyl, benzyl, phenethyl, and a bond to $L_n$; provided that one of $R^1$ and $R^3$ is a bond to $L_n$;
- $R^2$ is independently selected from the group: 2-benzimidazolylmethyl, 2-guanidinoethyl, 2-amino-2-pyridyl, 2-amino-2-pyridylmethyl, 5-amino-2-imidazolylmethyl, and 2-imidazolylmethyl;
- $R^4$ is independently selected from H, $C_{1-6}$ alkyl or benzyl;
- $R^{2a}$ is $(CH_2)_3R^{3a}$;
- $R^{3a}$ is selected from the group:

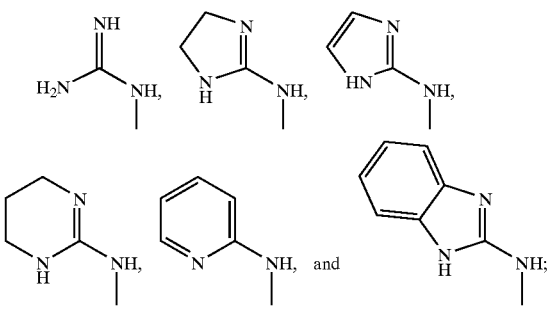

$R^{4a}$ is independently selected from $C_{1-6}$ alkyl substituted with a bond to $L_n$ or benzyl substituted with a bond to $L_n$;

$R^{2b}$ is independently selected from the group:

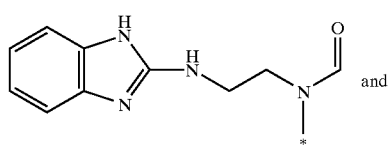
and

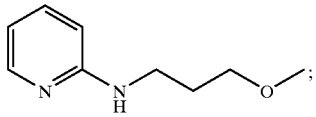

the asterisks * denote optional positions for attaching $L_n$; or Q is a peptide selected from the group:

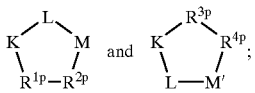

- $R^{1p}$ is L-valine, D-valine or L-lysine optionally substituted on the. amino group with a bond to $L_n$;
- $R^{2p}$ is L-phenylalanine, D-phenylalanine, D-1-naphthylalanine, 2-aminothiazole-4-acetic acid or tyrosine, the tyrosine optionally substituted on the hydroxy group with a bond to $L_n$;
- $R^{3p}$ is D-valine;
- $R^{4p}$ is D-tyrosine substituted on the hydroxy group with a bond to $L_n$;
- provided that one of $R^{1p}$ and $R^{2p}$ in each Q is substituted with a bond to $L_n$, and further provided that when $R^{2p}$ is 2-aminothiazole-4-acetic acid, K is N-methylarginine;
- provided that at least one Q is a compound of Formula Ia Ib, or Ic;
- d is selected from 1, 2, 3, 4, 5, 6, 7, 8, 9, and 10;
- d' is 1–100;
- $L_n$ is a linking group having the formula:

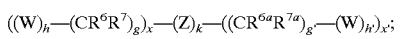

- W is independently selected at each occurrence from the group: O, S, NH, NHC(=O), C(=O)NH, $NR^8C(=O)$, C(=O)N $R^8$, C(=O), C(=O)O, OC(=O), NHC(=S) NH, NHC(=O)NH, $SO_2$, $SO_2NH$, $(OCH_2CH_2)_s$, $(CH_2CH_2O)_{s'}$, $(OCH_2CH_2CH_2)_{s''}$, $(CH_2CH_2CH_2O)_t$, and $(aa)_{t'}$;
- aa is independently at each occurrence an amino acid;
- Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;
- $R^6$, $R^{6a}$, $R^7$, $R^{7a}$, and $R^8$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, $NHC(=O)R^{11}$, $C(=O)NHR^{11}$, $NHC(=O)NHR^{11}$, $NHR^{11}$, $R^{11}$, and a bond to $C_h$;
- $R^{10}$ is independently selected at each occurrence from the group: a bond to $C_h$, $COOR^{11}$, $C(=O)NHR^{11}$, NHC(=O)$R^{11}$, OH, $NHR^{11}$, $SO_3H$, $PO_3H$, $—OPO_3H_2$, $—OSO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;
- $R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, polyalkylene glycol substituted with 0–1 $R^{12}$, carbohydrate substituted with 0–1 $R^{12}$, cyclodextrin substituted with 0–1 $R^{12}$, amino acid substituted with 0–1 $R^{12}$, polycarboxyalkyl substituted with 0–1 $R^{12}$, polyazaalkyl substituted with 0–1 $R^{12}$, peptide substituted with 0–1 $R^{12}$, wherein the peptide is comprised of 2–10 amino acids, 3,6-O-disulfo-B-D-galactopyranosyl, bis(phosphonomethyl)glycine, and a bond to $C_h$;

$R^{12}$ is a bond to $C_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$C_h$ is a metal bonding unit having a formula selected from the group:

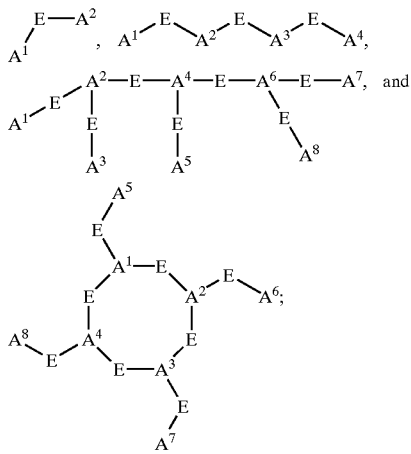

$A^1$, $A^2$, $A^3$, $A^4$, $A^5$, $A^6$, $A^7$, and $A^8$ are independently selected at each occurrence from the group: $NR^{13}$, $NR^{13}R^{14}$, S, SH, S(Pg), O, OH, $PR^{13}$, $PR^{13}R^{14}$, $P(O)R^{15}R^{16}$, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{13}$ and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, $C_{1-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form =C($R^{20}$)($R^{21}$);

$R^{15}$ and $R^{16}$ are each independently selected from the group: a bond to $L_n$, —OH, $C_1$–$C_{10}$ alkyl substituted with 0–3 $R^{17}$, $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{17}$ is independently selected at each occurrence from the group: a bond to $L_n$, =O, F, Cl, Br, I, —$CF_3$, —CN, —$CO_2R^{18}$, —C(=O)$R^{18}$, —C(=O)N($R^{18}$)$_2$, —CHO, —$CH_2OR^{18}$, —OC(=O)$R^{18}$, —OC(=O)$OR^{18a}$, —$OR^{18}$, —OC(=O)N($R^{18}$)$_2$, —$NR^{19}$C(=O)$R^{18}$, —$NR^{19}$C(=O)$OR^{18a}$, —$NR^{19}$C(=O)N($R^{18}$)$_2$, —$NR^{19}SO_2$N($R^{18}$)$_2$, —$NR^{19}SO_2R^{18a}$, —$SO_3H$, —$SO_2R^{18a}$, —$SR^{18}$, —S(=O)$R^{18a}$, —$SO_2$N($R^{18}$)$_2$, —N($R^{18}$)$_2$, —NHC(=S)$NHR^{18}$, =$NOR^{18}$, $NO_2$, —C(=O)$NHOR^{18}$, —C(=O)$NHNR^{18}R^{18a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{18}$, and a 5–10 membered heterocyclic ring system containing 1–4 heteroatoms independently selected from N, S, and O;

$R^{18}$, $R^{18a}$, and $R^{19}$ are independently selected at each occurrence from the group: a bond to $L_n$, H, $C_1$–$C_6$ alkyl, phenyl, benzyl, $C_1$–$C_6$ alkoxy, halide, nitro, cyano, and trifluoromethyl;

Pg is a thiol protecting group;

$R^{20}$ and $R^{21}$ are independently selected from the group: H, $C_1$–$C_{10}$ alkyl, —CN, —$CO_2R^{25}$, —C(=O)$R^{25}$, —C(=O)N($R^{25}$)$_2$, $C_2$–$C_{10}$ 1-alkene substituted with 0–3 $R^{23}$, $C_2$–$C_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted with 0–3 $R^{23}$, and unsaturated $C_{3-10}$ carbocycle substituted with 0–3 $R^{23}$;

alternatively, $R^{20}$ and $R^{21}$, taken together with the divalent carbon radical to which they are attached form:

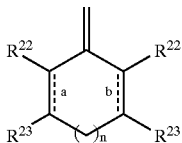

$R^{22}$ and $R^{23}$ are independently selected from the group: H, $R^{24}$, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and $C_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: =O, F, Cl, Br, I, —$CF_3$, —CN, —$CO_2R^{25}$, —C(=O)$R^{25}$, —C(=O)N($R^{25}$)$_2$, —N($R^{25}$)$_3^+$, —$CH_2OR^{25}$, —OC(=O)$R^{25}$, —OC(=O)O$R^{25a}$, —$OR^{25}$, —OC(=O)N($R^{25}$)$_2$, —$NR^{26}$C(=O)$R^{25}$, —$NR^{26}$C(=O)O$R^{25a}$, —$NR^{26}$C(=O)N($R^{25}$)$_2$, —$NR^{26}SO_2$N($R^{25}$)$_2$, —$NR^{26}SO_2R^{25a}$, —$SO_3H$, —$SO_2R^{25a}$, —$SR^{25}$, —S(=O)$R^{25a}$, —$SO_2$N($R^{25}$)$_2$, —N($R^{25}$)$_2$, =$NOR^{25}$, —C(=O)NHO$R^{25}$, —$OCH_2CO_2H$, and 2-(1-morpholino)ethoxy; and, $R^{25}$, $R^{25a}$, and $R^{26}$ are each independently selected at each occurrence from the group: hydrogen and $C_1$–$C_6$ alkyl; and a pharmaceutically acceptable salt thereof.

In a more preferred embodiment, the present invention provides a compound wherein:

d is selected from 1, 2, 3, 4, and 5;

d' is 1–50;

W is independently selected at each occurrence from the group: O, NH, NHC(=O), C(=O)NH, $NR^8$C(=O), C(=O)$NR^8$, C(=O), C(=O)O, OC(=O), NHC(=S) NH, NHC(=O)NH, $SO_2$, ($OCH_2CH_2$)$_s$, ($CH_2CH_2O$)$_{s'}$, ($OCH_2CH_2CH_2$)$_{s''}$, ($CH_2CH_2CH_2O$)$_t$, and (aa)$_{t'}$;

aa is independently at each occurrence an amino acid;

z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, and $R^8$ are independently selected at each occurrence from the group: H, =O, COOH, $SO_3H$, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O)$NHR^{11}$, NHC(=O)$NHR^{11}$, $NHR^{11}$, $R^{11}$, and a bond to $C_h$;

k is 0 or 1;

s is selected from 0, 1, 2, 3, 4, and 5;

s' is selected from 0, 1, 2, 3, 4, and 5;

s" is selected from 0, 1, 2, 3, 4, and 5;

t is selected from 0, 1, 2, 3, 4, and 5;

$A^1$, $A^2$, $A^3$, $A^4$, $A^5$, $A^6$, $A^7$, and $A^8$ are independently selected at each occurrence from the group: $NR^{13}$, $NR^{13}R^{14}$, S, SH, S(Pg), OH, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, and a 5–10 membered heterocyclic ring system containing 1–4 heteroatoms independently selected from N, S, and O and substituted with 0–3 $R^{17}$;

$R^{13}$, and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form =C($R^{20}$)($R^{21}$);

$R^{17}$ is independently selected at each occurrence from the group: a bond to $L_n$, =O, F, Cl, Br, I, —$CF_3$, —CN, —$CO_2R^{18}$, —C(=O)$R^{18}$, —C(=O)N($R^{18}$)$_2$, —$CH_2OR^{18}$, —OC(=O)$R^{18}$, —OC(=O)O$R^{18a}$, —$OR^{18}$, —OC(=O)N($R^{18}$)$_2$, —$NR^{19}$C(=O)$R^{18}$, —$NR^{19}$C(=O)O$R^{18a}$, —$NR^{19}$C(=O)N($R^{18}$)$_2$, —$NR^{19}SO_2$N($R^{18}$)$_2$, —$NR^{19}SO_2R^{18a}$, —$SO_3H$, —$SO_2R^{18a}$, —S(=O)$R^{18a}$, —$SO_2$N($R^{18}$)$_2$, —N($R^{18}$)$_2$, —NHC(=S)$NHR^{18}$, =$NOR^{18}$, —C(=O) $NHNR^{18}R^{18a}$, —$OCH_2CO_2H$, and 2-(1-morpholino) ethoxy;

$R^{18}$, $R^{18a}$, and $R^{19}$ are independently selected at each occurrence from the group: a bond to $L_n$, H, and $C_1$–$C_6$ alkyl;

$R^{20}$ and $R^{21}$ are independently selected from the group: H, $C_1$–$C_5$ alkyl, —$CO_2R^{25}$, $C_2$–$C_5$ 1-alkene substituted with 0–3 $R^{23}$, $C_2$–$C_5$ 1-alkyne substituted with 0–3 $R^{23}$, aryl substituted with 0–3 $R^{23}$, and unsaturated 5–10 membered heterocyclic ring system containing 1–4 heteroatoms independently selected from N, S, and O and substituted with 0–3 $R^{23}$;

alternatively, $R^{20}$ and $R^{21}$, taken together with the divalent carbon radical to which they are attached form:

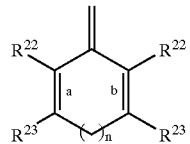

$R^{22}$ and $R^{23}$ are independently selected from the group: H, and $R^{24}$;

alternatively, $R^{22}$, $R^{23}$ taken together form a fused aromatic or a 5–10 membered heterocyclic ring system containing 1–4 heteroatoms independently selected from N, S, and O;

$R^{24}$ is independently selected at each occurrence from the group: —$CO_2R^{25}$, —C(=O)N($R^{25}$)$_2$, —$CH_2OR^{25}$, —OC(=O)$R^{25}$, —$OR^{25}$, —$SO_3H$, —N($R^{25}$)$_2$, and —$OCH_2CO_2H$; and, $R^{25}$ is independently selected at each occurrence from the group: H and $C_1$–$C_3$ alkyl.

In an even more preferred embodiment, the present invention provides a compound wherein:

$R^{4a}$ is benzyl substituted with a bond to $L_n$;

$R^{2b}$ is 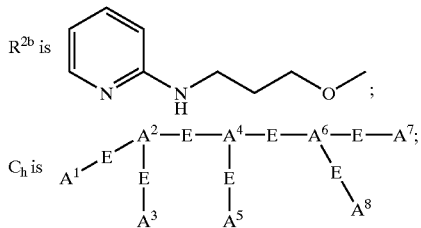

$C_h$ is 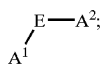

$A^1$ is selected from the group: OH, and a bond to $L_n$;
$A^2$, $A^4$, and $A^6$ are each N;
$A^3$, $A^5$, and $A^8$ are each OH;
$A^7$ is a bond to $L_n$ or NH-bond to $L_n$;
E is a $C_2$ alkyl substituted with 0–1 $R^{17}$;
$R^{17}$ is =O;
alternatively, $C_h$ is

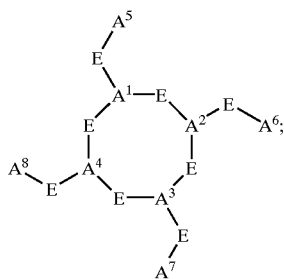

$A^1$ is selected from the group: OH, and a bond to $L_n$;
$A^2$, $A^3$ and $A^4$ are each N;
$A^5$, $A^6$ and $A^8$ are each OH;
$A^7$ is a bond to $L_n$;
E is a $C_2$ alkyl substituted with 0–1 $R^{17}$;
$R^{17}$ is =O;
alternatively, $C_h$ is $A^1$—E—$A^2$;

$A^1$ is $NH_2$ or $N=C(R^{20})(R^{21})$;
E is a bond;
$A^2$ is $NHR^{13}$;
$R^{13}$ is a heterocycle substituted with $R^{17}$, the heterocycle being selected from pyridine and pyrimidine;
$R^{17}$ is selected from a bond to $L_n$, C(=O)$NHR^{18}$ and C(=O) $R^{18}$;
$R^{18}$ is a bond to $L_n$;
$R^{24}$ is selected from the group: —$CO_2R^{25}$, —$OR^{25}$, —$SO_3H$, and —$N(R^{25})_2$; and,
$R^{25}$ is independently selected at each occurrence from the group: hydrogen and methyl.

In another even more preferred embodiment, the present invention provides a compound selected from the group:

(S,S,S)-4-(N-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)propyl) carbamoyl)-4-(4-carboxy-2-(2-(1,4,7,10-tetraaza-4,7,10-tris(carboxymethyl) cyclodecyl)acetylamino) butanoyl amino)butanoic acid;

(S)-2-(2,5-diaza-5-(6((6-((1-aza-2-(2-sulfophenyl)vinyl) amino)(3-pyridyl))carbonylamino)hexyl)-9-(N-(benzimidazol-2-ylmethyl)-N-methylcarbamoyl)-4-oxobicyclo [5.4.0]undeca-1(7),8,10-trien-3-yl) acetic acid;

(S)-2-(2,5-diaza-9-(N-(6-((6-((1-aza-2-(2-sulfophenyl) vinyl)amino)(3-pyridyl))carbonylamino)hexyl)-N-(benzimidazol-2-ylmethyl)carbamoyl)-5-methyl-4-oxobicyclo [5.4.0]undeca-1(7),8,10-trien-3-yl)acetic acid;

(S,S)-2-(2-aza-2-((5-(N-(1,3-bis(N-(6-(aminohexyl-4-oxobicyclo[5.4.0]undeca-1(7),8,10-trien-3-yl)acetic acid)(2-(2,5-diaza-9-(N-(benzimidazol-2-ylmethyl) propyl)carbamoyl)(2-pyridyl))amino)vinyl) benzenesulfonic acid;

(S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-4-(4-carboxy-2-(2-(1,4,7,10-tetraaza-4,7,10-tris(carboxymethyl) cyclododecyl)acetylamino) butanoylamino) butanoic acid;

(S,S)-3-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-3-(2-(1,4,7,10-tetraaza-4,7,10-tris (carboxymethyl) cyclododecyl)acetylamino)propanoic acid;

(S,S,S,S,S,S,S,S)-4-(N-1,3-bis(N-3-carboxy-1-(N-(3-(3, 6-diaza-10-(N-(benzimidazol-2-ylmethyl)-N-methylcarbamoyl)-5-(carboxymethyl)-4-oxobicyclo [5.4.0]undeca-1(7),8,10-trien-3-yl)propyl)carbamoyl)-4,4-dihydroxypentyl) carbamoyl)propyl)carbamoyl)-4-(5,5-dihydroxy-2-(2-(1,4,7,10-tetraaza-4,7,10-tris (carboxymethyl)cyclodecyl)acetylamino) butanoic acid;

(S,S,S,S,S,S,S,S,S,S)-2-(4-(N-(1,3-bis(N-(3-(N-(3-(3,6-diaza-10-(N-(benzimidazol-2-ylmethyl)-N-methylcarbamoyl)-5-((methoxycarbonyl)methyl)-4-oxobicyclo [5.4.0]undeca-1(7),8,10-trien-3-yl)propyl) carbamoyl)-1-(methoxycarbonyl)propyl)carbamoyl) propyl)carbamoyl propyl)carbamoyl)-4-(2-(2-(1,4,7, 10-tetraaza-4,7,10-tris(carboxymethyl)cyclodecyl) acetylamino)-4-carboxybutanoylamino)-4-carboxybutanoylamino)butanoylamino)-4-(N-(3-(3,6-diaza-10-(N-(benzimidazol-2-ylmethyl)-N-methyl carbamoyl)-5-((methoxycarbonyl)methyl)-4-oxobicyclo[5.4.0] undeca-1(7),8,10-trien-3-yl)propyl) carbamoyl)butanoic acid;

(S)-2-(2,5-diaza-5-(3-(2-(2-(3-((6-((1-aza-2-(2-sulfophenyl)vinyl)amino)(3-pyridyl))carbonylamino) propoxy)ethoxy)ethoxy)propyl)-9-(N-(benzimidazol-2-ylmethyl)-N-methylcarbamoyl)-4-oxobicyclo[5.4.0] undeca-1(7),8,10-trien-3-yl)acetic acid;

(S,S,S,S)-4-(N-(1,3-bis(N-(3-(2-(2-(3-(3,6-diaza-10-(N-(benzimidazol-2-ylmethyl)-N-methylcarbamoyl)-5-(carboxymethyl)-4-oxobicyclo[5.4.0]undeca-1(7),8, 10-trien-3-yl)propoxy)ethoxy)ethoxy)propyl) carbamoyl) propyl)carbamoyl)-4-(5,5-dihydroxy-2-(2-(1,4,7,10-tetraaza-4,7,10-tris(carboxy methyl) cyclododecyl)acetylamino) hexanoylamino)butanoic acid;

(S,S,S)-2-(2,5-diaza-9-(N-(benzimidazol-2-ylmethyl)-N-methylcarbamoyl)-4-oxo-5-(6-(4-(N-((R,S,S,S)-2,3,4, 5,6-pentahydroxyhexyl)carbamoyl)-2-(4-(N-((R,S,S, S)-2,3,4,5,6-pentahydroxy hexyl)carbamoyl)-2-(2-(1, 4,7,10-tetraaza-4,7,10-tris(carboxymethyl)cyclodecyl)

acetylamino)butanoylamino)butanoylamino)hexyl) bicyclo[5.4.0]undeca-1(7),8,10-trien-3-yl)acetic acid;

(S,S,S,S)-2-(4-(N-(1-(N-(1-(N-(6-(3,6-diaza-10-(N-(benzimidazol-2-ylmethyl)-N-methylcarbamoyl)-5-(carboxymethyl)-4-oxobicyclo[5.4.0]undeca-1(7),8, 10-trien-3-yl)hexyl)carbamoyl)-3-(N-cyclo{Lys-Arg (Mtr)-Gly-Asp(OtBu)-D-Phe}[gamma-LysNH] carbamoyl)propyl)carbamoyl)-3-carboxypropyl) carbamoyl)-4-(2-(1,4,7,10-tetraaza-4,7,10-tris (carboxymethyl) cyclododecyl)acetylamino)butanoic acid;

4-[N-(3-{(2R)-7-[N-(benzimidazol-2-ylmethyl)-N-methylcarbamoyl]-2-(carboxymethyl)-3-oxo(1H, 2H,5H-benzo[f]1,4-diazepin-4-yl)}propyl)carbamoyl] (4S)-4-[(4S)-4-(N-{(1S)-1-[N-(3-{(2S)-7-[N-(benzimidazol-2-ylmethyl)-N-methylcarbamoyl]-2-(carboxymethyl)-3-oxo (1H,2H,5H-benzo[f]1,4-diazepin-4-yl)}propyl)carbamoyl]-3-carboxypropyl}carbamoyl)-4-{2-[1,4,7,10-tetraaza-4,7,10-tris(carboxymethyl)cyclododecyl] acetylamino}butanoyl amino]butanoic acid;

2-(4-{3-[(6-{[(1E)-1-aza-2-(2-sulfophenyl)vinyl]amino} (3-pyridyl))carbonylamino]propyl} (2S)-7-{N-[2-(amidinoamino)ethyl]-N-methylcarbamoyl}-3-oxo-1H,2H,5H-benzo[f]1,4-diazepin-2-yl)acetic acid; and 2-[9-(N-{6-[(6-{[(1E)-1-aza-2-(2-sulfophenyl)vinyl] amino}(3-pyridyl))carbonylamino]hexyl}-N-(benzimidazol-2-ylmethyl)carbamoyl)(5S)-5,6,11-trihydro-dibenzo[b,e][7]annulen-5-yl]acetic acid;

or a pharmaceutically acceptable salt form thereof.

In a further preferred embodiment, the present invention provides a kit comprising a compound of the present invention, or a pharmaceutically acceptable salt form thereof and a pharmaceutically acceptable carrier.

In an even further preferred embodiment, the kit further comprises one or more ancillary ligands and a reducing agent.

In a still further preferred embodiment, the ancillary ligands are tricine and TPPTS.

In another still further preferred embodiment, the reducing agent is tin(II).

In a second embodiment, the present invention provides a novel diagnostic or therapeutic metallopharmaceutical composition, comprising: a metal, a chelator capable of chelating the metal and a targeting moiety, wherein the targeting moiety is bound to the chelator, is a benzodiazepine, benzodiazepinedione, or dibenzotrihydroannulene nonpeptide and binds to a receptor that is upregulated during angiogenesis and the compound has 0–1 linking groups between the targeting moiety and chelator.

In a preferred embodiment, the metallopharmaceutical is a diagnostic radiopharmaceutical, the metal is a radioisotope selected from the group: $^{99m}$Tc, $^{95}$Tc, $^{111}$Tn, $^{62}$Cu, $^{64}$Cu, $^{67}$Ga, and $^{68}$Ga, and the linking group is present between the targeting moiety and chelator.

In another preferred embodiment, the targeting moiety is a benzodiazepine, benzodiazepinedione, or dibenzotrihydroannulene and the receptor is $\alpha_v\beta_3$ or $\alpha_v\beta_5$.

In another preferred embodiment, the radioisotope is $^{99m}$Tc or $^{95}$Tc, the radiopharmaceutical further comprises a first ancillary ligand and a second ancillary ligand capable of stabilizing the radiopharmaceutical.

In another preferred embodiment, the radioisotope is $^{99m}$Tc.

In another preferred embodiment, the radiopharmaceutical is selected from the group:

$^{99m}$Tc((S)-2-(2,5-diaza-5-(6((6-(diazenido)(3-pyridyl)) carbonylamino)hexyl)-9-(N-(benzimidazol-2-ylmethyl)-N-methylcarbamoyl)-4-oxobicyclo [5.4.0] undeca-1(7),8,10-trien-3-yl) acetic acid)(tricine) (TPPTS) and $^{99m}$Tc((S)-2-(2,5-diaza-9-(N-(6-((6-(diazenido)(3-pyridyl))carbonylamino)hexyl)-N-(benzimidazol-2-ylmethyl)carbamoyl)-5-methyl-4-oxobicyclo [5.4.0] undeca-1(7),8,10-trien-3-yl)acetic acid)(tricine) (TPPTS);

In another preferred embodiment, the radioisotope is $^{111}$In.

In another preferred embodiment, the radiopharmaceutical is selected from the group:

$^{111}$In complex of 6-(N-(3-(3-aza-10-(N-(benzimidazol-2-ylmethyl)-N-methylcarbamoyl)-5-(carboxymethyl)-4-oxobicyclo [5.4.0]undeca-1(7),8,10-trien-3-yl)propyl) carbamoyl)-3-(2-((2-((carboxymethyl)(2-((carboxymethyl)methylamino)ethyl)amino) ethyl)(2-((carboxymethyl)ethylamino)ethyl)amino)-acetylamino)-4-oxooctane-1,8-dicarboxylic acid;

$^{111}$In complex of (S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8, 10-trien-3-yl)propyl) carbamoyl)-4-(4-carboxy-2-(2-(1,4,7,10-tetraaza-4,7,10-tris(carboxymethyl) cyclododecyl)acetylamino)butanoylamino) butanoic acid; and $^{111}$In complex of (S,S)-3-(N-(3-(3,6-diaza-5-(carboxymethyl)-10-(N-(imidazol-2-ylmethyl)-N-benzylcarbamoyl)-4-oxobicyclo[5.4.0]undeca-1(7),8, 10-trien-3-yl)propyl) carbamoyl)-3-(2-(1,4,7,10-tetraaza-4,7,10-tris(carboxymethyl) cyclododecyl) acetylamino)propanoic acid.

In another preferred embodiment wherein the metallopharmaceutical is a therapeutic radiopharmaceutical, the metal is a radioisotope selected from the group: $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir, and the linking group is present between the targeting moiety and chelator.

In another preferred embodiment, the targeting moiety is a benzodiazepine, benzodiazepinedione, or dibenzotrihydroannulene and the receptor is $\alpha_v\beta_3$ or $\alpha_v\beta_5$.

In another preferred embodiment, the radioisotope is $^{149}$Pm.

In another preferred embodiment, the radiopharmaceutical is selected from the group:

the Pm-149 complex of (S,S,S)-4-(N-(3-(3,6-diaza-10-(N-(benzimidazol-2-ylmethyl)-N-methylcarbamoyl)-5-(carboxymethyl)-4-oxobicyclo[5.4.0]undeca-1(7),8, 10-trien-3-yl)propyl)carbamoyl)-4-(4-carboxy-2-(2-(1, 4,7,10-tetraaza-4,7,10-tris(carboxymethyl) cyclodecyl) acetylamino)butanoyl amino)butanoic acid; and the Pm-149 complex of (S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8, 10-trien-3-yl)propyl) carbamoyl)-4-(4-carboxy-2-(2-(1,4,7,10-tetraaza-4,7,10-tris(carboxymethyl) cyclododecyl)acetylamino)butanoylamino) butanoic acid.

In another preferred embodiment, the radioisotope is $^{177}$Lu.

In another preferred embodiment, the radiopharmaceutical is selected from the group:

the Lu-177 complex of (S,S,S)-4-(N-(3-(3,6-diaza-10-(N-(benzimidazol-2-ylmethyl)-N-methylcarbamoyl)-5-

(carboxymethyl)-4-oxobicyclo[5.4.0]undeca-1(7),8,
10-trien-3-yl)propyl)carbamoyl)-4-(4-carboxy-2-(2-(1,
4,7,10-tetraaza-4,7,10-tris(carboxymethyl) cyclodecyl)
acetylamino)butanoyl amino)butanoic acid; and the Lu-177 complex of (S,S,S)-4-(N-(3-(3,6-diaza-5-
(carboxymethyl)-10-(N-(imidazol-2-ylmethyl)-N-
benzylcarbamoyl)-4-oxobicyclo[5.4.0]undeca-1(7),8,
10-trien-3-yl)propyl) carbamoyl)-4-(4-carboxy-2-(2-
(1,4,7,10-tetraaza-4,7,10-tris(carboxymethyl)
cyclododecyl)acetylamino)butanoylamino) butanoic
acid; and the Lu-177 complex of (S,S)-3-(N-(3-(3,6-diaza-5-
(carboxymethyl)-10-(N-(imidazol-2-ylmethyl)-N-
benzylcarbamoyl)-4-oxobicyclo[5.4.0]undeca-1(7),8,
10-trien-3-yl)propyl) carbamoyl)-3-(2-(1,4,7,10-
tetraaza-4,7,10-tris(carboxymethyl) cyclododecyl)
acetylamino)propanoic acid.

[24] In another preferred embodiment, the radioisotope is $^{90}Y$

[25] In another preferred embodiment, the radiopharmaceutical is selected from the group:

the Y-90 complex of (S,S,S)-4-(N-(3-(3,6-diaza-10-(N-
(benzimidazol-2-ylmethyl)-N-methylcarbamoyl)-5-
(carboxymethyl)-4-oxobicyclo[5.4.0]undeca-1(7),8,
10-trien-3-yl)propyl)carbamoyl)-4-(4-carboxy-2-(2-(1,
4,7,10-tetraaza-4,7,10-tris(carboxymethyl) cyclodecyl)
acetylamino)butanoyl amino)butanoic acid; and the Y-90 complex of (S,S,S)-4-(N-(3-(3,6-diaza-5-
(carboxymethyl)-10-(N-(imidazol-2-ylmethyl)-N-
benzylcarbamoyl)-4-oxobicyclo[5.4.0]undeca-1(7),8,
10-trien-3-yl)propyl) carbamoyl)-4-(4-carboxy-2-(2-
(14,7,10-tetraaza-4,7,10-tris(carboxymethyl)
cyclododecyl)acetylamino)butanoylamino) butanoic
acid; and the Y-90 complex of(S,S)-3-(N-(3-(3,6-diaza-5-
(carboxymethyl)-10-(N-(imidazol-2-ylmethyl)-N-
benzylcarbamoyl)-4-oxobicyclo[5.4.0]undeca-1(7),8,
10-trien-3-yl)propyl) carbamoyl)-3-(2-(1,4,7,10-
tetraaza-4,7,10-tris(carboxymethyl) cyclododecyl)
acetylamino)propanoic acid.

In another preferred embodiment wherein the metallopharmaceutical is a MRI contrast agent, the metal is a paramagnetic metal ion selected from the group: Gd(III), Dy(III), Fe(III), and Mn(II), and the linking group is present between the targeting moiety and chelator.

In another preferred embodiment, the targeting moiety is a benzodiazepine, benzodiazepinedione, or dibenzotrihydroannulene and the receptor is $\alpha_v\beta_3$ or $\alpha_v\beta_5$.

In another preferred embodiment, the metal ion is Gd(III).

In yet another preferred embodiment wherein the metallopharmaceutical is a X-ray contrast agent, the metal is selected from the group: Re, Sm, Ho, Lu, Pm, Y, Bi, Pd, Gd, La, Au, Au, Yb, Dy, Cu, Rh, Ag, and Ir, and the linking group is present between the targeting moiety and chelator.

In another preferred embodiment, the present invention provides a novel method of treating rheumatoid arthritis in a patient comprising: administering a therapeutic radiopharmaceutical of claim 18 capable of localizing in new angiogenic vasculature to a patient by injection or infusion.

In another preferred embodiment, the present invention provides a novel method of treating cancer in a patient comprising: administering to a patient in need thereof a therapeutic radiopharmaceutical of claim 18 by injection or infusion.

In another preferred embodiment, the present invention provides a novel method of treating restenosis in a patient comprising: administering to a patient, either systemically or locally, a therapeutic radiopharmaceutical of claim 18 capable of localizing in the restenotic area and delivering an effective dose of radiation.

In another preferred embodiment, the present invention provides a novel method of imaging cancer in a patient comprising: (1) administering a diagnostic radiopharmaceutical of claim 11 to a patient by injection or infusion; (2) imaging the patient using planar or SPECT gamma scintigraphy, or positron emission tomography.

In another preferred embodiment, the present invention provides a novel method of imaging cancer in a patient comprising: (1) administering a MRI contrast agent of claim 26; and (2) imaging the patient using magnetic resonance imaging.

In another preferred embodiment, the present invention provides a novel method of imaging cancer in a patient comprising: (1) administering an X-ray contrast agent of claim 29; and (2) imaging the patient using X-ray computed tomography.

In another preferred embodiment, the present invention provides a novel method of imaging therapeutic angiogenesis in a patient comprising: (1) administering a diagnostic radiopharmaceutical, a MRI contrast agent, or a X-ray contrast agent of claim 10 to a patient by injection or infusion; (2) imaging the area of the patient wherein the desired formation of new blood vessels is located.

In another preferred embodiment, the present invention provides a novel method of imaging atherosclerosis in a patient comprising: (1) administering a diagnostic radiopharmaceutical, a MRI contrast agent, or a X-ray contrast agent of claim 10 to a patient by injection or infusion; (2) imaging the area of the patient wherein the atherosclerosis is located.

In another even more preferred embodiment, the present invention provides a novel method of imaging restenosis in a patient comprising: (1) administering a diagnostic radiopharmaceutical, a MRI contrast agent, or a X-ray contrast agent of claim 10 to a patient by injection or infusion; (2) imaging the area of the patient wherein the restenosis is located.

In another even more preferred embodiment, the present invention provides a novel method of imaging cardiac ischemia in a patient comprising: (1) administering a diagnostic radiopharmaceutical, a MRI contrast agent, or a X-ray contrast agent of claim 10 to a patient by injection or infusion; (2) imaging the area of the myocardium wherein the ischemic region is located.

In another even more preferred embodiment, the present invention provides a novel method of imaging myocardial reperfusion injury in a patient comprising: (1) administering a diagnostic radiopharmaceutical, a MRI contrast agent, or a X-ray contrast agent of claim 10 to a patient by injection or infusion; (2) imaging the area of myocardium wherein the reperfusion injury is located.

In a third embodiment, the present invention provides a novel compound, comprising: a targeting moiety and a surfactant, wherein the targeting moiety is bound to the surfactant, is a benzodiazepine, benzodiazepinedione, or dibenzotrihydroannulene nonpeptide, and binds to a receptor that is upregulated during angiogenesis and the compound has 0–1 linking groups between the targeting moiety and surfactant.

In a preferred embodiment, the receptor is the integrin $\alpha_v\beta_3$ or $\alpha_v\beta_5$ and the compound is of the formula:

$$(Q)_d\text{-}L_n\text{-}S_f$$

wherein, Q is a compound of Formulae (Ia), (Ib) or (Ic):

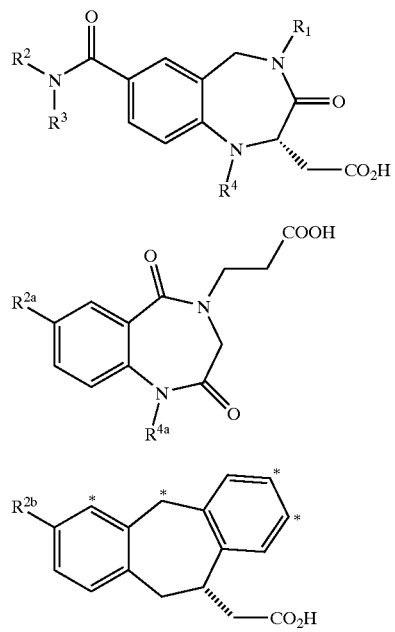

(Ia)

(Ib)

(Ic)

wherein:

R$^1$ and R$^3$ are independently selected from the group: C$_1$–C$_6$ alkyl, benzyl, phenethyl, and a bond to L$_n$; provided that one of R$^1$ and R$^3$ is a bond to L$_n$;

R$^2$ is independently selected from the group: 2-benzimidazolylmethyl, 2-guanidinoethyl, 2-amino-2-pyridyl, 2-amino-2-pyridylmethyl, 5-amino-2-imidazolylmethyl, and 2-imidazolylmethyl;

R$^4$ is independently selected from H, C$_{1-6}$ alkyl or benzyl;

R$^{2a}$ is (CH$_2$)$_3$R$^{3a}$;

R$^{3a}$ is selected from the group:

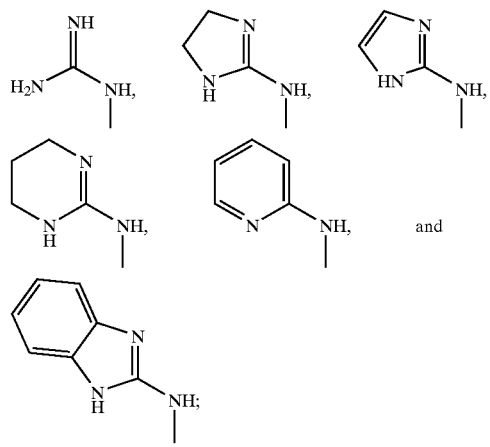

R$^{4a}$ is independently selected from C$_{1-6}$ alkyl substituted with a bond to L$_n$ or benzyl substituted with a bond to L$_n$;

R$^{2b}$ is independently selected from the group:

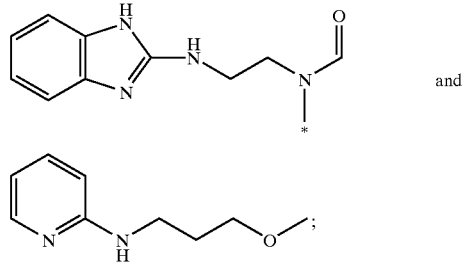

and the asterisks * denote optional positions for attaching L$_n$; or Q is a peptide selected from the group:

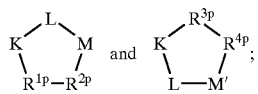

and

R$^{1p}$ is L-valine, D-valine or L-lysine optionally substituted on the .amino group with a bond to L$_n$;

R$^{2p}$ is L-phenylalanine, D-phenylalanine, D-1-naphthylalanine, 2-aminothiazole-4-acetic acid or tyrosine, the tyrosine optionally substituted on the hydroxy group with a bond to L$_n$;

R$^{3p}$ is D-valine;

R$^{4p}$ is D-tyrosine substituted on the hydroxy group with a bond to L$_n$;

provided that one of R$^{1p}$ and R$^{2p}$ in each Q is substituted with a bond to L$_n$, and further provided that when R$^{2p}$ is 2-aminothiazole-4-acetic acid, K is N-methylarginine;

provided that at least one Q is a compound of Formula Ia Ib, or Ic;

d is selected from 1, 2, 3, 4, 5, 6, 7, 8, 9, and 10;

L$_n$ is a linking group having the formula:

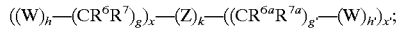

W is independently selected at each occurrence from the group: O, S, NH, NHC(=O), C(=O)NH, NR$^8$C(=O), C(=O)N R$^8$, C(=O), C(=O)O, OC(=O), NHC(=S) NH, NHC(=O)NH, SO$_2$, SO$_2$NH, (OCH$_2$CH$_2$)$_{20\text{-}200}$, (CH$_2$CH$_2$O)$_{20\text{-}200}$, (OCH$_2$CH$_2$CH$_2$)$_{20\text{-}200}$, (CH$_2$CH$_2$CH$_2$O)$_{20\text{-}200}$, and (aa)$_t$;

aa is independently at each occurrence an amino acid;

Z is selected from the group: aryl substituted with 0–3 R$^{10}$, C$_{3-10}$ cycloalkyl substituted with 0–3 R$^{10}$, and a 5–10 membered heterocyclic ring system containing 1–4 heteroatoms independently selected from N, S, and O and substituted with 0–3 R$^{10}$;

R$^6$, R$^{6a}$, R$^7$, R$^{7a}$, and R$^8$ are independently selected at each occurrence from the group: H, =O, COOH, SO$_3$H, PO$_3$H, C$_1$–C$_5$ alkyl substituted with 0–3 R$^{10}$, aryl substituted with 0–3 R$^{10}$, benzyl substituted with 0–3 R$^{10}$, and C$_1$–C$_5$ alkoxy substituted with 0–3 R$^{10}$, NHC(=O)R$^{11}$, C(=O)NHR$^{11}$, NHC(=O)NHR$^{11}$, NHR$^{11}$, R$^{11}$, and a bond to S$_f$;

R$^{10}$ is independently selected at each occurrence from the group: a bond to S$_f$, COOR$^{11}$, C(=O)NHR$^{11}$, NHC (=O)R$^{11}$, OH, NHR$^{11}$, SO$_3$H, PO$_3$H, —OPO$_3$H$_2$, —OSO$_3$H, aryl substituted with 0–3 R$^{11}$, C$_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, and a bond to $S_f$;

$R^{12}$ is a bond to $S_f$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$S_f$ is a surfactant which is a lipid or a compound of the formula:

$$\begin{array}{c} E^1\!\!-\!\!A^{10}; \\ / \\ A^9 \end{array}$$

$A^9$ is selected from the group: OH and $OR^{27}$;

$A^{10}$ is $OR^{27}$;

$R^{27}$ is $C(=O)C_{1-20}$ alkyl;

$E^1$ is $C_{1-10}$ alkylene substituted with 1–3 $R^{28}$;

$R^{28}$ is independently selected at each occurrence from the group: $R^{30}$, $-PO_3H-R^{30}$, $=O$, $-CO_2R^{29}$, $-C(=O)R^{29}$, $-C(=O)N(R^{29})_2$, $-CH_2OR^{29}$, $-OR^{29}$, $-N(R^{29})_2$, $C_1-C_5$ alkyl, and $C_2-C_4$ alkenyl;

$R^{29}$ is independently selected at each occurrence from the group: $R^{30}$, H, $C_1-C_6$ alkyl, phenyl, benzyl, and trifluoromethyl;

$R^{30}$ is a bond to $L_n$;

and a pharmaceutically acceptable salt thereof.

In another preferred embodiment, the compound is of the formula:

$$Q\!-\!L_n\!-\!S_f$$

wherein: Q is a compound of Formulae (Ia), (Ib), or (Ic):

(Ia)

(Ib)

(Ic)

$R^{4a}$ is benzyl substituted with a bond to $L_n$;

$R^{2b}$ is

Z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, and $R^8$ are independently selected at each occurrence from the group: H, $=O$, COOH, $SO_3H$, $C_1-C_5$ alkyl substituted with 0–1 $R^{10}$, aryl substituted with 0–1 $R^{10}$, benzyl substituted with 0–1 $R^{10}$, and $C_1-C_5$ alkoxy substituted with 0–1 $R^{10}$, NHC(=O)$R^{11}$, C(=O)NH$R^{11}$, NHC(=O)NH$R^{11}$, NH$R^{11}$, $R^{11}$, and a bond to $S_f$;

k is 0 or 1;

$S_f$ is a surfactant which is a lipid or a compound of the formula:

$$\begin{array}{c} E^1\!\!-\!\!A^{10}; \\ / \\ A^9 \end{array}$$

$A^9$ is $OR^{27}$;

$A^{10}$ is $OR^{27}$;

$R^{27}$ is $C(=O)C_{1-15}$ alkyl;

$E^1$ is $C_{1-4}$ alkylene substituted with 1–3 $R^{28}$;

$R^{28}$ is independently selected at each occurrence from the group: $R^{30}$, $-PO_3H-R^{30}$, $=O$, $-CO_2R^{29}$, $-C(=O)R^{29}$, $-CH_2OR^{29}$, $-OR^{29}$, and $C_1-C_5$ alkyl;

$R^{29}$ is independently selected at each occurrence from the group: $R^{30}$, H, $C_1-C_6$ alkyl, phenyl, and benzyl;

$R^{30}$ is a bond to $L_n$;

and a pharmaceutically acceptable salt thereof.

In another preferred embodiment, the compound selected from the group:

Sodium 1,2-dipalmitoyl-sn-glycero-3-phosphatidylethanolamine-(S)-2-(2,5-diaza-9-(N-(benzimidazol-2-ylmethyl)-N-methylcarbamoyl)-5-(6-aminohexyl)-4-oxobicyclo[5.4.0]undeca-1(7),8,10-trien-3-yl)acetic acid-dodecoanoate conjugate;

DPPE-PEG$_{3400}$-[(S) -2-(2,5-diaza-9-(N-(benzimidaz-2-ylmethyl)-N-methylcarbamoyl)-5-(6-aminohexyl)-4-oxobicyclo[5.4.0]undeca-1(7),8,10-trien-3-yl)acetic acid]-dodecoanoate conjugate; and

[(S)-2-(2-aza-(2-((5-(N-(1,3-bis-N-(6-(aminohexyl-4-oxobicyclo[5.4.0]undeca-1(7),8,10-trien-3-yl)acetic acid)(2-(2,5-diaza-9-(N-(benzimidazol-2-ylmethyl) carbamoyl)propyl)carbamoyl]-w-amino-PEG$_{3400}$-dodecanoate-DPPE conjugate.

In another more preferred embodiment, the present invention provides a novel ultrasound contrast agent composition, comprising:

(a) a compound of claim 41, comprising: a benzodiazepine, benzodiazepinedione, or dibenzotrihydroannulene that binds to the integrin $\alpha_v\beta_3$, or $\alpha_v\beta_5$, a surfactant and a linking group between the benzodiazepine and the surfactant;

(b) a parenterally acceptable carrier; and, (c) an echogenic gas.

In another preferred embodiment, the present invention provides a novel ultrasound contrast agent composition, further comprising: 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

In another preferred embodiment, the echogenic gas is a $C_{2-5}$ perfluorocarbon.

In another preferred embodiment, the present invention provides a method of imaging cancer in a patient comprising: (1) administering, by injection or infusion, a ultrasound contrast agent composition of claim 45 to a patient; and (2) imaging the patient using sonography.

In another preferred embodiment, the present invention provides a method of imaging therapeutic angiogenesis in a patient comprising: (1) administering, by injection or infusion, an ultrasound contrast agent composition of claim 45 to a patient; (2) imaging the area of the patient wherein the desired formation of new blood vessels is located.

In another preferred embodiment, the present invention provides a method of imaging atherosclerosis in a patient comprising: (1) administering, by injection or infusion, an ultrasound contrast agent composition of claim 45 to a patient; (2) imaging the area of the patient wherein the atherosclerosis is located.

In another preferred embodiment, the present invention provides a method of imaging restenosis in a patient comprising: (1) administering, by injection or infusion, an ultrasound contrast agent composition of claim 45 to a patient; (2) imaging the area of the patient wherein the restenosis is located.

[52] In another preferred embodiment, the present invention provides a method of imaging cardiac ischemia in a patient comprising: (1) administering, by injection or infusion, an ultrasound contrast agent composition of claim 45 to a patient; (2) imaging the area of the myocardium wherein the ischemic region is located.

In another preferred embodiment, the present invention provides a method of imaging myocardial reperfusion injury in a patient comprising: (1) administering, by injection or infusion, an ultrasound contrast agent composition of claim 45 to a patient; (2) imaging the area of myocardium wherein the reperfusion injury is located.

In another preferred embodiment, the present invention provides a novel therapeutic radiopharmaceutical composition, comprising:

(a) a therapeutic radiopharmaceutical of claim 19; and, (b) a parenterally acceptable carrier.

In another preferred embodiment, the present invention provides a novel diagnostic radiopharmaceutical composition, comprising:

(a) a diagnostic radiopharmaceutical, a MRI contrast agent, or a X-ray contrast agent of claim 10; and, (b) a parenterally acceptable carrier.

Another aspect of the present invention are diagnostic kits for the preparation of radiopharmaceuticals useful as imaging agents for cancer. Diagnostic kits of the present invention comprise one or more vials containing the sterile, non-pyrogenic, formulation comprised of a predetermined amount of a reagent of the present invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The inclusion of one or two ancillary ligands is required for diagnostic kits comprising reagent comprising a hydrazine or hydrazone bonding moiety. The one or more vials that contain all or part of the formulation can independently be in the form of a sterile solution or a lyophilized solid.

Another aspect of the present invention contemplates a method of imaging cancer in a patient involving: (1) synthesizing a diagnostic radiopharmaceutical of the present invention, using a reagent of the present invention, capable of localizing in tumors; (2) administering said radiopharmaceutical to a patient by injection or infusion; (3) imaging the patient using planar or SPECT gamma scintigraphy, or positron emission tomography.

Another aspect of the present invention contemplates a method of imaging cancer in a patient involving: (1) administering a paramagnetic metallopharmaceutical of the present invention capable of localizing in tumors to a patient by injection or infusion; and (2) imaging the patient using magnetic resonance imaging.

Another aspect of the present invention contemplates a method of imaging cancer in a patient involving: (1) administering a X-ray contrast agent of the present invention capable of localizing in tumors to a patient by injection or infusion; and (2) imaging the patient using X-ray computed tomography.

Another aspect of the present invention contemplates a method of imaging cancer in a patient involving: (1) administering a ultrasound contrast agent of the present invention capable of localizing in tumors to a patient by injection or infusion; and (2) imaging the patient using sonography.

Another aspect of the present invention contemplates a method of treating cancer in a patient involving: (1) administering a therapeutic radiopharmaceutical of the present invention capable of localizing in tumors to a patient by injection or infusion.

Definitions

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present invention. The D and L-isomers of a particular amino acid are designated herein using the conventional 3-letter abbreviation of the amino acid, as indicated by the following examples: D-Leu, or L-Leu.

When any variable occurs more than one time in any substituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —N($R^{53}$)$_2$, each of the two $R^{53}$ substituents on N is independently selected from the defined list of possible $R^{53}$. Combinations of substituents and/or variables are permissible only if such combinations result in stable compounds. When a bond to a substituent is shown to cross the bond connecting two atoms in a ring, then such substituent may be bonded to any atom on the ring.

The term "nonpeptide" means preferably less than three amide bonds in the backbone core of the targeting moiety or preferably less than three amino acids or amino acid mimetics in the targeting moiety.

The term "metallopharmaceutical" means a pharmaceutical comprising a metal. The metal is the cause of the imageable signal in diagnostic applications and the source of the cytotoxic radiation in radiotherapeutic applications. Radiopharmaceuticals are metallopharmaceuticals in which the metal is a radioisotope.

By "reagent" is meant a compound of this invention capable of direct transformation into a metallopharmaceutical of this invention. Reagents may be utilized directly for the preparation of the metallopharmaceuticals of this invention or may be a component in a kit of this invention.

The term "binding agent" means a metallopharmaceutical of this invention having affinity for and capable of binding to the vitronectin receptor. The binding agents of this invention have Ki<1000 nM.

By "stable compound" or "stable structure" is meant herein a compound that is sufficiently robust to survive isolation to a useful degree of purity from a reaction mixture, and formulation into an efficacious pharmaceutical agent.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the CRC Handbook of Chemistry and Physics, 65th Edition, CRC Press, Boca Raton, Fla., 1984, as any substance which yields ions, other than hydrogen or hydroxyl ions. As used herein, "pharmaceutically acceptable salts" refer to derivatives of the disclosed compounds modified by making acid or base salts. Examples of pharmaceutically acceptable salts include, but are not limited to, mineral or organic acid salts of basic residues such as amines; alkali or organic salts of acidic residues such as carboxylic acids; and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

As used herein, "alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, hexyl, heptyl, octyl, nonyl, and decyl; "cycloalkyl" or "carbocycle" is intended to include saturated and partially unsaturated ring groups, including mono-, bi- or poly-cyclic ring systems, such as cyclopropyl, cyclobutyl, cyclopentyl, cyclohexyl, cycloheptyl, cyclooctyl and adamantyl; "bicycloalkyl" or "bicyclic" is intended to include saturated bicyclic ring groups such as [3.3.0]bicyclooctane, [4.3.0] bicyclononane, [4.4.0]bicyclodecane (decalin), [2.2.2] bicyclooctane, and so forth.

As used herein, the term "alkene" or "alkenyl" is intended to include hydrocarbon chains having the specified number of carbon atoms of either a straight or branched configuration and one or more unsaturated carbon-carbon bonds which may occur in any stable point along the chain, such as ethenyl, propenyl, and the like.

As used herein, the term "alkyne" or "alkynyl" is intended to include hydrocarbon chains having the specified number of carbon atoms of either a straight or branched configuration and one or more unsaturated carbon-carbon triple bonds which may occur in any stable point along the chain, such as propargyl, and the like.

As used herein, "aryl" or "aromatic residue" is intended to mean phenyl or naphthyl, which when substituted, the substitution can be at any position.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7- membered monocyclic or bicyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

As used herein, the term "alkaryl" means an aryl group bearing an alkyl group of 1–10 carbon atoms; the term "aralkyl" means an alkyl group of 1–10 carbon atoms bearing an aryl group; the term "arylalkaryl" means an aryl group bearing an alkyl group of 1–10 carbon atoms bearing an aryl group; and the term "heterocycloalkyl" means an alkyl group of 1–10 carbon atoms bearing a heterocycle.

A "polyalkylene glycol" is a polyethylene glycol, polypropylene glycol or polybutylene glycol having a molecular weight of less than about 5000, terminating in either a hydroxy or alkyl ether moiety.

A "carbohydrate" is a polyhydroxy aldehyde, ketone, alcohol or acid, or derivatives thereof, including polymers thereof having polymeric linkages of the acetal type.

A "cyclodextrin" is a cyclic oligosaccharide. Examples of cyclodextrins include, but are not limited to, α-cyclodextrin, hydroxyethyl-α-cyclodextrin, hydroxypropyl-α-cyclodextrin, β-cyclodextrin, hydroxypropyl-β-cyclodextrin, carboxymethyl-β-cyclodextrin, dihydroxypropyl-β-cyclodextrin, hydroxyethyl-β-cyclodextrin, 2,6 di-O-methyl-β-cyclodextrin, sulfated-β-cyclodextrin, γ-cyclodextrin, hydroxypropyl-γ-cyclodextrin, dihydroxypropyl-γ-cyclodextrin, hydroxyethyl-γ-cyclodextrin, and sulfated γ-cyclodextrin.

As used herein, the term "polycarboxyalkyl" means an alkyl group having between two and about 100 carbon atoms and a plurality of carboxyl substituents; and the term "polyazaalkyl" means a linear or branched alkyl group having between two and about 100 carbon atoms, interrupted by or substituted with a plurality of amine groups.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with a metal ion that is stable enough to prevent unwanted side-reactions but labile enough to be converted to a metallopharmaceutical. The formation of the intermediate complex is kinetically favored while the formation of the metallopharmaceutical is thermodynamically favored. Transfer ligands useful in the preparation of metallopharmaceuticals and in diagnostic kits useful for the preparation of diagnostic radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into a radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal ion through the formation of chemical bonds with one or more donor atoms.

The term "binding site" means the site in vivo or in vitro that binds a biologically active molecule.

A "diagnostic kit" or "kit" comprises a collection of components, termed the formulation, in one or more vials which are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

Therapeutic radiopharmaceuticals, X-ray contrast agent pharmaceuticals, ultrasound contrast agent pharmaceuticals and metallopharmaceuticals for magnetic resonance imaging contrast are provided to the end user in their final form in a formulation contained typically in one vial, as either a lyophilized solid or an aqueous solution. The end user reconstitutes the lyophilized with water or saline and withdraws the patient dose or just withdraws the dose from the aqueous solution formulation as provided.

A "lyophilization aid" is a component that has favorable physical properties for lyophilization, such as the glass transition temperature, and is added to the formulation to improve the physical properties of the combination of all the components of the formulation for lyophilization.

A "stabilization aid" is a component that is added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceutical.

A "solubilization aid" is a component that improves the solubility of one or more other components in the medium required for the formulation.

A "bacteriostat" is a component that inhibits the growth of bacteria in a formulation either during its storage before use of after a diagnostic kit is used to synthesize a radiopharmaceutical.

The following abbreviations are used herein:

| | |
|---|---|
| Acm | acetamidomethyl |
| b-Ala, beta-Ala or bAla | 3-aminopropionic acid |
| ATA | 2-aminothiazole-5-acetic acid or 2-aminothiazole-5-acetyl group |
| Boc | t-butyloxycarbonyl |
| CBZ, Cbz or Z | Carbobenzyloxy |
| Cit | citrulline |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate |
| hynic | boc-hydrazinonicotinyl group or 2-[[[5-[carbonyl]-2-pyridinyl]hydrazono]methyl]-benzenesulfonic acid, |
| NMeArg or MeArg | a-N-methyl arginine |
| NMeAsp | a-N-methyl aspartic acid |
| NNM | N-methylmorpholine |
| OcHex | O-cyclohexyl |
| OBzl | O-benzyl |
| oSu | O-succinimidyl |
| TBTU | 2-(1H-Benzotriazol-1-yl)1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are NOT used herein:

Ala = alanine
Arg = arginine
Asn = asparagine
Asp = aspartic acid
Cys = cysteine
Gln = glutamine
Glu = glutamic acid
Gly = glycine
His = histidine
Ile = isoleucine
Leu = leucine
Lys = lysine
Met = methionine
Nle = norleucine
Orn = ornithine
Phe = phenylalanine
Phg = phenylglycine
Pro = proline
Sar = sarcosine
Ser = serine
Thr = threonine -continued Trp = tryptophan
Tyr = tyrosine
Val = valine As used herein, the term "bubbles", as used herein, refers to vesicles which are generally characterized by the presence of one or more membranes or walls surrounding an internal void that is filled with a gas or precursor thereto. Exemplary bubbles include, for example, liposomes, micelles and the like.

As used herein, the term "lipid" refers to a synthetic or naturally-occurring amphipathic compound which comprises a hydrophilic component and a hydrophobic component. Lipids include, for example, fatty acids, neutral fats, phosphatides, glycolipids, aliphatic alchols and waxes, terpenes and steroids.

As used herein, the term "lipid composition" refers to a composition which comprises a lipid compound. Exemplary lipid compositions include suspensions, emulsions and vesicular compositions.

As used herein, the term "lipid formulation" refers to a composition which comprises a lipid compound and a bioactive agent.

As used herein, the term "vesicle" refers to a spherical entity which is characterized by the presence of an internal void. Preferred vesicles are formulated from lipids, including the various lipids described herein. In any given vesicle, the lipids may be in the form of a monolayer or bilayer, and the mono- or bilayer lipids may be used to form one of more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

As used herein, the term "vesicular composition" refers to a composition which is formulate from lipids and which comprises vesicles.

As used herein, the term "vesicle formulation" refers to a composition which comprises vesicles and a bioactive agent.

As used herein, the term "lipsomes" refers to a generally spherical cluster or aggregate of amphipathic compounds, including lipid compounds, typically in the form of one or more concentric layers, for example, bilayers. They may also be referred to herein as lipid vesicles.

Angiogenesis is the process of formation of new capillary blood vessels from existing vasculature. It is an important component of a variety of physiological processes including ovulation, embryonic development, wound repair, and collateral vascular generation in the myocardium. It is also central to a number of pathological conditions such as tumor growth and metastasis, diabetic retinopathy, and macular degeneration. The process begins with the activation of existing vascular endothelial cells in response to a variety of cytokines and growth factors. The activated endothelial cells secrete enzymes that degrade the basement membrane of the vessels. The endothelial cells then proliferate and migrate into the extracellular matrix first forming tubules and subsequently new blood vessels.

Under normal conditions, endothelial cell proliferation is a very slow process, but it increases for a short period of time during embryogenesis, ovulation and wound healing. This temporary increase in cell turnover is governed by a combination of a number of growth stimulatory factors and growth suppressing factors. In pathological angiogenesis, this normal balance is disrupted resulting in continued increased endothelial cell proliferation. Some of the pro-angiogenic factors that have been identified include basic fibroblast growth factor (bFGF), angiogenin, TGF-alpha, TGF-beta, and vascular endothelium growth factor (VEGF), while interferon-alpha, interferon-beta and thrombospondin are examples of angiogenesis suppressors.

Angiogenic factors interact with endothelial cell surface receptors such as the receptor tyrosine kinases EGFR, FGFR, PDGFR, Flk-1/KDR, Flt-1, Tek, Tie, neuropilin-1, endoglin, endosialin, and Axl. The receptors Flk-1/KDR, neuropilin-1, and Flt-1 recognize VEGF and these interactions play key roles in VEGF-induced angiogenesis. The Tie subfamily of receptor tyrosine kinases are also expressed prominently during blood vessel formation.

The proliferation and migration of endothelial cells in the extracellular matrix is mediated by interaction with a variety of cell adhesion molecules. Integrins are a diverse family of heterodimeric cell surface receptors by which endothelial cells attach to the extracellular matrix, each other and other cells. Angiogenesis induced by bFGF or TNF-alpha depend on the agency of the integrin avb3, while angiogenesis induced by VEGF depends on the integrin avb5 (Cheresh et. al., Science, 1995, 270, 1500–2). Induction of expression of the integrins a1b1 and a2b1 on the endothelial cell surface is another important mechanism by which VEGF promotes angiogenesis (Senger, et. al., Proc. Natl. Acad, Sci USA, 1997, 94, 13612–7).

The pharmaceuticals of the present invention are comprised of a non-peptide targeting moiety for the vitronectin receptor that is expressed or upregulated in angiogenic tumor vasculature.

The ultrasound contrast agents of the present invention comprise a plurality of vitronectin receptor targeting moieties attached to or incorporated into a microbubble of a biocompatible gas, a liquid carrier, and a surfactant microsphere, further comprising an optional linking moiety, $L_n$, between the targeting moieties and the microbubble. In this context, the term liquid carrier means aqueous solution and the term surfactant means any amphiphilic material which produces a reduction in interfacial tension in a solution. A list of suitable surfactants for forming surfactant microspheres is disclosed in EP0727225A2, herein incorporated by reference. The term surfactant microsphere includes nanospheres, liposomes, vesicles and the like. The biocompatible gas can be air, or a fluorocarbon, such as a $C_3$–$C_5$ perfluoroalkane, which provides the difference in echogenicity and thus the contrast in ultrasound imaging. The gas is encapsulated or contained in the microsphere to which is attached the biodirecting group, optionally via a linking group. The attachment can be covalent, ionic or by van der Waals forces. Specific examples of such contrast agents include lipid encapsulated perfluorocarbons with a plurality of tumor neovasculature receptor binding peptides, polypeptides or peptidomimetics.

X-ray contrast agents of the present invention are comprised of one or more vitronectin receptor targeting moieties attached to one or more X-ray absorbing or "heavy" atoms of atomic number 20 or greater, further comprising an optional linking moiety, $L_n$, between the targeting moieties and the X-ray absorbing atoms. The frequently used heavy atom in X-ray contrast agents is iodine. Recently, X-ray contrast agents comprised of metal chelates (Wallace, R., U.S. Pat. No. 5,417,959) and polychelates comprised of a plurality of metal ions (Love, D., U.S. Pat. No. 5,679,810) have been disclosed. More recently, multinuclear cluster complexes have been disclosed as X-ray contrast agents (U.S. Pat. No. 5,804,161, PCT WO91/14460, and PCT WO 92/17215).

MRI contrast agents of the present invention are comprised of one or more vitronectin receptor targeting moieties attached to one or more paramagnetic metal ions, further comprising an optional linking moiety, $L_n$, between the targeting moieties and the paramagnetic metal ions. The paramagnetic metal ions are present in the form of metal complexes or metal oxide particles. U.S. Pat. Nos. 5,412,148, and 5,760,191, describe examples of chelators for paramagnetic metal ions for use in MRI contrast agents. U.S. Pat. No. 5,801,228, U.S. Pat. No. 5,567,411, and U.S. Pat. No. 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents.

The pharmaceuticals of the present invention have the formulae, $(Q)_d-L_n-(C_h-X)$, $(Q)_d-L_n-(C_h-X^1)_{d'}$, $(Q)_d-L_n-(X^2)_{d''}$, and $(Q)_d-L_n-(X^3)$, wherein Q represents a non-peptide that binds to a receptor expressed in angiogenic tumor vasculature, d is 1–10, $L_n$ represents an optional linking group, $C_h$ represents a metal chelator or bonding moiety, X represents a radioisotope, $X^1$ represents paramagnetic metal ion, $X^2$ represents a paramagnetic metal ion or heavy atom containing insoluble solid particle, d" is 1–100, and $X^3$ represents a surfactant microsphere of an echogenic gas. The interaction of the non-peptide recognition sequences of the vitronectin receptor binding portion of the pharmaceuticals with the $\alpha_v\beta_3$ receptor results in localization of the pharmaceuticals in angiogenic tumor vasculature, which express the $\alpha_v\beta_3$ receptor.

The pharmaceuticals of the present invention can be synthesized by several approaches. One approach involves the synthesis of the targeting non-peptide moiety, Q, and direct attachment of one or more moieties, Q, to one or more metal chelators or bonding moieties, $C_h$, or to a paramagnetic metal ion or heavy atom containing solid particle, or to an echogenic gas microbubble. Another approach involves the attachment of one or more moieties, Q, to the linking group, $L_n$, which is then attached to one or more metal chelators or bonding moieties, $C_h$, or to a paramagnetic metal ion or heavy atom containing solid particle, or to an echogenic gas microbubble. Another approach involves the synthesis of a non-peptide, Q, bearing a fragment of the linking group, $L_n$, one or more of which are then attached to the remainder of the linking group and then to one or more metal chelators or bonding moieties, $C_h$, or to a paramagnetic metal ion or heavy atom containing solid particle, or to an echogenic gas microbubble.

The non-peptide vitronectin binding moieties, Q, optionally bearing a linking group, $L_n$, or a fragment of the linking group, can be synthesized using standard synthetic methods known to those skilled in the art. Preferred methods include but are not limited to those methods described below.

The attachment of linking groups, $L_n$, to the non-peptides, Q; chelators or bonding units, $C_h$, to the non-peptides, Q, or to the linking groups, $L_n$; and non-peptides, bearing a fragment of the linking group to the remainder of the linking group, in combination forming the moiety, $(Q)_d-L_n$, and then to the moiety $C_h$; can all be performed by standard techniques. These include, but are not limited to, amidation, esterification, alkylation, and the formation of ureas or thioureas. Procedures for performing these attachments can be found in Brinkley, M., *Bioconjugate Chemistry* 1992, 3(1), which is incorporated herein by reference.

A number of methods can be used to attach the non-peptides, Q, to paramagnetic metal ion or heavy atom containing solid particles, $X^2$, by one of skill in the art of the surface modification of solid particles. In general, the targeting moiety Q or the combination $(Q)_d L_n$ is attached to a coupling group that react with a constituent of the surface of the solid particle. The coupling groups can be any of a number of silanes which react with surface hydroxyl groups on the solid particle surface, as described in co-pending U.S. patent application Ser. No. 09/356,178, and can also include polyphosphonates, polycarboxylates, polyphosphates or mixtures thereof which couple with the surface of the solid particles, as described in U.S. Pat. No. 5,520,904.

A number of reaction schemes can be used to attach the non-peptides, Q, to the surfactant microsphere, $X^3$. These are illustrated in following reaction schemes where $S_f$ represents a surfactant moiety that forms the surfactant microsphere.

Acylation Reaction:

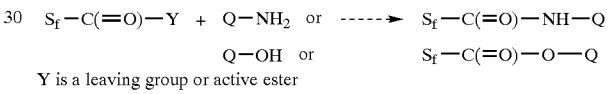

Y is a leaving group or active ester

Disulfide Coupling:

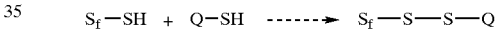

Sulfonamide Coupling:

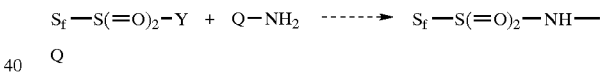

Reductive Amidation:

In these reaction schemes, the substituents $S_f$ and Q can be reversed as well.

The linking group $L_n$ can serve several roles. First it provides a spacing group between the metal chelator or bonding moiety, $C_h$, the paramagnetic metal ion or heavy atom containing solid particle, $X^2$, and the surfactant microsphere, $X^3$, and the one or more of the non-peptides, Q, so as to minimize the possibility that the moieties $C_h-X$, $C_h-X^1$, $X^2$, and $X^3$, will interfere with the interaction of the recognition sequences of Q with angiogenic tumor vasculature receptors. The necessity of incorporating a linking group in a reagent is dependent on the identity of Q, $C_h-X$, $C_h-X^1$, $X^2$, and $X^3$. If $C_h-X$, $C_h-X^1$, $X^2$, and $X^3$, cannot be attached to Q without substantially diminishing its affinity for the receptors, then a linking group is used. A linking group also provides a means of independently attaching multiple non-pepetides, Q, to one group that is attached to $C_h-X$, $C_h-X^1$, $X^2$, or $X^3$.

The linking group also provides a means of incorporating a pharmacokinetic modifier into the pharmaceuticals of the present invention. The pharmacokinetic modifier serves to direct the biodistribution of the injected pharmaceutical other than by the interaction of the targeting moieties, Q, with the vitronectin receptors expressed in the tumor neovasculature. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals. Preferred pharmacokinetic modifiers are those that result in moderate to fast blood clearance and enhanced renal excretion.

The metal chelator or bonding moiety, $C_h$, is selected to form stable complexes with the metal ion chosen for the particular application. Chelators or bonding moieties for diagnostic radiopharmaceuticals are selected to form stable complexes with the radioisotopes that have imageable gamma ray or positron emissions, such as $^{99m}Tc$, $^{95}Tc$, $^{111}In$, $^{62}Cu$, $^{60}Cu$, $^{64}Cu$, $^{67}Ga$, $^{68}Ga$, $^{86}Y$.

Chelators for technetium, copper and gallium isotopes are selected from diaminedithiols, monoamine-monoamidedithiols, triamide-monothiols, monoamine-diamide-monothiols, diaminedioximes, and hydrazines. The chelators are generally tetradentate with donor atoms selected from nitrogen, oxygen and sulfur. Preferred reagents are comprised of chelators having amine nitrogen and thiol sulfur donor atoms and hydrazine bonding units. The thiol sulfur atoms and the hydrazines may bear a protecting group which can be displaced either prior to using the reagent to synthesize a radiopharmaceutical or preferably in situ during the synthesis of the radiopharmaceutical.

Exemplary thiol protecting groups include those listed in Greene and Wuts, "Protective Groups in Organic Synthesis" John Wiley & Sons, New York (1991), the disclosure of which is hereby incorporated by reference. Any thiol protecting group known in the art can be used. Examples of thiol protecting groups include, but are not limited to, the following: acetamidomethyl, benzamidomethyl, 1-ethoxyethyl, benzoyl, and triphenylmethyl.

Exemplary protecting groups for hydrazine bonding units are hydrazones which can be aldehyde or ketone hydrazones having substituents selected from hydrogen, alkyl, aryl and heterocycle. Particularly preferred hydrazones are described in co-pending U.S. Ser. No. 08/476,296 the disclosure of which is herein incorporated by reference in its entirety.

The hydrazine bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

Chelators for $^{111}In$ and $^{86}Y$ are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic) acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine. Procedures for synthesizing these chelators that are not commercially available can be found in Brechbiel, M. and Gansow, O., *J. Chem. Soc. Perkin Trans.* 1992, 1, 1175; Brechbiel, M. and Gansow, O., *Bioconjugate Chem.* 1991, 2, 187; Deshpande, S., et. al., *J. Nucl. Med.* 1990, 31, 473; Kruper, J., U.S. Pat. No. 5,064,956, and Toner, J., U.S. Pat. No. 4,859,777, the disclosures of which are hereby incorporated by reference in their entirety.

The coordination sphere of metal ion includes all the ligands or groups bound to the metal. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

Preferred technetium radiopharmaceuticals of the present invention are comprised of a hydrazido or diazenido bonding unit and an ancillary ligand, $A_{L1}$, or a bonding unit and two types of ancillary $A_{L1}$ and $A_{L2}$, or a tetradentate chelator comprised of two nitrogen and two sulfur atoms. Ancillary ligands $A_{L1}$ are comprised of two or more hard donor atoms such as oxygen and amine nitrogen (sp$^3$ hybridized). The donor atoms occupy at least two of the sites in the coordination sphere of the radionuclide metal; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis (hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris(hydroxymethyl)methylglycine).

The most preferred technetium radiopharmaceuticals of the present invention are comprised of a hydrazido or diazenido bonding unit and two types of ancillary designated $A_{L1}$ and $A_{L2}$, or a diaminedithiol chelator. The second type of ancillary ligands $A_{L2}$ are comprised of one or more soft donor atoms selected from the group: phosphine phosphorus, arsine arsenic, imine nitrogen ($sp^2$ hybridized), sulfur ($sp^2$ hybridized) and carbon (sp hybridized); atoms which have p-acid character. Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom. We have disclosed in co-pending U.S. Ser. No. 08/415,908, and U.S. Ser. Nos. 60/013360 and 08/646,886, the disclosures of which are herein incorporated by reference in their entirety, that radiopharmaceuticals comprised of one or more ancillary or co-ligands $A_{L2}$ are more stable compared to radiopharmaceuticals that are not comprised of one or more ancillary ligands, $A_{L2}$; that is, they have a minimal number of isomeric forms, the relative ratios of which do not change significantly with time, and that remain substantially intact upon dilution.

The ligands $A_{L2}$ that are comprised of phosphine or arsine donor atoms are trisubstituted phosphines, trisubstituted arsines, tetrasubstituted diphosphines and tetrasubstituted diarsines. The ligands $A_{L2}$ that are comprised of imine nitrogen are unsaturated or aromatic nitrogen-containing, 5 or 6-membered heterocycles. The ligands that are comprised of sulfur ($sp^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Patent 0107734 and in U.S. Pat. No. 4,988,827, herein incorporated by reference.

Preferred ancillary ligands $A_{L2}$ are trisubstituted phosphines and unsaturated or aromatic 5 or 6 membered heterocycles. The most preferred ancillary ligands $A_{L2}$ are trisubstituted phosphines and unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands which may affect the biological properties of the radiopharmaceuticals, such as altering the distribution into non-target tissues, cells or fluids, and the mechanism and rate of elimination from the body.

Chelators or bonding moieties for therapeutic radiopharmaceuticals are selected to form stable complexes with the radioisotopes that have alpha particle, beta particle, Auger or Coster-Kronig electron emissions, such as $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir. Chelators for rhenium, copper, palladium, platinum, iridium, rhodium, silver and gold isotopes are selected from diaminedithiols, monoamine-monoamidedithiols, triamide-monothiols, monoamine-diamide-monothiols, diaminedioximes, and hydrazines. Chelators for yttrium, bismuth, and the lanthanide isotopes are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

Chelators for magnetic resonance imaging contrast agents are selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine.

The technetium and rhenium radiopharmaceuticals of the present invention comprised of a hydrazido or diazenido bonding unit can be easily prepared by admixing a salt of a radionuclide, a reagent of the present invention, an ancillary ligand $A_{L1}$, an ancillary ligand $A_{L2}$, and a reducing agent, in an aqueous solution at temperatures from 0 to 100° C. The technetium and rhenium radiopharmaceuticals of the present invention comprised of a tetradentate chelator having two nitrogen and two sulfur atoms can be easily prepared by admixing a salt of a radionuclide, a reagent of the present invention, and a reducing agent, in an aqueous solution at temperatures from 0 to 100° C.

When the bonding unit in the reagent of the present invention is present as a hydrazone group, then it must first be converted to a hydrazine, which may or may not be protonated, prior to complexation with the metal radionuclide. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention comprised of a hydrazido or diazenido bonding unit can be prepared by first admixing a salt of a radionuclide, an ancillary ligand $A_{L1}$, and a reducing agent in an aqueous solution at temperatures from 0 to 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of a radionuclide, an ancillary ligand $A_{L1}$, a reagent of the present invention, and a reducing agent in an aqueous solution at temperatures from 0 to 100° C. to form an intermediate radionuclide complex, and then adding an ancillary ligand $A_{L2}$ and reacting further at temperatures from 0 to 100° C.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the reagent of the present invention used to prepare the technetium and rhenium radiopharmaceuticals of the present invention can range from 0.01 µg to 10 mg, or more preferably from 0.5 µg to 200 µg. The amount used will be dictated by the amounts of the other reactants and the identity of the radiopharmaceuticals of the present invention to be prepared.

The amounts of the ancillary ligands $A_{L1}$ used can range from 0.1 mg to 1 g, or more preferably from 1 mg to 100 mg. The exact amount for a particular radiopharmaceutical is a function of identity of the radiopharmaceuticals of the present invention to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary, ligands $A_{L2}$ used can range from 0.001 mg to 1 g, or more preferably from 0.01 mg to 10 mg. The exact amount for a particular radiopharmaceutical is a function of the identity of the radiopharmaceuticals of the present invention to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the reagent bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention comprised of a hydrazido or diazenido bonding unit will depend on the identity of the reagent of the present invention used, the identity of any ancillary ligand $A_{L1}$, the identity of any ancillary ligand $A_{L2}$, and the identity of the radionuclide. Radiopharmaceuticals comprised of a hydrazido or diazenido bonding unit synthesized using concentrations of reagents of <100 µg/mL, will be comprised of one hydrazido or diazenido group. Those synthesized using >1 mg/mL concentrations will be comprised of two hydrazido or diazenido groups from two reagent molecules. For most applications, only a limited amount of the biologically active molecule can be injected and not result in undesired side-effects, such as chemical toxicity, interference with a biological process or an altered biodistribution of the radiopharmaceutical. Therefore, the radiopharmaceuticals which require higher concentrations of the reagents comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

The indium, copper, gallium, silver, palladium, rhodium, gold, platinum, bismuth, yttrium and lanthanide radiopharmaceuticals of the present invention can be easily prepared by admixing a salt of a radionuclide and a reagent of the present invention, in an aqueous solution at temperatures from 0 to 100° C. These radionuclides are typically obtained as a dilute aqueous solution in a mineral acid, such as hydrochloric, nitric or sulfuric acid. The radionuclides are combined with from one to about one thousand equivalents of the reagents of the present invention dissolved in aqueous solution. A buffer is typically used to maintain the pH of the reaction mixture between 3 and 10.

The gadolinium, dysprosium, iron and manganese metallopharmaceuticals of the present invention can be easily prepared by admixing a salt of the paramagnetic metal ion and a reagent of the present invention, in an aqueous solution at temperatures from 0 to 100° C. These paramagnetic metal ions are typically obtained as a dilute aqueous solution in a mineral acid, such as hydrochloric, nitric or sulfuric acid. The paramagnetic metal ions are combined with from one to about one thousand equivalents of the reagents of the present invention dissolved in aqueous solution. A buffer is typically used to maintain the pH of the reaction mixture between 3 and 10.

The total time of preparation will vary depending on the identity of the metal ion, the identities and amounts of the reactants and the procedure used for the preparation. The preparations may be complete, resulting in >80% yield of the radiopharmaceutical, in 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

Buffers useful in the preparation of metallopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of metallopharmaceuticals and in diagnostic kits useful for the preparation of radiopharmaceuticals include but are not limited to ascorbic acid, cysteine, monothioglycerol, sodium bisulfite, sodium metabisulfite, gentisic acid, and inositol.

Solubilization aids useful in the preparation of metallopharmaceuticals and in diagnostic kits useful for the preparation of radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of metallopharmaceuticals and in diagnostic kits useful for the preparation of radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. No. 5,155,215; U.S. Pat. No. 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The ultrasound contrast agents of the present invention are administered by intravenous injection in an amount of 10 to 30 μL of the echogenic gas per kg body weight or by infusion at a rate of approximately 3 μL/kg/min. Imaging is performed using known techniques of sonography.

Other features of the invention will become apparent in the course of the following descriptions of exemplary embodiments which are given for illustration of the invention and are not intended to be limiting thereof.

EXAMPLES

Representative materials and methods that may be used in preparing the compounds of the invention are described further below.

Manual solid phase peptide synthesis was performed in 25 mL polypropylene filtration tubes purchased from BioRad Inc., or in 60 mL hour-glass reaction vessels purchased from Peptides International. Oxime resin (substitution level=0.96 mmol/g) was prepared according to published procedure (DeGrado and Kaiser, *J. Org. Chem.* 1980, 45, 1295), or was purchased from Novabiochem (substitution level=0.62 mmol/g). All chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA), 1,2,4-triazole, stannous chloride dihydrate, and tris(3-sulfonatophenyl)phosphine trisodium salt (TPPTS) were purchased from Aldrich Chemical Company. Bis(3-sulfonatophenyl)phenylphosphine disodium salt (TPPDS) was prepared by the published procedure (Kuntz, E., U.S. Pat. No. 4,248,802). (3-Sulfonatophenyl)diphenylphosphine monosodium salt (TPPMS)was purchased from TCI America, Inc. Tricine was obtained from Research Organics, Inc. Technetium-99m-pertechnetate ($^{99m}TcO_4^-$) was obtained from a DuPont Pharma $^{99}Mo/^{99m}Tc$ Technelite® generator. In-111-chloride (Indichlor®) was obtained from Amersham Medi-Physics, Inc. Sm-153-chloride and Lutetium-177-chloride were obtained from the University of Missouri Research Reactor (MURR). Yttrium-90 chloride was obtained from the Pacific Northwest Research Laboratories. Dimethylformamide (DMF), ethyl acetate, chloroform ($CHCl_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were commercially obtained. Absolute ethanol was obtained from Quantum Chemical Corporation.

Synthesis of Boc-Glu-(OTFP)-OTFP

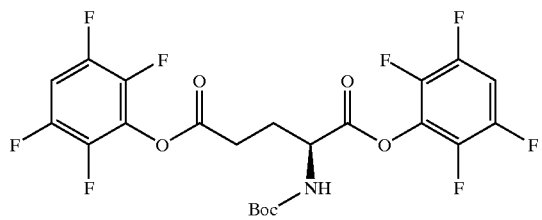

To a solution of Boc-Glu-OH (28.9 g, 117 mmol) in DMF (500 mL) at room temperature, and under nitrogen, was added a solution of 2,3,5,6-tetrafluorophenol (48.2 g, 290 mmol) in DMF (50 mL). After stirring for 10 min. EDC (55.6 g, 290 mmol) was added and the reaction mixture was stirred for about 96 h. The volatiles were removed in vacuo and the residue was triturated in 0.1 N HCl (750 mL). To this mixture was added ethyl acetate (600 mL), the layers separated. The aqueous layer was extracted with ethyl acetate (3×~500 mL), and all the ethyl acetate fractions were combined, washed with water (300 mL) and brine (300 mL), dried ($MgSO_4$), and concentrated to give a tan solid (62 g). The tan solid was washed with acetonitrile to give the title compound (45.5 g, 73%) in purified form.

ESMS: Calculated for $C_{22}H_{17}F_8NO_6$, 543.09; found, 566.0 $[M+Na]^{+1}$.

Example 1

Preparation of (S,S,S)-4-(N-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)propyl)carbamoyl)-4-(4-carboxy-2-(2-(1,4,7,10-tetraaza-4,7,10-tris(carboxymethyl)cyclodecyl)acetylamino)butanoyl amino)butanoic Acid

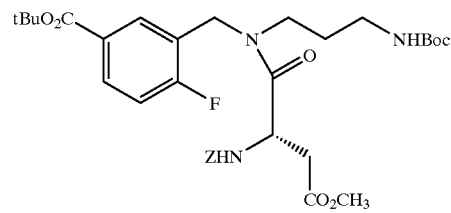

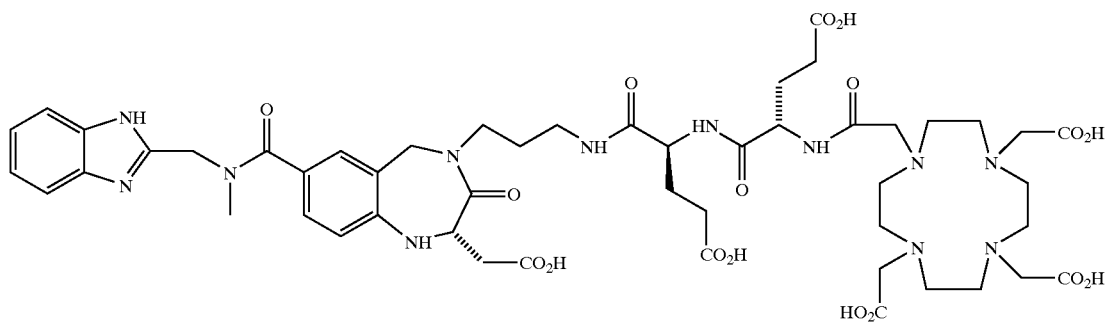

Step 1A. Synthesis of tert-butyl 3-(((3-((tert-butoxy)carbonylamino)propyl)methylamino)methyl)-4-fluorobenzoate

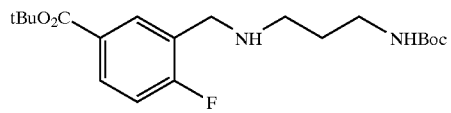

Crude tert-butyl-4-fluoro-3(alpha-bromomethyl)benzoate (4.6 g., 16 mmol), prepared as described in (WO 95/18619, PCT/US95/00248), was dissolved in 100 mL THF, along with 3-tert-butoxycarbonylamino-1-propylamine hydrochloride (2.9 g., 16.6 mmol) and diisopropylethylamine added (4.6 g., 36 mmol). The solution was stirred overnight, diluted with 1N NaOH, and extracted with three portions of ether. The combined organics were washed with water and sat. NaCl, dried over $MgSO_4$, and concentrated under vacuum to 5.7 g. of a yellow oil. This was purified by flash chromatography ($CH_2Cl_2$/EtOAc) to afford the product as a clear oil (2.04 g., ~35%). $^1$HNMR (600 MHz, DMSO-d6): 7.99 (dd, J=2, 5.1 Hz, 1H), 7.78 (ddd, J=2.3, 2.8, 3.0 Hz, 1H), 7.22 (dd, J=8.8, 0.7, 1H), 6.73 (b, 1H), 3.68 (s, 2H), 2.94 (m, 2H), 2.15 (b, 1H), 1.51 (s, 9H), 1.49 (m, 2H), 1.33 (s, 9H); MS (ES): 765.4 $[2M+H]^+$, 383.3 $[M+H]^+$.

Step 1B. Synthesis of methyl (S)-3-N-(3-((tert-butoxyl)carbonyl amino)propyl)-N-((5-((tert-butyl)oxycarbonyl)-2-fluorophenyl) methyl)carbamoyl)-3-((phenylmethoxy)carbonylamino)propanoate The product of Step A (2 g, 5.3 mmol) was dissolved in 20 mL dry DMF, along with N-Cbz-L-aspartic acid β-methyl ester (1.65 g, 5.9 mmol), and 1-hydroxybenzotriazole hydrate (800 mg, 5.9 mmol) under a nitrogen atmosphere. Dicyclohexylcarbodiimide (1M in $CH_2Cl_2$, 5.9 mL, 5.9 mmol) was added via syringe, and the solution stirred 18 hr.

Ether (25 mL) was added and the solids were filtered and rinsed with ether. The filtrate was concentrated, redissolved in ether, filtered, and the filtrate washed with sat. bicarbonate, water, and sat. NaCl. It was dried ($Na_2SO_4$), filtered and concentrated to a yellow oil which was purified by flash chromatography (4:1 CH2Cl2/EtOAc) to afford the product (3.0 g, 87%) as a clear oil. $^1$HNMR (600 MHz, DMSO-d6): mixture of amide rotamers: 7.82 (m, 2H), 7.71 (m, 1H), 7.3 (m,6H), 6.72 (bd, 1H), 5.02 (dd, J=12.5, 25.7 Hz, 1H), 4.44–4.88 (m, 4H), 3.52 (d, 2H), 3.27 (d, 3H), 3.10–3.45 (m, 4H)2.45–2.90 (m, 4H), 1.55 (m, 2H), 1.49 (s, 9H), 1.31 (s, 9H); MS-ES: 590.3 $[(M-tBu)+H]^+$, 646.4 $[M+H]^+$, 668.4 $[M+Na]^+$.

Step 1C: Synthesis of methyl (S)-3-amino-3-(N-(3-((tert-butoxy)carbonylamino)propyl)-N-((5-((tert-butyl)oxycarbonyl)-2-fluorophenyl)methyl)carbamoyl)propanoate

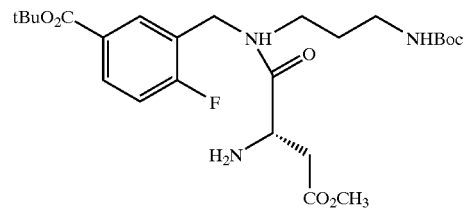

The product of step B (2.8 g, 4.4 mmol) was dissolved in MeOH (50 mL) with 10% Pd/C (530 mg) and shaken under a hydrogen atmosphere (50 psi) in a Parr shaker for 2 hr. The reaction mixture was filtered through Celite® and concentrated to a clear oil (2.14 g, 94%) under vacuum, which was not further purified. MS-ES: 512.4 [M+H]$^+$, 1023.5 [2M+H]$^+$;

Step 1D: Synthesis of methyl (S)-2-(2,5-diaza-9-((tert-butyl) oxycarbonyl)-5-(3-((tert-butoxy)carbonylamino) propyl)-4-oxobicyclo[5.4.0]undeca-1(7),8,10-trien-3-yl) acetate

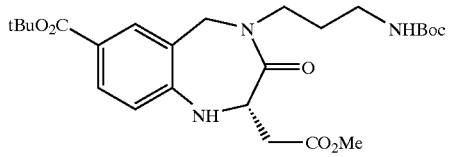

The crude oil from C (2.14 g, 4.0 mmol) was dissolved in dry N-methylpyrollidinone (50 mL) along with 2,6-di-tert-butylpyridine (2.1 mL, 9.2 mmol) under nitrogen. The solution was heated at 125° C. in an oil bath for 43 hours. The solution was cooled, poured into 100 mL water, and extracted with ethyl acetate. The organics were concentrated to an oil and purified by flash chromatography (CH$_2$Cl$_2$/EtOAc) to afford 1.0 g (46%) of the product. MS-ES: 392.3 [(M-tBoc)+H]$^+$436.3 [(M-tBu)+H]$^+$492.4 [M+H]$^+$, 983.6 [2M+H]$^+$;

Step 1E: Synthesis of (S)-2,5-diaza-5-(3-((tert-butoxy) carbonylamino)propyl)-3-((methoxycarbonyl)methyl)-4-oxobicyclo[5.4.0]undeca-1(7),8,10-trien-9-carboxylic acid

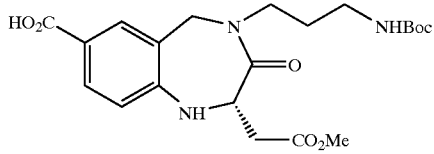

The ester from D (880 mg, 1.8 mmol) was dissolved in dichloromethane (12 mL) and trifluoroacetic acid (6 mL) added with stirring under nitrogen. The reaction was stirred 2 hours, concentrated under vacuum, and redissolved in 7 mL dichloromethane. Acetonitrile (7 mL) was added, followed by di-tert-butyldicarbonate (590 mg, 2.7 mmol) and diisopropylethylamine (1.4 mL, 7.6 mmol). The reaction was stirred overnight under nitrogen. EtOAc (15 mL) was added and the entire solution was washed with 5% citric acid and brine, dried (MgSO4), and concentrated to 1.12 g of oil. This was purified by flash chromatography (CH2Cl2/EtOAc/MeOH) and the residue dissolved in 0.1% TFA/acetonitrile (50 mL) and lyophilized to afford the product (680 mg, 69%) as a white powder. $^1$HNMR (600 MHz, DMSO-d6): 12.14 (b, 1H), 7.62 (d, J=1.8 Hz, 1H), 7.53 (dd, J=1.9 Hz, 8.5 Hz, 1H), 6.66 (bt, J=5.4 Hz, 1H), 6.56 (d, J=8.5 Hz, 1H), 6.55 (m, 1H) 5.41 (d, J=16.6 Hz)1H), 5.15 (dd, J=5 Hz, 8.8 Hz, 1H), 4.02 (d, 16.7 Hz, 1H), 3.60 (s, 3H), 3.38 (m, 2H), 2.84 (m, 2H), 2.82 (dd, J=8.8 Hz, 16.6 Hz, 1H), 2.67 (dd, J=5.3 Hz, 16.6 Hz, 1H), 1.50 (m, 2H), 1.36 (s, 9H); LRMS(ES): 380.3 [(M-tBu)+H]$^+$, 436.3 [M+H]$^+$.

Step 1F. Synthesis of methyl (S)-2-(2,5-diaza-9-(N-(benzimidazol-2-ylmethyl)-N-methylcarbamoyl)-5-(3-((tert-butoxy)carbonylamino)propyl)-4-oxobicyclo[5.4.0] undeca-1(7),8,10-trien-3-yl)acetate

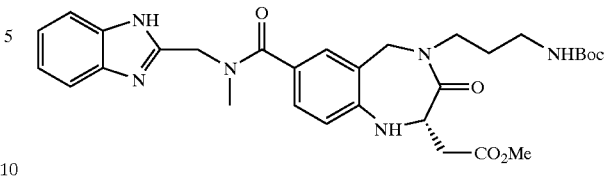

The product of step 1E (476 mg, 1.09 mmol) was dissolved in dry dimethylformamide along with 2-(methylaminomethyl)benzimidazole dihydrochloride (290 mg, 1.25 mmol, prepared according to F. Ali et. al., WO 96/00730), hydroxybenzotriazole hydrate (HOBT) (154 mg, 1.14 mmol), ethyl dimethylaminopropylcarbodiimide hydrochloride (261 mg, 1.36 mmol), and diisopropylethylamine (1.1 mL, 6 mmol). The solution was stirred for 23 hr under nitrogen and then concentrated. The residue was partitioned with ethyl acetate/water, and the aqueous layer extracted with 2 portions of ethyl acetate. The combined organic layers were washed with water and brine and concentrated. The residue was purified by flash chromatography on silica (95:5 ethyl acetate/methanol) and the product fractions concentrated to afford the product (435 mg, 69%) as a crunchy foam after drying under vacuum. LRMS(ES): 579.4 [(M+H]$^+$. $^1$HNMR (600.1300 MHz, DMSO-d6): 12.34 (b, 1H), 7.58 (d, J=1.8 Hz, 1H), 7.48 (dd, J=1.9 Hz, 8.5 Hz, 1H), 7.24 (s, 1H), 7.17 (m, 3H), 6.64 (t, 1H), 6.56 (d, 1H), 6.55 (m, 1H) 6.21 (s, 1H), 5.41 (d, J=16.6 Hz, 1H), 5.10 (dd, J=5 Hz, 8.8 Hz, 1H), 4.76 (q, 2H), 3.89 (d, 16.6 Hz, 1H), 3.60 (s, 3H), 3.37 (m, 2H), 3.04 (s, 3H), 2.82 (m, 3H), 2.64 (dd, J=5.3 Hz, 16.6 Hz, 1H), 1.48 (m, 2H), 1.34 (s, 9H).

Step 1G: Synthesis of (S,S)-7-((tert-butyl)oxycarbonyl)-2-(2-((tert-butyl)oxycarbonyl)ethyl)-3-oxo-5-((phenylmethoxy)carbonyl amino)carbonyl)heptanoic acid

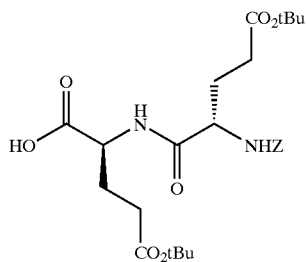

Gamma-tert-butoxy-Z-glutamic acid succinimide ester (2.0 g, 4.75 mmol) was dissolved in dimethylformamide, and gamma-tert-butoxyglutamic acid (0.98 g, 4.8 mmol) added, followed by diisopropylethylamine (1.75 mL, 10.1 mmol). The solution was stirred 18 hr, concentrated, and the residue partitioned into ethyl acetate/10% citric acid. The aqueous fraction was extracted with ethyl acetate and the combined organics were washed with water, 10% potassium hydrogen sulfate, and brine, and then concentrated. The residual oil was purified by flash chromatography on silica (CH$_2$Cl$_2$/EtOAc/EtOH, 1:1:0.5%) and the product fractions combined and evaporated to yield the product (1.3 g, 53%) as a gummy solid. LRMS (ES): 523.4 [M+H]$^+$, 467.4; $^1$HNMR (600.1330 MHz, CDCl$_3$) 7.30 (m, 6H), 5.80 (d, 1H), 5.09 (m, 2H), 4.53 (m, 1H), 4.29 (m, 1H), 2.36 (m, 4H), 1.88–2.16 (m, 4H), 1.42 (s, 9 H), 1.41 (s, 9H).

Step 1H: Synthesis of tert-butyl (S,S,S)-4-(N-(3-(3,6-diaza-5-((methoxycarbonyl)methyl)-10-(N-(benzimidazol-2-ylmethyl)-N-methylcarbamoyl)-4-oxobicyclo[5.4.0]undeca-1(7),8,10-trien-3-yl)propyl)carbamoyl)-4-(4-((tert-butyl)oxycarbonyl)-2-((phenylmethoxycarbonylamino)butanoylamino)butanoate 2.25–2.45 (m, 4H) 2.05–2.16 (m, 2H), 1.96 (m, 2H), 1.71 (m, 2H), 1.46 (s, 9 H), 1.44 (s, 9H).

Step 1I: Synthesis of tert-butyl (S,S,S)-4-amino-4-(N-(3-(3,6-diaza-5-((methoxycarbonyl)methyl)-10-(N-(benzimidazol-2-ylmethyl)-N-methylcarbamoyl)-4-oxobicyclo[5.4.0]undeca-1(7),8,10-trien-3-yl)propyl)carbamoyl)-3-((tert-butyl) oxycarbonyl)propyl)carbamoyl)butanoate acetate salt

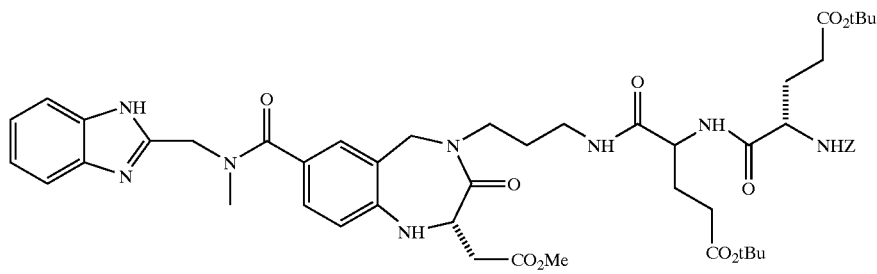

The product of 1F (40 mg, 70 µmol) was dissolved in dichloromethane (1 mL) under nitrogen. To this was added triethylsilane (110 uL, 0.7 mmol) and trifluoroacetic acid (1 mL). The reaction was stirred 60 min, concentrated, and reconcentrated with 5 mL toluene. The residue was dis-

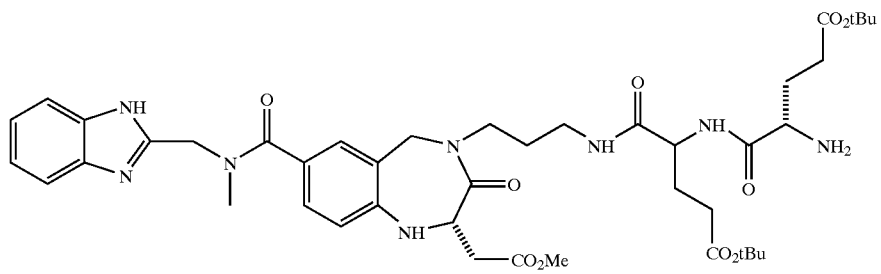

solved in dry dimethylformamide (1 mL) and the product of step 1G (40 mg, 77 µmol) added, along with HBTU (33.2 mg, 87 µmol) and diisopropylethylamine (100 µL, 560 µmol). This was stirred for 18 hr. The reaction was concentrated, and the residue dissolved in ethyl acetate. The organics were washed with water, 10% potassium hydrogen sulfate, water, and brine, and then concentrated. The residual oil was purified by flash chromatography on silica (EtOAc/2-PrOH, 1%->10%) and the product fractions combined and evaporated to yield the product (36 mg, 53%) as a white solid. LRMS (ES): 983.6 [M+H]$^+$, 492.5 [M+2H]$^{+2}$; HRMS (ESI): Calculated for $C_{51}H_{67}N_8O_{12}$—983.4878, found—983.4860; $^1$HNMR (600.1300 MHz, CDCl$_3$) 7.63 (b, 2H), 7.45 (b, 1H) 7.22–7.41 (m, 11H), 6.90 (b, 1H), 6.54 (d, 1H), 5.99 (b, 1H) 5.39 (d, J=16.6 Hz, 1H), 5.12 (m, 3H), 4.78–4.98 (m, 2H), 4.51 (b, 1H), 4.40 (b, 1H),4.25 (b, 1H), 3.87 (d, J=16.6 Hz 1H), 3.76 (s, 3H), 3.66 (b, 1H), 3.45 (b, 1H), 3.19 (s, 3H), 3.17 (m, 1H), 3.03 (m, 2H), 2.69 (dd, 1H), The product of Step 1H (33 mg, 33 µmol) was hydrogenated with 10% palladium on carbon (15 mg) in methanol (6 mL) with acetic acid (0.1 mL) on a Parr shaker at 40 psi for 1.5 hr. The solution was filtered on Celite, rinsed with methanol and concentrated. The residue was dissolved in 20 mL 1:1 acetonitrile/water, frozen, and lyophilized to afford the product as a white powder (21 mg, 75%). LRMS (ES): 849.5 [M+H]$^+$, 425.5 [M+2H]$^{+2}$;

Step J: Synthesis of tert-butyl (S,S,S)-4-(N-(1-(N-(3-(3,6-diaza-10-(N-(benzimidazol-2-ylmethyl)-N-methylcarbamoyl)-5-((methoxy carbonyl)methyl)-4-oxobicyclo[5.4.0]undeca-1(7),8,10-trien-3-yl)propyl)carbamoyl)-3-((tert-butyl)oxycarbonyl) carbamoyl)-4-(2-(1,4,7,10-tetraaza-4,5,10-tris(((tert-butyl)oxycarbonyl)methyl)cyclododecyl)acetylamino)butanoate trifluoroacetate

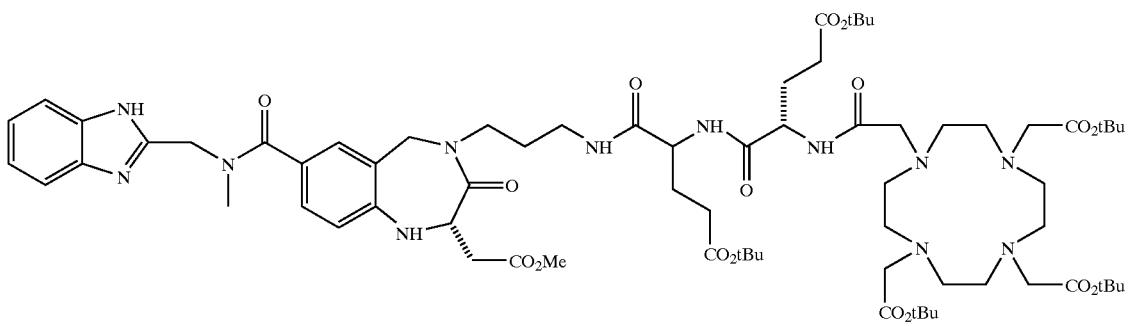

The product of step 1I (20 mg, 16.8 μmol) was dissolved in DMF (1 mL) along with DOTA(OtBu)3-OH (26 mg, 25 μmol), HBTU (20 mg, 53 μmol), diisopropylethylamine (29.1 mg, 225 μmol) and HOBT hydrate (2.5 mg, 18 μmol). This was stirred for 18 hr under nitrogen, concentrated under vacuum, and purified by preparative HPLC (Vydac C-18, 2.5 cm×15 cm, 0.1% TFA/acetonitrile gradient). The product fractions were pooled and lyophilized to afford 17.5 mg of product as a white powder. LRMS (ES) 589.5, 617.8, 646.1, 674.5 [(M-ntBu)+2H]+2, 702.8 [M+2H]+2, 1403.9 [M+H]+

Step 1K: Synthesis of (S,S,S)-4-(N-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)propyl)carbamoyl)-4-(4-carboxy-2-(2-(14,7,10-tetraaza-4,7,10-tris(carboxymethyl)cyclodecyl)acetylamino)butanoyl amino)butanoic acid The product of I (16 mg, 7.67 μmol (as 6TFA salt)) was dissolved in THF/MeOH (1:1, 1 mL) and lithium hydroxide added (26 μL of a 3M solution in water). The reaction was stirred for 2 hr, concentrated, and treated with trifluoroacetic acid (0.8 mL) and triethylsilane (0.2 mL) under nitrogen. The solution was stirred for 21 hr, concentrated under vacuum, and purified by preparative HPLC (Vydac C-18, 21.5 mm×15 cm, 0.1% TFA/acetonitrile gradient). The product fractions were pooled and lyophilized to afford the product (6.5 mg, 55%) as a white powder. LRMS (ES): 370.9 [M+3H]+3, 555.6 [M+2H]+2, 1109.5 [M+H]+; HRMS: Calculated for $C_{50}H_{69}O_{17}N_{12}$: 1109.4904, found: 1109.4890.

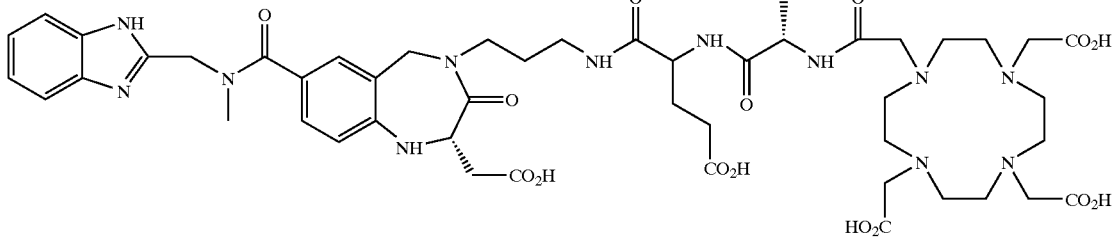

Example 2

Preparation of (S)-2-(2,5-diaza-5-(6((6-((1-aza-2-(2-sulfophenyl)vinyl)amino)(3-pyridyl))carbonylamino)hexyl)-9-(N-(benzimidazol-2-ylmethyl)-N-methylcarbamoyl)-4-oxobicyclo[5.4.0]undeca-1(7),8,10-trien-3-yl) acetic acid trifluoroacetate salt

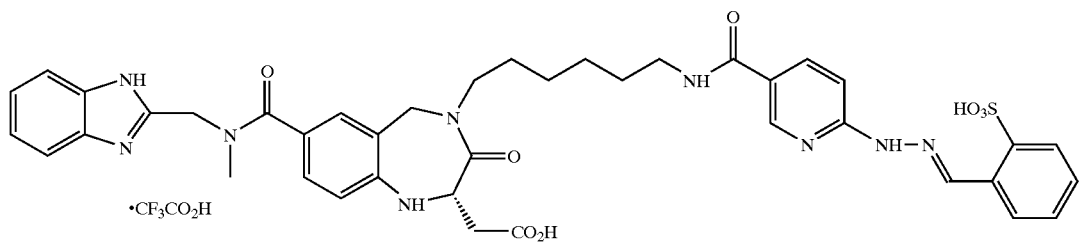

Step 2A: Synthesis of tert-butyl 3-(((6-((tert-butoxy)carbonylamino)hexyl)amino)methyl)-4-fluorobenzoate

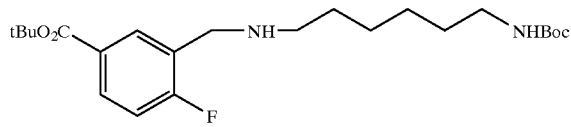

This was prepared in the same fashion as Example 1A from tert-butyl-4-fluoro-3(alpha-bromomethyl)benzoate (5.4 g., 18 mmol) and 6-tert-butoxycarbonylamino-1-hexylamine hydrochloride (5.0 g., 19.8 mmol), affording 3.1 g (41%) of product as a yellow oil. LRMS: 425.2 [M+H]$^+$; $^1$HNMR (270 MHz, DMSO-d6): 7.95 (dd, 1H), 7.87 (dd, 1H), 7.04 (t, 1H), 4.50 (bs, 1H), 3.83 (s, 2H), 3.07 (q, 2H), 2.59 (t, 2H), 1.57 (s, 9H), 1.42 (s, 9H), 1.60–1.20 (m, 8H);

Step 2B: Synthesis of methyl (S)-3-N-(6-((tert-butoxyl)carbonyl amino)hexyl)-N-((5-((tert-butyl)oxycarbonyl)-2-fluorophenyl) methyl)carbamoyl)-3-((phenylmethoxy)carbonylamino)propanoate

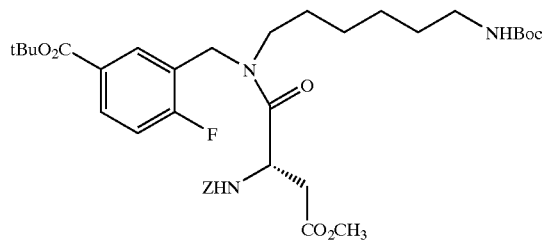

This was prepared as in Example 1B, starting with 3.06 g of amine, affording 4.4 g(88%) of the product as a viscous oil. LRMS: 688.4 [M+H]$^+$; $^1$HNMR (270 MHz, DMSO-d6): Mixture of amide rotamers, 7.85 (m, 2H), 7.80 (d, 1H), 7.4–7.2 (m, 6H), 6.73 (br t, 1H), 5.10–4.40 (m, 4H), 3.56, 3.53 (2s, 3H), 3.35 (m, 2H), 3.00–2.55 (m, 4H), 1.51 (s, 9H), 1.35 (s, 9H), 1.70–1.10 (m, 8H);

Step 2C: Synthesis of methyl (S)-3-amino-3-(N-(6-((tert-butoxy)carbonylamino)hexyl)-N-((5-((tert-butyl)oxycarbonyl)-2-fluorophenyl)methyl)carbamoyl)propanoate

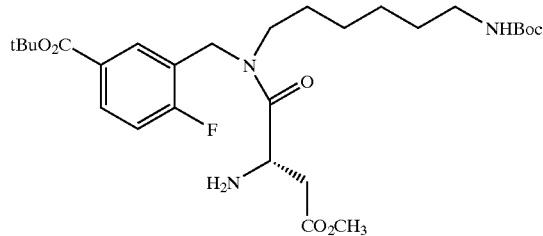

This step was done in the same fashion as Example 1C, starting with 2.3 g of CbZ protected compound, affording 1.71 g (92%) of the amine as a pale yellow oil. LRMS: 554.3 [M+H]$^+$; $^1$HNMR (270 MHz, DMSO-d6) mixture of amide rotamers: 7.90–7.70 (m, 2H), 7.29 (m, 1H), 6.75 (br, 1H), 4.80 (q, 1H), 4.54 (s, 2H), 4.10 (q, 1H), 3.89 (2t, 1H), 3.53 (2s, 3H) 2.87 (m, 2H), 2.55 (m, 2H), 1.90 (bs, 1H), 1.52 (s, 9H), 1.35 (s, 9H), 1.70–1.10 (m, 8H);

Step 2D: Synthesis of methyl (S)-2-(2,5-diaza-9-((tert-butyl) oxycarbonyl)-5-(6-((tert-butoxy)carbonylamino)hexyl)-4-oxobicyclo[5.4.0]undeca-1(7),8,10-trien-3-yl) acetate

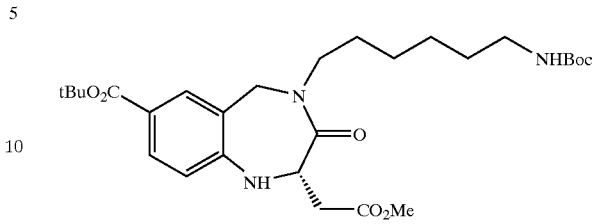

This step was done in the same fashion as Example 1D, starting with 1.66 g of amine, affording 706 mg (44%) of the benzodiazepine as a pale yellow foam. LRMS: 534.3 [M+H]$^+$; $^1$HNMR (270 MHz, DMSO-d6) mixture of amide rotamers: 7.55 (d, 1H), 7.50 (dd, 1H), 6.70 (br t, 1H), 6.55 (br, 1H), 6.54 (d, 1H), 5.40 (d, 1H), 5.14 (m, 1H), 3.99 (d, 1H), 3.59 (s, 3H) 2.78 (m, 2H), 2.65 (q, 2H), 1.49 (s, 9H), 1.35 (s, 9H), 1.30–1.00 (m, 8H);

Step 2E: Synthesis of (S)-2,5-diaza-5-(6-((tert-butoxy)carbonylamino)hexyl)-3-((methoxycarbonyl)methyl)-4-oxobicyclo[5.4.0]undeca-1(7),8,10-trien-9-carboxylic acid

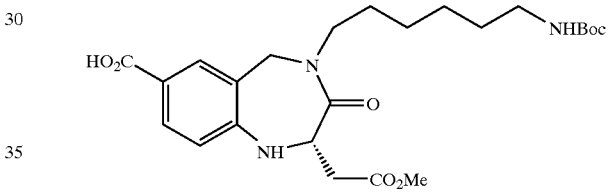

This step was done in the same fashion as Example 1E, starting with 301 mg of ester, affording the crude product (394 mg) as a yellow foam, which was used directly in the next step without purification. LRMS: 478.2 [M+H]$^+$.

Step 2F: Synthesis of methyl (S)-2-(2,5-diaza-9-(N-(benzimidazol-2-ylmethyl)-N-methylcarbamoyl)-5-(6-((tert-butoxy)carbonyl amino)hexyl)-4-oxobicyclo[5.4.0] undeca-1(7),8,10-trien-3-yl)acetate

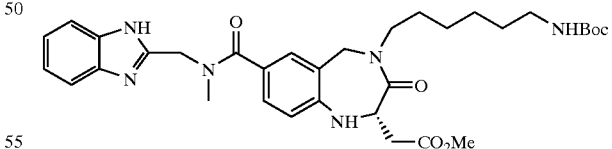

The reaction was carried out as in Example 1F, obtaining 306 mg of crude solid, which was further purified by flash chromatography to afford the desired product (164 mg, 47% from Step D) as a pale yellow solid. LRMS: 621.3 [M+H]$^+$; $^1$HNMR (270 MHz, DMSO-d6): 12.40 (br, 1H), 7.53 (bs, 2H), 7.20 (m, 4H), 6.71 (br, 1H), 6.52 (d, 1H), 6.23 (bd, 1H), 5.40 (d, 1H), 5.10, (m, 1H), 4.76 (s, 2H), 3.85 (bd, 1H), 3.59 (s, 3H), 3.04 (s, 3H), 2.90–2.55 (m, 2H), 1.35 (s, 9H), 1.40–1.20 (m, 8H).

Step 2G: Synthesis of (S)-2-(2,5-diaza-9-(N-(benzimidazol-2-ylmethyl)-N-methylcarbamoyl)-5-(6-((tert-butoxy)carbonylamino) hexyl)-4-oxobicyclo[5.4.0]undeca-1(7),8,10-trien-3-yl)acetic acid

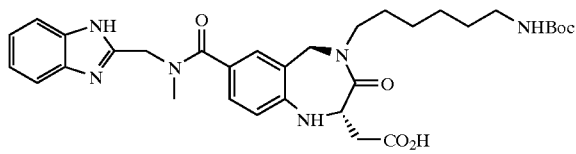

The product of step F (152 mg, 245 μmol) was stirred with lithium hydroxide (21 mg, 500 μmol) in THF/H2O (3 mL/2 mL) for 22 hr. THF was removed under vacuum, the residue diluted with water and acidified with solid citric acid. The precipitated solid and solution was extracted with dichloromethane, washed with brine, dried (Na$_2$SO$_4$), and concentrated to afford the acid product (120 mg, 81%) as a pale yellow powder, which was not purified further. LRMS: 607.2 [M+H]$^+$.

Step 2H: Synthesis of (S)-2-(2,5-diaza-5-(6((6-((1-aza-2-(2-sulfophenyl)vinyl)amino)(3-pyridyl))carbonylamino) hexyl)-9-(N-(benzimidazol-2-ylmethyl)-N-methylcarbamoyl)-4-oxobicyclo [5.4.0]undeca-1(7),8,10-trien-3-yl)acetic acid trifluoroacetate

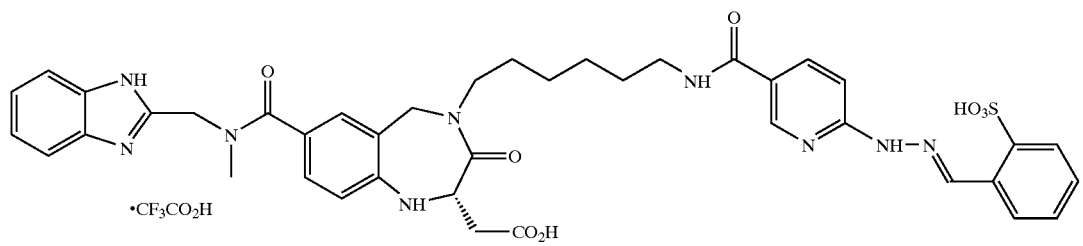

The product of step G (87 mg, 143 μmol) was dissolved in CH$_2$Cl$_2$ (4 mL) and trifluoroacetic acid (2 mL) added with stirring under nitrogen. The solution was stirred for one hour, concentrated under vacuum, and the residue redissolved in dry DMF (2.5 mL). To this was added sodium 2-[[[5-[[(2,5-dioxo-1-pyrollidinyl) oxy]carbonyl]-2-pyridinyl] hydrazono]methyl]-benzenesulfonate (75 mg, 170 μmol) and diisopropylethylamine (500 μL, 2.87 mmol) with stirring under nitrogen. The reaction was stirred overnight, concentrated, and the residue purified by preparative HPLC (Vydac C-18, 2.5 cm×15 cm, 0.1% TFA/acetonitrile gradient). The product fractions were combined and lyophilized to afford the product as a pale yellow powder (47.3 mg, 35%). LRMS (ES): 810.3 [M+H]$^+$. $^1$HNMR (600.1300 MHz, DMSO-d6): 12.40 (b, 2H), 9.24 (bs, 1H), 8.59 (bs, 1H), 8.50 (s, 1H), 8.24 (bs, 1H), 8.20 (bs, 1H), 7.80 (d, 3H), 7.53 (m, 2H), 7.41 (m, 2H), 7.20 (m, 3H), 6.57 (d, 1H), 6.32 (bs, 1H), 5.40 (d, 1H, J=16.4 Hz), 5.10 (m, 1H), 4.76 (s, 2H), 3.85 (d, 1H, J=16.4 Hz), 3.55 (m, 2H), 3.21 (m, 2H), 3.04 (s, 3H), 2.79 (dd, 1 H, J=16.5 Hz, 9 Hz), 2.55 (dd, 1H, J=16.5 Hz, 5 Hz), 1.60 (m, 2H), 1.51 (m, 2H), 1.26 (m, 2H), 1.19 (m, 2H).

Example 3

Synthesis of (S)-2-(2,5-diaza-9-(N-(6-((6-((1-aza-2-(2-sulfophenyl)vinyl)amino)(3-pyridyl)) carbonylamino)hexyl)-N-benzimidazol-2-ylmethyl) carbamoyl)-5-methyl-4-oxobicyclo [5.4.0]undeca-1(7),8,10-trien-3-yl)acetic acid trifluoroacetate

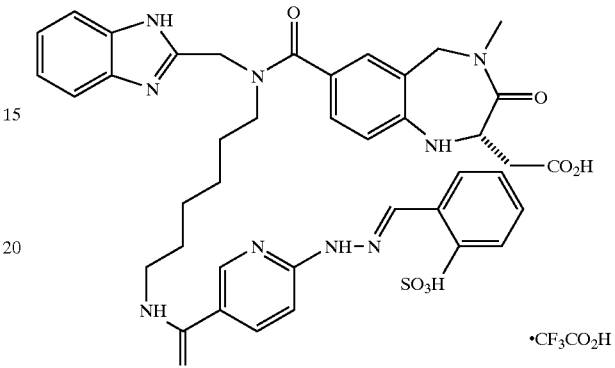

Step 3A: Synthesis of N-(6-((benzimidazol-2-ylmethyl) amino) hexyl)(phenylmethoxy)formamide dihydrochloride

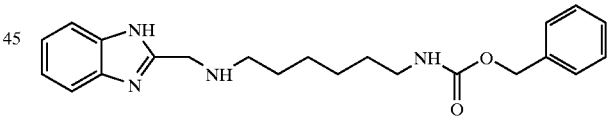

Both α-bromomethyl-(N-tert-butoxycarbonyl) benzimidazole (3.42 g, 11 mmol, prepared according to WO96/00730) and N-(mono-benzyloxycarbonyl)-hexanediamine (4.58 g, 16 mmol, prepared according to Bioconj. Chem., 1997, 8, 611) were dissolved in THF (100 mL), along with diisopropylethylamine (8 mL, 45.9 mmol) and water (3 mL). The mixture was stirred for 20 hr, concentrated, and the residue partitioned between 1N NaOH and dichloromethane. The aqueous was reextracted and concentrated to afford a yellow semi-solid product which was dissolved in ether/dichloromethane (2:1, 300 mL) and treated with 4N HCl in dioxane (40 mL, 160 mmol) with stirring at room temperature for 18 hr. The resulting solids were filtered, dissolved in a minimum amount of 10% sodium carbonate, extracted into dichloromethane and concentrated to an oil. This was purified by flash chromatography on silica (9:1 EtOAc/EtOH, 0.1% NH$_4$OH) and the product fractions concentrated, dissolved in ether, and treated with 4N HCl/dioxane. The resulting solids were filtered and washed with ether to afford 745 mg of a white powder. LRMS: 381.3 [M+H]$^+$; $^1$HNMR (270 MHz, DMSO-d6): 10.04 (b, 2H), 7.78 (m, 2H), 7.44 (m, 2H), 7.34 (m, 6H) 6.76 (b, 2H), 4.99 (s, 2H), 4.60 (s, 2H), 3.10 (m, 2H), 2.99 (m, 2H), 1.67 (m, 2H), 1.41 (m, 2H), 1.29 (m, 4H)

Step 3B: Synthesis of methyl (S)-2-(2,5-diaza-9-(N-(benzimidazol-2-ylmethyl)-N-(6-((phenylmethoxy) carbonylamino) hexyl)carbamoyl)-5-methyl-4-oxobicyclo [5.4.0]undeca-1(7),8,10-trien-3-yl)acetate

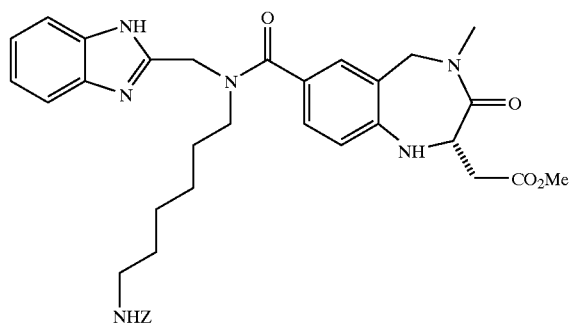

The product of Step 3A (300 mg, 0.66 mmol), methyl (S)-(-)-7-carboxy-2,3,4,5-tetrahydro-4-methyl-3-oxo-1H-1,4-benzodiazepine-2-acetate (172 mg, 0.55 mmol, prepared according to PCT/US95/00248, WO 95/18619), HOBT (89 mg, 0.66 mmol), and diisopropylethylamine (380 μL, 2.18 mmol) were dissolved in dry DMF (5 mL) in dry glassware under nitrogen. EDC (89 mg, 0.66 mmol) was added in one portion and the reaction stirred 20 hr. The solution was concentrated, partitioned between water and ethyl acetate, and the aqueous layer extracted with two additional portions of ethyl acetate. The combined organics were washed with water and brine, and concentrated. The crude oil was purified by flash chromatography on silica gel (EtOAc, 0.5% EtOH). The product fractions were combined and concentrated to yield 145 mg (40%) of product as a light brown solid. LRMS (ES): 655.3 [M+H]$^+$; $^1$HNMR (600.1343 MHz, DMSO-d6): 12.38 (b, 1H), 7.51 (m, 2H), 7.30 (m, 6H), 7.14 (m, 4H), 6.51 (d, 1H), 6.16 (d, 1H), 5.42 (d, 1H, J=16 Hz), 5.08 (m, 1H), 4.96 (s, 2H), 4.73 (s, 2H), 3.88 (d, 1H, J=16 Hz), 3.57 (s, 3H), 3.33 (m, 2H), 2.89 (m, 2H), 2.85 (s, 3H), 2.78 (dd, 1 H, J=16.5 Hz, 9 Hz), 2.61 (dd, J=16.5 Hz, 5 Hz), 1.52 (m, 2H), 1.30 (m, 2H), 1.15 (m, 4H); $^{13}$C NMR (600.1343 MHz, DMSO-d6): 170.9, 169.1, 165.6, 156.0, 151.3, 147.4, 137.3, 129.3, 128.3, 127.8, 127.7, 127.3, 123.0, 118.1, 114.9, 65.0, 59.7, 51.6, 51.3, 50.1, 50.0, 37.4, 35.0, 29.5, 29.2, 26.6, 20.7, 14.1

Step 3C: Synthesis of methyl (S)-2-(9-(N-(6-aminohexyl)-N-(benzimidazol-2-ylmethyl)carbamoyl)-2,5-diaza-5-methyl-4-oxobicyclo[5.4.0]undeca-1(7),8,10-trien-3-yl)acetate

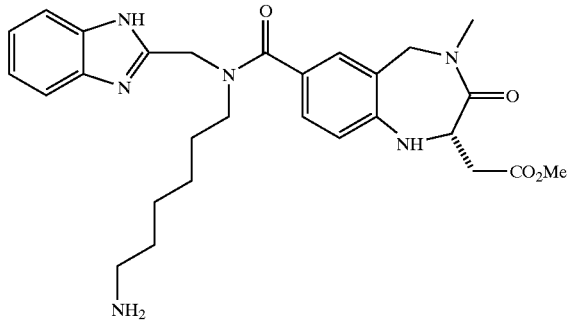

The product of 3B (140 mg, 214 μmol) was dissolved in methanol (6 mL) with 10% palladium on carbon (30 mg). The slurry was hydrogenated at one atmosphere pressure for 5.5 hr, filtered through Celite® and concentrated to yield the product (100 mg, 90%) as a clear oil which was not further purified, but taken directly into the next step. LRMS (ES) 521.4 [M+H]$^+$, 275.3, 261.3, 245.2, 231.3.

Step 3D: Synthesis of (S)-2-(9-(N-(6-aminohexyl)-N-(benzimidazol-2-ylmethyl)carbamoyl)-2,5-diaza-5-methyl-4-oxobicyclo[5.4.0]undeca-1(7),8,10-trien-3-yl)acetic acid

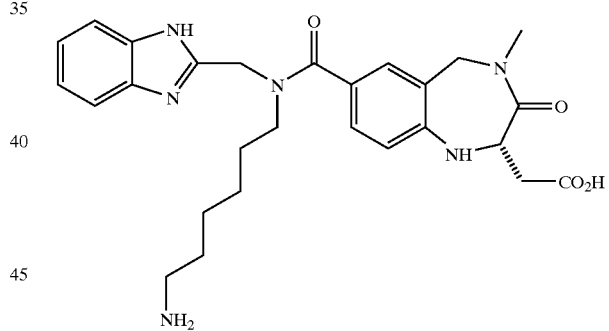

The product of Step 3C (100 mg, 192 μmol) was dissolved in methanol/tetrahydrofuran (2:1, 1 mL) and lithium hydroxide hydrate (23 mg, 550 μmol) dissolved in 0.5 mL water was added. The reaction was stirred for 4 hr, neutralized with 10% potassium hydrogen sulfate solution, and concentrated. The solids were dissolved in methanol, filtered, and the filtrate concentrated to an oil, which was dissolved in water/acetonitrile and lyophilized to afford 93 mg (96%) of the product as a white solid. LRMS (ES): 507.3 [M+H]$^+$, 459.4, 254.4 [M+2H]$^{+2}$; $^1$HNMR (600.1300 MHz, DMSO-d6): 12.35 (b, 1H), 10.49 (b, 3H), 7.59 (m, 2H), 7.53 (m, 2H), 7.16 (bs, 4H), 6.53 (d, 1H, J=7.4 Hz), 6.18 (s, 1H), 5.44 (d, 1H, J=16.4 Hz), 5.08 (m, 1H), 4.76 (s, 2H), 3.80 (bd, 1H, J=12 Hz), 3.38 (m, 2H), 2.88 (s, 3H), 2.78 (dd, 1 H, J=16.7 Hz, 9 Hz), 2.71 (m, 2H), 2.61 (dd, 1H, J=16.7 Hz, 5 Hz), 1.55 (m, 2H), 1.47 (m, 2H), 1.18 (m, 2H), 1.03 (m, 2H)

Step 3E: Synthesis of 2-(2,5-diaza-9-(N-(6-((6-((1-aza-2-(2-sulfophenyl)vinyl)amino)(3-pyridyl))carbonylamino)hexyl)-N-(benzimidazol-2-ylmethyl)carbamoyl)-5-methyl-4-oxobicyclo [5.4.0]undeca-1(7),8,10-trien-3-yl)acetic acid trifluoroacetate

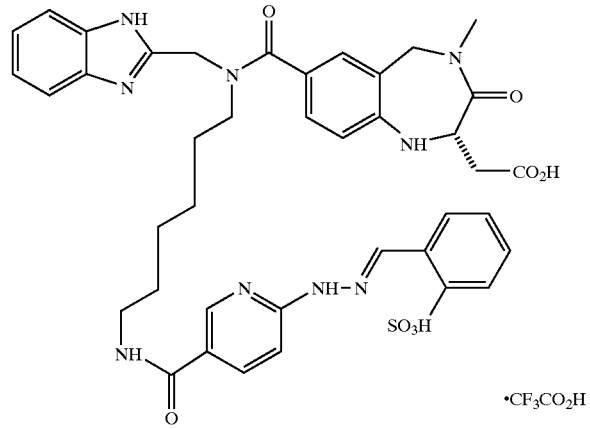

The product of Step D (80 mg, 160 μmol) was dissolved in dry dimethylformamide, along with sodium 2-[[[5-[[(2,5-dioxo-1-pyrolidinyl) oxy]carbonyl]-2-pyridinyl] hydrazono]methyl]-benzenesulfonate (88 mg, 250 μmol) and diisopropylethylamine (280 μL, 1.6 mmol) with stirring under nitrogen. The reaction was stirred overnight, concentrated, and the residue purified by preparative HPLC (Vydac C-18, 21.5 mm×25 cm, 0.1% TFA/acetonitrile gradient). The product fractions were combined and lyophilized to afford the product as a white solid (24 mg, 18%). LRMS (ES): 810.3 [M+H]$^+$, 4764.3, 399.3; HRMS (ESI): Calculated for $C_{40}H_{44}N_9O_8S$ (M+H)—810.3033, found—810.3052. $^1$HNMR (600.1300 MHz, DMSO-d6): 12.40 (b, 2H), 9.24 (bs, 1H), 8.59 (bs, 1H), 8.50 (s, 1H), 8.24 (bs, 1H), 8.20 (bs, 1H), 7.80 (d, 3H), 7.53 (m, 2H), 7.41 (m, 2H), 7.20 (m, 3H), 6.57 (d, 1H), 6.32 (bs, 1H), 5.47 (d, 1H, J=16.4 Hz), 5.08 (m, 1H), 4.98 (s, 2H), 3.83 (d, 1H, J=16.4 Hz), 3.50 (m, 2H), 3.21 (m, 2H), 2.89 (s, 3H), 2.75 (dd, 1 H, J=16.7 Hz, 9 Hz), 2.53 (dd, 1H, J=16.7 Hz, 5 Hz), 1.65 (m, 2H), 1.48 (m, 2H), 1.26 (m, 2H), 1.19 (m, 2H)

Example 4

Preparation of (S,S)-2-(2-aza-2-((5-(N-(1,3-bis(N-(6-(aminohexyl-4-oxobicyclo[5.4.0]undeca-1(7),8,10-trien-3-yl)acetic acid)(2-(2,5-diaza-9-(N-(benzimidazol-2-ylmethyl)propyl)carbamoyl)(2-pyridyl))amino)vinyl) benzenesulfonic acid

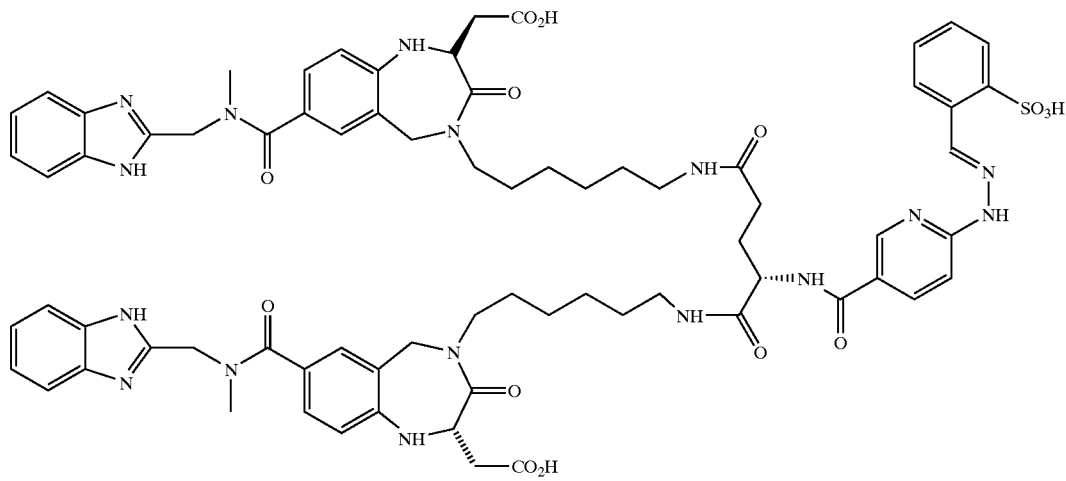

Step 4A. Synthesis of (S)-2-(2,5-diaza-9-(N-(benzimidazol-2-ylmethyl)-N-methylcarbamoyl)-5-(6-aminohexyl)-4-oxobicyclo[5.4.0]undeca-1(7),8,10-trien-3-yl)acetic acid

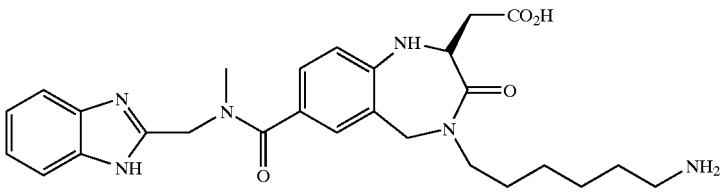

The product of Step 2E (350 mg, 564 μmol) was dissolved in methanol/tetrahydrofuran (2:1, 8 mL) with stirring. Lithium hydroxide hydrate (95 mg, 2.25 mmol) was dissolved in water (5 mL) and added to this solution. It was stirred for two hours, neutralized with 10% potassium hydrogen sulfate and concentrated to a gummy solid. This was added to a solution of trifluoroacetic acid in dichloromethane (4 mL/6 mL) and stirred for two hours. The solids were filtered off, and the filtrate concentrated to afford an oil, which was redissolved in water/acetonitrile and lyophilized to a white powder which was not further purified. LRMS (ES): 507.4 [M+H]$^+$, 254.4 [M+2H]$^{+2}$.

Step 4B. Synthesis of (S,S)-2-(2,5-diaza-(9-(N-benzimidazol-2-ylmethyl))-5-(6-(4-(N-(6-(3,6-diaza-5-(carboxymethyl)-4-oxobicyclo[5.4.0]undeca-1(7),8,10-trien-3-yl)hexyl)carbamoyl)-2-((tert-butoxy)carbonylamino)butanoylamino)hexyl)-4-oxobicyclo[5.4.0]undeca-1(11),7(8),9-trien-3-yl)acetic acid The product of 4A (31 mg, 36.5 μmol) was dissolved in dry dimethylformamide (1.5 mL), along with diisopropylethylamine (51 μL, 300 μmol). To this was added bis-(N-hydroxysuccinimide)-N-(tert-butoxycarbonyl)-glutamate (7.7 mg, 17.5 μmol) with stirring. The solution was allowed to stir for three hours, when it was concentrated and purified by preparative HPLC (Vydac C-18, 21.5 mm×25 cm, 0.1% TFA/acetonitrile gradient). The product fractions were combined and lyophilized to afford the product as a white solid (12 mg, 33%). LRMS (ES): 1224.7 [M+H]$^+$, 613.1 [M+2H]$^+_2$, 409.3 [M+3H]$^{+3}$. HRMS (ESI): Calculated for $C_{64}H_{82}N_{13}O_{12}$—1224.6206, found—1224.619.

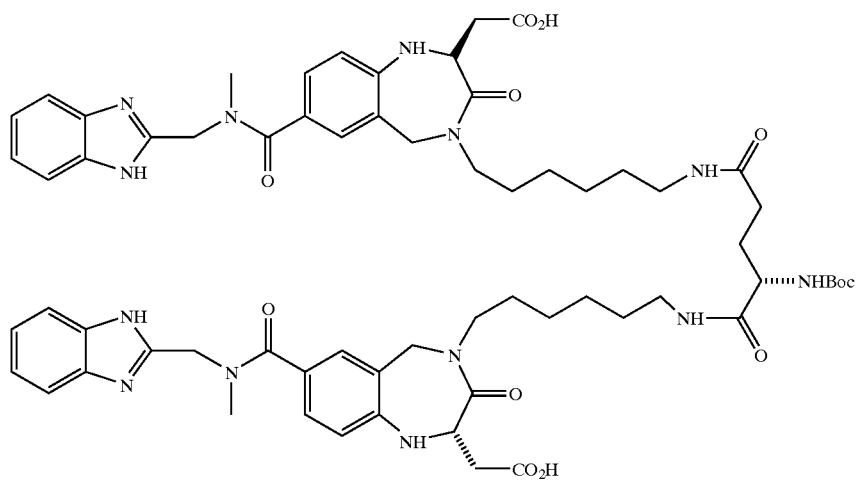

Step 4C. Synthesis of (S,S)-2-(2-aza-2-((5-(N-(1,3-bis(N-(6-(aminohexyl-4-oxobicyclo[5.4.0]undeca-1(7),8,10-trien-3-yl)acetic acid)(2-(2,5-diaza-9-(N-(benzimidazol-2-ylmethyl)propyl)carbamoyl)(2-pyridyl))amino)vinyl)benzenesulfonic acid

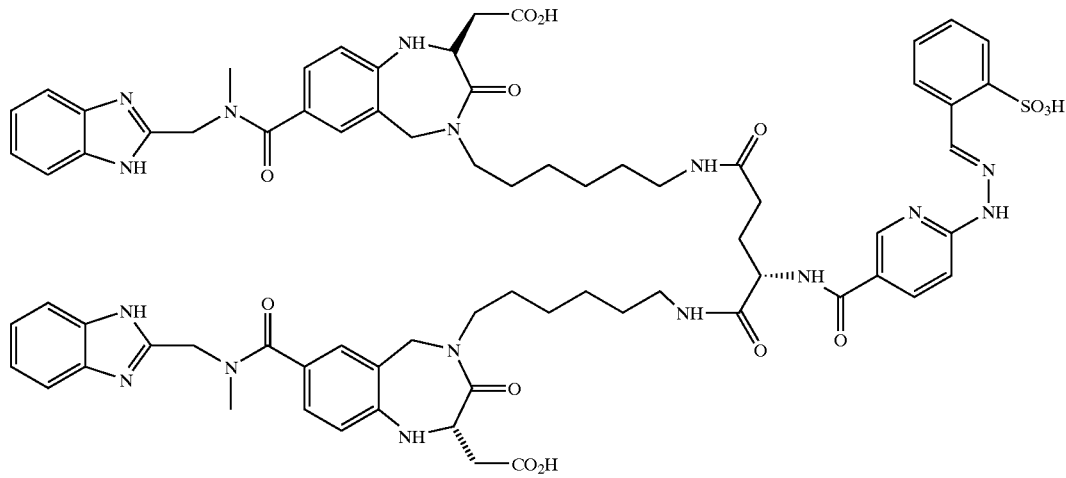

The product of 4B (10 mg, 5.5 μmol of 4TFA salt) was dissolved in dichloromethane:triflouroacetic acid (1.5 mL/0.5 mL) under nitrogen. It was stirred 20 minutes and concentrated to an oil, which was resuspended in toluene and reconcentrated to remove residual TFA. The residue was treated as in step 3E to afford 2.5 mg (31%) of the product as a white lyophilized solid. LRMS (ES): 1428.2 [M+H]$^+$, 714.5 [M+2H]$^{+2}$, 477.3 [M+3H]$^{+3}$. HRMS (ESI): Calculated for $C_{72}H_{83}N_{16}O_{14}S$—1427.5995, found—1427.601.

Example 5

Preparation of (S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-4-(4-carboxy-2-(2-(1,4,7,10-tetraaza-4,7,10-tris(carboxymethyl)cyclododecyl)acetylamino)butanoylamino) butanoic acid

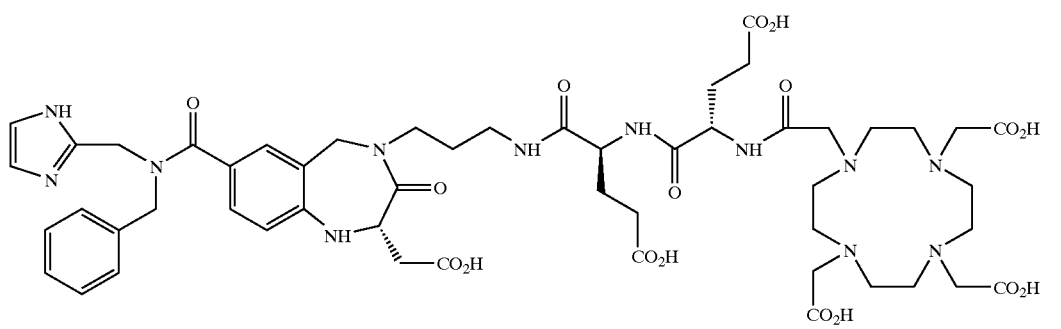

Step 5A. Synthesis of benzyl((1-(triphenylmethyl)imidazol-2-yl)methyl)amine

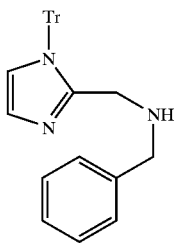

N-tritylimidazole-2-carboxaldehyde (338 mg, 1 mmol, prepared according to K. L. Kirk; *J.Org.Chem.*, 1978, 43, 4381) was dissolved in dry toluene (7 mL) and anhydrous magnesium sulfate (602 mg, 5 mmol) added with stirring under nitrogen. Benzylamine (131 μL, 1.2 mmol) was added and the solution stirred for 3.5 hr. The solids were filtered under nitrogen and the reaction concentrated. The residue is redissolved in 1,2-dichloroethane (25 mL) and cooled to 0° C. Sodium triacetoxyborohydride (1.06 g, 5 mmol) was added slowly. The solution was allowed to warm to room temperature over 2.5 hours. The reaction mixture was added to water/ethyl acetate and the layers separated. The aqueous layer was extracted with two portions of ethyl acetate and the combined organic layers washed with sat. bicarbonate, water, and brine. The solution was concentrated to an oil and purified by flash chromatography on silica gel (99:1 EtOAc/EtOH with 0.1% triethylamine) to afford 330 mg (77%) of product as an oil which solidified on standing. LRMS (ES): 430.4 [M+H]$^+$, 243.2; $^1$HNMR (600.1328 MHz, DMSO-d6): 7.37 (m, 11H), 7.04 (m, 9 H), 6.92 (d, 1H), 6.64 (d, 1H), 3.34 (s, 2H), 2.77 (2H).

Step 5B. Synthesis of methyl (S)-2-(2,5-diaza-5-(3-((tert-butoxy)carbonylamino)propyl)-4-oxo-9-(N-benzyl-N-((2-(triphenylmethyl)imidazol-2-yl)methyl)carbamoyl)bicyclo[5.4.0]undeca-1(7),8,10-trien-3yl)acetate

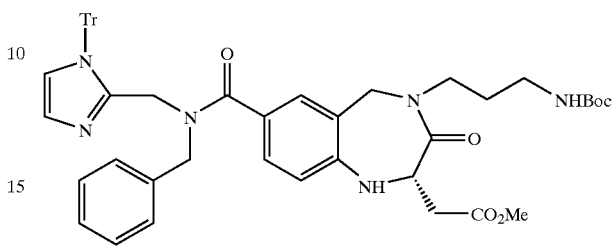

The product of step 5E (150 mg, 0.345 mmol) was treated in the same manner as step 1F, affording the product (250 mg, 85%) as a thick oil. LRMS (ES): 847.5 [M+H]$^+$, 430.5, 243.2; $^1$HNMR (600.1330 MHz, CDCl$_3$) This sample gave broad peaks with little fine splitting, even when refiltered, and was qualitatively similar to 1E for the benzodiazepine nucleus.

Step 5C. Synthesis of methyl (S)-2-(5-(3-aminopropyl)-2,5-diaza-9-(N-(imidazol-2-ylmethyl)-N-benzylcarbamoyl)-4-oxobicyclo [5.4.0]undeca-1(7),8,10-trien-3-yl)acetate

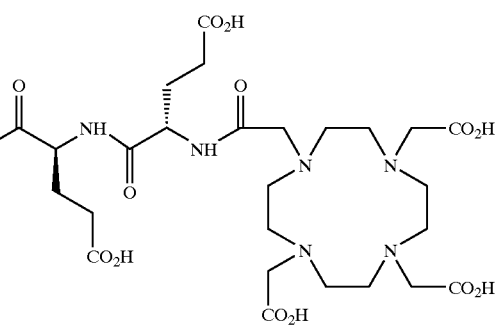

The product of step 5B (220 mg, 0.26 mmol) was added to neat trifluoroacetic acid (4 mL) containing triethylsilane (1 mL) under nitrogen and stirred for 1.5 hr. The solution was concentrated and residual acid removed by reconcentration with toluene. This product was not purified, but was used directly in the following step. LRMS (ES): 505.4 [M+H]$^+$, 253.4.

Step 5D. Synthesis of tert-butyl (S,S,S)-4-(N-(3-(3,6-diaza-10-(N-(imidazol-2-ylmethyl)-N-benzylcarbamoyl)-5-((methoxycarbonyl) methyl-4-oxobicyclo[5.4.0]undeca-1(7),8,10-trien-3-yl)propyl) carbamoyl)-4-(4-((tert-butyl)oxycarbonyl)-2-((phenylmethoxy) carbonylamino) butanoylamino)butanoate

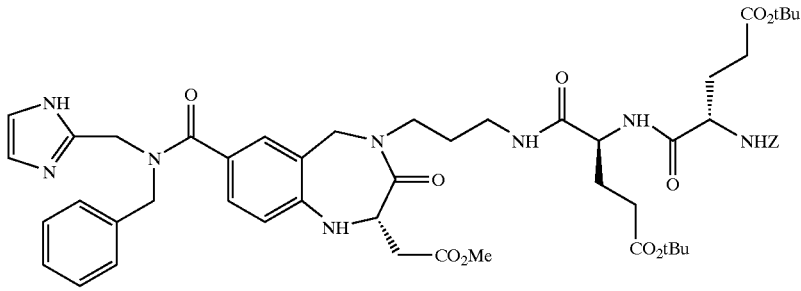

A portion of the product of step 5C (65 mg, 130 μmol) was reacted with step 1G as in Step 1H to afford the product (64 mg, 49% from 5B) as an oil. LRMS (ES): 1009.7 [M+H]$^+$, 505.6 [M+2H]$^{+2}$; HRMS (ESI): Calculated for $C_{53}H_{69}N_8O_{12}$—1009.5035, found—1009.502; $^1$HNMR (600.1330 MHz, CDCl$_3$) 7.47 (b, 1H), 7.22–7.41 (m, 14H), 6.99 (s, 2H), 6.93 (b, 1H), 6.44 (d, 1H), 5.98 (b, 1H) 5.32 (d, 1H), 5.13 (d, 1H), 5.05 (m, 2H) 4.68 (m, 3H), 4.48 (b, 1H), 4.36 (b, 1H), 4.24 (b, 1H), 3.71 (s, 3H), 3.68 (m, 1H), 3.60 (b, 1H), 3.38 (b, 1H), 3.11 (b, 1H), 2.97 dd, 1H), 2.94 (m, 1H), 2.65 (dd, 1H), 2.25–2.45 (m, 4H) 1.88–2.16 (m, 4H), 1.65 (m, 2H), 1.45 (s, 9 H), 1.41 (s, 9H).

Step 5E: Synthesis of tert-butyl (S,S,S)-4-amino-4-(N-(1-(N-(3-(3,6-diaza-10-(N-(imidazol-2-ylmethyl)-N-benzylcarbamoyl)-5-((methoxycarbonyl)methyl)-4-oxobicyclo[5.4.0]undeca-1(7),8,10-trien-3-yl)propyl) carbamoyl)-3-((tert-butyl)oxycarbonyl) propyl)carbamoyl) butanoate The product of 5D (58 mg, 57 μmol) was hydrogenated according to the procedure of step 1I, to yield the product (44 mg, 88%) as a white solid, which was not further purified but was lyophilized in 0.1% aqueous trifluoroacetic acid/acetonitrile (1:1) and used as the trifluoroacetate salt in the next step. LRMS (ES): 875.6 [M+H]$^+$, 438.5 [M+2H]$^{+2}$;

Step 5F: Synthesis of tert-butyl (S,S,S)-4-(N-(1-(N-(3-(3,6-diaza-10-(N-(imidazol-2-ylmethyl)-N-benzylcarbamoyl)-5-((methoxycarbonyl)methyl)-4-oxobicyclo[5.4.0]undeca-1(7),8,10-trien-3-yl)propyl)carbamoyl)-3-((tert-butyl)oxycarbonyl) propyl)carbamoyl)-4-(2-(1,4,7,10-tetraaza-4,7,10-tris(((tert-butyl)oxycarbonyl)methyl)cyclododecyl) acetylamino)butanoate

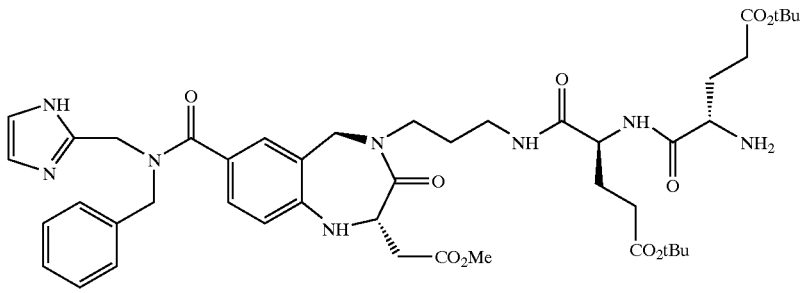

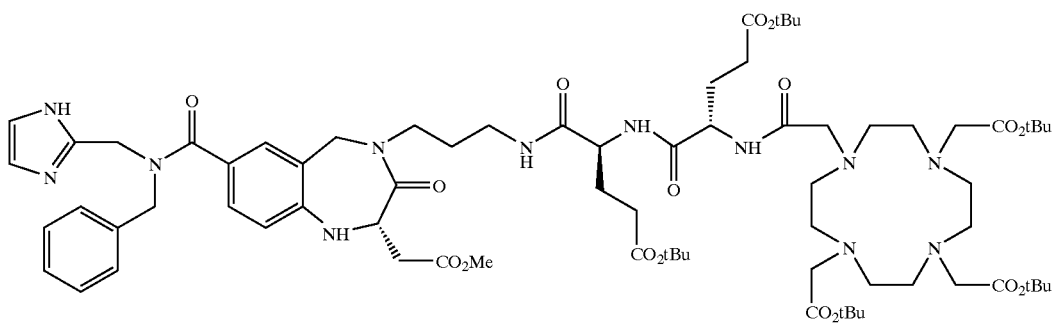

The product of 5E (24.4 mg, 20 μmol) was reacted with DOTA tri-tert-butyl ester as in step 1J, to afford the product (19.6 mg, 55%) as a trifluoroacetate salt after lyophilization.

LRMS (ES): 1430.0 [M+H]$^+$, 715.7 [M+2H]$^{+2}$, 477.8 [M+3H]$^{+3}$; HRMS(ESI): Calculated for $C_{73}H_{113}N_{12}O_{17}$—1429.8347, found 1429.838;

Step 5G: Synthesis of (S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-4-(4-carboxy-2-(2-(1,4,7,10-tetraaza-4,7,10-tris(carboxymethyl)cyclododecyl) acetylamino)butanoylamino) butanoic acid Step 6A: Synthesis of tert-butyl (S,S)-3-(N-(3-(3,6-diaza-10-(N-(imidazol-2-ylmethyl)-N-benzylcarbamoyl)-5-((methoxycarbonyl) methyl)-4-oxobicyclo[5.4.0]undeca-1(7),8,10-trien-3-yl)propyl) carbamoyl)-3-((phenylmethoxy) carbonylamino)propanoate

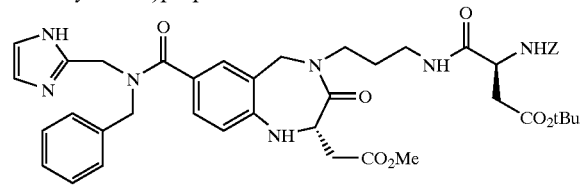

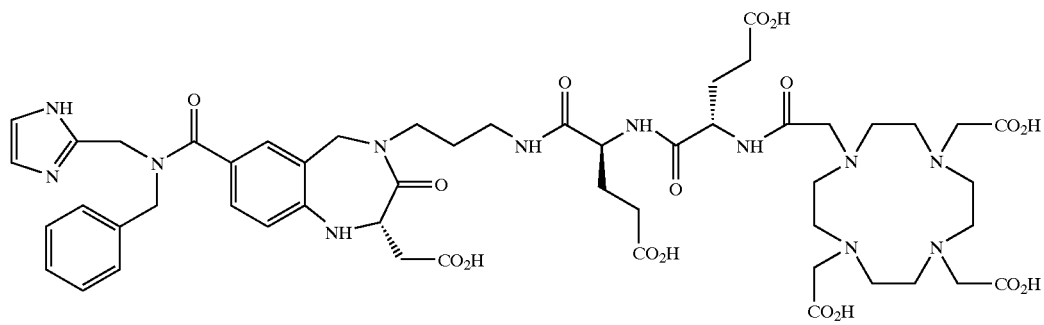

The product of 5F (13 mg, 7.4 μmol) was deprotected and purified as in step 1K, to afford the product (6.5 mg, 55%) as a trifluoroacetate salt after lyophilization. LRMS (ES): 1135.6 [M+H]$^+$, 568.5 [M+2H]$^{+2}$, 379.6 [M+3H]$^{+3}$; HRMS (ESI): Calculated for $C_{52}H_{71}N_{12}O_{17}$—1135.5060, found—1135.503;

Example 6

Preparation of (S,S)-3-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-3-(2-(1,4,7,10-tetraaza-4,7,10-tris(carboxymethyl) cyclododecyl) acetylamino)propanoic acid The product of step 5D (65 mg, 130 μmol) was reacted with N-(carbobenzyloxy)-β-(tert-butyl)-□-(N-hydroxysuccinimidyl) aspartate (66 mg, 156 μmol) and diisopropylethylamine (181 μL, 1.04 mmol) in dimethylformamide (1.5 mL) with stirring at room temperature under nitrogen for 20 hr. The reaction was concentrated, and the residue dissolved in ethyl acetate. The organics were washed with water, 10% potassium hydrogen sulfate, water, and brine, and then concentrated. The residual oil was purified by flash chromatography on silica (EtOAc/MeOH, 1%->10%) and the product fractions combined and evaporated to yield the product (76 mg, 73%) as an oil. LRMS (ES): 810.5 [M+H]$^+$, 378.0; HRMS (ESI): Calculated for $C_{43}H_{52}N_7O_9$—810.3826, found—810.3819; $^1$HNMR (600.1323 MHz, CDCl$_3$) 7.25–7.38 (m, 12H), 7.18 (m, 2H), 7.07 (b, 1H), 6.99 (s, 2H), 6.39 (d, 1H), 6.18 (b, 1H) 5.30 (d,

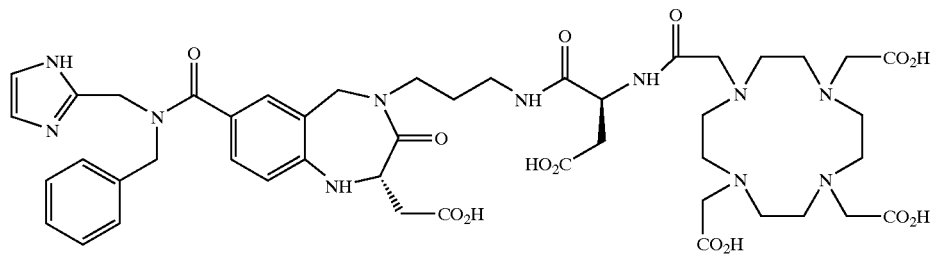

J=16.2 Hz, 1H), 5.09 (m, 2H), 5.04 (m, 1H) 4.67 (m, 4H), 4.50 (b, 1H), 4.36 (b, 1H), 3.69 (s, 3H), 3.62 (d, J=18.6 Hz, 1H), 3.45 (b, 1H), 3.14 (m, 1H), 2.94 (dd, 1H), 2.86 (m, 2H), 2.62 (m, 2H), 1.60 (m, 2H), 1.39 (s, 9 H).

Step 6B: Synthesis of tert-butyl (S,S)-3-amino-3-(N-(3-(3,6-diaza-10-(N-(imidazol-2-ylmethyl)-N-benzylcarbamoyl)-5-((methoxycarbonyl) methyl)-4-oxobicyclo[5.4.0]undeca-1(7),8,10-trien-3-yl)propyl) carbamoyl)propanoate

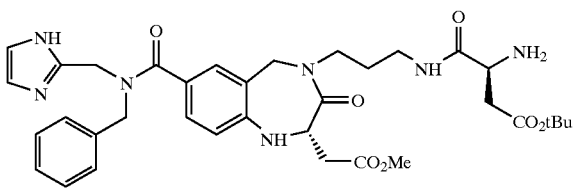

The product of 6A (70 mg, 86 μmol) was hydrogenated according to the procedure of step 1I, to yield the product (55 mg, 95%) as a white solid, which was not further purified but was lyophilized in 0.1% aqueous trifluoroacetic acid/acetonitrile (1:1) and used as the trifluoroacetate salt in the next step. LRMS (ES): 676.5 [M+H]$^+$, 339.0 [M+2H]$^{+2}$, 310.9.

Step 6C: Synthesis of tert-butyl (S,S)-3-(N-(3-(3,6-diaza-10-(N-(imidazol-2-ylmethyl)-N-benzylcarbamoyl)-5-((methoxycarbonyl) methyl)-4-oxobicyclo[5.4.0]undeca-1(7),8,10-trien-3-yl)propyl) carbamoyl)-3-(2-(1,4,7,10-tetraaza-4,7,10-tris(((tert-butyl) oxycarbonyl)methyl) cyclododecyl)acetylamino)propanoate The product of 6B (22.4 mg, 22 μmol) was reacted with DOTA tri-tert-butyl ester and purified as in step 1J, to afford the product (16.6 mg, 44%) as a trifluoroacetate salt after lyophilization. LRMS (ES): 1230.9 [M+H]$^+$, 616.2 [M+2H]$^{+2}$, 411.3 [M+3H]$^{+3}$; HRMS(ESI): Calculated for $C_{63}H_{96}N_{11}O_{14}$—1230.7138, found—1230.715;

Step 6D: Synthesis of (S,S)-3-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-3-(2-(1,4,7,10-tetraaza-4,7,10-tris(carboxymethyl) cyclododecyl)acetylamino) propanoic acid

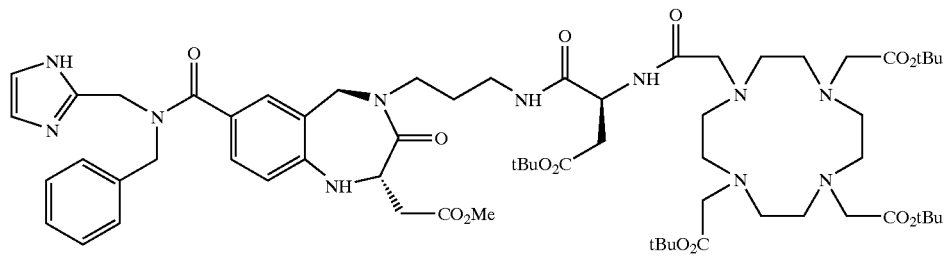

50

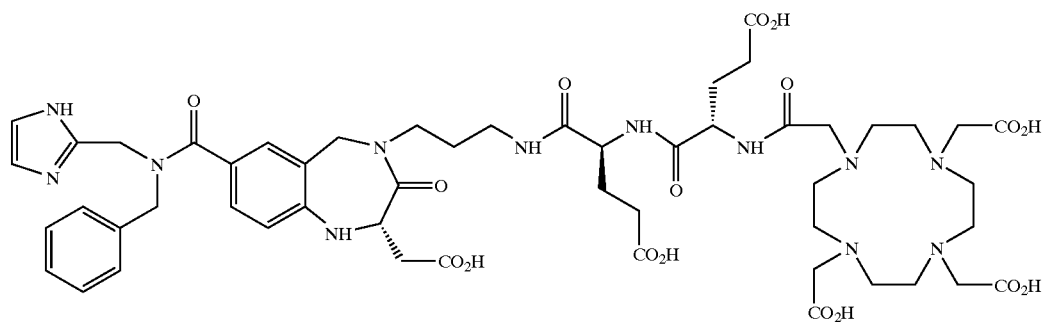

The product of 5F (14 mg, 8.3 μmol) was deprotected and purified as in step 1K, to afford the product (4.6 mg, 47%) as a trifluoroacetate salt after lyophilization. LRMS (ES): 992.6 [M+H]$^+$, 497.0 [M+2H]$^{+2}$, 331.8 [M+3H]$^{+3}$; HRMS (ESI): Calculated for $C_{46}H_{62}N_{11}O_{14}$—992.4478, found— 992.4457;

Example 7

Synthesis of (S,S,S,S,S,S,S,S)-4-(N-1,3-bis(N-3-carboxy-1-(N-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl) propyl)carbamoyl)-4,4-dihydroxypentyl) carbamoyl) propyl)carbamoyl)-4-(5,5-dihydroxy-2-(2-(1,4,7,10-tetraaza-4,7,10-tris(carboxymethyl)cyclodecyl) acetylamino) butanoic acid

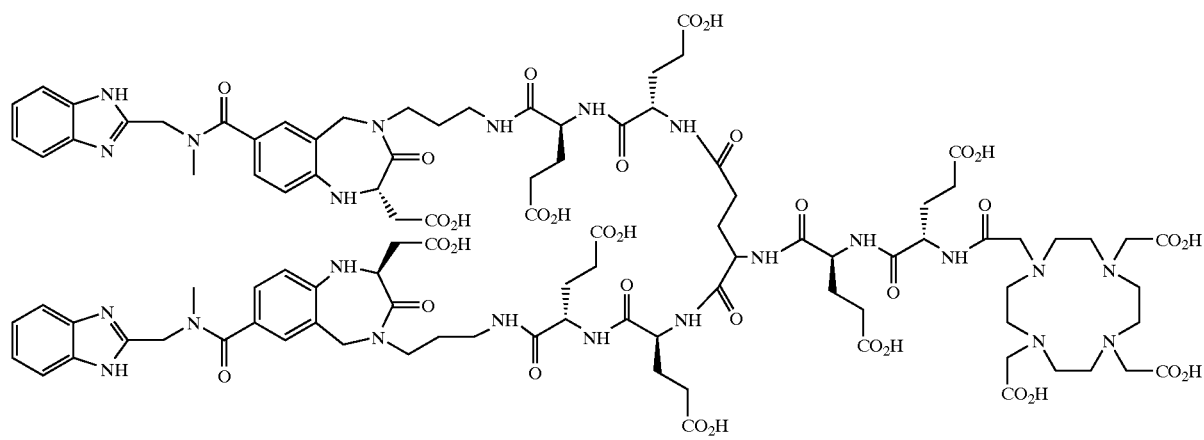

Step 7A: Synthesis of tert-butyl (S,S,S,S,S,S,S)4-(N-(1-(N-(3-(3,6-diaza-10-10-(N-(benzimidazol-2-ylmethyl)-N-methylcarbamoyl)-5-((methoxy carbonyl)methyl)-4-oxobicyclo[5.4.0]undeca-1(7),8,10-trien-3-yl)propyl) carbamoyl)-4-(4-(N-(1-(N-(1-(N-(3-(3,6-diaza-10-10-(N-(benzimidazol-2-ylmethyl)-N-methylcarbamoyl)-5-((methoxy carbonyl)methyl)-4-oxobicyclo[5.4.0]undeca-1 (7),8,10-trien-3-yl)propyl)carbamoyl)-3-((tert-butyl) oxycarbonyl)propyl) carbamoyl)-2-((phenylmethoxy) carbonylamino) butanoylamino) butanoate

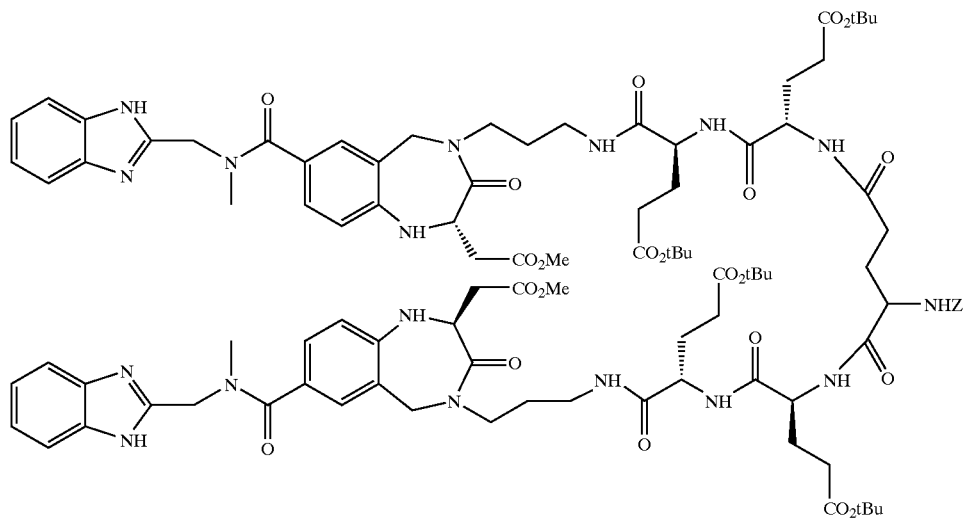

The product of step 1I (65 mg, 54.6 μmol) is dissolved in DMF (1 mL) along with HBTU (25 mg, 65 μmol), N-carbobenzyloxy-L-glutamic acid (7.3 mg, 26 μmol), HOBT (7 mg, 52 μmol), and diisopropylethylamine (40 μL, 225 μmol) under nitrogen. After stirring for 2 hrs, the reaction is concentrated and purified by preparative HPLC (0.1% TFA/acetonitrile gradient, Zorbax C8, 21.5 mm×25 cm). The product may be obtained as the trifluoroacetate salt after lyophilization.

Step 7B: Synthesis of tert-butyl (S,S,S,S,S,S)-4-(2-amino-4-(N-(1-(N-(3-(3,6-diaza-10-10-(N-(benzimidazol-2-ylmethyl)-N-methylcarbamoyl)-5-((methoxycarbonyl) methyl)-4-oxobicyclo [5.4.0]undeca-1(7),8,10-trien-3-yl) propyl)carbamoyl)-3-((tert-butyl)oxycarbonyl)propyl) carbamoyl)-3-((tert-butyl)oxycarbonyl) propyl)carbamoyl) butanoylamino)-4-(N-(1-(N-(3-(3,6-diaza-10-10-(N-(benzimidazol-2-ylmethyl)-N-methylcarbamoyl)-5-((methoxy carbonyl)methyl)-4-oxobicyclo[5.4.0]undeca-1(7),8,10-trien-3-yl)propyl)carbamoyl)-3-((tert-butyl)oxycarbonyl)propyl) carbamoyl)butanoate The product of step 7A is hydrogenated and isolated as in step 1I. This material is not further purified, but used directly in the following step.

Step 7C: Synthesis of tert-butyl (S,S,S,S,S,S,S,S)-4-(N-(1,3-bis(N-(3-((tert-butyl)oxycarbonyl)-1-(N-3-((tert-butyl) oxycarbonyl)-1-(N-(3-(3,6-diaza-10-10-(N-(benzimidazol-2-ylmethyl)-N-methylcarbamoyl)-5-((methoxy carbonyl) methyl)-4-oxobicyclo[5.4.0]undeca-1(7),8,10-trien-3-yl) propyl) carbamoyl)propyl)carbamoyl)propyl) carbamoyl) propyl)carbamoyl)-4-(4-((tert-butyl)oxycarbonyl)-2-((phenylmethoxy)carbonylamino) butanoylamino)butanoate

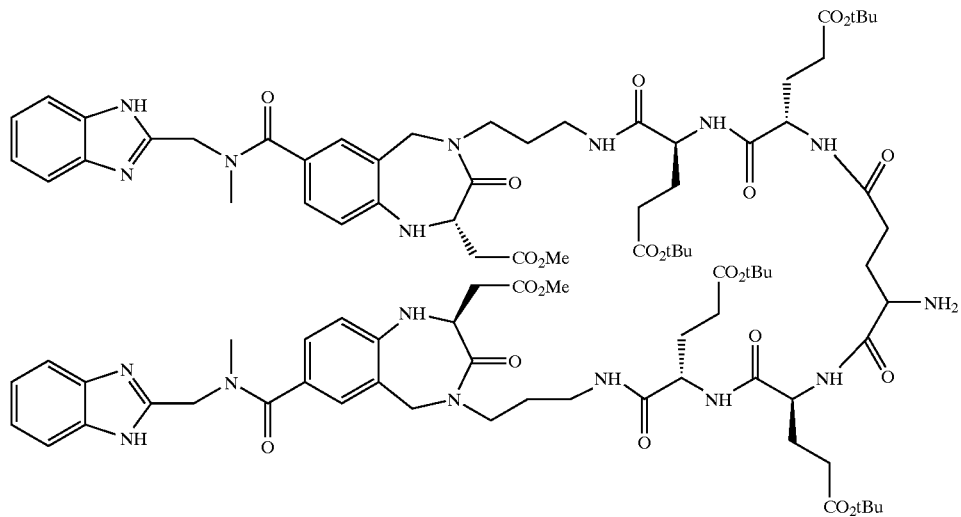

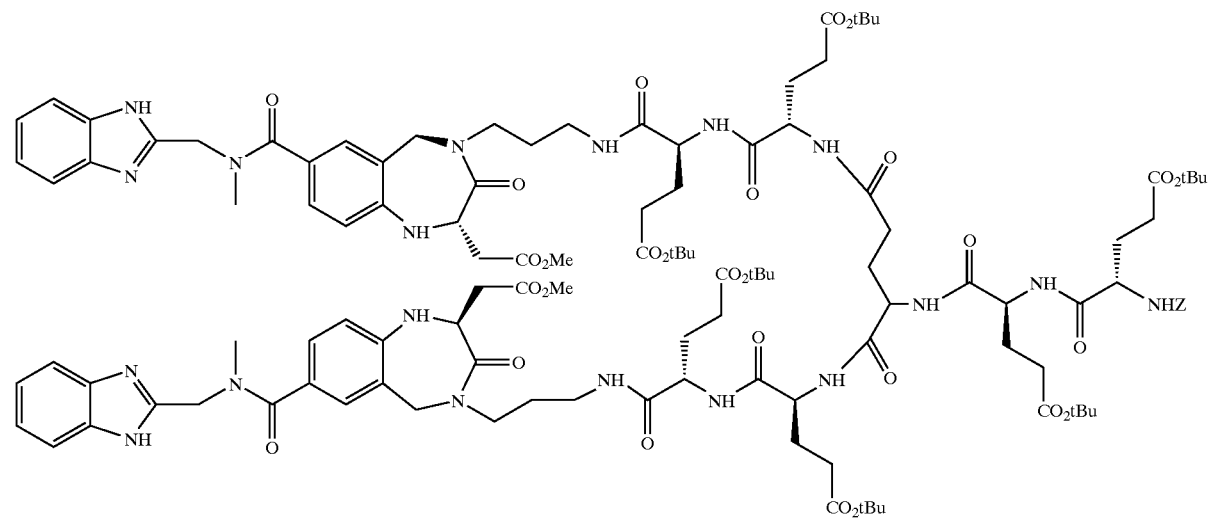

The product of step 7B is reacted as in step 5D to afford the product, which is purified by preparative HPLC.

Step 7D: Synthesis of tert-butyl (S,S,S,S,S,S,S,S)-4-amino-4-(N-(1-(N-(1,3-bis(N-(3-((tert-butyl)oxycarbonyl)-1-(N-3-((tert-butyl)oxycarbonyl)-1-(N-(3-(3,6-diaza-10-10-(N-(benzimidazol-2-ylmethyl)-N-methyl carbamoyl)-5-((methoxy carbonyl)methyl)-4-oxobicyclo[5.4.0]undeca-1(7),8,10-trien-3-yl)propyl)carbamoyl) propyl)carbamoyl) propyl)carbamoyl)propyl)carbamoyl)-3-((tert-butyl)oxycarbonyl)propyl)carbamoyl)butanoate The product of step 7D is reacted with DOTA(OtBu)3-OH as in step 1J to afford the product as a solid after preparative HPLC purification and lyophilization. Alternatively, the product of 7B is reacted with the product of 7I in the presence of HBTU, HOBT, and diisopropylethylamine in dry dimethylformamide for 2 hours, after which the reaction is concentrated and the residue purified by preparative HPLC to afford the product as a solid after lyophilization.

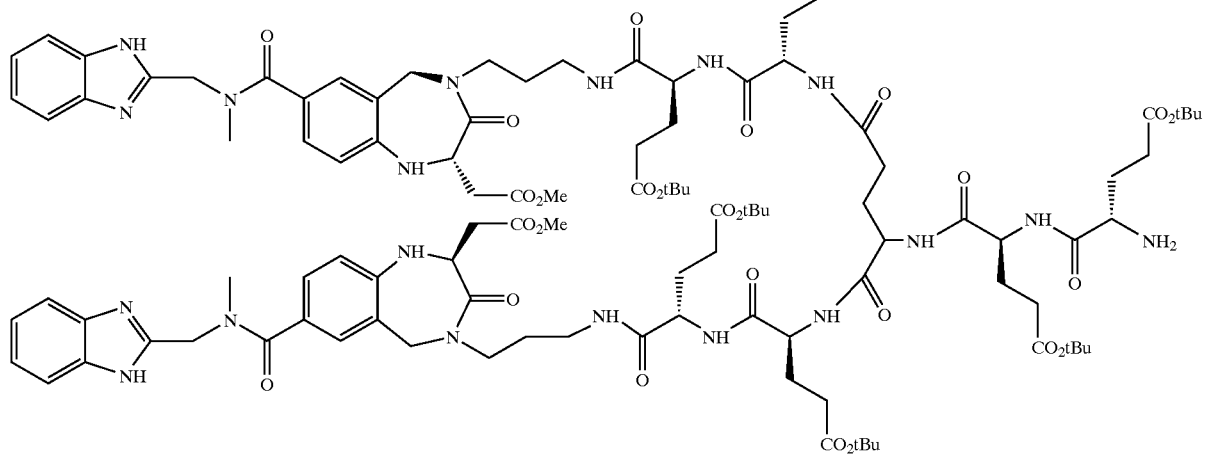

The product of step 7C is hydrogenated as in step 1I to afford the amine, which is not further purified but used directly in the next step.

Step 7E: Synthesis of tert-butyl (S,S,S,S,S,S,S,S)-4-(N-(1-(N-(1,3-bis(N-(3-((tert-butyl)oxycarbonyl)-1-(N-3-((tert-butyl) oxycarbonyl)-1-(N-(3-(3,6-diaza-10-10-(N-(benzimidazol-2-ylmethyl)-N-methylcarbamoyl)-5-((methoxycarbonyl)methyl)-4-oxobicyclo[5.4.0]undeca-1(7),8,10-trien-3-yl))propyl)carbamoyl) propyl)carbamoyl) propyl)carbamoyl)propyl)carbamoyl)-3-((tert-butyl)oxycarbonyl)propyl)carbamoyl)-4-(2-(1,4,7,10-tetraaza-4,7,10-tris(((tert-butyl)oxycarbonyl)methyl)cyclododecyl) acetylamino)butanoate Step 7F: Synthesis of (S,S,S,S,S,S,S,S)-4-(N-1,3-bis(N-3-carboxy-1-(N-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)propyl) carbamoyl)-4,4-dihydroxypentyl) carbamoyl)propyl) carbamoyl)-4-(5,5-dihydroxy-2-(2-(1,4,7,10-tetraaza-4,7,10-tris(carboxymethyl)cyclodecyl)acetylamino) butanoic acid

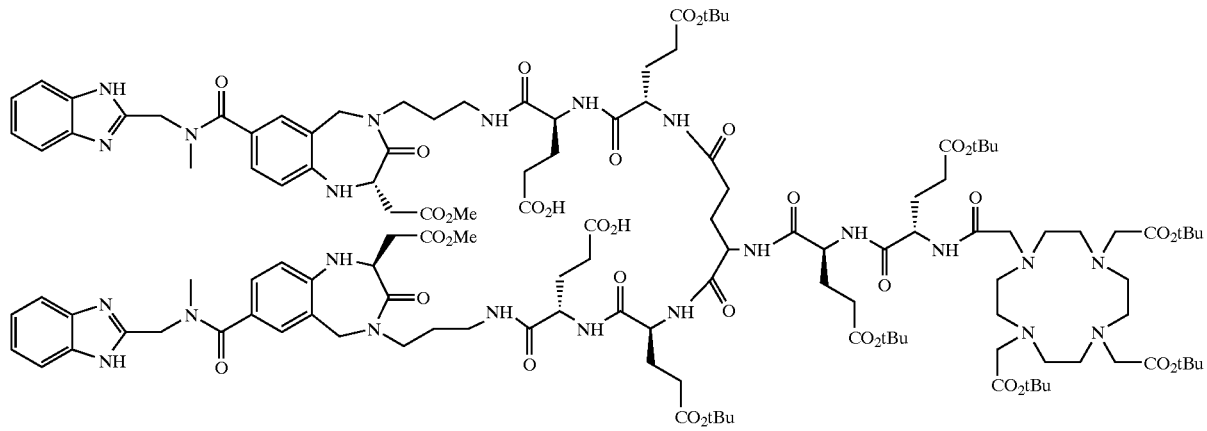

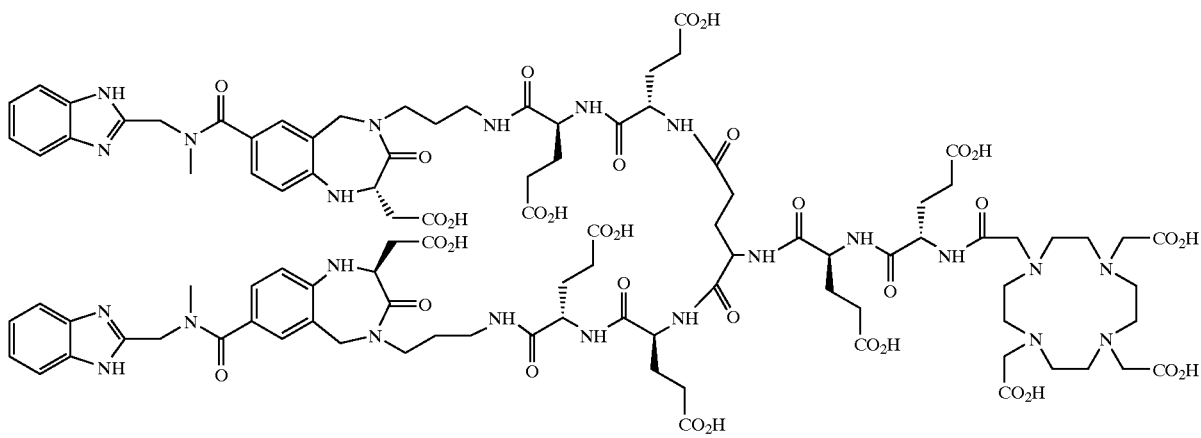

The product of step 7D is deprotected as in step 1K to afford the product as a solid after preparative HPLC purification and lyophilization.

Step 7G: Synthesis of tert-butyl (S,S)-3,3-dimethyl-3-silabutyl 2-(4-((tert-butyl)oxycarbonyl)-2-((phenylmethoxy)carbonylamino) butanoylamino)pentane-1,5-dioate

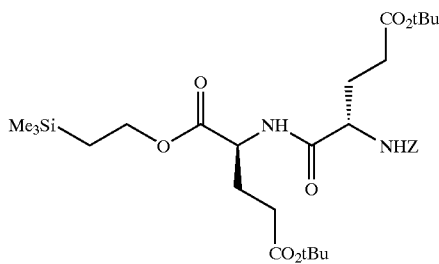

The product of step 1G (1.25 g, 2.4 mmol) was reacted with 2-trimethylsilylethanol (296 mg, 2.5 mmol) in the presence of ethyl [3-(N,N-dimethylaminopropyl]-carbodiimide hydrochloride (480 mg, 2.5 mmol) and dimethylaminopyridine (250 mg, 1.2 mmol) in dimethylformamide (10 mL) at 0° C. The reaction was allowed to warm slowly to room temperature and stirred overnight. It was concentrated and the residue partitioned between ethyl acetate and water. The aqueous layer was extracted twice with ethyl acetate, and the combined organics washed with water, 10% potassium hydrogen sulfate, and brine, and concentrated. The residue was purified by flash chromatography (ethyl acetate/hexane) to afford the product as an oil (1.1 g, 73%). LRMS (ES): 623.5 [M+H]$^+$.

Step 7H: Synthesis of tert-butyl (S,S)-3,3-dimethyl-3-silabutyl 2-(2-amino-4-((tert-butyl)oxycarbonyl) butanoylamino)pentane-1,5-dioate The product of step 7G (1.09 g) was dissolved in 2-propanol (75 mL) with 10% palladium on carbon (300 mg) and hydrogenated on a Parr shaker at 45 psi for one hour. The reaction mixture was filtered on a bed of Celite, washed with 2-propanol, and concentrated to yield the product (803 mg, 94%) as a clear oil. LRMS (ES): 489.5 [M+H]$^+$, 977.7 [2M+H]$^+$. $^1$HNMR (600.1343 MHz, CDCl$_3$): 7.78 (m, 1H), 4.53 (m, 1H), 4.22 (m, 2H), 3.53 (m, 1H), 1.80–2.41 (m, 10H), 1.43 (s, 18H), 1.01 (m, 2H), 0.02 (s, 9H).

Step 7I: Synthesis of tert-butyl (S,S)-3,3-dimethyl-3-silabutyl 2-(4-((tert-butyl)oxycarbonyl)-2-(2-bromoacetylamino) butanoylamino)pentane-1,5-dioate

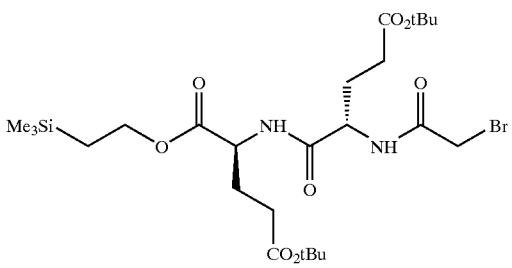

The product of step 7H (397 mg, 0.813 mmol) was dissolved in dry tetrahydrofuran (5 mL) with diisopropylethylamine (180 μL, 1.05 mmol) and cooled to −10° C. under nitrogen. Bromoacetyl bromide (85 μL, 0.98 mmol), dissolved in 10 mL tetrahydrofuran, was added dropwise to the cold solution, keeping T≦−5° C. The reaction was stirred in the cold for 1.5 hr, and 25 μL methanol added. The solids were filtered and rinsed and the combined filtrate concentrated to a brown oil, which was purified by flash chromatography (dichloromethane/ethyl acetate) to afford the product (388 mg, 78%) as a light tan oil. LRMS (ES): 609.3/611.3 [M+H]$^+$, 631.3/633.3 [M+Na]$^+$, 185.3, 144.2. $^1$HNMR (600.1343 MHz, CDCl$_3$): 7.32 (m, 1H), 7.09 (m, 1H), 4.50 (m, 2H), 4.21 (m, 2H), 3.87 (m, 2H), 2.31 (m, 2H), 2.13 (m, 2H), 1.99 (m, 2H), 1.97 (m, 2H), 1.45 (s, 9H), 1.43 (s, 9H), 1.01 (m, 2H), 0.04 (s, 9H).

Step 7J: Synthesis of (S,S)-4-((tert-butyl)oxycarbonyl)-2-(4-((tert-butyl)oxycarbonyl)-2-(2-(1,4,7,10-tetraaza-4,7,10-tris(((tert-butyl)oxycarbonyl)methyl)cyclododecyl) acetylamino) butanoylamino)butanoic acid

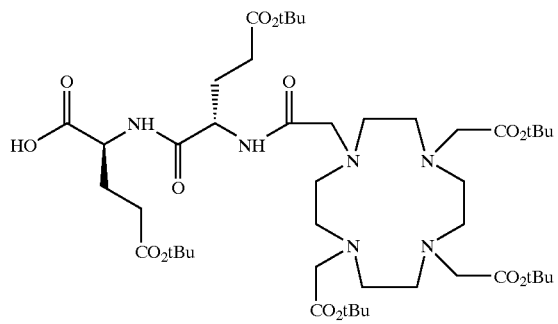

The product of step 7H (214 mg, 0.416 mmol) was dissolved in dimethylformamide (3 mL) and added to a solution of triethylamine (250 μL) and DO3A tri-tert-butyl ester in dimethylformamide (3 mL). The reaction was stirred for 4 days at room temperature, concentrated, and the residue dissolved in ethyl acetate. This was washed with water and brine, dried, and concentrated to an oil which was not further purified but reacted directly with tetra-butylammonium fluoride (1.0M in tetrahydrofuran, 1.25 mL) in tetrahydrofuran (2.5 mL). After stirring for 2 hours, the reaction was treated with ether (50 mL) and water (50 mL) and the layers separated. The aqueous layer was extracted with three portions of ethyl acetate, and the combined organic layers concentrated to an oil. This was purified by preparative HPLC (0.1% trifluoroacetic acid/acetonitrile, Zorbax C-8, 21.5 mm×25 cm) and the product fractions lyophilized to afford 127 mg (32% for two steps) of the product as a white solid. LRMS (ES): 943.3 [M+H]$^+$, 887.2, 831.2, 775.5, 719.3, 663.2 (loss of 1–5 tert-butyl) 444.3, 416.2, 388.3, 360.1, 332.1 [M-(1–5 tert butyl)+2H]$^{+2}$. $^1$HNMR (600.1343 MHz, CDCl$_3$): 9.05 (b, 1H), 8.2 (b, 4H) 7.36 (b, 1H), 4.34 (m, 2H), 2.77–4.23 (very broad humps, 24H), 2.31 (m, 4H), 2.13 (m, 2H), 1.93 (m, 2H), 1.47 (d, 18H), 1.43 (m, 27H).

Example 8

Synthesis of (S,S,S,S,S,S,S,S,S,S)-2-(4-(N-(1,3-bis (N-(3-(N-(3-(3,6-diaza-10-(N-(benzimidazol-2-ylmethyl)-N-methylcarbamoyl)-5-((methoxycarbonyl)methyl)-4-oxobicyclo [5.4.0] undeca-1(7),8,10-trien-3-yl)propyl)carbamoyl)-1-(methoxycarbonyl)propyl)carbamoyl)propyl) carbamoyl)propyl) carbamoyl)-4-(2-(2-(1,4,7,10-tetraaza-4,7,10-tris(carboxymethyl) cyclodecyl) acetylamino)-4-carboxybutanoylamino)-4-carboxybutanoylamino)butanoylamino)-4-(N-(3-(3,6-diaza-10-(N-(benzimidazol-2-ylmethyl)-N-methyl carbamoyl)-5-((methoxycarbonyl)methyl)-4-oxobicyclo[5.4.0] undeca-1(7),8,10-trien-3-yl) propyl)carbamoyl)butanoic acid

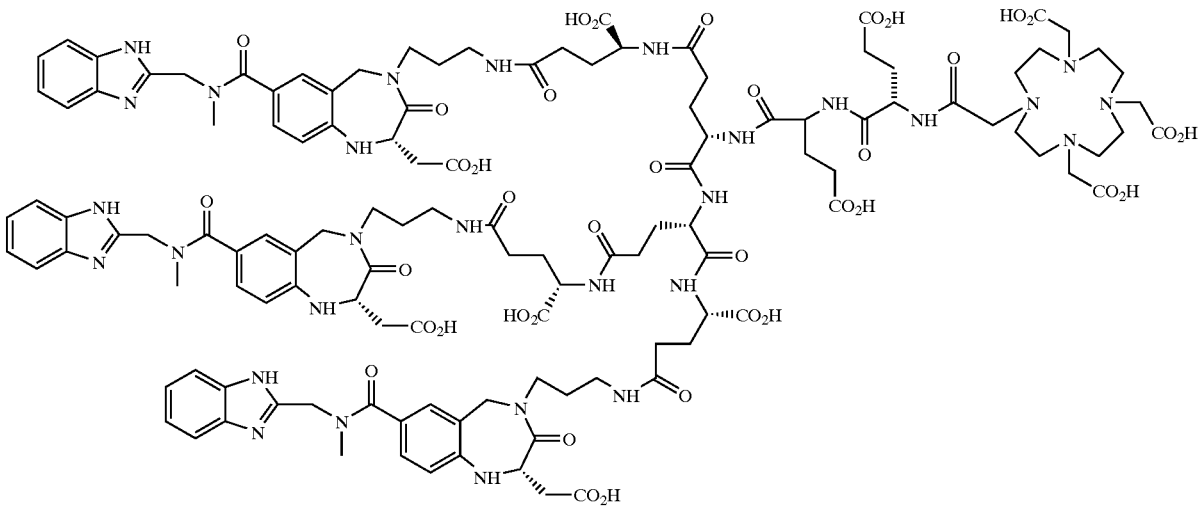

Step 8A: Synthesis of ditert-butyl (S,S)-2-(4-((tert-butyl) oxycarbonyl)-2-((phenylmethoxy)carbonylamino) butanoylamino) pentane-1,5-dioate

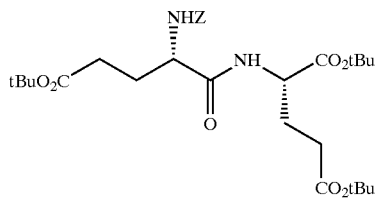

Gamma-tert-butyl-N-carbobenzyloxyglutamic acid N-hydroxy-succinimide ester is dissolved in DMF with diisopropylethylamine. Bis(tert-butyl)glutamate hydrochloride is added and the reaction stirred for one hour. The reaction is concentrated, water added, and the mixture extracted with ethyl acetate. The combined organic layers are washed with water, 10% potassium hydrogen sulfate, and brine, and then concentrated. The product is purified by flash chromatography.

Step 8B: Synthesis of tert-butyl methyl (S,S,S,S,S)-2-(4-(N-(1,3-bis(N-(3-((tert-butyl)oxycarbonyl)-1-(methoxycarbonyl) propyl)carbamoyl)propyl)carbamoyl)-4-((phenylmehtoxycarbonyl amino)butanoylamino) pentane-1,5-dioate methylcarbamoyl)-5-((methoxycarbonyl)methyl)-4-oxobicyclo[5.4.0]undeca-1(7),8,10-trien-3-yl)propyl) carbamoyl)-2-(4-(N-(1,3-bis(N-(3-(N-(3,6-diaza-10-(N-(benzimidazol-2-ylmethyl)-N-methylcarbamoyl)-5-((methoxycarbonyl)methyl)-4-oxobicyclo[5.4.0]undeca-1(7),8,10-trien-3-yl)propyl)carbamoyl)-1-(methoxycarbonyl) propyl) carbamoyl)propyl)carbamoyl)-4-((phenylmethoxy) carbonyl amino)butanoylamino)butanoate

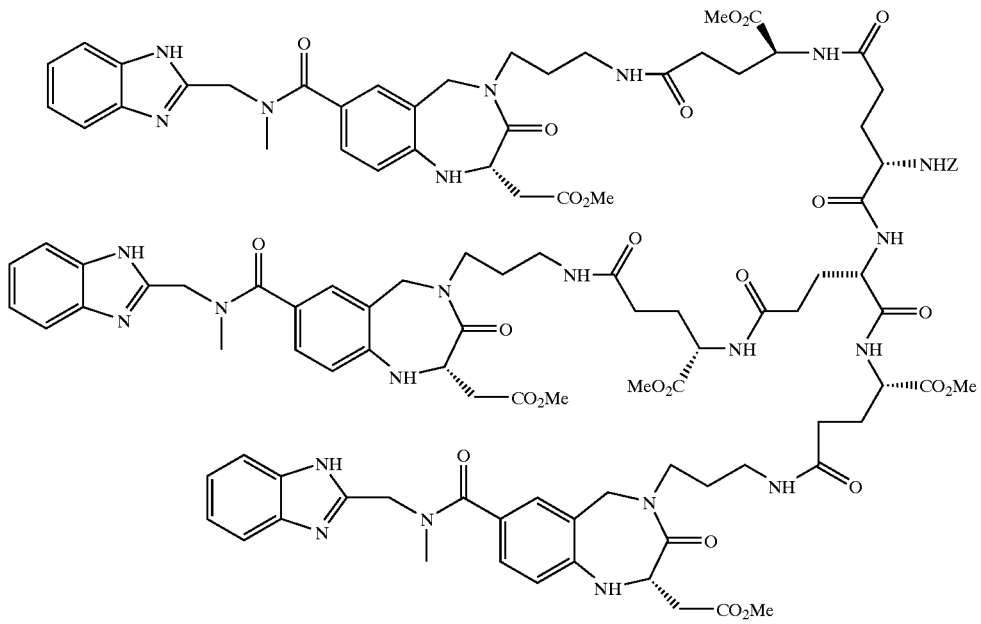

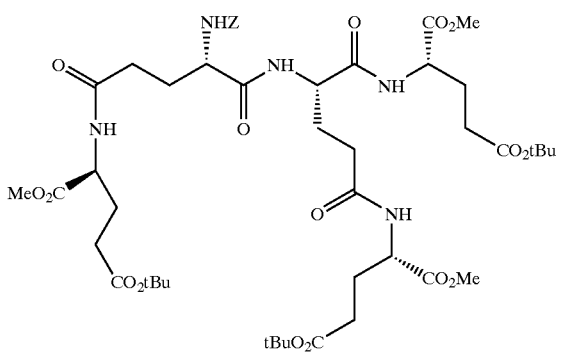

The product of 8a is dissolved in one volume of dichloromethane and treated with excess triethylsilane and one volume of trifluoroacetic acid. The reaction is stirred under nitrogen for three hours and then concentrated to an oil. The triacid residue is dissolved in dimethylformamide and treated with excess gamma-tert-butyl-alpha-methyl glutamate, HBTU, HOBT, and diisopropylethylamine with stirring under nitrogen for 4-5 hours. The reaction is concentrated, partitioned into water/ethyl acetate and extracted with more ethyl acetate. The combined organics are washed with water and brine and concentrated to an oil, which is purified by flash chromatography using dichloromethane/ethyl acetate/methanol.

Step 8C: Synthesis of methyl (S,S,S,S,S,S,S,S)-4-(N-(3-(3,6-diaza-10-(N-(benzimidazol-2-ylmethyl)-N-

The product of 8b is dissolved in one volume of dichloromethane and treated with excess triethylsilane and one volume of trifluoroacetic acid. The reaction is stirred under nitrogen for three hours and then concentrated to an oil.

A threefold excess of the product of step 1F is treated in the same fashion with trifluoroacetic acid and triethylsilane and concentrated to an oil. The two residues are dissolved in dimethylformamide, combined, and treated with HBTU, HOBT, and diisopropylethylamine with stirring under nitrogen, following disappearance of starting material by HPLC. When complete, the reaction is concentrated, partitioned into water/ethyl acetate and extracted with more ethyl acetate. The combined organics are washed with water and brine and concentrated to an oil, which is purified by preparative HPLC using a 0.1% trifluoroacetic acid/acetonitrile gradient to afford the product as a powder after lyophilization.

Step 8D: Synthesis of methyl (S,S,S,S,S,S,S,S)-2-(4-amino-4-(N-(1,3-bis(N-(3-(N-(3-(3,6-diaza-10-(N-(benzimidazol-2-ylmethyl)-N-methylcarbamoyl)-5-((methoxycarbonyl)methyl)-4-oxobicyclo[5.4.0]undeca-1(7),8,10-trien-3-yl)propyl)carbamoyl)-1-(methoxycarbonyl) propyl)carbamoyl)propyl)carbamoyl)butanoylamino)-4-(N-(3-(3,6-diaza-10-(N-(benzimidazol-2-ylmethyl)-N-methylcarbamoyl)-5-((methoxycarbonyl)methyl)-4-oxobicyclo[5.4.0]undeca-1(7),8,10-trien-3-yl)propyl) carbamoyl)butanoate

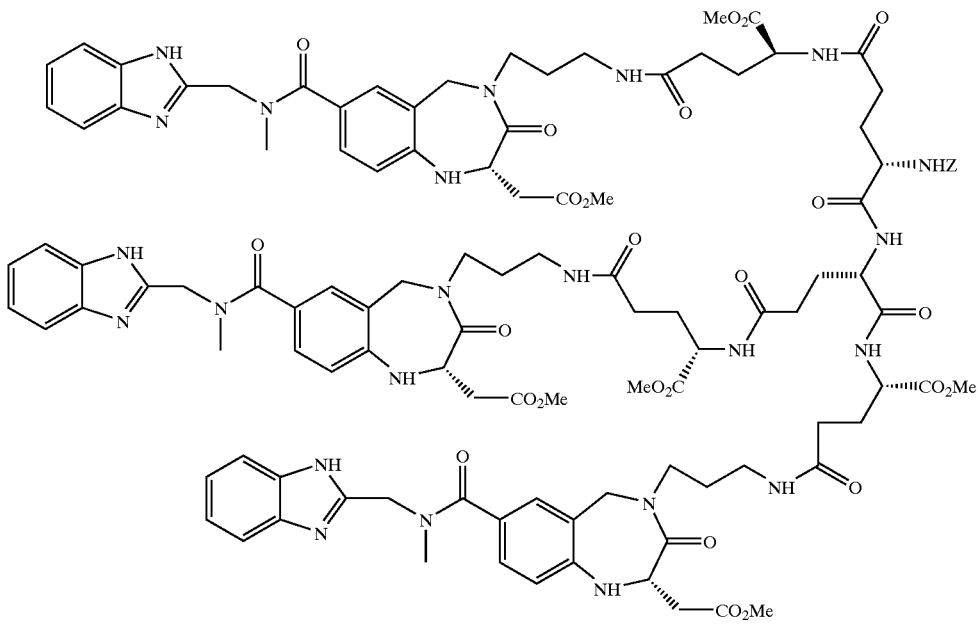

The product of step 8C is dissolved in methanol with 10% palladium on carbon and 2 equivalents of acetic acid in a Parr bottle. The mixture is hydrogenated at 55 psi in a Parr shaker, following by HPLC until all the starting material has been reacted. The reaction is filtered through Celite, concentrated, and the residual oil lyophilized from water/acetonitrile to yield the product as a powder, to be used directly in the next step.

Step 8E: Conjugation of 8D with 7I

Step 8F: Synthesis of (S,S,S,S,S,S,S,S,S,S)-2-(4-(N-(1,3-bis(N-(3-(N-(3-(3,6-diaza-10-(N-(benzimidazol-2-ylmethyl)-N-methylcarbamoyl)-5-((methoxycarbonyl)methyl)-4-oxobicyclo [5.4.0]undeca-1(7),8,10-trien-3-yl)propyl)carbamoyl)-1-(methoxycarbonyl)propyl)carbamoyl)propyl)carbamoyl)propyl) carbamoyl)-4-(2-(2-(1,4,7,10-tetraaza-4,7,10-tris(carboxymethyl) cyclodecyl)acetylamino)-4-carboxybutanoylamino)-4-

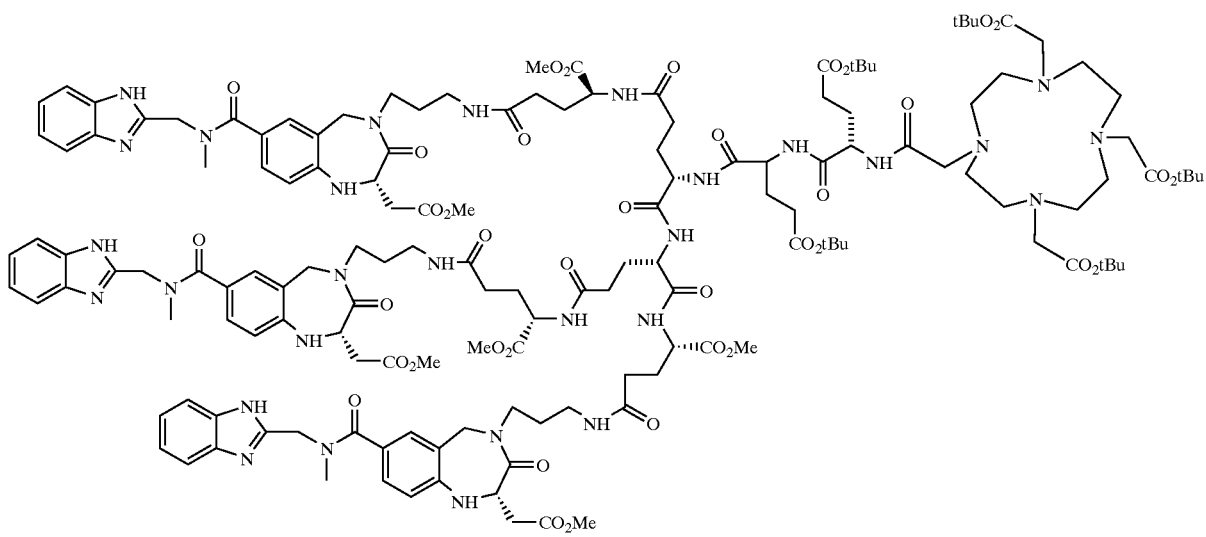

The product of step 8D is reacted with the product of step 7I as described in the alternate synthesis of 7E to afford the product as a solid after preparative HPLC purification and lyophilization.

carboxybutanoylamino)butanoylamino)-4-(N-(3-(3,6-diaza-10-(N-(benzimidazol-2-ylmethyl)-N-methyl carbamoyl)-5-((methoxycarbonyl)methyl)-4-oxobicyclo[5.4.0] undeca-1(7),8,10-trien-3-yl)propyl)carbamoyl)butanoic acid

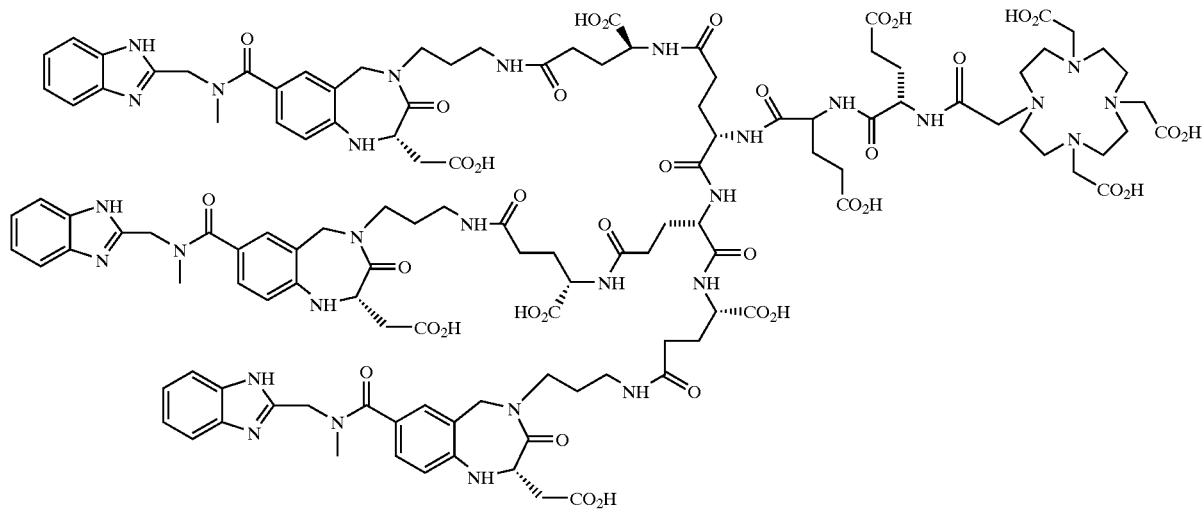

The product of step 8E is dissolved in 2:1 methanol/tetrahydrofuran and excess lithium hydroxide (3M solution) added. The solution is stirred, following by HPLC, until all the methyl esters have been hydrolyzed. The reaction is quenched with solid citric acid, concentrated, and redissolved in one volume of dichloromethane. The solids are filtered and the filtrate treated with excess triethylsilane and one volume of trifluoroacetic acid. The solution is stirred under nitrogen, following by HPLC, until all of the tert-butyl esters have been hydrolyzed. The reaction mixture is concentrated and directly purified by preparative HPLC using 0.1% formic acid/acetonitrile gradient on a Zorbax C-8 column to afford the product after lyophilization.

Example 9

Preparation of (S)-2-(2,5-diaza-5-(3-(2-(2-(3-((6-((1-aza-2-(2-sulfophenyl)vinyl)amino)(3-pyridyl))carbonylamino) propoxy)ethoxy)ethoxy)propyl)-9-(N-(benzimidazol-2-ylmethyl)-N-methylcarbamoyl)-4-oxobicyclo[5.4.0]undeca-1(7),8,10-trien-3-yl) acetic acid Step 9A: Synthesis of N-(3-(2-(2-(3-aminopropoxy) ethoxy) ethoxy)propyl)(tert-butoxy)formamide

A solution of at least three equivalents of 4,7,10-trioxa-1,13-tridecanediamine in tetrahydrofuran is cooled to 0° C., and a solution of one equivalent of di-tert-butyl dicarbonate in acetonitrile is added dropwise with stirring. The solution is stirred under nitrogen overnight and then concentrated. The residue is dissolved in ether and washed with five portions of saturated sodium chloride. The organic layer is dried over magnesium sulfate, filtered and concentrated to an oil, which is purified by flash chromatography to afford the monoamine.

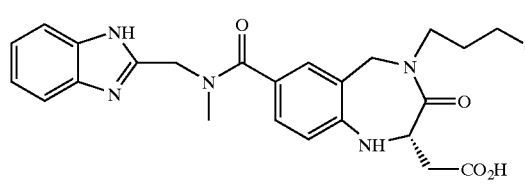 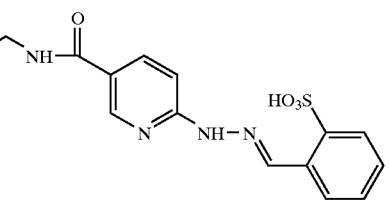

Step 9B: Synthesis of tert-butyl 3-(((3-(2-(2-(3-((tert-butoxy)carbonylamino)propoxy)ethoxy)ethoxy)propyl)amino)m ethyl)-4-fluorobenzoate

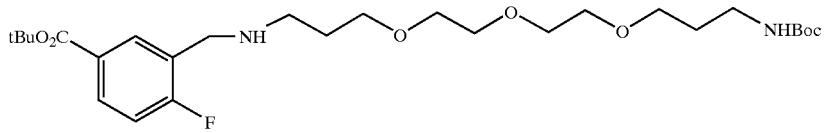

The product of step 9A is treated with crude tert-butyl-4-fluoro-3(alpha-bromomethyl)benzoate, as described in step 1A, to afford the product after flash chromatography.

Step 9C: Synthesis of methyl (S)-3-(N-(3-(2-(2-(3-((tert-butoxy)carbonyl amino)propoxy)ethoxy)ethoxy)propyl)-N-((5-((tert-butyl)oxy carbonyl)-2-fluorophenyl)methyl) carbamoyl)-3-((phenylmethoxy) carbonylamino)propanoate

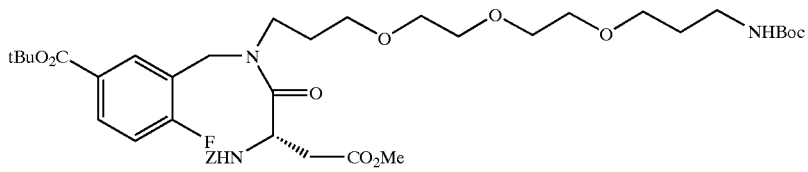

The product of step 9B is treated with Z-aspartic acid-β-methyl ester as described in step 1B, to afford the product after flash chromatography.

Step 9D: Synthesis of methyl (S)-3-amino-3-(N-(3-(2-(2-(3-((tert-butoxy)carbonylamino)propoxy)ethoxy)ethoxy) propyl)-N-((5-((tert-butyl)oxycarbonyl)-2-fluorophenyl) methyl)carbamoyl)propanoate

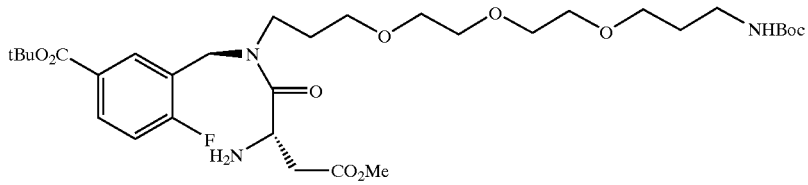

The product of step 9C is treated as in step 1C, and used directly in the following step.

Step 9E: Synthesis of methyl (S)-2-(2,5-diaza-9-((tert-butyl) oxycarbonyl-5-(3-(2-(2-(3-((tert-butoxy) carbonylamino) propoxy)ethoxy)ethoxy)propyl)-4-oxobicyclo[5.4.0]undeca-1(7),8,10-trien-3-yl)acetate

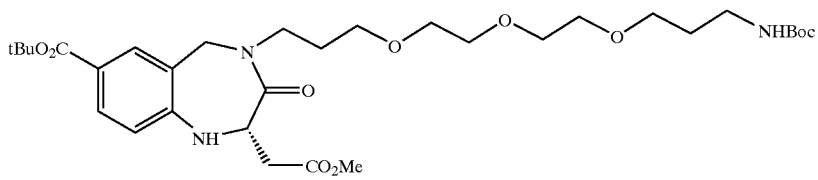

The product of step 9D is treated as in step 1D, to afford the product after flash chromatography.

Step 9F: Synthesis of (S)-2,5-diaza-5-(3-(2-(2-(3-((tert-butoxy)carbonylamino)propoxy)ethoxy)ethoxy)propyl)-3-((methoxycarbonyl)methyl)-4-oxobicyclo[5.4.0]undeca-1(7),8,10-trien-9-carboxylic acid

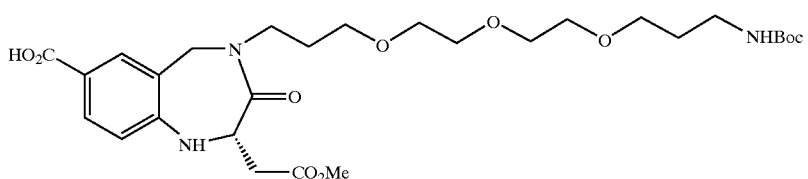

The product of step 9E is treated as in step 1E, to afford the product after flash chromatography.

Step 9G: Synthesis of methyl (S)-2-(2,5-diaza-9-(N-(benzimidazol-2-ylmethyl)-N-methylcarbamoyl)-5-(3-(2-(2-(3-((tert-butoxy) carbonylamino)propoxy)ethoxy) ethoxy)propyl)-4-oxobicyclo [5.4.0]undeca-1(7),8,10-trien-3-yl)acetate

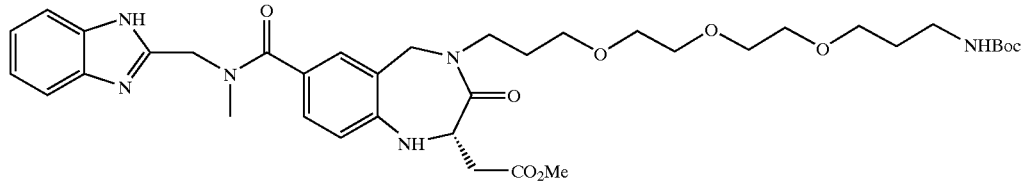

The product of step 9F is treated as in step 1F, to afford the product after flash chromatography.

Step 9H: Synthesis of (S)-2-(2,5-diaza-5-(3-(2-(2-(3-((6-((1-aza-2-(2-sulfophenyl)vinyl)amino)(3-pyridyl)) carbonylamino) propoxy)ethoxy)ethoxy)propyl)-9-(N-(benzimidazol-2-ylmethyl)-N-methylcarbamoyl)-4-oxobicyclo[5.4.0]undeca-1(7),8,10-trien-3-yl)acetic acid

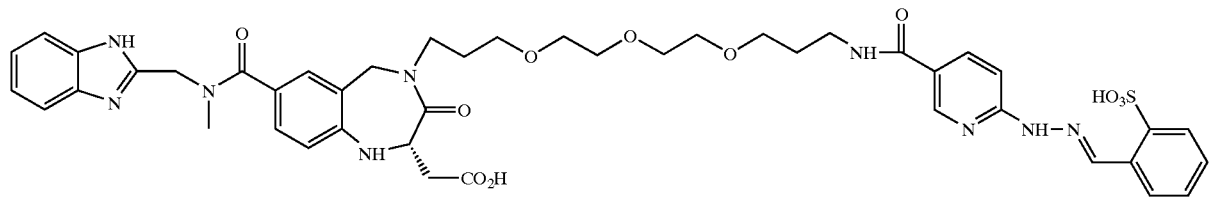

The product of step 9G is treated as in step 2G, and the isolated residue then directly treated as in step 2H to afford the product after preparative HPLC and lyophilization.

Example 10

Preparation of (S,S,S,S,S)-4-(N-(1,3-bis(N-(3-(2-(2-(3-(3,6-diaza-10-(N-(benzimidazol-2-ylmethyl)-N-methylcarbamoyl)-5-(carboxymethyl)-4-oxobicyclo [5.4.0]undeca-1(7),8,10-trien-3-yl)propoxy)ethoxy) ethoxy)propyl)carbamoyl) propyl)carbamoyl)-4-(5, 5-dihydroxy-2-(2-(1,4,7,10-tetraaza-4,7,10-tris (carboxy methyl)cyclododecyl)acetylamino) hexanoylamino)butanoic acid

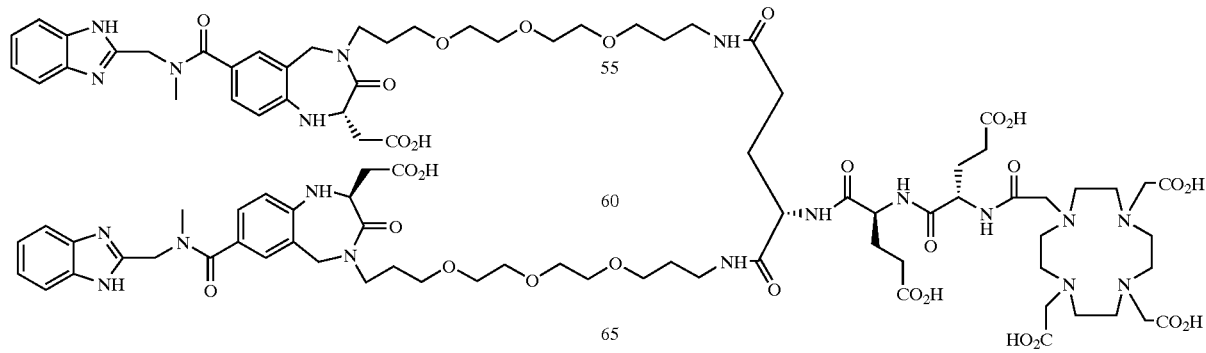

Step 10A: Synthesis of methyl (S)-2-(5-(3-(2-(2-(3-aminopropoxy)ethoxy)ethoxy)propyl)-2,5-diaza-9-(N-(benzimidazol-2-ylmethyl)-N-methylcarbamoyl)-4-oxobicyclo[5.4.0]undeca-1(7),8,10-trien-3-yl)acetate

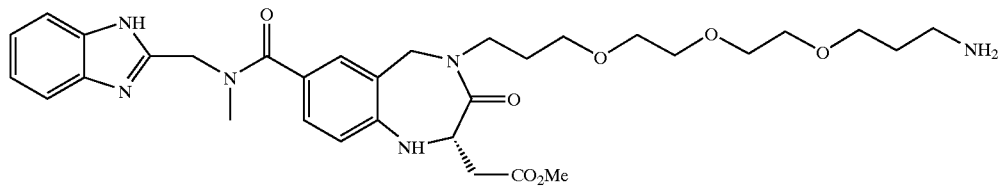

The product of step 9G is treated with trifluoroacetic acid and triethylsilane in dichloromethane for 30 minutes and the reaction then concentrated to an oil. Toluene is added and the solution reconcentrated to an oil, which is used directly in the next step.

Step 10B: Synthesis of (S,S,S,S,S)-4-(N-(1,3-bis(N-(3-(2-(2-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)propoxy)ethoxy)ethoxy)propyl)carbamoyl)propyl)carbamoy l)-4-(5,5-dihydroxy-2-(2-(1,4,7,10-tetraaza-4,7,10-tris(carboxy methyl)cyclododecyl)acetylamino)hexanoylamino)butanoic acid

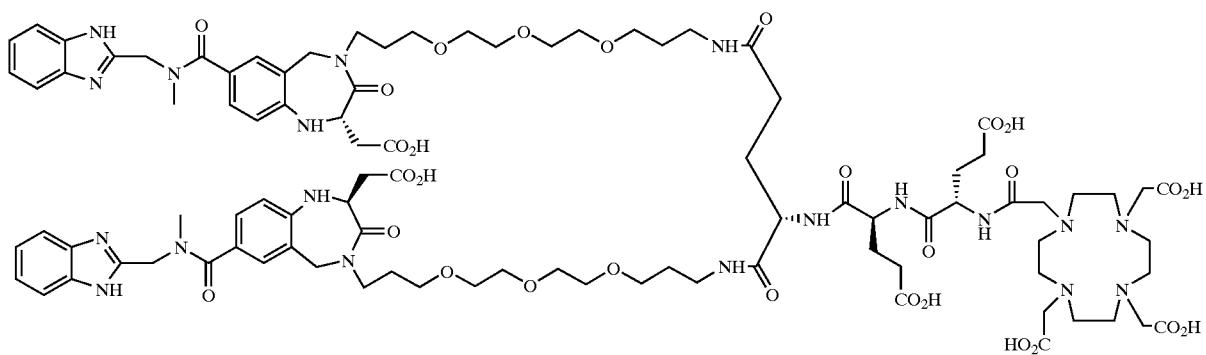

The product of step 10A is treated in several steps as defined in example 7, steps 7A-7F, substituting step 10A product for step 1I product as a starting material in step 7A. The product is obtained as a solid after preparative HPLC purification and lyophilization.

Example 11

Synthesis of (S,S,S)-2-(2,5-diaza-9-(N-(benzimidazol-2-ylmethyl)-N-methylcarbamoyl)-4-oxo-5-(6-(4-(N-((R,S,S,S)-2,3,4,5,6-pentahydroxyhexyl)carbamoyl)-2-(4-(N-((R,S,S,S)-2,3,4,5,6-pentahydroxy hexyl)carbamoyl)-2-(2-(1,4,7,10-tetraaza-4,7,10-tris(carboxymethyl)cyclodecyl)acetylamino)butanoylamino)butanoylamino)hexyl)bicyclo[5.4.0]undeca-1(7),8,10-trien-3-yl)acetic acid

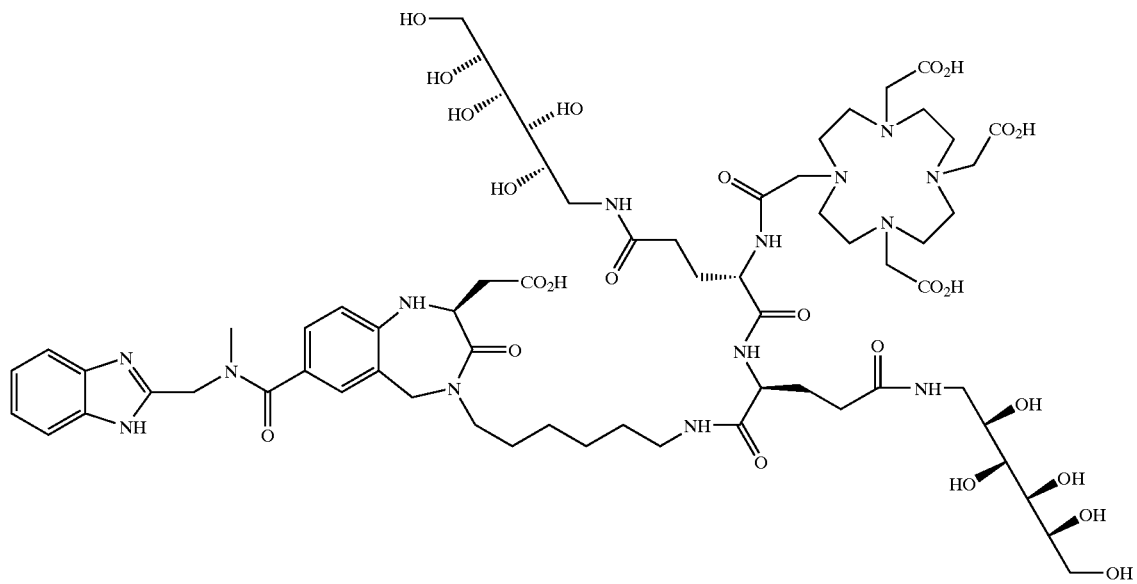

Step 11A: Synthesis of tert-butyl methyl (S,S)-2-(4-((tert-butyl)oxycarbonyl)-2-((phenylmethoxy)carbonylamino)butanoylamino)pentane-1,5-dioate

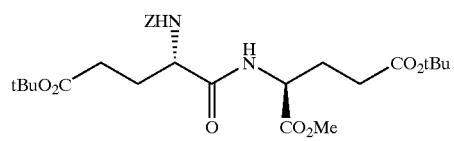

This process is carried out as in step 1G, except starting with alpha-methyl-gamma-tert-butylglutamate.

Step 11B: Synthesis of methyl (S,S)-4-(N-((R,S,S,S)-2,3,4,5,6-pentahydroxy hexyl)carbamoyl)-2-(4-(N-((R,S,S,S)-2,3,4,5,6-pentahydroxyhexyl)carbamoyl)-2-((phenylmethoxy)carbonylamino) butanoylamino)butanoate The product of step 11A is dissolved in dichloromethane, followed by addition of trifluoroacetic acid (to form a 35% solution). This is stirred under nitrogen until the starting material and monoacid have disappeared by HPLC, and then the solution is concentrated. The residue is dissolved in dimethylformamide along with 2.5 equivalents of 1-amino-1-deoxysorbitol, 2.5 equivalents of HBTU, 2 equivalents of hydroxybenzotriazole hydrate, and 3 equivalents diisopropylethylamine. The solution is stirred for two hours, concentrated, and the residue purified by preparative HPLC.

Step 11C: Synthesis of (S,S)-4-(N-((R,S,S,S)-2,3,4,5,6-pentahydroxyhexyl) carbamoyl)-2-(4-(N-((R,S,S,S)-2,3,4,5,6-pentahydroxyhexyl)carbamoyl)-2-((phenylmethoxy)carbonylamino) butanoylamino)butanoic acid

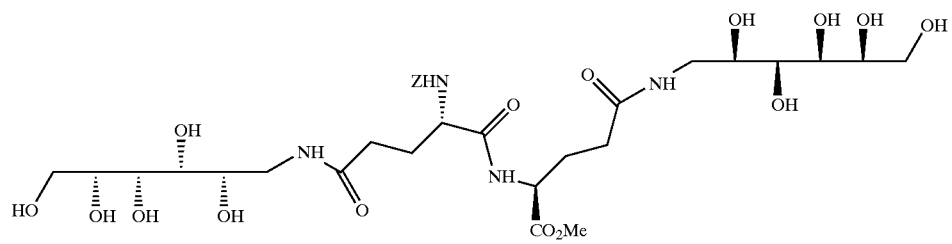

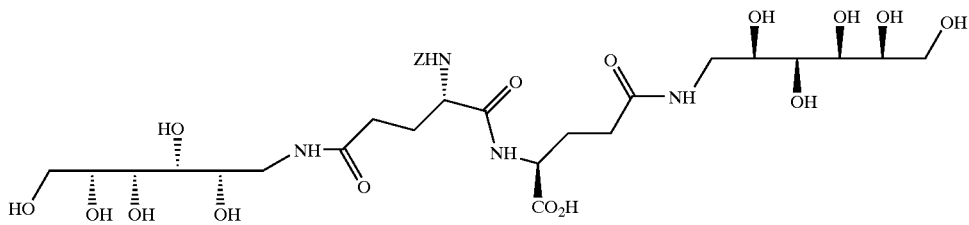

The product of step 11B is dissolved in tetrahydrofuran/methanol (1:1) and treated with excess 3N aqueous lithium hydroxide. The reaction is followed by HPLC for disappearance of starting material. The reaction is concentrated, diluted with additional water, and purified by passage down an acidic ion exchange column. The product fractions are lyophilized to afford the product as a solid.

Step 11D: Synthesis of methyl (S,S,S)-2-(2,5-diaza-9-(N-(benzimidazol-2-ylmethyl)-N-methylcarbamoyl)-4-oxo-5-(6-(4-(N-((R,S,S,S)-2,3,4,5,6-pentahydroxyhexyl)carbamoyl)-2-(4-(N-((R,S,S,S)-2,3,4,5,6-pentahydroxyhexyl)carbamoyl)-2-(phenylmethoxy)carbonylamino)butanoylamino)butanoylamino) hexyl)bicyclo[5.4.0]undeca-1(7),8,10-trien-3-yl)acetate The product of step 2G is dissolved in dichloromethane and stirred with trifluoroacetic acid and triethylsilane for 15 minutes. The solution is concentrated, and the residue dissolved in dimethylformamide with the product of step 11C, HBTU, hydroxybenzotriazole hydrate, and diisopropylethylamine. The reaction is stirred, following by HPLC for disappearance of starting materials. When complete, the solution is concentrated and the residue purified by preparative HPLC. The product solutions are lyophilized to afford the product.

Step 11E: Synthesis of methyl (S,S,S)-2-(5-(6-(2-(2-amino-4-(-N-((R,S,S,S)-2,3,4,5,6-pentahydroxyhexyl) carbamoyl) butanoylamino)-4-(N-((R,S,S,S)-2,3,4,5,6-pentahydroxyhexyl) carbamoyl)butanoylamino)hexyl)-2,5-diaza-9-(N-(benzimidazol-2-ylmethyl)-N-methylcarbamoyl)-4-oxo-bicyclo[5.4.0]undeca-1(7),8,10-trien-3-yl)acetate

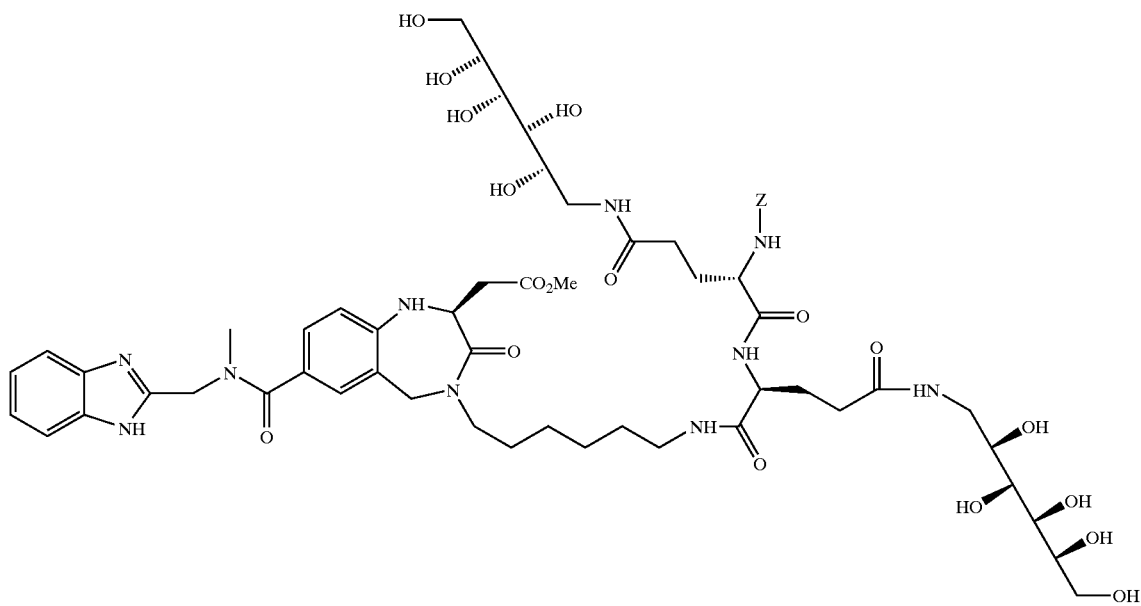

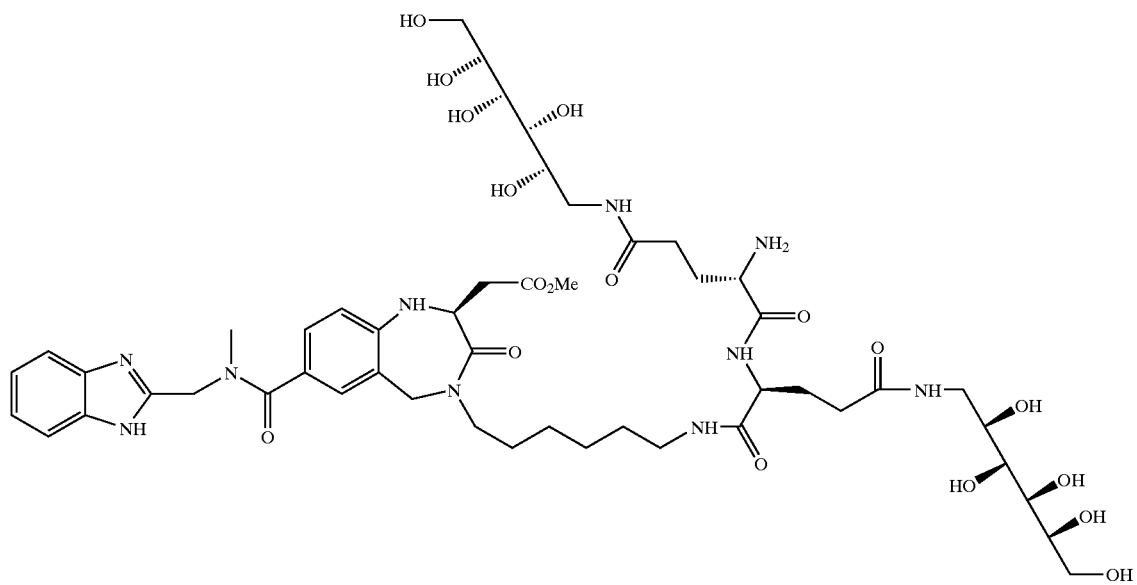

The product of step 11D is treated as in step 1I, to afford the amine after concentration.

Step 11F: Synthesis of (S,S,S)-2-(2,5-diaza-9-(N-(benzimidazol-2-ylmethyl)-N-methylcarbamoyl)-4-oxo-5-(6-(4-(N-((R,S,S,S)-2,3,4,5,6-pentahydroxyhexyl)carbamoyl)-2-(4-(N-((R,S,S,S)-2,3,4,5,6-pentahydroxyhexyl)carbamoyl)-2-(2-(1,4,7,10-tetraaza-4,7,10-tris(((tert-butyl)oxycarbonyl)methyl)cyclododecyl)acetylamino)butanoylamino)butanoylamino)hexyl)bicyclo[5.4.0]undeca-1(7),8,10-trien-3-yl)acetic acid

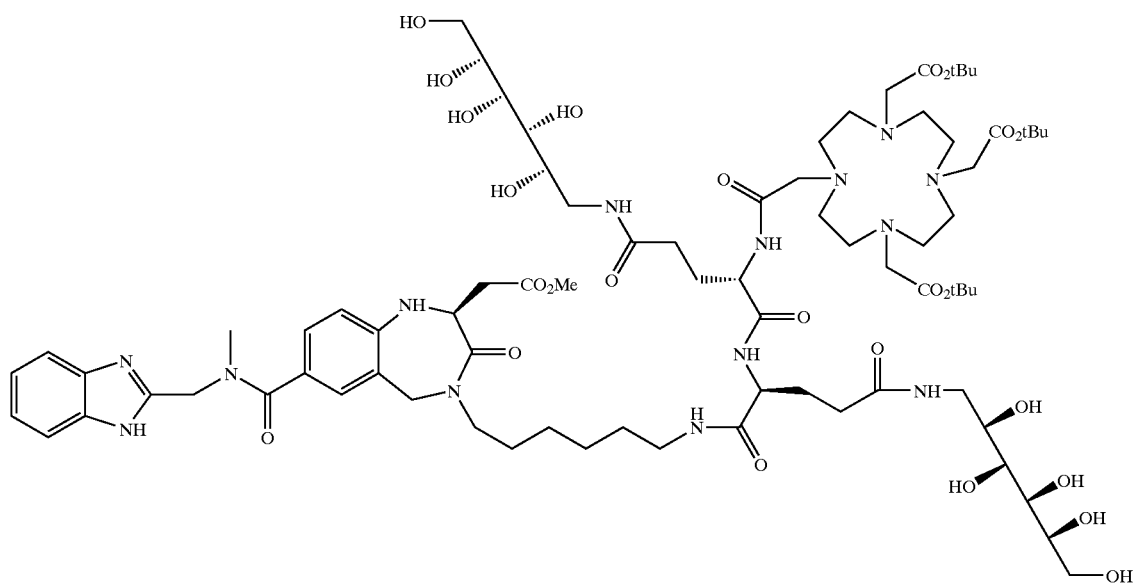

The product of step 11E is reacted as in step 1J to afford the product after preparative HPLC purification.

Step 11G: Synthesis of (S,S,S)-2-(2,5-diaza-9-(N-(benzimidazol-2-ylmethyl)-N-methylcarbamoyl)-4-oxo-5-(6-(4-(N-((R,S,S,S)-2,3,4,5,6-pentahydroxyhexyl) carbamoyl)-2-(4-(N-((R,S,S,S)-2,3,4,5,6-pentahydroxy hexyl)carbamoyl)-2-(2-(1,4,7,10-tetraaza-4,7,10-tris (carboxymethyl)cyclodecyl)acetylamino)butanoylamino) butanoylamino)hexyl)bicyclo[5.4.0]undeca-1(7),8,10-trien-3-yl)acetic acid

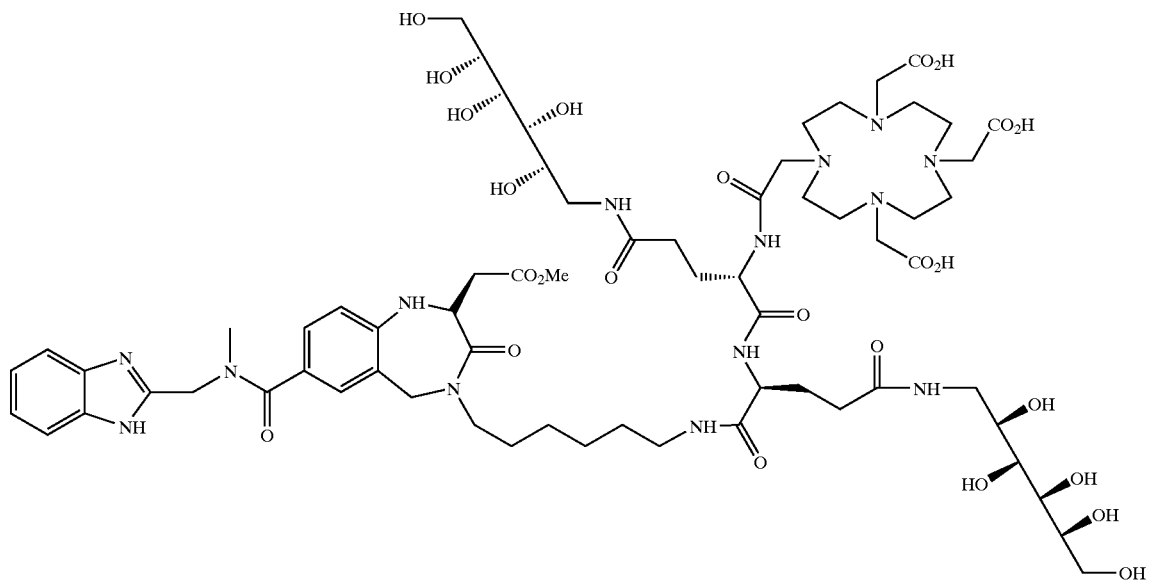

The product of step 11F is treated as in step 1K, to afford the product after preparative HPLC purification.

Example 12

Synthesis of (S,S,S,S)-2-(4-(N-(1-(N-(1-(N-(6-(3,6-diaza-10-(N-(benzimidazol-2-ylmethyl)-N-methylcarbamoyl)-5-(carboxymethyl)-4-oxobicyclo [5.4.0]undeca-1(7),8,10-trien-3-yl)hexyl) carbamoyl)-3-(N-cyclo{Lys-Arg(Mtr)-Gly-Asp (OtBu)-D-Phe}[gamma-LysNH] carbamoyl)propyl) carbamoyl)-3-carboxypropyl) carbamoyl)-4-(2-(1,4, 7,10-tetraaza-4,7,10-tris(carboxymethyl) cyclododecyl)acetylamino)butanoic acid

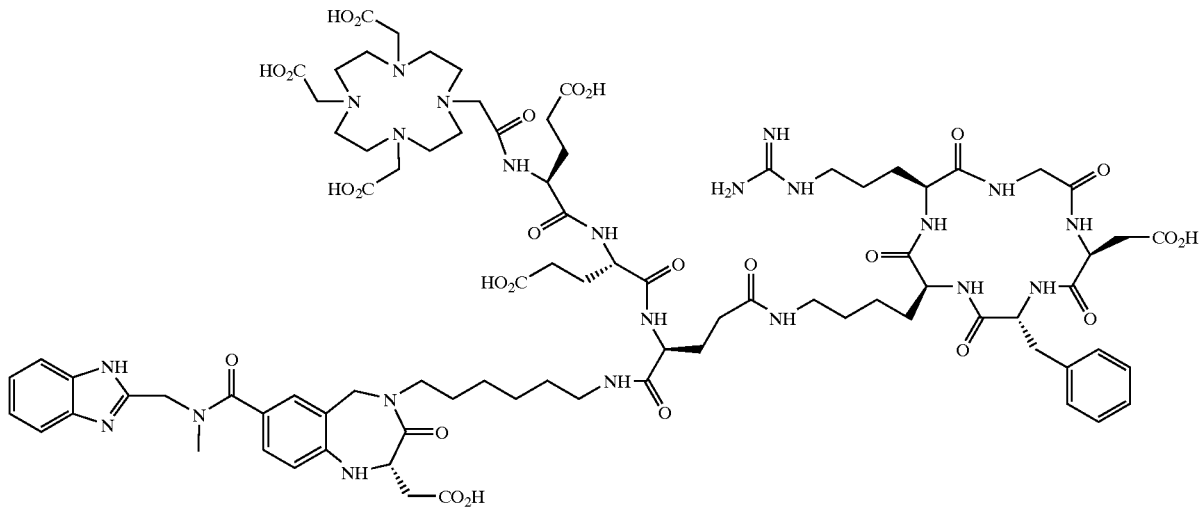

Step 12A: Synthesis of H-Asp(OtBu)-D-Phe-Lys(Cbz)-Arg(Mtr)-Gly-OH

This peptide is prepared using an Advanced Chemtech Model 90 synthesizer using standard Fmoc protocols. The starting resin is 4-[4-hydroxymethyl)-3-methoxy-phenoxy] butanoyl benzhydrylamine resin preloaded with Fmoc-glycine (Fmoc-Gly-HMPB-BHA). Synthesis of the protected linear peptide is achieved through sequential coupling (for 3 hrs) of the amino acids N-alpha-Fmoc-N$^9$-4-methoxy-2,3,6-trimethylbenzenesulfonyl-1-arginine, N-alpha-Fmoc-N-epsilon-benzyloxycarbonyl-L-lysine, Fmoc-phenylalanine, and Fmoc-gamma-tert-butyl aspartic acid, using HBTU and HOBT as coupling agents. The couplings are carried out with five equivalents of amino acid, HBTU, HOBT, and diisopropylethylamine in dimethylformamide. Fmoc deprotections are accomplished with 20% piperidine in DMF for 30 minutes. The protected linear peptide is cleaved from the resin with 1% trifluoroacetic acid in dichloromethane and the peptide solution collected in 10% pyridine in methanol. The crude peptide is obtained by concentrating the solvents in vacuo and triturating with diethyl ether. The peptide is purified by preparative HPLC and the product fractions are lyophilized.

Step 12B: Synthesis of cyclo{Lys(Cbz)-Arg(Mtr)-Gly-Asp(OtBu)-D-Phe}

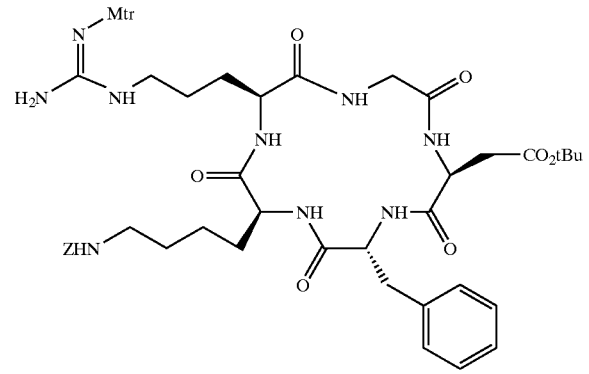

ethyl acetate and dried under vacuum to afford the product, which is used directly in the next step.

Step 12C: Synthesis of cyclo{Lys-Arg(Mtr)-Gly-Asp(OtBu)-D-Phe}

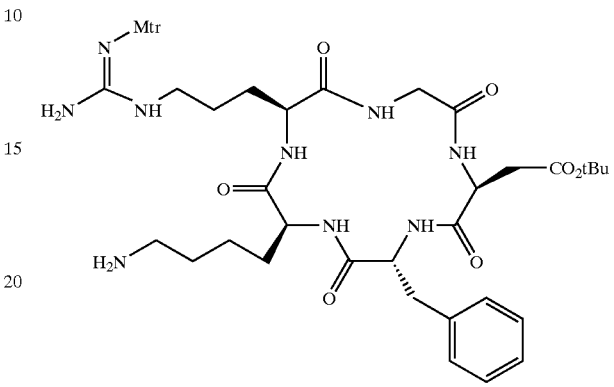

The product of step 12 B is dissolved in 2-propanol and 10% palladium on carbon added with stirring. Hydrogen gas is gently bubbled into the reaction mixture until all of the starting material is consumed by HPLC analysis. The reaction mixture is filtered through a bed of Celite and the filtrate concentrated. The residue is not further purified but used directly in the following step.

Step 12D: Synthesis of tert-butyl (S,S)-4-(N-(6-(3,6-diaza-10-(N-(benzimidazol-2-ylmethyl)-N-methylcarbamoyl)-5-((methoxycarbonyl)methyl)-4-oxobicyclo[5.4.0]undeca-1(7),8,10-trien-3-yl)hexyl)carbamoyl)-4-(((phenylmethoxy) carbonylamino)butanoate

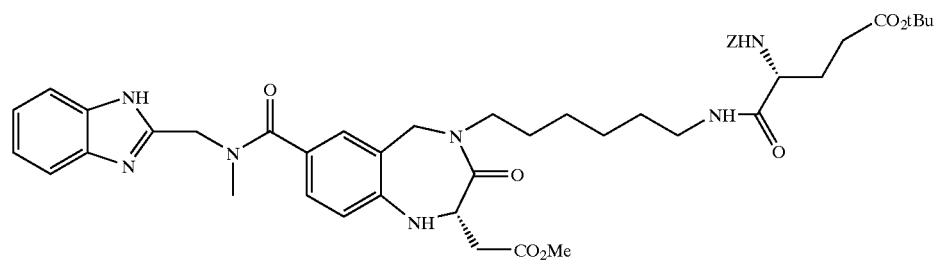

HBTU (0.7 mmol) and hydroxybenzotriazole (0.5 mmol) are dissolved in dimethylformamide (10 mL). The solution is warmed to 60° C. under nitrogen and a solution of the product of step 12 A (0.4 g) and diisopropylethylamine (1.5 mmol) in dimethylformamide (10 mL) added slowly. The solution is stirred at this temperature for 4 hours under nitrogen. The solution is concentrated and the residue triturated with ethyl acetate. The resulting solids are washed with The product of step 2F is dissolved in dichloromethane and trifluoroacetic acid added (30% solution). The reaction is stirred 30 minutes and concentrated. The residue is dissolved in dimethylformamide and N-carbobenzyloxy-gamma-tert-butyl-alpha-N-hydroxysuccinimidylglutamate added, along with excess diisopropylethylamine. The reaction is stirred for four hours and concentrated. The residue is purified by preparative HPLC and the fractions lyophilized to afford the product as a solid.

Step 12E: Synthesis of (S,S)-4-(N-(6-(3,6-diaza-10-(N-(benzimidazol-2-ylmethyl)-N-methylcarbamoyl)-5-((methoxycarbonyl)methyl)-4-oxobicyclo[5.4.0]undeca-1(7),8,10-trien-3-yl)hexyl)carbamoyl)-4-(((phenylmethoxy)carbonylamino) butanoyl-cyclo{Lys-Arg(Mtr)-Gly-Asp(OtBu)-D-Phe} conjugate

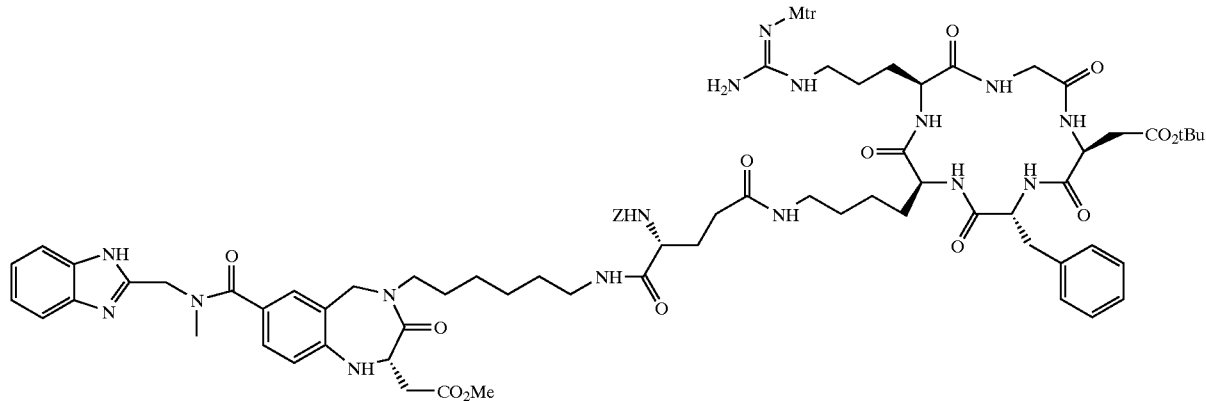

The product of step 12D is dissolved in one volume of dichloromethane, followed by one volume of trifluoroacetic acid and 5 equivalents of triethylsilane. The solution is stirred for four hours and concentrated. The residue is dissolved in dimethylformamide containing the product of step 12C, HBTU, and hydroxybenzotriazole hydrate. Diisopropylethylamine is added to this mixture with stirring under nitrogen, following by HPLC for disappearance of the starting materials. When complete, the reaction is concentrated and the residue purified by preparative HPLC. The product fractions are combined and lyophilized.

Step 12F: Synthesis of (S,S)-4-(N-(6-(3,6-diaza-10-(N-(benzimidazol-2-ylmethyl)-N-methylcarbamoyl)-5-((methoxycarbonyl)methyl)-4-oxobicyclo[5.4.0]undeca-1(7),8,10-trien-3-yl)hexyl)carbamoyl)-4-amino)butanoyl)-cyclo{Lys-Arg(Mtr)-Gly-Asp(OtBu)-D-Phe} conjugate The product of step 12E is treated as in step 8D. The product is not further purified, but used directly in the next step.

Step 12G: Synthesis of tert-butyl (S,S,S,S)-4-(N-(1-N-(1-(N-(6-(3,6-diaza-10-(N-(benzimidazol-2-ylmethyl)-N-methylcarbamoyl)-4-oxobicyclo[5.4.0]undeca-1(7),8,10-trien-3-yl)hexyl)carbamoyl)-3-(N-cyclo{Lys-Arg(Mtr)-Gly-Asp(OtBu)-D-Phe}carbamoyl)propyl) carbamoyl-3-((tert-butyl)oxycarbonyl)propyl)carbamoyl)-4-(2-(1,4,7,10-tetraaza-4,7,10-tris(((tert-butyl)oxycarbonyl) methyl) cyclcododecyl)acetylamino)butanoate

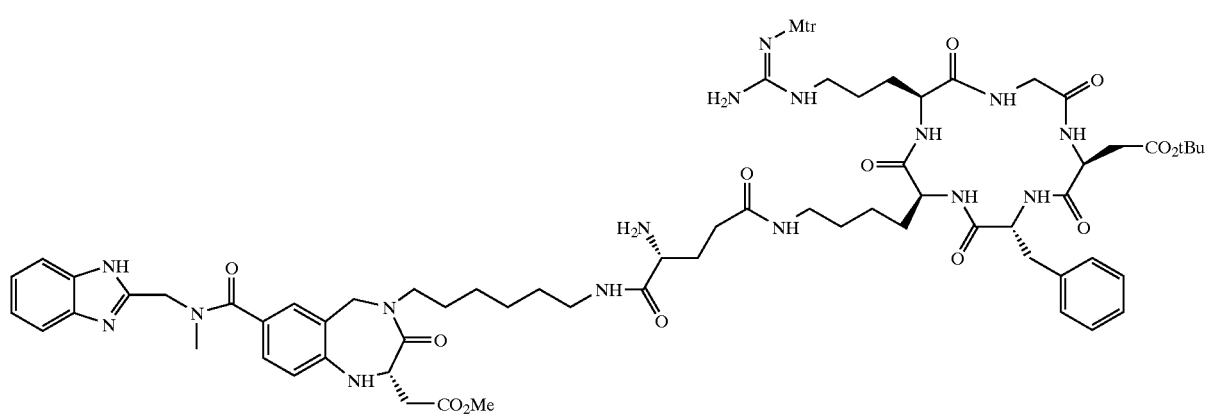

The product of step 12F is treated as in step 8E to afford the product after preparative HPLC purification.

Step 12H: Synthesis of (S,S,S,S)-2-(4-(N-(1-(N-(1-(N-(6-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)hexyl)carbamoyl)-3-(N-cyclo{Lys-Arg(Mtr)-Gly-Asp(OtBu)-D-Phe}[gamma-LysNH] carbamoyl)propyl)carbamoyl)-3-carboxypropyl)carbamoyl)-4-(2-(1,4,7,10-tetraaza-4,7,10-tris (carboxymethyl)cyclcododecyl) acetylamino)butanoic acid The product of step 12G is dissolved in tetrahydrofuran and excess lithium hydroxide added as a 3N solution in water. The solution is stirred under nitrogen, following by HPLC for disappearance of starting material. When this is complete, the reaction is acidified with 10% potassium hydrogen sulfate and concentrated. The residue is dissolved in neat trifluoroacetic acid containing thioanisole and stirred at room temperature under nitrogen, following the multiple deprotections by HPLC, until complete. The reaction is concentrated and the crude residue purified by preparative HPLC.

The following procedure describe the synthesis of radiopharmaceuticals of the present invention of the formula $^{99m}$Tc(VnA)(tricine)(phosphine), in which (VnA) represents a vitronectin receptor antagonist compound of the present invention bonded to the Tc through a diazenido (—N=N—) or hydrazido (=N—NH—) moiety. The diazenido or hydrazido moiety results from the reaction of the hydrazinonicotinamido group, present either as the free hydrazine or protected as a hydrazone, with the Tc-99m. The other two ligands in the Tc coordination sphere are tricine and a phosphine.

Examples 13–14

Synthesis of Complexes [$^{99m}$Tc (HYNIC-VnA) (tricine) (TPPTS)]

To a lyophilized vial containing 4.84 mg TPPTS, 6.3 mg tricine, 40 mg mannitol, succinic acid buffer, pH 4.8, and 0.1% Pluronic F-64 surfactant, was added 1.1 mL sterile water for injection, 0.2 mL (20 µg) of the appropriate HYNIC-conjugated vitronectin antagonist (VnA) in deionized water or 50% aqueous ethanol, and 0.2 mL of $^{99m}$TcO$_4^-$ (50±5 mCi) in saline. The reconstituted kit was heated in a 100° C. water bath for 15 minutes, and was allowed to cool 10 minutes at room temperature. A sample of the reaction mixture was analyzed by HPLC. The RCP results are listed in the table 1.

TABLE 1

Analytical and Yield Data for
$^{99m}$Tc (VnA) (tricine) (TPPTS) Complexes

| Example No. | Reagent No. | Ret. Time (min) | % Yield |
|---|---|---|---|
| 13 | 2 | 8.9* | 86 |
| 14 | 3 | 22.5** | 46 |

*The HPLC method using a reverse phase $C_{18}$ Zorbax column (4.6 mm × 25 cm, 80 Å pore size) at a flow rate of 1.0 mL/min with a gradient mobile phase from 100% A (25 mM pH 8.0 phosphate buffer) to 20% B (acetonitrile) at 20 min.
**The HPLC method using a reverse phase $C_{18}$ Zorbax column (4.6 mm × 25 cm, 80 Å pore size) at a flow rate of 1.0 mL/min with a gradient mobile phase from 100% A (10 mM pH 6.0 phosphate buffer) to 25% B (acetonitrile) at 40 min.

Examples 15–22

Synthesis of $^{177}$Lu and $^{90}$Y Complexes

To a clean sealed 10 mL vial was added 0.5 mL of a solution of the appropriate conjugate (200 μg/mL in 0.25 M ammonium acetate buffer, pH 7.0), followed by 0.05–0.1 mL of gentisic acid (sodium salt, 10 mg/mL in 0.25 M ammonium acetate buffer, pH 7.0) solution, 0.3 mL of 0.25 M ammonium acetate buffer (pH 7.0), and 0.05 mL of $^{177}$LuCl$_3$ solution (~200 mCi/mL) or $^{90}$YCl$_3$ solution (100–200 mCi/mL) in 0.05 N HCl. The resulting mixture was heated at 100° C. for 35 min. After cooling to room temperature, a sample of the resulting solution was analyzed by radio-HPLC and ITLC. For $^{90}$Y complexes, the sample has to be diluted 15–20 fold before the radio-HPLC analysis. The ITLC method used GS silica-gel paper strips and a 1:1 mixture of acetone and saline as eluant. The analytical and yield data are shown in Table 2.

TABLE 2

Analytical and Yield Data for Lu-177 and Y-90 Complexes

| Example No. | Reagent Ex. No. | Isotope | Ret. Time (min) | % RCP |
|---|---|---|---|---|
| 15 | 1 | $^{177}$Lu | 14.3 | 94 |
| 16 | 1 | $^{90}$Y | 14.0 | 92 |
| 17 | 1 | $^{149}$Pm | 14.0 | 94 |
| 18 | 5 | $^{177}$Lu | 14.1 | 94 |
| 19 | 5 | $^{90}$Y | 14.7 | 93 |
| 20 | 5 | $^{149}$Pm | 15.0 | 94 |
| 21 | 6 | $^{177}$Lu | 17.1 | 94 |
| 22 | 6 | $^{90}$Y | 17.4 | 84 |

HPLC Method

Column: Zorbax C18 , 25 cm×4.6 mm
Flow rate: 1.0 mL/min
Solvent A: 25 mM sodium phosphate buffer, pH 6.0
Solvent B: 100% CH$_3$CN
Gradient I

| t (min) | 0 | 20 | 21 | 30 | 31 | 40 |
|---|---|---|---|---|---|---|
| % Solvent B | 0 | 20 | 60 | 60 | 0 | 0 |

The identity of the Lu-177 complexes of Examples 15, 18, and 21 were further confirmed by LC-MS. The MS data are shown in Table 3.

TABLE 3

Mass Spec. Data for Lu-177 Complexes

| Example No. | Formula | Atomic Weight | M + H⁺ |
|---|---|---|---|
| 15 | $C_{50}H_{65}LuN_{12}O_{17}$ | 1280.4 | 1282.0 |
| 18 | $C_{52}H_{67}LuN_{12}O_{17}$ | 1306.4 | 1307.3 |
| 21 | $C_{46}H_{58}LuN_{11}O_{17}$ | 1163.4 | 1164.2 |

Example 23

Synthesis of the $^{111}$In Complex of the Conjugate of Example 1

To a lead shielded and closed autosampler vial was added 65 μg of the conjugate of Example 1 and 1.5 mg gentisic acid, sodium salt dissolved in 65 μL ammonium acetate buffer (0.4 M, pH 4.7) followed by the addition of 1.8 mCi, 15 μL In-111 in 0.05 N HCl (specific activity: 36 μg/mCi). The reaction mixture was heated at 70–80° C. for 60 min and analyzed by HPLC and ITLC. The radiolabeling yield was 91% and the retention time was 9.8 min.

HPLC Method

Column: Zorbax C18 , 25 cm×4.6 mm
Flow rate : 1.0 mL/min
Solvent A: 10 mM sodium phosphate buffer, pH 6.0
Solvent B : 100% CH$_3$CN Gradient I

| t (min) | 0 | 20 | 21 | 30 | 31 | 40 |
|---|---|---|---|---|---|---|
| % Solvent B | 5 | 20 | 60 | 60 | 5 | 5 |

The ITLC method used GS silica-gel paper strips and a 1:1 mixture of acetone and saline as eluant.

Examples 24–25

Synthesis of the $^{111}$In Complex of the Conjugates of Example 5 and 6

To a lead shielded and closed autosampler vial was added 100 μg of the appropriate conjugate of the present invention dissolved in 100 μL ammonium acetate buffer (0.2 M, pH 4.7) followed by 2.3 mCi, 25 μL In-111 in 0.05 N HCl. The solutions were heated at 100° C. for 30 min and analyzed by HPLC and ITLC. The radiolabeling yield for Example 24 was 76% and the retention time was 9.4 min. The radiolabeling yield for Example 25 was 87% and the retention time was 17.2 min.

The ITLC method used GS silica-gel paper strips and a 1:1 mixture of acetone and saline as eluant.

HPLC Method (Example 24)

Column: Zorbax C18 , 25 cm×4.6 mm
Flow rate: 1.0 mL/min
Solvent A: 10 mM sodium phosphate buffer, pH 6.0
Solvent B: 100% CH$_3$CN Gradient I

| t (min) | 0 | 20 | 21 | 30 | 31 | 40 |
|---|---|---|---|---|---|---|
| % Solvent B | 5 | 20 | 60 | 60 | 5 | 5 |

HPLC Method (Example 25)

Column: Zorbax C18, 25 cm×4.6 mm
Flow rate: 1.0 mL/min
Solvent A: 0.1% TFA in water
Solvent B : 100% CH$_3$CN Gradient I

| t (min) | 0 | 20 | 21 | 30 | 31 | 40 |
|---|---|---|---|---|---|---|
| % Solvent B | 5 | 20 | 60 | 60 | 5 | 5 |

Example 26

Preparation of sodium 1,2-dipalmitoyl-sn-glycero-3-phosphatidylethanolamine-(S)-2-(2,5-diaza-9-(N-(benzimidazol-2-ylmethyl)-N-methylcarbamoyl)-5-(6-aminohexyl)-4-oxobicyclo[5.4.0]undeca-1(7),8,10-trien-3-yl)acetic acid-dodecoanoate conjugate Step 26B: Preparation of contrast agent composition The product of step 13A is admixed with three other lipids, 1,2-dipalmitoyl-sn-glycero-3-phosphotidic acid, 1,2-dipalmitoyl-sn-glycero-3-phosphatidyl choline, and N-(methoxypolyethylene glycol 5000)carbamoyl)-1,2-dipalmitoyl-sn-glycero-3-phosphoethanolamine in relative amounts of 1 wt %:6 wt %:54 wt %:41 wt %. An aqueous solution of this lipid admixture (1 mg/mL), sodium chloride (7 mg/mL), glycerin (0.1 mg/mL), and propylene glycol (0.1 mL/mL) at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 seconds to form a milky white solution.

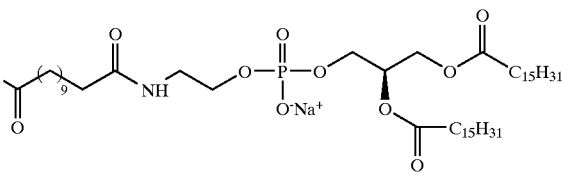

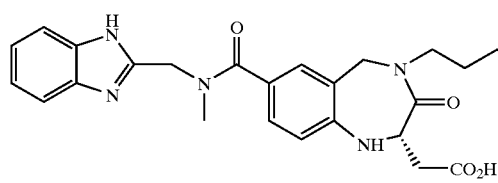

Step 26A: Synthesis of sodium 1,2-dipalmitoyl-sn-glycero-3-phosphatidylethanolamine-(S)-2-(2,5-diaza-9-(N-(benzimidazol-2-ylmethyl)-N-methylcarbamoyl)-5-(6-aminohexyl)-4-oxobicyclo[5.4.0]undeca-1(7),8,10-trien-3-yl)acetic acid-dodecoanoate conjugate Example 27

Preparation of DPPE-PEG$_{3400}$-[(S)-2-(2,5-diaza-9-(N-(benzimidazol-2-ylmethyl)-N-methylcarbamoyl)-5-(6-aminohexyl)-4-oxobicyclo[5.4.0]undeca-1(7),8,10-trien-3-yl)acetic acid]-dodecoanoate conjugate

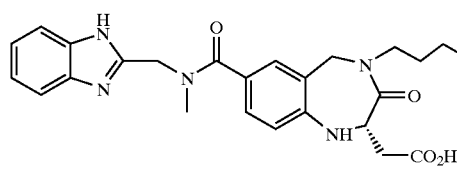

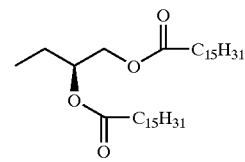

1,2-Dipalmitoyl-sn-glycero-3-phosphoethanolamine monosodium salt (DPPE) (1.25 g, 0.5 mmol) is dissolved under nitrogen in chloroform (15 mL) along with disuccinimidyl dodecanoate (0.212 g, 0.5 mmol and the product of step 4A (367 mg, 0.5 mmol). They are stirred for 5 minutes, when sodium carbonate (0.5 mmol) and sodium sulfate (0.5 mmol) is added. The reaction is stirred 18 hrs, filtered, and concentrated. The residue is purified to obtain the title compound.

Step 27A: Synthesis of ω-amino-PEG$_{3400}$-[(S)-2-(2,5-diaza-9-(N-(benzimidazol-2-ylmethyl)-N-methylcarbamoyl)-5-(6-aminohexyl)-4-oxobicyclo[5.4.0]undeca-1(7),8,10-trien-3-yl)acetic acid]

A solution of N-Boc-ω-amino-PEG$_{3400}$-succinimidyl ester (1 mmol) and the product of step 4A (1 mmol) in DMF (15 mL) is treated with diisopropylethylamine (3 mmol) and stirred under nitrogen for 18 hr. The solution is concentrated and the residue dissolved in dichloromethane (8 mL) to which trifluoroacetic acid (6 mL) is added. The solution is stirred for 30 minutes, and then concentrated under vacuum. The product is isolated by trituration with diethyl ether.

Step 27B: Synthesis of DPPE-PEG$_{3400}$-[(S)-2-(2,5-diaza-9-(N-(benzimidazol-2-ylmethyl)-N-methylcarbamoyl)-5-(6-aminohexyl)-4-oxobicyclo[5.4.0]undeca-1(7),8,10-trien-3-yl)acetic acid]-dodecoanoate conjugate A solution of disuccinimidyl dodecanoate (0.5 mmol), DPPE (0.5 mmol), and the product of step 14A (0.5 mmol) are added to 10 mL chloroform with stirring under nitrogen. Sodium carbonate (1 mmol) and sodium sulfate (1 mmol) are added and the solution is stirred at room temperature for 18 hrs. The reaction is filtered, the solvent concentrated, and the residue purified to obtain the title compound.

Step 27C: Preparation of contrast agent composition

The product of step 14B is admixed with three other lipids, 1,2-dipalmitoyl-sn-glycero-3-phosphotidic acid, 1,2-dipalmitoyl-sn-glycero-3-phosphatidyl choline, and N-(methoxypolyethylene glycol 5000)carbamoyl)-1,2-dipalmitoyl-sn-glycero-3-phosphoethanolamine in relative amounts of 1 wt %:6 wt %:54 wt %:41 wt %. An aqueous solution of this lipid admixture (1 mg/mL), sodium chloride (7 mg/mL), glycerin (0.1 mg/mL), and propylene glycol (0.1 mL/mL) at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 seconds to form a milky white solution.

Example 28

Preparation of [(S)-2-(2-aza-(2-((5-(N-(1,3-bis-N-(6-(aminohexyl-4-oxobicyclo[5.4.0]undeca-1(7),8,10-trien-3-yl)acetic acid)(2-(2,5-diaza-9-(N-(benzimidazol-2-ylmethyl)carbamoyl)propyl)carbamoyl]-□-amino-PEG$_{3400}$-dodecanoate-DPPE conjugate Step 28A: Synthesis of [(S)-2-(2-aza-(2-((5-(N-(1,3-bis-N-(6-(aminohexyl-4-oxobicyclo[5.4.0]undeca-1(7),8,10-trien-3-yl)acetic acid)(2-(2,5-diaza-9-(N-(benzimidazol-2-ylmethyl)carbamoyl)propyl)carbamoyl]-ω-amino-PEG$_{3400}$ The product of step 4B (1 mmol) was deprotected as described in step 4C and added to a solution of N-Boc-ω-amino-PEG$_{3400}$-succinimidyl ester (1 mmol) in DMF (15 mL). Diisopropylethylamine (3 mmol) is added and the solution stirred under nitrogen for 18 hr. The solution is concentrated and the residue dissolved in dichloromethane (8 mL) to which trifluoroacetic acid (6 mL) is added. The solution is stirred for 30 minutes, and then concentrated under vacuum. The product is isolated by trituration with diethyl ether.

Step 28B: Synthesis of DPPE-PEG$_{3400}$-[(S)-2-(2,5-diaza-9-(N-(benzimidazol-2-ylmethyl)carbamoyl)-N-methylcarbamoyl)-5-(6-aminohexyl)-4-oxobicyclo[5.4.0]undeca-1(7),8,10-trien-3-yl)acetic acid]-dodecoanoate conjugate A solution of disuccinimidyl dodecanoate (0.5 mmol), DPPE (0.5 mmol), and the product of step 15A (0.5 mmol) are added to 10 mL chloroform with stirring under nitrogen. Sodium carbonate (1 mmol) and sodium sulfate (1 mmol) are added and the solution is stirred at room temperature for 18 hrs. The reaction is filtered, the solvent concentrated, and the residue purified to obtain the title compound.

Step 28C: Preparation of contrast agent composition

The product of step 15B is admixed with three other lipids, 1,2-dipalmitoyl-sn-glycero-3-phosphotidic acid, 1,2-dipalmitoyl-sn-glycero-3-phosphatidyl choline, and N-(methoxypolyethylene glycol 5000)carbamoyl)-1,2-dipalmitoyl-sn-glycero-3-phosphoethanolamine in relative amounts of 1 wt %:6 wt %:54 wt %:41 wt %. An aqueous solution of this lipid admixture (1 mg/mL), sodium chloride (7 mg/mL), glycerin (0.1 mg/mL), and propylene glycol (0.1 mL/mL) at pH 6–7 is then prepared in a 2 cc glass vial. The air in the vial is evacuated and replaced with perfluoropropane and the vial is sealed. The ultrasound contrast agent composition is completed by agitating the sealed vial in a dental amalgamator for 30–45 seconds to form a milky white solution.

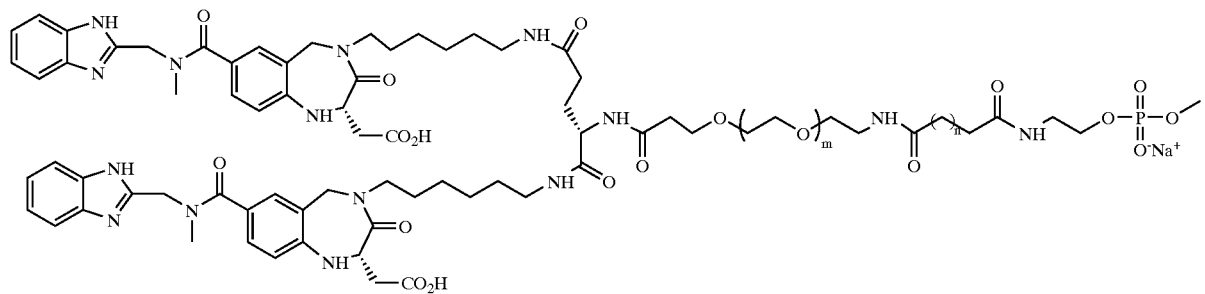

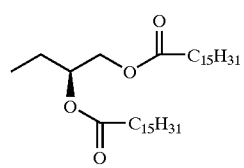

Example 29

Synthesis of 4-[N-(3-{(2R)-7-[N-(benzimidazol-2-ylmethyl)-N-methylcarbamoyl]-2-(carboxymethyl)-3-oxo(1H, 2H,5H-benzo[f]1,4-diazepin-4-yl)}propyl)carbamoyl] (4S)-4-[(4S)-4-(N-{(1S)-1-[N-(3-{(2S)-7-[N-(benzimidazol-2-ylmethyl)-N-methylcarbamoyl]-2-(carboxymethyl)-3-oxo (1H, 2H,5H-benzo[f]1,4-diazepin-4-yl)}propyl)carbamoyl]-3-carboxypropyl}carbamoyl)-4-{2-[1,4,7,10-tetraaza-4,7,10-tris(carboxymethyl)cyclododecyl]acetylamino}butanoylamino]butanoic acid luoroacetic acid (4 mL) and triethylsilane (160 uL) under nitrogen. The reaction was stirred for 25 minutes and concentrated under vacuum, treated with toluene (5 mL) and reconcentrated. The residue was dissolved in DMF (2 mL) and treated with tert-butyl 2,5-dioxopyrrolidinyl (2S)-2-[(phenylmethoxy)carbonyl-amino]pentane-1,5-dioate (85 mg, 0.19 mmol) and di;sopropylethylamine (135 uL, 0.775 mmol). The mixture was stirred under nitrogen for 1 hour and then partitioned into ethyl acetate/water (1:1, 100 mL). The layers were separated and the aqueous layer extracted with two more portions of ethyl acetate. The combined organic layer was washed with water and brine, dried over sodium sulfate, filtered, and concentrated to afford the product as a pale oil which solidified under vacuum (145

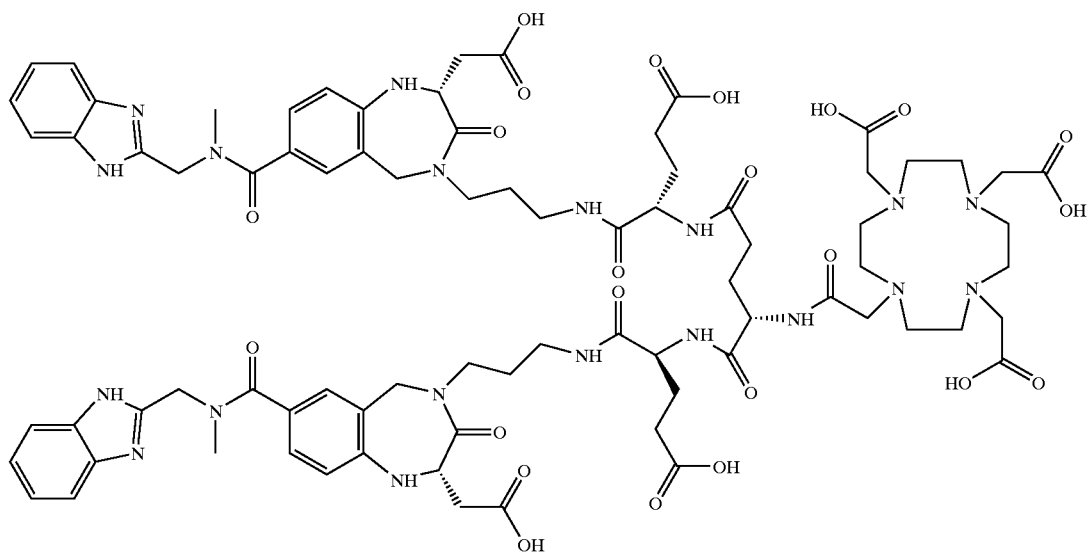

Step 29A: Synthesis of

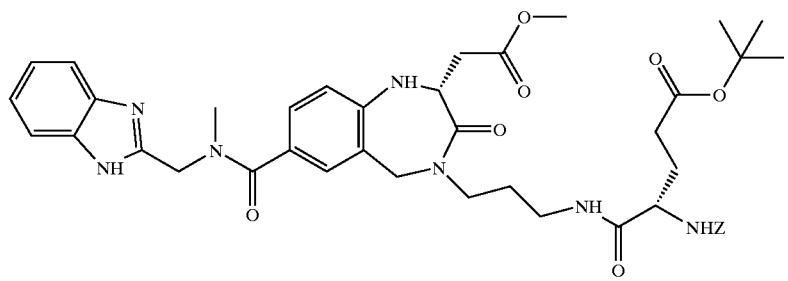

The product of step 1F (100 mg, 0.172 mmol) was dissolved in dichloromethane (4 mL) and treated with trifmg, 105%). This was used directly in the next step. LRMS (ES): 798.4 [M+H]$^+$, 100%

Step 29B: Synthesis of

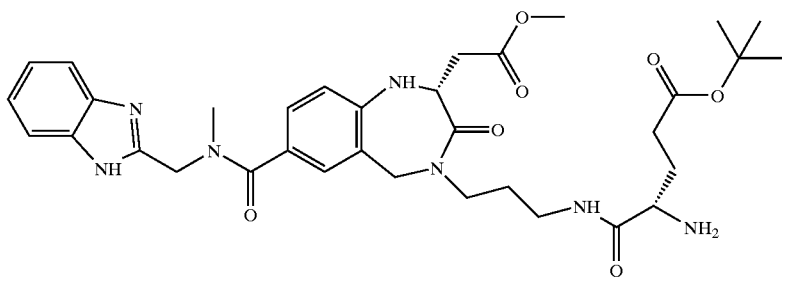

The product of step 29A is deprotected as in step 6B to afford an impure oil. This was purified by preparative HPLC (Vydac C18, 2.25×25 cm, 90% acetonitrile/water/0.1% TFA; 5–55% B over 25 minutes), the product fractions combined, frozen, and lyophilized to afford the product as the bis-TFA salt (100 mg, 97%). LRMS (ES): 664.4 ([M+H]+, 20%), 333.0 ([M+2H]+2, 100%).

Step 29C: Synthesis of bis-2,3,5,6-tetrafluorophenyl (2S)-2-[(tert-butoxy)carbonylamino]pentane-1,5-dioate

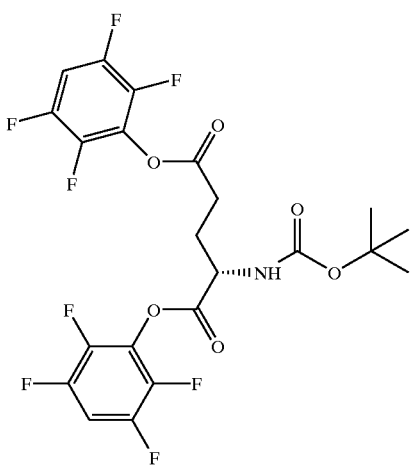

Boc-Glutamic acid (4.0 g, 16.2 mmol) was dissolved in DMF (60 mL) with 2,3,5,6-tetrafluorophenol (6.5 g, 39 mmol). To this was added (3-dimethylaminopropyl)ethyl carbodiimide hydrochloride (7.4 g, 39 mmol) and the solution was stirred 18 hr. The reaction was concentrated and the residue partitioned between ethyl acetate and water. The aqueous layer was extracted three times with ethyl acetate, and the combined organic layer was washed with 0.1N HCl, water, and brine. It was concentrated to a white solid which was washed with two portions of acetonitrile and dried under vacuum to afford the product as a white solid (6.2 g, 70%) with mp=123.5–124.5C. LRMS: 566.0 [M+Na]+. $^1$HNMR (600.1343 MHz, CDCl$_3$): 7.02 (m, 2H), 5.14 (m, 1H), 4.80 (m, 1H), 2.92 (m, 2H), 2.53 (m, 1H), 2.80 (m, 1H), 1.47 (s, 9H).

Step 29D: Synthesis of

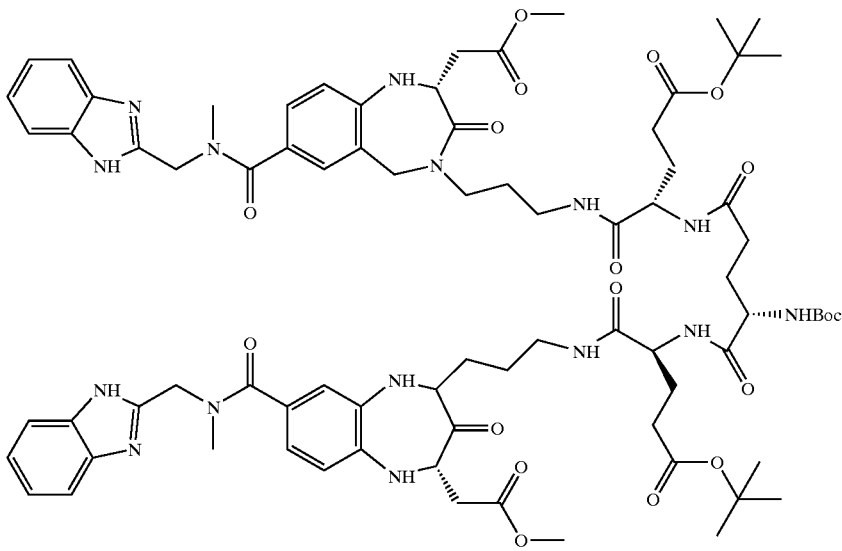

The product of step 29B (95 mg, 94 umol) was treated with the product of 29C (24.4 mg, 45 umol) and diisopropylethylamine (99 uL, 570 umol) in DMF and allowed to stir under nitrogen for 20 hr. The reaction was concentrated, water added and extracted three times with ethyl acetate. The combined organics were washed with 0.1N NaOH, water, and brine, dried over magnesium sulfate, filtered and concentrated to a white film (63 mg, 91%) which was not further purified but used directly in the next step. LRMS (ES): 1538.1 ([M+H]$^+$, 5%), 770.0 ([M+2H]$^{+2}$, 100%), 514.0 ([M+3H]$^{+3}$, 25%).

Step 29E: Synthesis of solution stirred for 1.5 hr. The reaction was concentrated and chased with toluene (2×5 mL). The residue was dissolved in THF/methanol (1:1, 3 mL) and treated with a 3N solution of lithium hydroxide in water (260 uL, 390 umol). After stirring for 12 hours, another aliquot of lithium hydroxide (130 uL) was added and stirring continued for five hours. The reaction was acidified with 0.1N HCl to pH=2 and concentrated. Purification by preparative HPLC (Vydac C18, 2.25×25 cm, 90% acetonitrile/water/0.1% TFA; 5–35% B over 50 minutes), combining product fractions, and lyophilizing afforded the product as a white solid (23 mg 45%). LRMS (ES): 1298.4 ([M+H]$^+$, 10%), 649.9 ([M+2H]$^{+2}$, 30%), 433.6 ([M+3H]$^{+3}$, 100%).

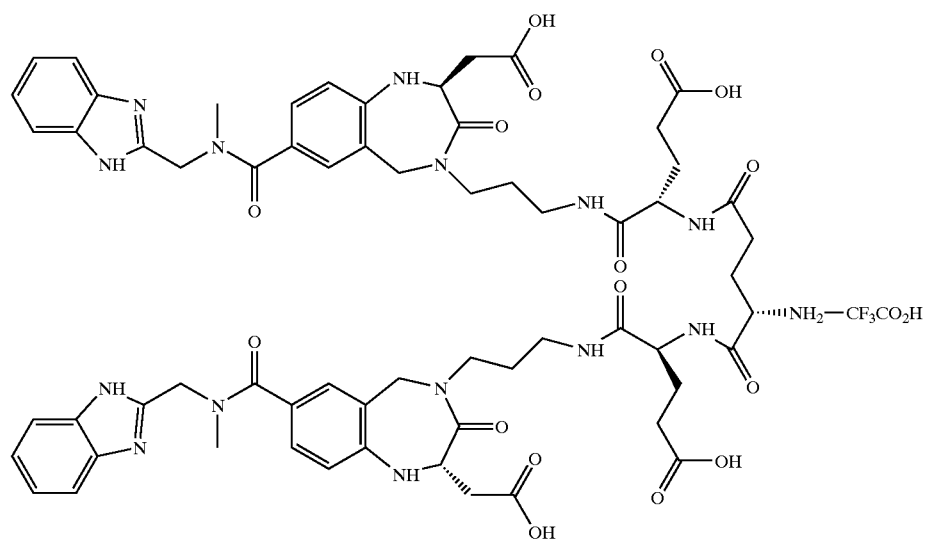

The product of step 29D (60 mg, 39 umol) was dissolved in dichloromethane (2.5 mL) under nitrogen. Trifluoroacetic acid (2.5 mL) and triethylsilane were added (100 uL) and the Step 29F: Synthesis of

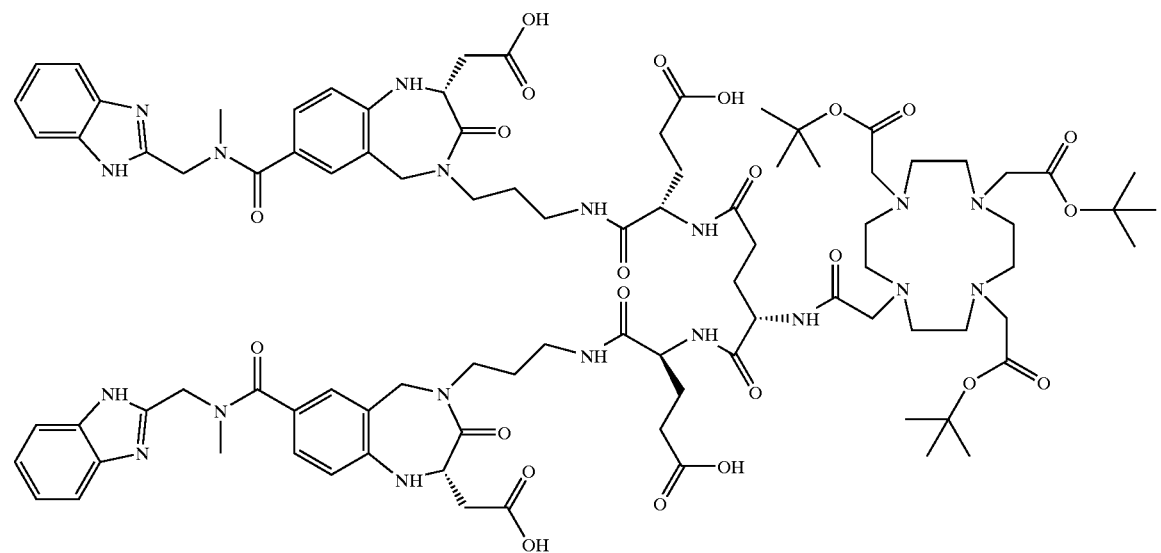

The product of step 29E (20 mg, 14.1 umol) was dissolved in dry DMF (0.5 mL) with diisopropylethylamine (15 μL, 85 umol) under nitrogen. In another flask under nitrogen, DOTA(OtBu)$_3$-OH (17 mg, 21 umol) was dissolved in DMF with diisopropylethylamine (15 uL, 85 umol) and HBTU (6.7 mg, 18 umol) and stirred 10 minutes. The activated DOTA solution is added in one portion to the amine and stirred for 30 minutes. The reaction was concentrated and purified by preparative HPLC (Vydac C18, 2.25×25 cm, 90% acetonitrile/water/0.1% TFA; 15–535% B over 50 minutes), combining product fractions, and lyophilizing afforded the product as a white solid (8 mg, 30%). LRMS (ES): 1853.0 [M+H]$^+$, Step 29G: Synthesis of The product of step 29F (7 mg) was dissolved in trifluoroacetic acid (2 mL) with triethylsilane (200 uL) under nitrogen and stirred for 30 minutes. The solution was concentrated and purified by prep HPLC (Vydac C18, 2.25× 25 cm, 50% acetonitrile/water/0.1% formic acid; 15–35% B over 50 minutes). The product fractions were combined and lyophilized to afford a white solid (2 mg). LRMS (ES): 1684.6 ( [M+H]$^+$, 5%), 843.0 ( [M+2H]$^{+2}$, 50%), 562.5 ([M+3H]$^{+3}$, 100%).

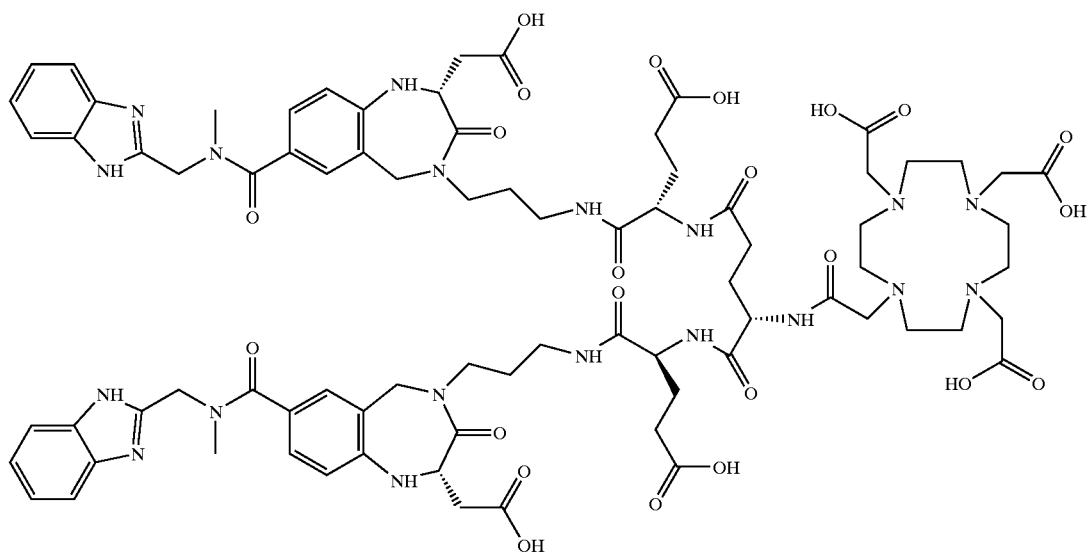

Example 30
Synthesis of 2-(4-{3-[(6-{[(1E)-1-aza-2-(2-sulfophenyl)vinyl]amino}(3-pyridyl) ) carbonylamino]propyl} (2S) -7-(N-[2-(amidinoamino)ethyl]-N-methylcarbamoyl}-3-oxo-1H,2H,5H-benzo[f]1,4-diazepin-2-yl)acetic acid

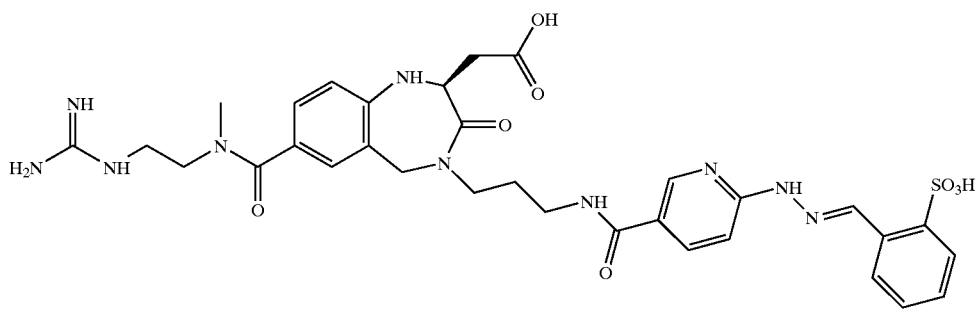

Step 30A: Synthesis of

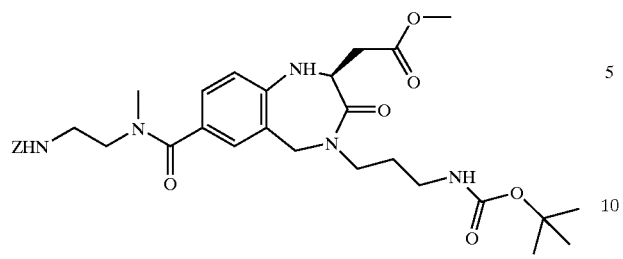

The product from step 1E (100 mg, 220 umol), N-[2-(methylamino)ethyl](phenylmethoxy)carboxamide hydrochloride (57 mg, 230 umol), (3-dimethylaminopropyl)ethyl carbodiimide hydrochloride (51 mg, 264 umol), and HOBT (31.2 mg, 230 umol) were dissolved in DMF (2.2 mL) under nitrogen and the solution was stirred 18 hr. The reaction was concentrated and the residue partitioned between ethyl acetate and water. The aqueous layer was extracted three times with ethyl acetate, and the combined organic layer was washed with 0.1N HCl, water, and brine. It was dried over sodium sulfate, filtered, and concentrated to a clear oil, which was purified by flash chromatography (2% methanol/ethyl acetate). Product fractions were combined and concentrated to yield the product as an oil (110 mg, 80%). LRMS (ES): 626.4 ([M+H]$^+$, 100%), 648.4 ([M+Na]$^+$, 100%) 1273.7 ([2M+Na]$^+$, 15%).

Step 30B: Synthesis of

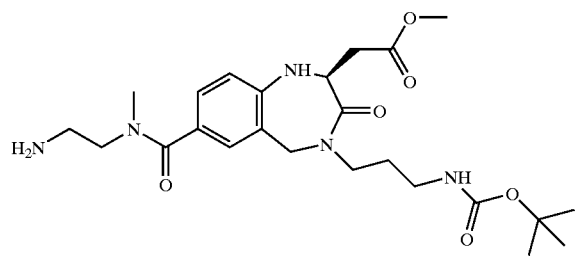

The product of Step 30A (110 mg) was treated as in step 1I to afford the product (98 mg, 100%) as a white solid. LRMS (ES): 492.4 ([M+H]$^+$, 100%), 514.4 ([M+Na]$^+$, 30%)

Step 30C: Synthesis of

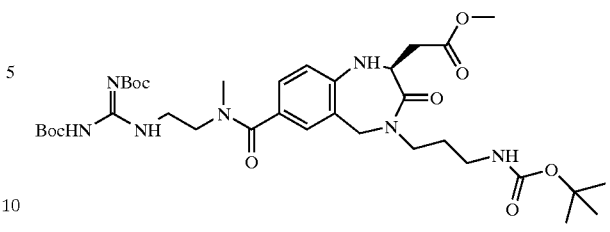

The product of step 30B (45 mg, 92 umol) was dissolved in DMF (0.6 mL) with diisopropylethylamine (33 uL, 185 umol), and tert-butyl-2-aza-3-[(tert-butoxy)carbonylamino]-3-methylthioprop-2-enoate (26.6 mg, 92 umol). Mercuric chloride (25 mg, 92 umol) was added and the reaction stirred 75 min. It was then diluted with ethyl acetate, filtered through Celite, and the solids rinsed. The combined filtrate was washed with water and brine, dried over sodium sulfate, filtered and concentrated to afford a crude oil, which was purified by prep HPLC (Vydac C18, 2.25×25 cm, 90% acetonitrile/water/0.1% TFA; 10–70% B over 30 minutes). The product fractions were combined and lyophilized to afford the product as a white solid (18 mg, 30%) which as a mixture of product and deprotected material, which was used directly in the next reaction. LRMS (ES): 734.4 [M+H]$^+$, 634.4 [M-Boc+H]$^+$.

Step 30D: Synthesis of

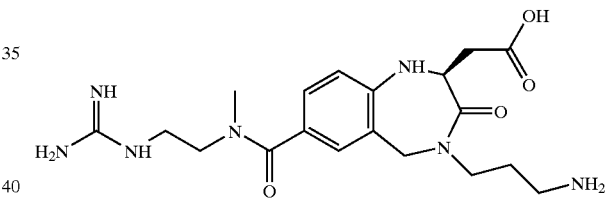

The product of step 30C (16 mg, 22 umol) was treated as in step 16E, and purified by prep HPLC (Vydac C18, 2.25×25 cm, 90% acetonitrile/water/0.1% TFA; 0–25% B over 30 minutes). The product fractions were combined and lyophilized to afford the product as a white solid (6 mg, 52%). LRMS (ES): 420.2 ([M+H]$^+$, 30%) 210.7 ([M+2H]$^{+2}$, 100%).

Step 30E: Synthesis of

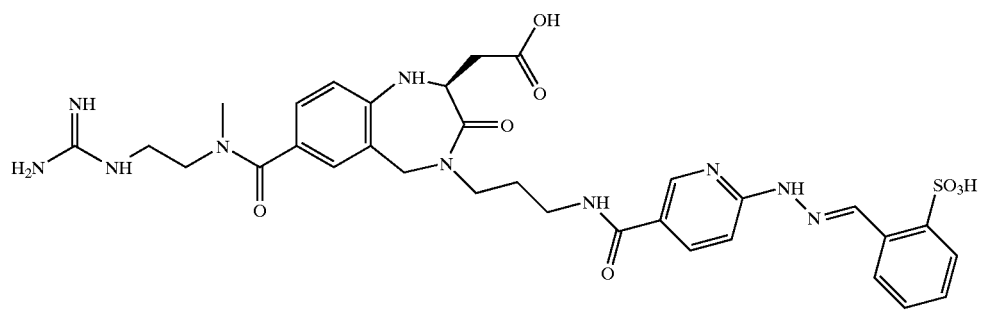

The product of step 30D is treated as in step 3E, purified by prep HPLC and lyophilized to afford the product.

Example 31

Synthesis of 2-[9-(N-{6-[(6-{[(1E)-1-aza-2-(2-sulfophenyl)vinyl]amino}(3-pyridyl))carbonylamino]hexyl}-N-(benzimidazol-2-ylmethyl)carbamoyl)(5S)-5,6,11-trihydro-dibenzo[b,e][7]annulen-5-yl]acetic acid

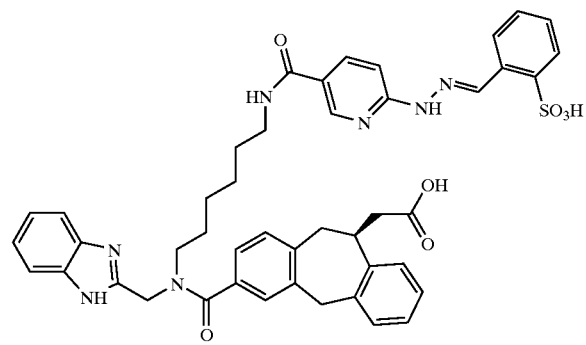

Step 31A: Synthesis of

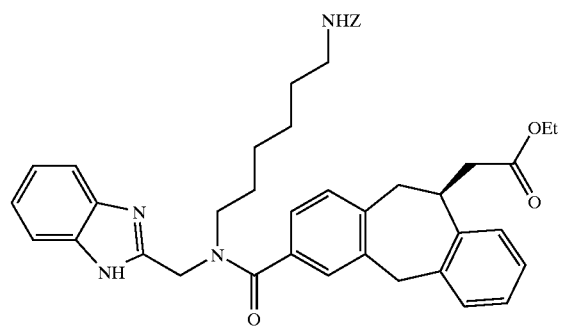

The product of step 3A (300 mg, 0.66 mmol) and 6-[(ethoxycarbonyl)methyl]-5,6,11-trihydrodibenzo [a,d][7] annulene-2-carboxylic acid (215 mg, 0.66 mmol, prepared according to W. H. Miller et al., Bioorg. Med. Chem. Lett., 9(1999) 1807–1812) are treated as in step 3B to yield the product after flash chromatography.

Step 31B: Synthesis of

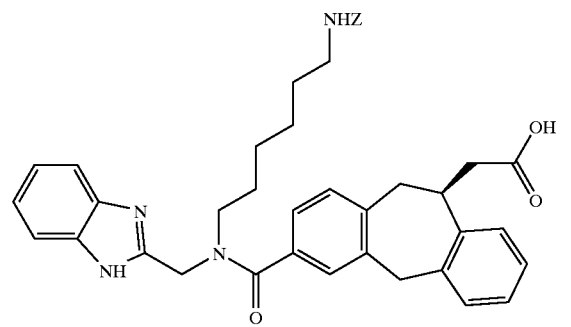

The product of step 31A (100 mg, 0.15 mmol) is dissolved THF (3 mL) with lithium hydroxide (3N solution in water, 0.5 mL, 1.5 mmol) and stirred, monitoring for disappearance of starting material by HPLC. When the reaction is complete, the solution is acidified to pH=2 with 0.1N HCl and the resulting solids are filtered and dried under vacuum to afford the product, which is used directly in the following step.

Step 31C: Synthesis of

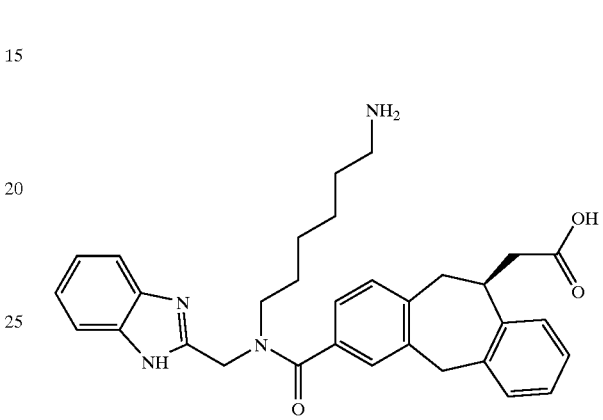

The product of step 31B is treated as in step 3C to afford the product as a solid after lyophilization.

Step 31D: Synthesis of

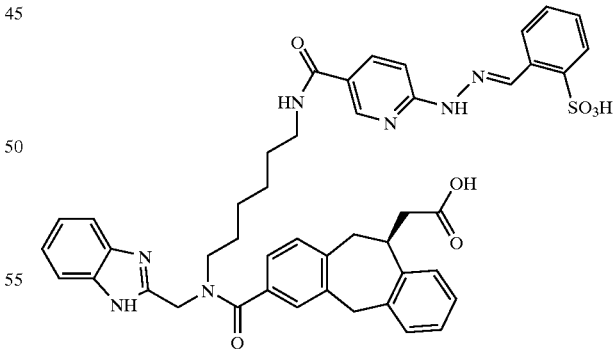

The product of step 31C is treated as in step 3E to afford the product as a yellow solid after prep HPLC purification and lyophilization.

Example 32

Synthesis of (2S)-2-[(2S)-4-(N-{(1S)-3-[N-(3-{(2S)-7-[N-(benzimidazol-2-ylmethyl)-N-methylcarbamoyl]-2-(carboxy methyl)-3-oxo(1H,2H,5H-benzo[f]1,4-diazepin-4-yl)}propyl)carbamoyl]-1-carboxypropyl}carbamoyl)-2-[(2S)-2-((2S)-4-carboxy-2-{2-[1,4,7,10-tetraaza-4,7,10-tris(carboxymethyl) cyclododecyl]acetylamino}butanoylamino)-4-carboxybutanoyl amino]butanoylamino]-4-[N-(3-{(2S)-7-[N-(benzimidazol-2-ylmethyl)-N-methylcarbamoyl]-2-(carboxymethyl)-3-oxo (1H,2H,5H-benzo[f]1,4-diazepin-4-yl)}propyl)carbamoyl] butanoic acid Cbz-glutamic acid (1 g, 3.56 mmol) was dissolved in DMF (20 mL) along with H-Glu(OtBu)OMe-HCl (1.9 g, 7.5 mmol), HBTU (3.4 g, 8.9 mmol), HOBT (1.01 g, 7.5 mmol), and diisopropylethylamine (2.2 mL, 12.5 mmol) under nitrogen. The reaction was stirred for 18 hours, concentrated, and partitioned between water and ethyl acetate. The solids were filtered and the filtrate layers separated. The aqueous layer was extracted with ethyl acetate and the combined organic layers washed with 10% sodium carbonate, water, 10% potassium hydrogen sulfate, water, and brine. The solution was dried over sodium sulfate, filtered, and concentrated to afford a golden oil which was purified by flash chromatog-

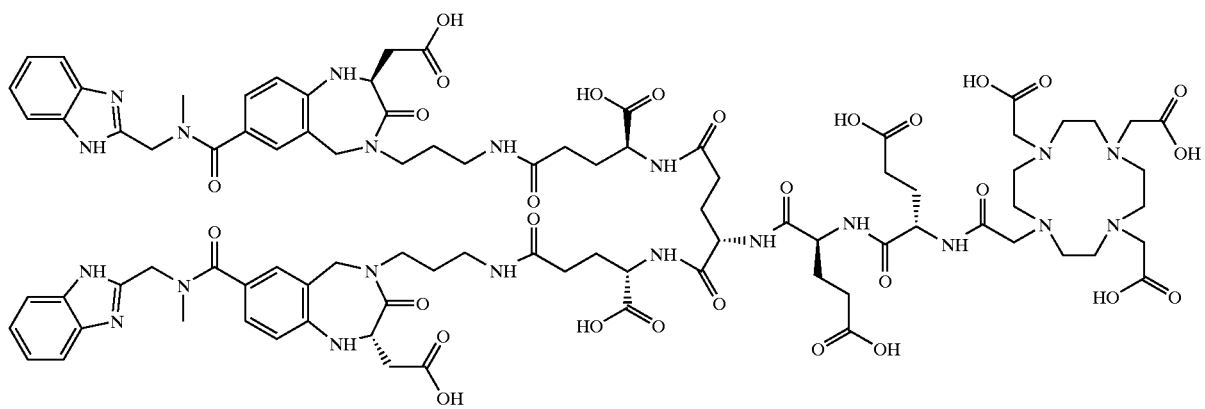

Step 32A: Synthesis of tert-butyl methyl (2S)-2-[(2S)-4-(N-{(1S)-3-[(tert-butyl)oxycarbonyl]-1-(methoxycarbonyl)propyl} carbamoyl)-2-[(phenylmethoxy)carbonylamino] butanoylamino] pentane-1,5-dioate

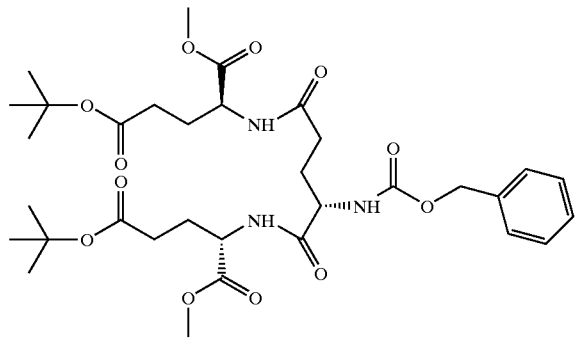

raphy (4:1 dichloromethane/ethyl acetate). The product fractions were combined and concentrated to afford the product as a clear oil (1.3 g, 54%) which solidified under vacuum. LRMS (ES): 680.5 ([M+H]$^+$, 100%), 702.5 ([M+Na]$^+$, 20%)

Step 32B: Synthesis of methyl (2S)-2-[(2S)-4-(N-{(1S)-3-[N-(3-{(2S)-7-[N-(benzimidazol-2-ylmethyl)-N-methylcarbamoyl]-2-[(methoxycarbonyl)methyl]-3-oxo(1H,2H,5H-benzo[f]1,4-diazepin-4-yl)}propyl)carbamoyl]-1-(methoxycarbonyl)propyl} carbamoyl)-2-[(phenylmethoxy)carbonylamino]butanoylamino]-4-[N-(3-{(2S)-7-[N-(benzimidazol-2-ylmethyl)-N-methyl carbamoyl]-2-[(methoxycarbonyl)methyl]-3-oxo(1H,2H,5H-benzo [f]1,4-diazepin-4-yl)}propyl)carbamoyl] butanoate

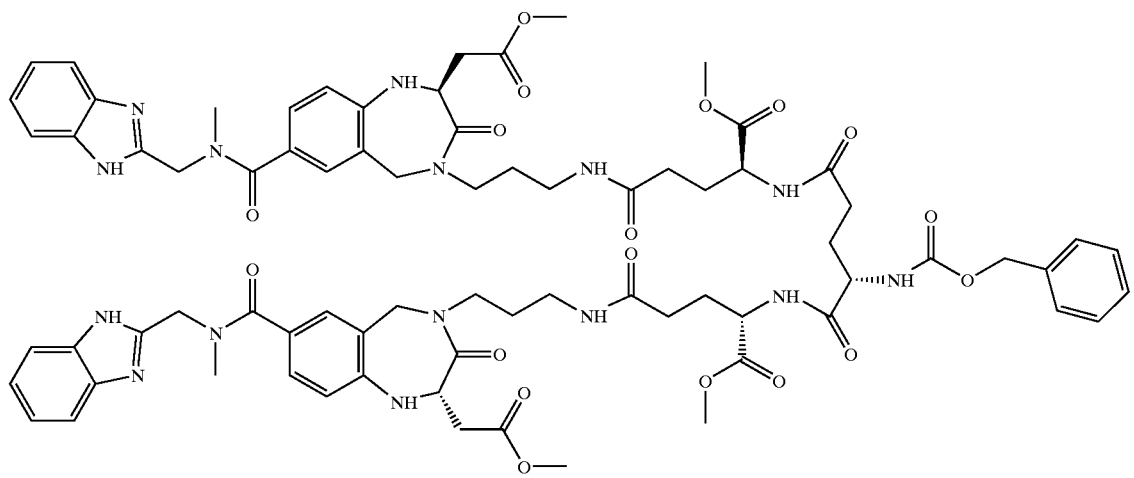

The product of step 1F (104 mg, 180 umol) was dissolved in dichloromethane (2 mL) and trifluoroacetic acid (1 mL) added with stirring under nitrogen. The solution was stirred for 1 hour, concentrated under vacuum, and reconcentrated methyl]-3-oxo(1H,2H,5H-benzo[f]1,4-diazepin-4-yl)}propyl)carbamoyl]-1-(methoxycarbonyl)propyl}carbamoyl)propyl]carbamoyl}-3-[(tert-butyl)oxycarbonyl]propyl)carbamoyl]-4-[(phenylmethoxy)carbonylamino]butanoate

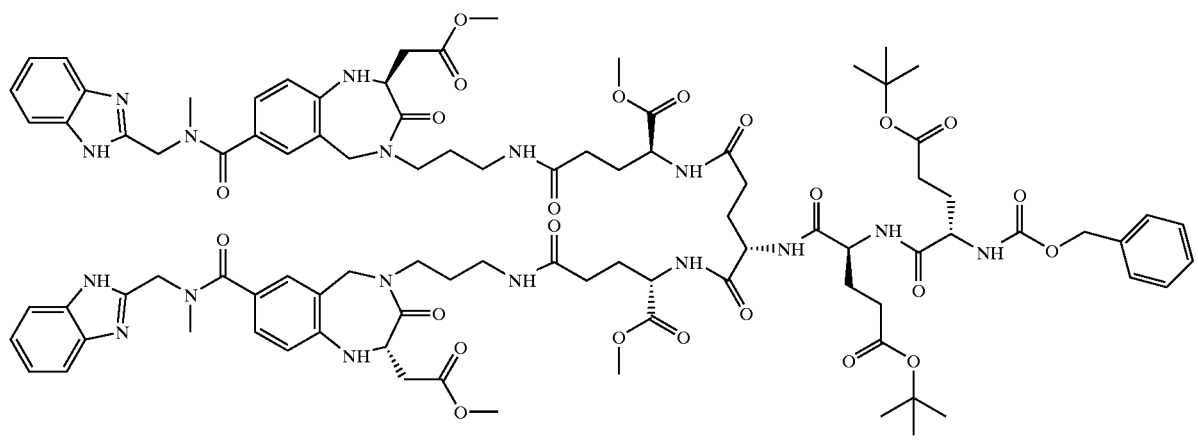

twice with toluene to afford the benzodiazepine amine as an oil which was used directly below.

The product of step 32A (43 mg, 63 umol) was dissolved in dichloromethane (0.5 mL) and trifluoroacetic acid (0.9 mL) added with stirring under nitrogen. The solution was stirred for 2 hours, concentrated under vacuum, and reconcentrated twice with toluene to afford the dicarboxylic acid as an oil which was used directly below.

Both of these products were dissolved in DMF (1.5 mL) under nitrogen, and HBTU (60 mg, 150 umol), HOBT (20 mg, 140 umol), and diisopropylethylamine (180 uL, 1.1 mmol) added. The solution was stirred for 18 hours, concentrated, and the residue purified by preparative HPLC (Vydac C18, 2.12×25 cm, 90% acetonitrile/water/0.1% TFA; 10–55% B over 25 minutes). The product fractions were combined and lyophilized to afford the product as a white solid (84 mg, 69%). LRMS (ES): 1488.7 ([M+H]$^+$, 10%), 745.1 ([M+2H]$^{+2}$, 100%), 497.3 ([M+3H]$^{+3}$, 100%)

Step 32C: Synthesis of tert-butyl (4S)-4-[N-((1S)-1-{N-[(1S)-1,3-bis(N-{(1S)-3-[N-(3-{(2S)-7-[N-(benzimidazol-2-ylmethyl)-N-methylcarbamoyl]-2-[(methoxycarbonyl)

The product of step 32B (70 mg, 47 umol) was dissolved in methanol (5 mL) and added to 10% palladium on carbon (40 mg) suspended in methanol (5 mL) under nitrogen in a pressure bottle. The slurry was hydrogenated at 55 psi on a Parr apparatus for two hours, additional catalyst (35 mg) added, and repressurized. The hydrogenation was continued for an additional 3 hours, at which time the reaction was filtered through Celite, rinsed with methanol, and the combined filtrate concentrated to a clear oil (49 mg). This was dissolved in dry DMF (1.5 mL), along with the product of step 1G (22 mg, 42 umol), HBTU (18 mg, 46 umol), HOBT (6.5 mg, 42 umol), and diisopropylethylamine (9 uL, 52 umol) in a flame-dried flask under nitrogen. The reaction was stirred for 5.5 hours, concentrated, and the residue purified by preparative HPLC (Vydac C18, 2.12×25 cm, 90% acetonitrile/water/0.1% TFA; 10–70% B over 30 minutes). The product fractions were combined and lyophilized to afford the product as a white solid (32 mg, 48%). LRMS (ES): 1859.2 ([M+H]$^+$, 5%), 930.1 ([M+2H]$^{+2}$, 85%), 620.8 ([M+3H]$^{+3}$, 100%)

Step 32D: Synthesis of tert-butyl (4S)-4-[N-((1S)-1-{N-[(1S)-1,3-bis(N-{(1S)-3-[N-(3-{(2S)-7-[N-(benzimidazol-2-ylmethyl)-N-methylcarbamoyl]-2-[(methoxycarbonyl)methyl]-3-oxo(1H,2H,5H-benzo[f]1,4-diazepin-4-yl)}propyl)carbamoyl]-1-(methoxycarbonyl)propyl}carbamoyl)propyl]carbamoyl}-3-[(tert-butyl)oxycarbonyl]propyl)carbamoyl]-4-[2-(1,4,7,10-tetraaza-4,7,10-tris{[(tert-butyl)oxycarbonyl]methyl} cyclododecyl)acetylamino]butanoate Step 32E: Synthesis of (2S)-2-[(2S)-4-(N-{(1S)-3-[N-(3-{(2S)-7-[N-(benzimidazol-2-ylmethyl)-N-methylcarbamoyl]-2-(carboxy methyl)-3-oxo{1H,2H,5H-benzo[f]1,4-diazepin-4-yl)}propyl)carbamoyl]-1-carboxypropyl}carbamoyl]-2-[(2S)-2-((2S)-4-carboxy-2-(2-[1,4,7,10-tetraaza-4,7,10-tris(carboxy methyl)cyclododecyl]acetylamino)butanoylamino)-4-carboxy

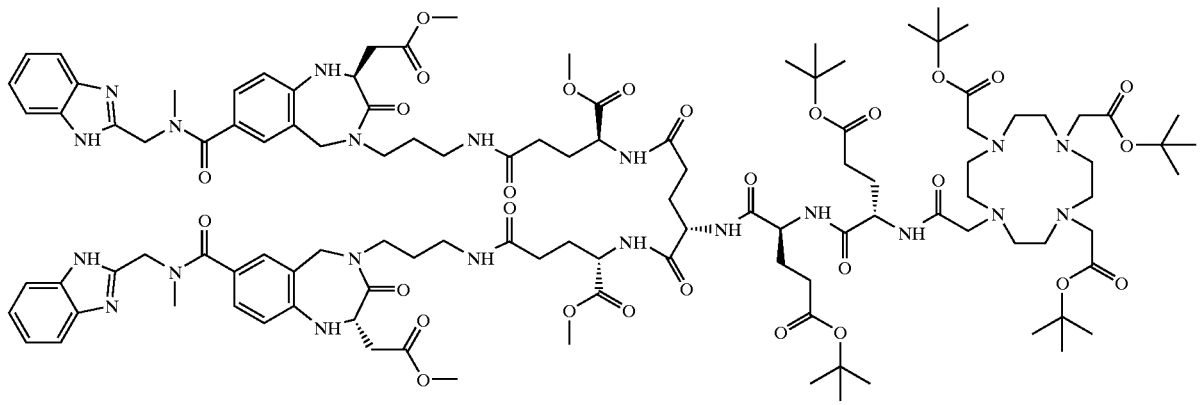

The product of step 32C (30 mg, 13.6 umol) was dissolved in methanol (6 mL) and added to 10% palladium on carbon (45 mg) in methanol (6 mL) and acetic acid (120 uL). The mixture was hydrogenated for 6.5 hours at 55 psi, butanoylamino]butanoylamino]-4-[N-(3-{(2S)-7-[N-(benzimidazol-2-ylmethyl)-N-methylcarbamoyl]-2-(carboxy methyl)-3-oxo (1H,2H,5H-benzo[f]1,4-diazepin-4-yl)}propyl) carbamoyl] butanoic acid

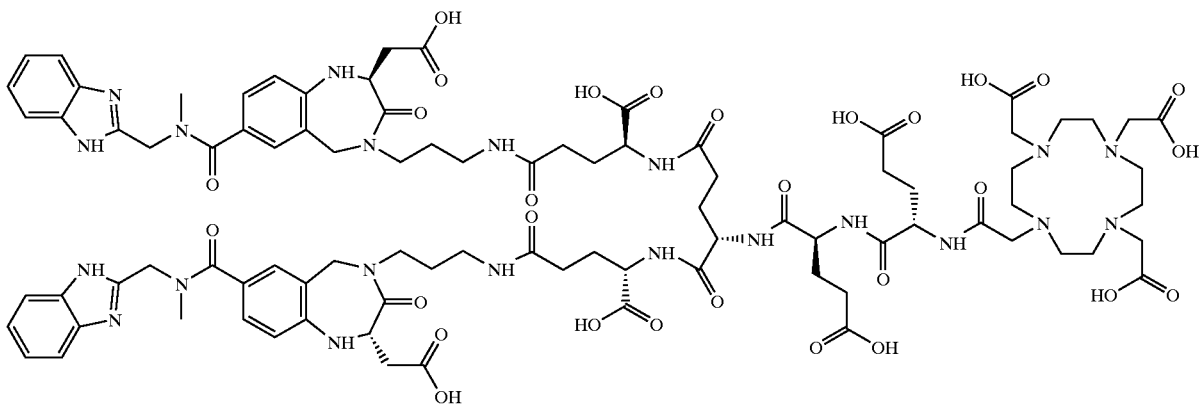

filtered, concentrated, and the residue dissolved in 50% water/acetonitrile (20 mL), frozen, and lyophilized to yield a white powder (20.6 mg). This was dissolved in dry DMF (1 mL) along with HBTU (20 mg, 53 umol), HOBT (2.3 mg, 15 umol), and diisopropylethylamine (15 uL, 75 umol). The reaction was stirred for 1.5 hours, concentrated, and the residue purified by preparative HPLC (Vydac C18, 2.12×25 cm, 90% acetonitrile/water/0.1% TFA; 50–75% B over 26 minutes). The product fractions were combined and lyophilized to afford the product as a white solid (9.6, 30% LRMS (ES): 2279.5 ([M+H]$^+$, 10%), 1140.3 ([M+2H]$^{+2}$, 20%), 760.8 ([M+3H]$^{+3}$, 100%). HRMS: Calculated for $C_{113}H_{164}N_{21}O_{29}$—2279.004; Found—2279.198.

The product of step 32D (8 mg, 3 umol) was dissolved in methanol/THF (1:1, 600 uL) and lithium hydroxide (3N solution, 10 uL, 30 umol) added. Additional aliquots of lithium hydroxide were added (20 uL at 1 hr, 3 hr, and 5 hr) and the reaction worked up at 6 hours. It was acidified with trifluoroacetic acid, concentrated, and the residue dissolved in dichloromethane (0.6 mL) along with trifluoroacetic acid (0.8 mL) and triethylsilane (100 uL). The solution was stirred under nitrogen for 20 hours, concentrated, and the residue purified by preparative HPLC (Vydac C18, 2.12×25 cm, 90% acetonitrile/water/0.1% TFA; 12–23% B over 50 minutes). The product fraction was lyophilized to afford the product as a white solid (2.1 mg, 38%). LRMS (ES): 1942.6 ([M+H]$^+$, 5%), 971.9 ([M+2H]$^{+2}$, 15%), 648.4 ([M+3H]$^{+3}$, 55%), 486.6 ([M+4H]$^{+4}$, 100%).

Example 33

Synthesis of 3-(7-[3-(amidinoamino)propyl]-2,5-dioxo-1-{[4-(3-{2-[1,4,7,10-tetraaza-4,7,10-tris(carboxymethyl)cyclododecyl]acetylamino}propoxy)phenyl]methyl}-3H-benzo [f] 1,4-diazaperhydroepin-4-yl)propanoic acid

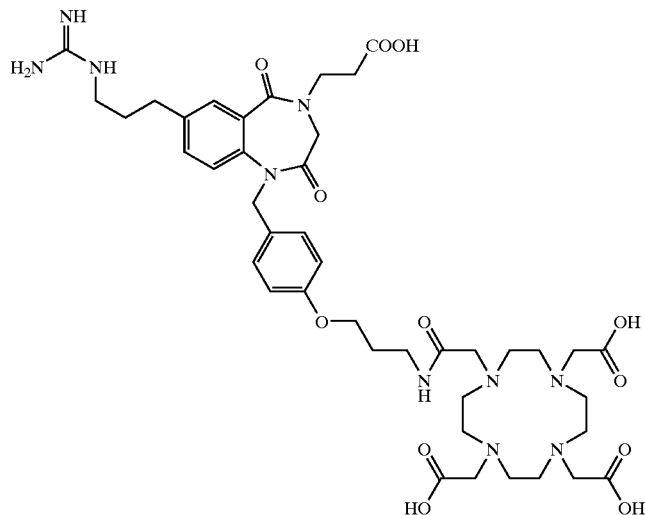

Example 34

Synthesis of 3-(8-[3-(amidinoamino)propyl]-2,5-dioxo-1-{[4-(3-{2-[1,4,7,10-tetraaza-4,7,10-tris(carboxymethyl)cyclododecyl]acetylamino}propoxy)phenyl]methyl}-3H-benzo[f] 1,4-diazaperhydroepin-4-yl)propanoic acid

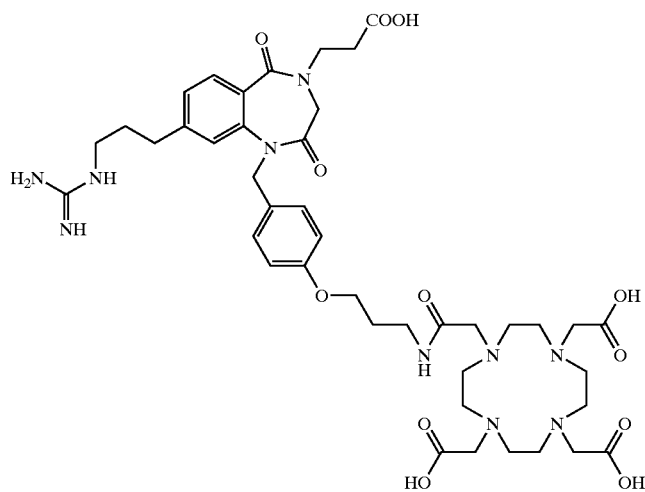

Compounds in Example 33 and Example 34 are prepared by the synthetic route shown in Scheme I.

The procedure described below elucidates Scheme I.

Step I: 7—Substituted or 8-substituted IB may be prepared via the alkylation of ethyl 3-(7-{3-[(tert-butoxy)carbonylamino]propyl}-2,5-dioxo-1H,3H-benzo[f]1,4-diazaperhydroepin-4-yl)propanoate or ethyl 3-(8-{3-[(tert-butoxy)carbonylamino]propyl}-2,5-dioxo-1H,3H-benzo[f] 1,4-diazaperhydroepin-4-yl)propanoate (IA) with 4-(2,4-dimethoxybenzyloxy)benzylbromide in the presence of base, followed by removal of the 2,4-dimethoxybenzyl protecting group. Alternately, 7-substituted or 8-substituted IB may be prepared from 1-aryl-6-iodoisatoic anhydride and 1-aryl-7-iodoisatoic anhydride by methods known in the art (McDowell, R. S. et al, J. Amer. Chem. Soc., 1994, 116, 5077–5083 and Blackburn, B. et al, PCT Intl. Appl., WO 9308174 A1 19930429 (CAS: 120:217745)). Step II: Compound IC is prepared by the alkylation of the hydroxyl group in IB with 3-Cbz-aminopropylbromide in the presence of base such as NaH in a solvent such as DMF. Step III: Intermediate ID is prepared by the deprotection of the Boc group with either trifluoroacetic acid or HCl-ethyl acetate followed by treatment of the intermediate with formamidinosulfonic acid in the presence of base (eg. 5% KHCO3).

Step IV: Removal of the benzyloxycarbonyl group (Z, Cbz) is achieved by hydrogenolysis (Pd/C) or TFA/triethylsilane to give IE.

Step V: The title compound IF is prepared by the conjugation of IE with DO3A-tri-t-butyl ester (Macrocyclics), followed by base and TFA hydrolyses of the ethyl and t-butyl esters, respectively. The desired compound is purified by reversed phase preparative HPLC.

Scheme I
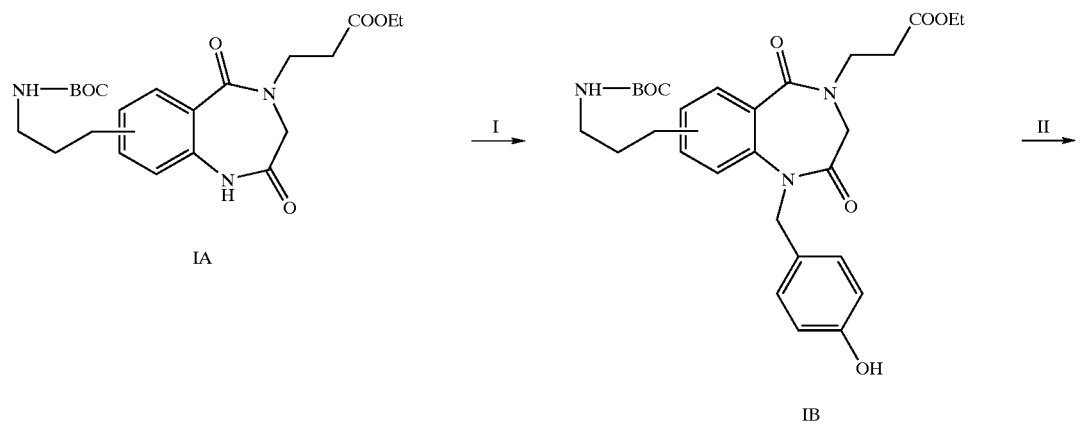
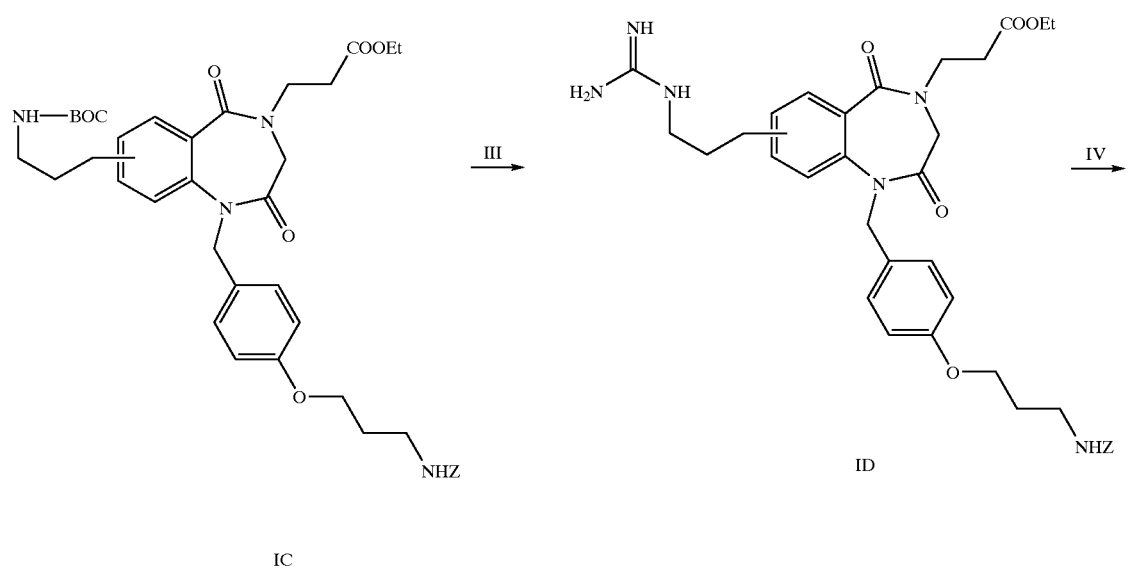
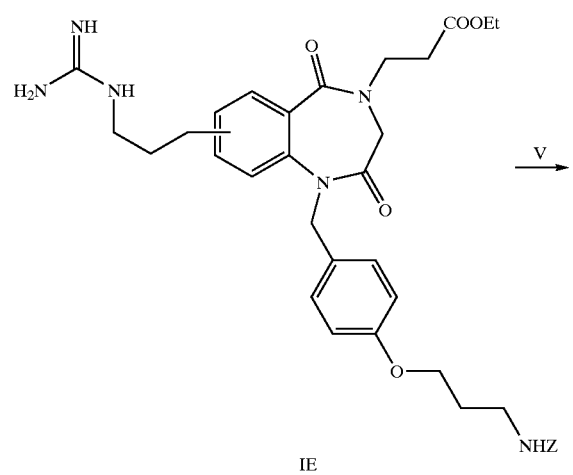

-continued

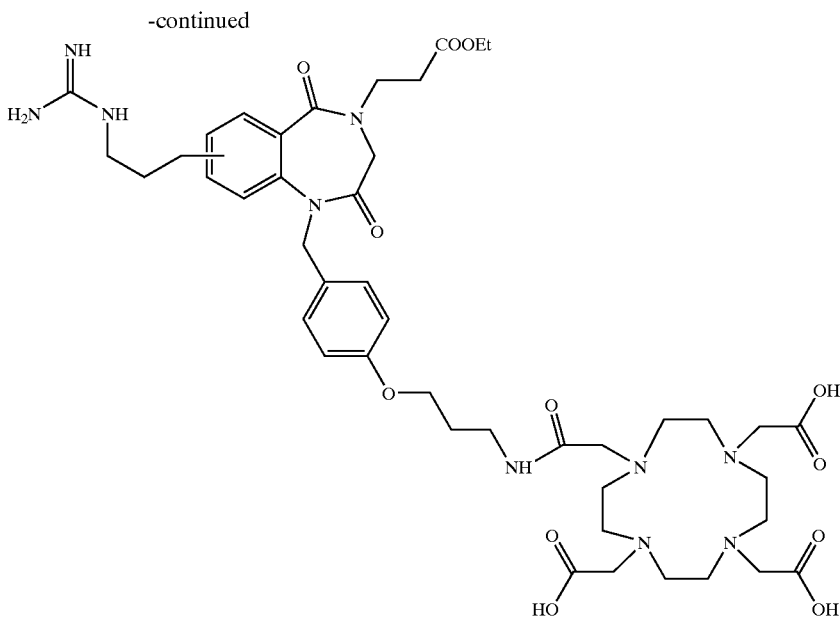

IF

Utility

The pharmaceuticals of the present invention are useful for imaging angiogenic tumor vasculature, therapeutic cardiovascular angiogenesis, and cardiac pathologies associated with the expression of vitronectin receptors in a patient or for treating cancer in a patient. The radiopharmaceuticals of the present invention comprised of a gamma ray or positron emitting isotope are useful for imaging of pathological processes involving angiogenic neovasculature, including cancer, diabetic retinopathy, macular degeneration, restenosis of blood vessels after angioplasty, and wound healing, as well as atherosclerotic plaque, myocardial reperfusion injury, and myocardial ischemia, stunning or infarction. The radiopharmaceuticals of the present invention comprised of a beta, alpha or Auger electron emitting isotope are useful for treatment of pathological processes involving angiogenic neovasculature, by delivering a cytotoxic dose of radiation to the locus of the angiogenic neovasculature. The treatment of cancer is affected by the systemic administration of the radiopharmaceuticals resulting in a cytotoxic radiation dose to tumors.

The compounds of the present invention comprised of one or more paramagnetic metal ions selected from gadolinium, dysprosium, iron, and manganese, are useful as contrast agents for magnetic resonance imaging (MRI) of pathological processes involving angiogenic neovasculature, as well as atherosclerotic plaque, myocardial reperfusion injury, and myocardial ischemia, stunning or infarction.

The compounds of the present invention comprised of one or more heavy atoms with atomic number of 20 or greater are useful as X-ray contrast agents for X-ray imaging of pathological processes involving angiogenic neovasculature, as well as atherosclerotic plaque, myocardial reperfusion injury, and myocardial ischemia, stunning or infarction.

The compounds of the present invention comprised of an echogenic gas containing surfactant microsphere are useful as ultrasound contrast agents for sonography of pathological processes involving angiogenic neovasculature, as well as atherosclerotic plaque, myocardial reperfusion injury, and myocardial ischemia, stunning or infarction.

Representative compounds of the present invention were tested in the following in vitro assays and in vivo models and were found to be active.

Immobilized Human Placental $\alpha_v\beta_3$ Receptor Assay

The assay conditions were developed and validated using [I-125]vitronectin. Assay validation included Scatchard format analysis (n=3) where receptor number (Bmax) and Kd (affinity) were determined. Assay format, is such that compounds are preliminarily screened at 10 and 100 nM final concentrations prior to IC50 determination. Three standards (vitronectin, anti-$\alpha_v\beta_3$ antibody, LM609, and anti-$\alpha_v\beta_5$, P1F6) and five reference peptides have been evaluated for IC50 determination. Briefly, the method involves immobilizing previously isolated receptors in 96 well plates and incubating overnight. The receptors were isolated from normal, fresh, non-infectious (HIV, hepatitis B and C, syphilis, and HTLV free) human placenta. The tissue was lysed and tissue debris removed via centrifugation. The lysate was filtered. The receptors were isolated by affinity chromatography using the immobilized $\alpha_v\beta_3$ antibody. The plates are then washed 3×with wash buffer. Blocking buffer is added and plates incubated for 120 minutes at room temperature. During this time compounds to be tested and [I-125]vitronectin are premixed in a reservoir plate. Blocking buffer is removed and compound mixture pipetted. Competition is carried out for 60 minutes at room temperature. Unbound material is then removed and wells are separated and counted via gamma scintillation.

Oncomouse® Imaging

The study involves the use of the c-Neu Oncomouse® and FVB mice simultaneously as controls. The mice are anesthetized with sodium pentobarbital and injected with approximately 0.5 mCi of radiopharmaceutical. Prior to injection, the tumor locations on each Oncomouse® are recorded and tumor size measured using calipers. The animals are positioned on the camera head so as to image the anterior or posterior of the animals. 5 Minute dynamic images are acquired serially over 2 hours using a 256×256 matrix and a zoom of 2×. Upon completion of the study, the images are evaluated by circumscribing the tumor as the target region of interest (ROI) and a background site in the neck area below the carotid salivary glands.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the rate of growth of the tumors in control mice versus those in the mice administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the tumors in the animal can be imaging using an ultrasound probe held proximate to the tumors. The effectiveness of the contrast agents can be readily seen by comparison to the images obtain from animals that are not administered a contrast agent.

Rabbit Matrigel Model

This model was adapted from a matrigel model intended for the study of angiogenesis in mice. Matrigel (Becton & Dickinson, USA) is a basement membrane rich in laminin, collagen IV, entactin, HSPG and other growth factors. When combined with growth factors such as bFGF [500 ng/ml] or VEGF [2 µg/ml] and injected subcutaneously into the midabdominal region of the mice, it solidifies into a gel and stimulates angiogenesis at the site of injection within 4–8 days. In the rabbit model, New Zealand White rabbits (2.5–3.0 kg) are injected with 2.0 ml of matrigel, plus 1 µg bFGF and 4 µg VEGF. The radiopharmaceutical is then injected 7 days later and the images obtained.

This model can also be used to assess the effectiveness of the radiopharmaceuticals of the present invention comprised of a beta, alpha or Auger electron emitting isotope. The radiopharmaceuticals are administered in appropriate amounts and the uptake at the angiogenic sites can be quantified either non-invasively by imaging for those isotopes with a coincident imageable gamma emission, or by excision of the angiogenic sites and counting the amount of radioactivity present by standard techniques. The therapeutic effect of the radiopharmaceuticals can be assessed by monitoring the rate of growth of the angiogenic sites in control rabbits versus those in the rabbits administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the angiogenic sites. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the angiogenic sites. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the angiogenic sites in the animal can be imaging using an ultrasound probe held proximate to the tumors. The effectiveness of the contrast agents can be readily seen by comparison to the images obtain from animals that are not administered a contrast agent.

Canine Spontaneous Tumor Model

Adult dogs with spontaneous mammary tumors were sedated with xylazine (20 mg/kg)/atropine (1 ml/kg). Upon sedation the animals were intubated using ketamine (5 mg/kg)/diazepam (0.25 mg/kg) for full anethesia. Chemical restraint was continued with ketamine (3 mg/kg)/xylazine (6 mg/kg) titrating as necessary. If required the animals were ventilated with room air via an endotrachael tube (12 strokes/min, 25 ml/kg) during the study. Peripheral veins were catheterized using 20G I.V. catheters, one to serve as an infusion port for compound while the other for exfusion of blood samples. Heart rate and EKG were monitored using a cardiotachometer (Biotech, Grass Quincy, Mass.) triggered from a lead II electrocardiogram generated by limb leads. Blood samples are generally taken at ~10 minutes (control), end of infusion, (1 minute), 15 min, 30 min, 60 min, 90 min, and 120 min for whole blood cell number and counting. Radiopharmaceutical dose was 300 µCi/kg administered as an i.v. bolus with saline flush. Parameters were monitored continuously on a polygraph recorder (Model 7E Grass) at a paper speed of 10 mm/min or 10 mm/sec.

Imaging of the laterals were for 2 hours with a 256×256 matrix, no zoom, 5 minute dynamic images. A known source is placed in the image field (20–90 µCi) to evaluate region of interest (ROI) uptake. Images were also acquired 24 hours post injection to determine retention of the compound in the tumor. The uptake is determined by taking the fraction of the total counts in an inscribed area for ROI/source and multiplying the known µCi. The result is µCi for the ROI.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the size of the tumors over time.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the tumors in the animal can be imaging using an ultrasound probe held proximate to the tumors. The effectiveness of the contrast agents can be readily seen by comparison to the images obtain from animals that are not administered a contrast agent.

Cardiovascular disease models that can be used to assess the diagnostic radiopharmaceuticals, magnetic resonance, X-ray and ultrasound contrast agents of the present invention are reviewed in J. Nucl. Cardiol., 1998, 5, 167–83. There are several well established rabbit models of atherosclerosis; one model produces predominantly proliferating smooth muscle cells by balloon deendothelialization of infradiaphragmatic abdominal aorta to simulate restenotic lesions; another model that produces simulated advanced human atherosclerotic plaque by balloon deendothelialization followed by a high cholesterol diet.

A model of congestive heart failure is described in Am. J. Physiol., 1998, 274, H1516-23. In general, Yorkshire pigs are randomly assigned to undergo 3 wks of rapid atrial pacing at 240 beats/min. or to be sham controls. The pigs are chronically instrumented to measure left ventricular function in the conscious state. The pigs are anesthetized. A shielded stimulating electrode is sutured onto the left atrium, connected to a modified programmable pace maker and buried in a subcutaneous pocket. The pericardium is closed loosely, the thoracotomy is closed, and the pleural space is evacuated of air. After a recovery period of 7–10 days, the pacemaker is activated in the animals selected to undergo chronic rapid pacing. The animals are sedated, the pacemaker is deactivated (pacing groups only. After a 30 min stabilization period, indexes of LV function and geometry are determined (by echocardiography as a control) by injecting the radiolabeled compound. For biodistribution, the animals are anesthetized, the heart extirpate and the LV apex and midventricular regions are evaluated.

A rat model of reversible coronary occlusion and reperfusion is described in McNulty et al., J. Am. Physiol., 1996, H2283-9.

Obviously, numerous modifications and variations of the present invention are possible in light of the above teachings. It is therefore to be understood that within the scope of the appended claims, the invention may be practiced otherwise that as specifically described herein.

What is claimed is described below:

1. A compound, comprising: a targeting moiety and a chelator, wherein the targeting moiety is bound to the chelator, is a benzodiazepinedione, or dibenzotrihydroannulene nonpeptide, and binds to a receptor that is upregulated during angiogenesis and the compound has 0–1 linking groups between the targeting moiety and chelator.

2. A compound according to claim 1, wherein the receptor is the integrin $\alpha_v\beta_3$ or $\alpha_v\beta_5$ and compound is of the formula:

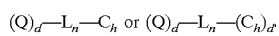

wherein, Q is a compound of Formulae (Ib) or (Ic):

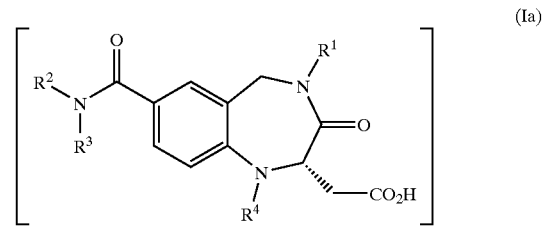

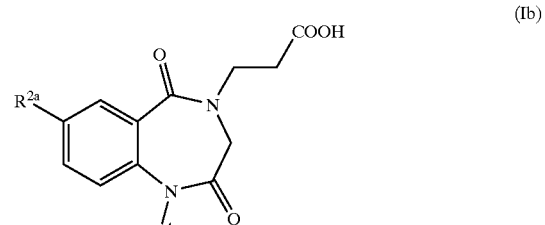

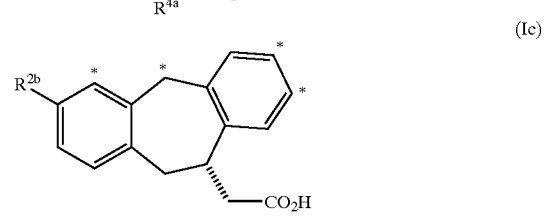

wherein:

$R^{2a}$ is $(CH_2)_3R^{3a}$;

$R^{3a}$ is selected from the group:

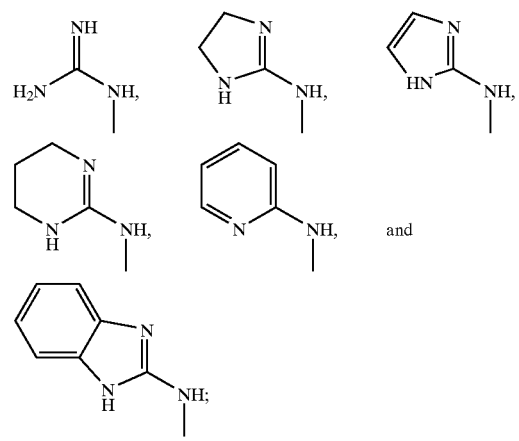

$R^{4a}$ is independently selected from $C_{1-6}$ alkyl substituted with a bond to $L_n$ or benzyl substituted with a bond to $L_n$;

$R^{2b}$ is independently selected from the group:

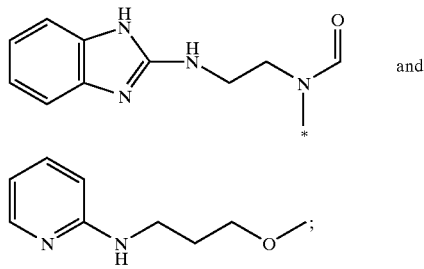
and the asterisks * denote optional positions for attaching $L_n$;
or Q is a peptide selected from the group:

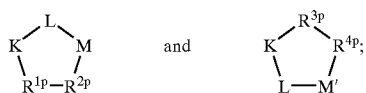

$R^{1p}$ is L-valine, D-valine or L-lysine optionally substituted on the ε amino group with a bond to $L_n$;

$R^{2p}$ is L-phenylalanine, D-phenylalanine, D-1-naphthylalanine, 2-aminothiazole-4-acetic acid or tyrosine, the tyrosine optionally substituted on the hydroxy group with a bond to $L_n$;

$R^{3p}$ is D-valine;

$R^{4p}$ is D-tyrosine substituted on the hydroxy group with a bond to $L_n$;

provided that one of $R^{1p}$ and $R^{2p}$ in each Q is substituted with a bond to $L_n$, and further provided that when $R^{2p}$ is 2-aminothiazole-4-acetic acid, K is N-methylarginine;

provided that at least one Q is a compound of Formula Ib, or Ic;

d is selected from 1, 2, 3, 4, 5, 6, 7, 8, 9, and 10;

d' is 1–100;

$L_n$ is a linking group having the formula:

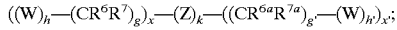

W is independently selected at each occurrence from the group: O, S, NH, NHC(=O), C(=O)NH, $NR^8$C(=O), C(=O)$NR^8$, C(=O), C(=O)O, OC(=O), NHC(=S)NH, NHC(=O)NH, $SO_2$, $SO_2$NH, $(OCH_2CH_2)_s$, $(CH_2CH_2O)_{s'}$, $(OCH_2CH_2CH_2)_{s''}$, $(CH_2CH_2CH_2O)_t$, and $(aa)_{t'}$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, and $R^8$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)$NHR^{11}$, NHC(=O)$NHR^{11}$, $NHR^{11}$, $R^{11}$, and a bond to $C_h$;

$R^{10}$ is independently selected at each occurrence from the group: a bond to $C_h$, $COOR^{11}$, C(=O)$NHR^{11}$, NHC(=O)$R^{11}$, OH, $NHR^{11}$, $SO_3H$, $PO_3H$, —$OPO_3H_2$, —$OSO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, polyalkylene glycol substituted with 0–1 $R^{12}$, carbohydrate substituted with 0–1 $R^{12}$, cyclodextrin substituted with 0–1 $R^{12}$, amino acid substituted with 0–1 $R^{12}$, polycarboxyalkyl substituted with 0–1 $R^{12}$, polyazaalkyl substituted with 0–1 $R^{12}$, peptide substituted with 0–1 $R^{12}$, wherein the peptide is comprised of 2–10 amino acids, 3,6-O-disulfo-B-D-galactopyranosyl, bis(phosphonomethyl)glycine, and a bond to $C_h$;

$R^{12}$ is a bond to $C_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$C_h$ is a metal bonding unit having a formula selected from the group:

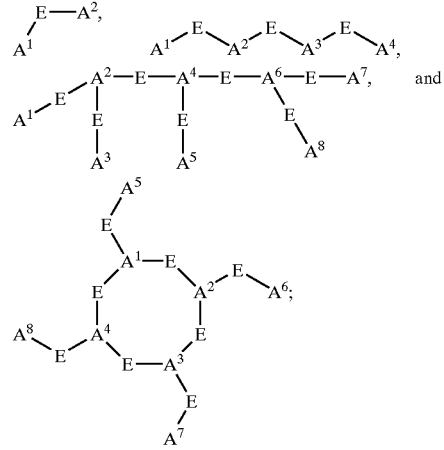

$A^1$, $A^2$, $A^3$, $A^4$, $A^5$, $A^6$, $A^7$, and $A^8$ are independently selected at each occurrence from the group: $NR^{13}$, $NR^{13}R^{14}$, S, SH, S(Pg), O, OH, $PR^{13}$, $PR^{13}R^{14}$, P(O)$R^{15}R^{16}$, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{13}$ and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, $C_{1-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form =C ($R^{20}$)($R^{21}$);

$R^{15}$ and $R^{16}$ are each independently selected from the group: a bond to $L_n$, —OH, $C_1$–$C_{10}$ alkyl substituted with 0–3 $R^{17}$, $C_1$–$C_{10}$ alkyl substituted with 0–3 $R^{17}$, aryl substituted with 0–3 $R^{17}$, $C_{3-10}$ cycloalkyl substituted with 0–3 $R^{17}$, heterocyclo-$C_{1-10}$ alkyl substituted with 0–3 $R^{17}$, wherein the heterocyclo group is a 5–10 membered heterocyclic ring system containing 1–4 heteroatoms independently selected from N, S, and O, $C_{6-10}$ aryl-$C_{1-10}$ alkyl substituted with 0–3 $R^{17}$, $C_{1-10}$ alkyl-$C_{6-10}$ aryl-substituted with 0–3 $R^{17}$, and a 5–10 membered heterocyclic ring system containing 1–4 heteroatoms independently selected from N, S, and O and substituted with 0–3 $R^{17}$;

$R^{17}$ is independently selected at each occurrence from the group: a bond to $L_n$, =O, F, Cl, Br, I, —$CF_3$, —CN, —$CO_2R^{18}$, —C(=O)$R^{18}$, —C(=O)N($R^{18}$)$_2$, —CHO, —$CH_2OR^{18}$, —OC(=O)$R^{18}$, —OC(=O)O$R^{18a}$, —O$R^{18}$, —OC(=O)N($R^{18}$)$_2$, —$NR^{19}$C(=O)$R^{18}$, —$NR^{19}$C(=O)O$R^{18a}$, —$NR^{19}$C(=O)N($R^{18}$)$_2$, —$NR^{19}$SO$_2$N($R^{18}$)$_2$, —$NR^{19}$SO$_2R^{18a}$, —$SO_3H$, —$SO_2R^{18a}$, —$SR^{18}$, —S(=O)$R^{18a}$, —$SO_2$N($R^{18}$)$_2$, —N($R^{18}$)$_2$, —NHC(=S)$NHR^{18}$, =NO$R^{18}$, $NO_2$, —C(=O)$NHOR^{18}$, —C(=O)$NHNR^{18}R^{18a}$, —$OCH_2CO_2H$, 2-(1-morpholino)ethoxy, $C_1$–$C_5$ alkyl, $C_2$–$C_4$ alkenyl, $C_3$–$C_6$ cycloalkyl, $C_3$–$C_6$ cycloalkylmethyl, $C_2$–$C_6$ alkoxyalkyl, aryl substituted with 0–2 $R^{18}$, and a 5–10 membered heterocyclic ring system containing 1–4 heteroatoms independently selected from N, S, and O;

$R^{18}$, $R^{18a}$, and $R^{19}$ are independently selected at each occurrence from the group: a bond to $L_n$, H, $C_1$–$C_6$ alkyl, phenyl, benzyl, $C_1$–$C_6$ alkoxy, halide, nitro, cyano, and trifluoromethyl;

Pg is a thiol protecting group;

$R^{20}$ and $R^{21}$ are independently selected from the group: H, $C_1$–$C_{10}$ alkyl, —CN, —$CO_2R^{25}$, —C(=O)$R^{25}$, —C(=O)N($R^{25}$)$_2$, $C_2$–$C_{10}$ 1-alkene substituted with 0–3 $R^{23}$, $C_2$–$C_{10}$ 1-alkyne substituted with 0–3 $R^{23}$, aryl substituted with 0–3 $R^{23}$, unsaturated 5–10 membered heterocyclic ring system containing 1–4 heteroatoms independently selected from N, S, and O and substituted with 0–3 $R^{23}$, and unsaturated $C_{3-10}$ carbocycle substituted with 0–3 $R^{23}$;

alternatively, $R^{20}$ and $R^{21}$, taken together with the divalent carbon radical to which they are attached form:

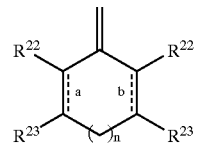

$R^{22}$ and $R^{23}$ are independently selected from the group: H, $R^{24}$, $C_1$–$C_{10}$ alkyl substituted with 0–3 $R^{24}$, $C_2$–$C_{10}$ alkenyl substituted with 0–3 $R^{24}$, $C_2$–$C_{10}$ alkynyl substituted with 0–3 $R^{24}$, aryl substituted with 0–3 $R^{24}$, a 5–10 membered heterocyclic ring system containing 1–4 heteroatoms independently selected from N, S, and O and substituted with 0–3 $R^{24}$, and $C_{3-10}$ carbocycle substituted with 0–3 $R^{24}$;

alternatively, $R^{22}$, $R^{23}$ taken together form a fused aromatic or a 5–10 membered heterocyclic ring system containing 1–4 heteroatoms independently selected from N, S, and O;

a and b indicate the positions of optional double bonds and n is 0 or 1;

$R^{24}$ is independently selected at each occurrence from the group: =O, F, Cl, Br, I, —$CF_3$, —CN, —$CO_2R^{25}$, —C(=O)$R^{25}$, —C(=O)N($R^{25}$)$_2$, —N($R^{25}$)$_{3+}$, —$CH_2OR^{25}$, —OC(=O)$R^{25}$, —OC(=O)O$R^{25a}$, —O$R^{25}$, —OC(=O)N($R^{25}$)$_2$, —$NR^{26}$C(=O)$R^{25}$, —$NR^{26}$C(=O)O$R^{25a}$, —$NR^{26}$C(=O)N($R^{25}$)$_2$, —$NR^{26}$SO$_2$N($R^{25}$)$_2$, —$NR^{26}$SO$_2R^{25a}$, —$SO_3H$, —$SO_2R^{25a}$, —$SR^{25}$, —S(=O)$R_{25a}$, —$SO_2$N($R^{25}$)$_2$, —N($R^{25}$)$_2$, =NO$R^{25}$, —C(=O)$NHOR^{25}$, —$OCH_2CO_2H$, and 2-(1-morpholino)ethoxy; and, $R^{25}$, $R^{25a}$, and $R^{26}$ are each independently selected at each occurrence from the group: hydrogen and $C_1$–$C_6$ alkyl;

and a pharmaceutically acceptable salt thereof.

3. A compound according to claim 2, wherein:

d is selected from 1, 2, 3, 4, and 5;

d' is 1–50;

W is independently selected at each occurrence from the group: O, NH, NHC(=O), C(=O)NH, $NR^8C$(=O), C(=O)N $R^8$, C(=O), C(=O)O, OC(=O), NHC(=S) NH, NHC(=O)NH, $SO_2$, $(OCH_2CH_2)_s$, $(CH_2CH_2O)_{s'}$, $(OCH_2CH_2CH_2)_{s''}$, $(CH_2CH_2CH_2O)_t$, and $(aa)_{t'}$;

aa is independently at each occurrence an amino acid;

Z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, and $R^8$ are independently selected at each occurrence from the group: H, =O, COOH, $SO_3H$, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O)$NHR^{11}$, NHC(=O)$NHR^{11}$, $NHR^{11}$, $R^{11}$, and a bond to $C_h$;

k is 0 or 1;

s is selected from 0, 1, 2, 3, 4, and 5;

s' is selected from 0, 1, 2, 3, 4, and 5;

s" is selected from 0, 1, 2, 3, 4, and 5;

t is selected from 0, 1, 2, 3, 4, and 5;

$A^1$, $A^2$, $A^3$, $A^4$, $A^5$, $A^6$, $A^7$, and $A^8$ are independently selected at each occurrence from the group: $NR^{13}$, $NR^{13}R^{14}$, S, SH, S(Pg), OH, and a bond to $L_n$;

E is a bond, CH, or a spacer group independently selected at each occurrence from the group: $C_1$–$C_{10}$ alkyl substituted with 0–3 $R^{17}$, aryl substituted with 0–3 $R^{17}$, $C_{3-10}$ cycloalkyl substituted with 0–3 $R^{17}$, and a 5–10 membered heterocyclic ring system containing 1–4 heteroatoms independently selected from N, S, and O and substituted with 0–3 $R^{17}$;

$R^{13}$, and $R^{14}$ are each independently selected from the group: a bond to $L_n$, hydrogen, $C_1$–$C_{10}$ alkyl substituted with 0–3 $R^{17}$, aryl substituted with 0–3 $R^{17}$, a 5–10 membered heterocyclic ring system containing 1–4 heteroatoms independently selected from N, S, and O and substituted with 0–3 $R^{17}$, and an electron, provided that when one of $R^{13}$ or $R^{14}$ is an electron, then the other is also an electron;

alternatively, $R^{13}$ and $R^{14}$ combine to form =C($R^{20}$)($R^{21}$);

$R^{17}$ is independently selected at each occurrence from the group: a bond to $L_n$, =O, F, Cl, Br, I, —$CF_3$, —CN, —$CO_2R^{18}$, —C(=O)$R^{18}$, —C(=O)N($R^{18}$)$_2$, —$CH_2OR^{18}$, —OC(=O)$R^{18}$, —OC(=O)$OR^{18a}$, —$OR^{18}$, —OC(=O)N($R^{18}$)$_2$, —$NR^{19}$C(=O)$R^{18}$, —$NR^{19}$C(=O)$OR^{18a}$, —$NR^{19}$C(=O)N($R^{18}$)$_2$, —$NR^{19}SO_2$N($R^{18}$)$_2$, —$NR^{19}SO_2R^{18a}$, —$SO_3H$, —$SO_2R^{18a}$, —S(=O)$R^{18a}$, —$SO_2$N($R^{18}$)$_2$, —N($R^{18}$)$_2$, —NHC(=S)NH$R^{18}$, =NO$R^{18}$, —C(=O)NHN$R^{18}R^{18a}$, —$OCH_2CO_2H$, and 2-(1-morpholino) ethoxy;

$R^{18}$, $R^{18a}$, and $R^{19}$ are independently selected at each occurrence from the group: a bond to $L_n$, H, and $C_1$–$C_6$ alkyl;

$R^{20}$ and $R^{21}$ are independently selected from the group: H, $C_1$–$C_5$ alkyl, —$CO_2R^{25}$, $C_2$–$C_5$ 1-alkene substituted with 0–3 $R^{23}$, $C_2$–$C_5$ 1-alkyne substituted with 0–3 $R^{23}$, aryl substituted with 0–3 $R^{23}$, and unsaturated 5–10 membered heterocyclic ring system containing 1–4 heteroatoms independently selected from N, S, and O and substituted with 0–3 $R^{23}$;

alternatively, $R^{20}$ and $R^{21}$, taken together with the divalent carbon radical to which they are attached form:

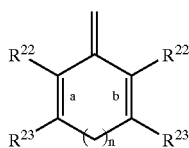

$R^{22}$ and $R^{23}$ are independently selected from the group: H, and $R^{24}$;

alternatively, $R^{22}$, $R^{23}$ taken together form a fused aromatic or a 5–10 membered heterocyclic ring system containing 1–4 heteroatoms independently selected from N, S, and O;

$R^{24}$ is independently selected at each occurrence from the group: —$CO_2R^{25}$, —C(=O)N($R^{25}$)$_2$, —$CH_2OR^{25}$, —OC(=O)$R^{25}$, —$OR^{25}$, —$SO_3H$, —N($R^{25}$)$_2$, and —$OCH_2CO_2H$; and, $R^{25}$ is independently selected at each occurrence from the group: H and $C_1$–$C_3$ alkyl.

4. A compound according to claim 3, wherein:

$R^{4a}$ is benzyl substituted with a bond to $L_n$;

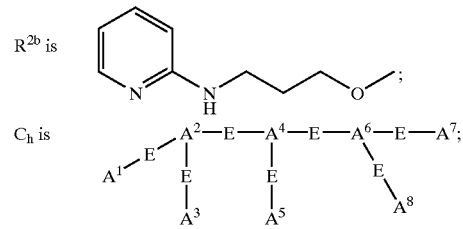

$R^{2b}$ is $C_h$ is $A^1$ is selected from the group: OH, and a bond to $L_n$;
$A^2$, $A^4$, and $A^6$ are each N;
$A^3$, $A^5$, and $A^8$ are each OH;
$A^7$ is a bond to $L_n$ or NH-bond to $L_n$;
E is a $C_2$ alkyl substituted with 0–1 $R^{17}$;
$R^{17}$ is =O;
alternatively, $C_h$ is

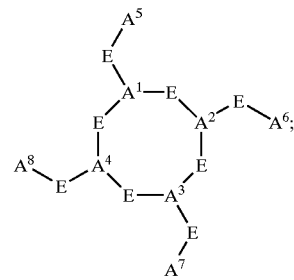

$A^1$ is selected from the group: OH, and a bond to $L_n$;
$A^2$, $A^3$ and $A^4$ are each N;
$A^5$, $A^6$ and $A^8$ are each OH;
$A^7$ is a bond to $L_n$;
E is a $C_2$ alkyl substituted with 0–1 $R^{17}$;
$R^{17}$ is =O;
alternatively, $C_h$ is

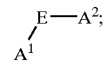

$A^1$ is $NH_2$ or N=C($R^{20}$)($R^{21}$);
E is a bond;
$A^2$ is $NHR^{13}$;
$R^{13}$ is a heterocycle substituted with $R^{17}$, the heterocycle being selected from pyridine and pyrimidine;
$R^{17}$ is selected from a bond to $L_n$, C(=O)NH$R^{18}$ and C(=O)$R^{18}$;
$R^{18}$ is a bond to $L_n$;
$R^{24}$ is selected from the group: —$CO_2R^{25}$, —$OR^{25}$, —$SO_3H$, and —N($R^{25}$)$_2$; and,
$R^{25}$ is independently selected at each occurrence from the group: hydrogen and methyl.

5. A compound according to claim 2, wherein the compound is selected from the group:

(S,S,S)-4-(N-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)propyl) carbamoyl)-4-(4-carboxy-2-(2-(1,4,7,10-tetraaza-4,7, 10-tris(carboxymethyl) cyclodecyl)acetylamino) butanoyl amino)butanoic acid;

(S)-2-(2,5-diaza-5-(6((6-((1-aza-2-(2-sulfophenyl)vinyl) amino)(3-pyridyl))carbonylamino)hexyl)-9-(N-(benzimidazol-2-ylmethyl)-N-methylcarbamoyl)-4-oxobicyclo[5.4.0]undeca-1(7),8,10-trien-3-yl) acetic acid;

(S)-2-(2,5-diaza-9-(N-(6-((6-((1-aza-2-(2-sulfophenyl) vinyl)amino)(3-pyridyl))carbonylamino)hexyl)-N-(benzimidazol-2-ylmethyl)carbamoyl)-5-methyl-4-oxobicyclo[5.4.0]undeca-1(7),8,10-trien-3-yl)acetic acid;

(S,S)-2-(2-aza-2-((5-(N-(1,3-bis(N-(6-(aminohexyl-4-oxobicyclo[5.4.0]undeca-1(7),8,10-trien-3-yl)acetic acid)(2-(2,5-diaza-9-(N-(benzimidazol-2-ylmethyl) propyl)carbamoyl)(2-pyridyl))amino)vinyl) benzene-sulfonic acid;

(S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-4-(4-carboxy-2-(2-(1,4,7,10-tetraaza-4,7, 10-tris(carboxymethyl) cyclododecyl)acetylamino) butanoylamino) butanoic acid;

(S,S)-3-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-3-(2-(1,4,7,10-tetraaza-4,7,10-tris (carboxymethyl) cyclododecyl)acetylamino)propanoic acid;

(S,S,S,S,S,S,S,S)-4-(N-1,3-bis(N-3-carboxy-1-(N-(3-(3, 6-diaza-10-(N-(benzimidazol-2-ylmethyl)-N-methylcarbamoyl)-5-(carboxymethyl)-4-oxobicyclo [5.4.0]undeca-1(7),8,10-trien-3-yl)propyl)carbamoyl)-4,4-dihydroxypentyl) carbamoyl)propyl)carbamoyl)-4-(5,5-dihydroxy-2-(2-(1,4,7,10-tetraaza-4,7,10-tris (carboxymethyl)cyclodecyl)acetylamino) butanoic acid;

(S,S,S,S,S,S,S,S,S,S)-2-(4-(N-(1,3-bis(N-(3-(N-(3-(3,6-diaza-10-(N-(benzimidazol-2-ylmethyl)-N-methylcarbamoyl)-5-((methoxycarbonyl)methyl)-4-oxobicyclo[5.4.0]undeca-1(7),8,10-trien-3-yl)propyl) carbamoyl)-1-(methoxycarbonyl)propyl)carbamoyl) propyl)carbamoyl)propyl)carbamoyl)-4-(2-(2-(1,4,7, 10-tetraaza-4,7,10-tris(carboxymethyl) cyclodecyl) acetylamino)-4-carboxybutanoylamino)-4-carboxybutanoylamino)butanoylamino)-4-(N-(3-(3,6-diaza-10-(N-(benzimidazol-2-ylmethyl)-N-methyl carbamoyl)-5-((methoxycarbonyl)methyl)-4-oxobicyclo[5.4.0] undeca-1(7),8,10-trien-3-yl)propyl) carbamoyl)butanoic acid;

(S)-2-(2,5-diaza-5-(3-(2-(2-(3-((6-((1-aza-2-(2-sulfophenyl)vinyl)amino)(3-pyridyl))carbonylamino) propoxy)ethoxy)ethoxy)propyl)-9-(N-(benzimidazol-2-ylmethyl)-N-methylcarbamoyl)-4-oxobicyclo[5.4.0] undeca-1(7),8,10-trien-3-yl)acetic acid;

(S,S,S,S,S)-4-(N-(1,3-bis(N-(3-(2-(2-(3-(3,6-diaza-10-(N-(benzimidazol-2-ylmethyl)-N-methylcarbamoyl)-5-(carboxymethyl)-4-oxobicyclo[5.4.0]undeca-1(7),8, 10-trien-3-yl)propoxy)ethoxy)ethoxy)propyl) carbamoyl)propyl)carbamoyl)-4-(5,5-dihydroxy-2-(2-(1,4,7,10-tetraaza-4,7,10-tris(carboxy methyl) cyclododecyl)acetylamino) hexanoylamino)butanoic acid;

(S,S,S)-2-(2,5-diaza-9-(N-(benzimidazol-2-ylmethyl)-N-methylcarbamoyl)-4-oxo-5-(6-(4-(N-((R,S,S,S)-2,3,4, 5,6-pentahydroxyhexyl)carbamoyl)-2-(4-(N-((R,S,S, S)-2,3,4,5,6-pentahydroxy hexyl)carbamoyl)-2-(2-(1, 4,7,10-tetraaza-4,7,10-tris(carboxymethyl)cyclodecyl) acetylamino)butanoylamino)butanoylamino)hexyl) bicyclo[5.4.0]undeca-1(7),8,10-trien-3-yl)acetic acid;

(S,S,S,S)-2-(4-(N-(1-(N-(1-(N-(6-(3,6-diaza-10-(N-(benzimidazol-2-ylmethyl)-N-methylcarbamoyl)-5-(carboxymethyl)-4-oxobicyclo[5.4.0]undeca-1(7),8, 10-trien-3-yl)hexyl)carbamoyl)-3-(N-cyclo{Lys-Arg (Mtr)-Gly-Asp(OtBu)-D-Phe}[gamma-LysNH] carbamoyl)propyl)carbamoyl)-3-carboxypropyl) carbamoyl)-4-(2-(1,4,7,10-tetraaza-4,7,10-tris (carboxymethyl) cyclododecyl)acetylamino)butanoic acid;

4-[N-(3-{(2R)-7-[N-(benzimidazol-2-ylmethyl)-N-methylcarbamoyl]-2-(carboxymethyl)-3-oxo(1H, 2H,5H-benzo[f]1,4-diazepin-4-yl)}propyl)carbamoyl] (4S)-4-[(4S)-4-(N-{(1S)-1-[N-(3-{(2S)-7-[N-(benzimidazol-2-ylmethyl)-N-methylcarbamoyl]-2-(carboxymethyl)-3-oxo (1H,2H,5H-benzo[f]1,4-diazepin-4-yl)}propyl)carbamoyl]-3-carboxypropyl}carbamoyl)-4-{2-[1,4,7,10-tetraaza-4, 7,10-tris(carboxymethyl)cyclododecyl] acetylamino}butanoyl amino]butanoic acid;

2-(4-{3-[(6-{[(1E)-1-aza-2-(2-sulfophenyl)vinyl]amino} (3-pyridyl))carbonylamino]propyl} (2S)-7-{N-[2-(amidinoamino)ethyl]-N-methylcarbamoyl}-3-oxo-1H,2H,5H-benzo[f]1,4-diazepin-2-yl)acetic acid; and 2-[9-(N-{6-[(6-{[(1E)-1-aza-2-(2-sulfophenyl)vinyl] amino}(3-pyridyl))carbonylamino]hexyl}—N-(benzimidazol-2-ylmethyl)carbamoyl)(5S)-5,6,11-trihydro-dibenzo[b,e][7]annulen-5-yl]acetic acid;

or a pharmaceutically acceptable salt form thereof.

6. A kit comprising a compound of claim 2, or a pharmaceutically acceptable salt form thereof and a pharmaceutically acceptable carrier.

7. A kit according to claim 6, wherein the kit further comprises one or more ancillary ligands and a reducing agent.

8. A kit according to claim 7, wherein the ancillary ligands are tricine and TPPTS.

9. A kit according to claim 7, wherein the reducing agent is tin(II).

10. A diagnostic or therapeutic metallopharmaceutical composition, comprising: a metal, a chelator capable of chelating the metal and a targeting moiety, wherein the targeting moiety is bound to the chelator, is a benzodiazepine, benzodiazepinedione, or dibenzotrihydroannulene nonpeptide and binds to a receptor that is upregulated during angiogenesis and the compound has 0–1 linking groups between the targeting moiety and chelator.

11. A composition according to claim 10, wherein the metallopharmaceutical is a diagnostic radiopharmaceutical, the metal is a radioisotope selected from the group: $^{99m}$Tc, $^{95}$Tc, $^{111}$In, $^{62}$Cu, $^{64}$Cu, $^{67}$Ga, and $^{68}$Ga, and the linking group is present between the targeting moiety and chelator.

12. A composition according to claim 11, wherein the targeting moiety is a benzodiazepine, benzodiazepinedione, or dibenzotrihydroannulene and the receptor is $\alpha_v\beta_3$ or $\alpha_v\beta_5$.

13. A composition according to claim 12, wherein the radioisotope is $^{99m}$Tc or $^{95}$Tc, the radiopharmaceutical further comprises a first ancillary ligand and a second ancillary ligand capable of stabilizing the radiopharmaceutical.

14. A composition according to claim 13, wherein the radioisotope is $^{99m}$Tc.

15. A composition according to claim 14, wherein the radiopharmaceutical is selected from the group:

$^{99m}$Tc((S)-2-(2,5-diaza-5-(6((6-(diazenido)(3-pyridyl))carbonylamino)hexyl)-9-(N-(benzimidazol-2-ylmethyl)-N-methylcarbamoyl)-4-oxobicyclo [5.4.0] undeca-1(7),8,10-trien-3-yl) acetic acid)(tricine) (TPPTS) and $^{99m}$Tc((S)-2-(2,5-diaza-9-(N-(6-((6-(diazenido)(3-pyridyl))carbonylamino)hexyl)-N-(benzimidazol-2-ylmethyl)carbamoyl)-5-methyl-4-oxobicyclo [5.4.0] undeca-1(7),8,10-trien-3-yl)acetic acid)(tricine) (TPPTS).

16. A composition according to claim 12, wherein the radioisotope is $^{111}$In.

17. A composition according to claim 16, wherein the radiopharmaceutical is selected from the group:

$^{111}$In complex of 6-(N-(3-(3-aza-10-(N-(benzimidazol-2-ylmethyl)-N-methylcarbamoyl)-5-(carboxymethyl)-4-oxobicyclo [5.4.0]undeca-1(7),8,10-trien-3-yl)propyl)carbamoyl)-3-(2-((2-((carboxymethyl)(2-((carboxymethyl)methylamino)ethyl)amino) ethyl)(2-((carboxymethyl)ethylamino)ethyl)amino)-acetylamino)-4-oxooctane-1,8-dicarboxylic acid;

$^{111}$In complex of (S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-4-(4-carboxy-2-(2-(1,4,7,10-tetraaza-4,7,10-tris(carboxymethyl) cyclododecyl)acetylamino)butanoylamino) butanoic acid; and $^{111}$In complex of (S,S)-3-(N-(3-(3,6-diaza-5-(carboxymethyl)-10-(N-(imidazol-2-ylmethyl)-N-benzylcarbamoyl)-4-oxobicyclo[5.4.0]undeca-1(7),8, 10-trien-3-yl)propyl) carbamoyl)-3-(2-(1,4,7,10-tetraaza-4,7,10-tris(carboxymethyl) cyclododecyl) acetylamino)propanoic acid.

18. A composition according to claim 10, wherein the metallopharmaceutical is a therapeutic radiopharmaceutical, the metal is a radioisotope selected from the group: $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, and $^{192}$Ir, and the linking group is present between the targeting moiety and chelator.

19. A composition according to claim 18, wherein the targeting moiety is a benzodiazepine, benzodiazepinedione, or dibenzotrihydroannulene and the receptor is $\alpha_v\beta_3$ or $\alpha_v\beta_5$.

20. A composition according to claim 19, wherein the radioisotope is $^{149}$Pm.

21. A composition according to claim 20, wherein the radiopharmaceutical is selected from the group:

the Pm-149 complex of (S,S,S)-4-(N-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)propyl)carbamoyl)-4-(4-carboxy-2-(2-(1,4,7,10-tetraaza-4,7,10-tris(carboxymethyl) cyclodecyl) acetylamino)butanoyl amino)butanoic acid; and the Pm-149 complex of (S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-4-(4-carboxy-2-(2-(1,4,7,10-tetraaza-4,7,10-tris(carboxymethyl) cyclododecyl)acetylamino)butanoylamino) butanoic acid.

22. A composition according to claim 19, wherein the radioisotope is $^{177}$Lu.

23. A composition according to claim 22, wherein the radiopharmaceutical is selected from the group:

the Lu-177 complex of (S,S,S)-4-(N-(3-(3,6-diaza-10-(N-(benzimidazol-2-ylmethyl)-N-methylcarbamoyl)-5-(carboxymethyl)-4-oxobicyclo[5.4.0]undeca-1(7),8,10-trien-3-yl)propyl)carbamoyl)-4-(4-carboxy-2-(2-(1,4,7,10-tetraaza-4,7,10-tris(carboxymethyl) cyclodecyl) acetylamino)butanoyl amino)butanoic acid; and the Lu-177 complex of (S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8,10-trien-3-yl)propyl) carbamoyl)-4-(4-carboxy-2-(2-(1,4,7,10-tetraaza-4,7,10-tris(carboxymethyl) cyclododecyl)acetylamino)butanoylamino) butanoic acid; and the Lu-177 complex of (S,S)-3-(N-(3-(3,6-diaza-5-(carboxymethyl)-10-(N-(imidazol-2-ylmethyl)-N-benzylcarbamoyl)-4-oxobicyclo[5.4.0]undeca-1(7),8, 10-trien-3-yl)propyl) carbamoyl)-3-(2-(1,4,7,10-tetraaza-4,7,10-tris(carboxymethyl) cyclododecyl) acetylamino)propanoic acid.

24. A composition according to claim 19, wherein the radioisotope is $^{90}$Y.

25. A composition according to claim 24, wherein the radiopharmaceutical is selected from the group:

the Y-90 complex of (S,S,S)-4-(N-(3-(3,6-diaza-10-(N-(benzimidazol-2-ylmethyl)-N-methylcarbamoyl)-5-(carboxymethyl)-4-oxobicyclo[5.4.0]undeca-1(7),8, 10-trien-3-yl)propyl)carbamoyl)-4-(4-carboxy-2-(2-(1,4,7,10-tetraaza-4,7,10-tris(carboxymethyl) cyclodecyl) acetylamino)butanoyl amino)butanoic acid; and the Y-90 complex of (S,S,S)-4-(N-(3-(3,6-diaza-5-(carboxymethyl)-10-(N-(imidazol-2-ylmethyl)-N-benzylcarbamoyl)-4-oxobicyclo[5.4.0]undeca-1(7),8, 10-trien-3-yl)propyl) carbamoyl)-4-(4-carboxy-2-(2-(1,4,7,10-tetraaza-4,7,10-tris(carboxymethyl) cyclododecyl)acetylamino)butanoylamino) butanoic acid; and the Y-90 complex of (S,S)-3-(N-(3-(3,6-diaza-5-(carboxymethyl)-10-(N-(imidazol-2-ylmethyl)-N-benzylcarbamoyl)-4-oxobicyclo[5.4.0]undeca-1(7),8, 10-trien-3-yl)propyl) carbamoyl)-3-(2-(1,4,7,10-tetraaza-4,7,10-tris(carboxymethyl) cyclododecyl) acetylamino)propanoic acid.

26. A composition according to claim 10, wherein the metallopharmaceutical is a MRI contrast agent, the metal is a paramagnetic metal ion selected from the group: Gd(III), Dy(III), Fe(III), and Mn(II), and the linking group is present between the targeting moiety and chelator.

27. A composition according to claim 26, wherein the targeting moiety is a benzodiazepine, benzodiazepinedione, or dibenzotrihydroannulene and the receptor is $\alpha_v\beta_3$ or $\alpha_v\beta_5$.

28. A composition according to claim 27, wherein the metal ion is Gd(III).

29. A composition according to claim 10, wherein the metallopharmaceutical is a X-ray contrast agent, the metal is selected from the group: Re, Sm, Ho, Lu, Pm, Y, Bi, Pd, Gd, La, Au, Au, Yb, Dy, Cu, Rh, Ag, and Ir, and the linking group is present between the targeting moiety and chelator.

30. A method of treating rheumatoid arthritis in a patient comprising: administering a therapeutic radiopharmaceutical of claim 18 capable of localizing in new angiogenic vasculature to a patient by injection or infusion.

31. A method of treating cancer in a patient comprising: administering to a patient in need thereof a therapeutic radiopharmaceutical of claim 18 by injection or infusion.

32. A method of treating restenosis in a patient comprising: administering to a patient, either systemically or locally, a therapeutic radiopharmaceutical of claim 18 capable of localizing in the restenotic area and delivering an effective dose of radiation.

33. A method of imaging cancer in a patient comprising: (1) administering a diagnostic radiopharmaceutical of claim 11 to a patient by injection or infusion; (2) imaging the patient using planar or SPECT gamma scintigraphy, or positron emission tomography.

34. A method of imaging cancer in a patient comprising: (1) administering a MRI contrast agent of claim 26; and (2) imaging the patient using magnetic resonance imaging.

35. A method of imaging cancer in a patient comprising: (1) administering an X-ray contrast agent of claim 29; and (2) imaging the patient using X-ray computed tomography.

36. A method of imaging therapeutic angiogenesis in a patient comprising: (1) administering a diagnostic radiopharmaceutical, a MRI contrast agent, or a X-ray contrast agent of claim 10 to a patient by injection or infusion; (2) imaging the area of the patient wherein the desired formation of new blood vessels is located.

37. A method of imaging atherosclerosis in a patient comprising: (1) administering a diagnostic radiopharmaceutical, a MRI contrast agent, or a X-ray contrast agent of claim 10 to a patient by injection or infusion; (2) imaging the area of the patient wherein the atherosclerosis is located.

38. A method of imaging restenosis in a patient comprising: (1) administering a diagnostic radiopharmaceutical, a MRI contrast agent, or a X-ray contrast agent of claim 10 to a patient by injection or infusion; (2) imaging the area of the patient wherein the restenosis is located.

39. A method of imaging cardiac ischemia in a patient comprising: (1) administering a diagnostic radiopharmaceutical, a MRI contrast agent, or a X-ray contrast agent of claim 10 to a patient by injection or infusion; (2) imaging the area of the myocardium wherein the ischemic region is located.

40. A method of imaging myocardial reperfusion injury in a patient comprising: (1) administering a diagnostic radiopharmaceutical, a MRI contrast agent, or a X-ray contrast agent of claim 10 to a patient by injection or infusion; (2) imaging the area of myocardium wherein the reperfusion injury is located.

41. A compound, comprising: a targeting moiety and a surfactant, wherein the targeting moiety is bound to the surfactant, is a benzodiazepine, benzodiazepinedione, or dibenzotrihydroannulene nonpeptide, and binds to a receptor that is upregulated during angiogenesis and the compound has 0–1 linking groups between the targeting moiety and surfactant.

42. A compound according to claim 41, wherein the receptor is the integrin $\alpha_v\beta_3$ or $\alpha_v\beta_5$ and the compound is of the formula:

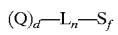

wherein, Q is a compound of Formulae (Ia), (Ib) or (Ic):

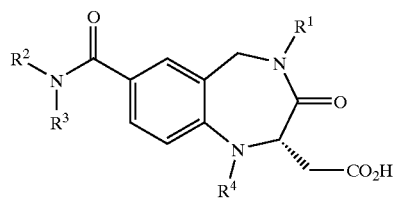

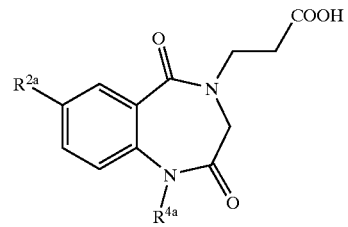

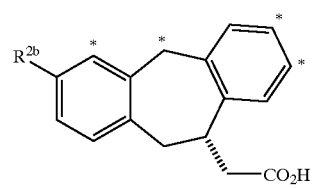

wherein:

$R^1$ and $R^3$ are independently selected from the group: $C_1$–$C_6$ alkyl, benzyl, phenethyl, and a bond to $L_n$; provided that one of $R^1$ and $R^3$ is a bond to $L_n$;

$R^2$ is independently selected from the group: 2-benzimidazolylmethyl, 2-guanidinoethyl, 2-amino-2-pyridyl, 2-amino-2-pyridylmethyl, 5-amino-2-imidazolylmethyl, and 2-imidazolylmethyl;

$R^4$ is independently selected from H, $C_{1-6}$ alkyl or benzyl;

$R^{2a}$ is $(CH_2)_3R^{3a}$;

$R^{3a}$ is selected from the group:

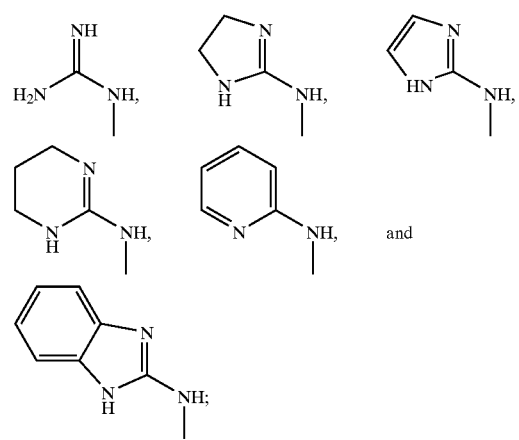

$R^{4a}$ is independently selected from $C_{1-6}$ alkyl substituted with a bond to $L_n$ or benzyl substituted with a bond to $L_n$;

$R^{2b}$ is independently selected from the group:

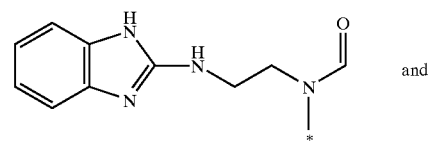

-continued

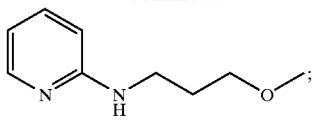

the asterisks * denote optional positions for attaching $L_n$; or Q is a peptide selected from the group:

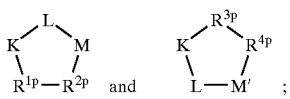

$R^{1p}$ is L-valine, D-valine or L-lysine optionally substituted on the ε amino group with a bond to $L_n$;

$R^{2p}$ is L-phenylalanine, D-phenylalanine, D-1-naphthylalanine, 2-aminothiazole-4-acetic acid or tyrosine, the tyrosine optionally substituted on the hydroxy group with a bond to $L_n$;

$R^{3p}$ is D-valine;

$R^{4p}$ is D-tyrosine substituted on the hydroxy group with a bond to $L_n$;

provided that one of $R^{1p}$ and $R^{2p}$ in each Q is substituted with a bond to $L_n$, and further provided that when $R^{2p}$ is 2-aminothiazole-4-acetic acid, K is N-methylarginine;

provided that at least one Q is a compound of Formula Ia Ib, or Ic;

d is selected from 1, 2, 3, 4, 5, 6, 7, 8, 9, and 10;

$L_n$ is a linking group having the formula:

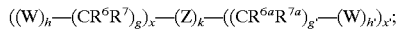

W is independently selected at each occurrence from the group: O, S, NH, NHC(=O), C(=O)NH, $NR^8$C(=O), C(=O)N $R^8$, C(=O), C(=O)O, OC(=O), NHC(=S) NH, NHC(=O)NH, $SO_2$, $SO_2$NH, $(OCH_2CH_2)_{20-200}$, $(CH_2CH_2O)_{20-200}$, $(OCH_2CH_2CH_2)_{20-200}$, $(CH_2CH_2CH_2O)_{20-200}$, and $(aa)_{t'}$;

aa is independently at each occurrence an amino acid;

Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;

$R^6$, $R^{6a}$, $R^7$, $R^{7a}$, and $R^8$ are independently selected at each occurrence from the group: H, =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, $NHC(=O)R^{11}$, $C(=O)NHR^{11}$, $NHC(=O)NHR^{11}$, $NHR^{11}$, $R^{11}$, and a bond to $S_f$;

$R^{10}$ is independently selected at each occurrence from the group: a bond to $S_f$, $COOR^{11}$, $C(=O)NHR^{11}$, NHC(=O)$R^{11}$, OH, $NHR^{11}$, $SO_3H$, $PO_3H$, $-OPO_3H_2$, $-OSO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, alkyl substituted with 0–1 $R^{12}$, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, and a bond to $S_f$;

$R^{12}$ is a bond to $S_f$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

$S_f$ is a surfactant which is a lipid or a compound of the formula:

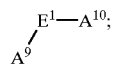

$A^9$ is selected from the group: OH and $OR^{27}$;

$A^{10}$ is $OR^{27}$;

$R^{27}$ is $C(=O)C_{1-20}$ alkyl;

$E^1$ is $C_{1-10}$ alkylene substituted with 1–3 $R^{28}$;

$R^{28}$ is independently selected at each occurrence from the group: $R^{30}$, $-PO_3H-R^{30}$, =O, $-CO_2R^{29}$, $-C(=O)R^{29}$, $-C(=O)N(R^{29})_2$, $-CH_2OR^{29}$, $-OR^{29}$, $-N(R^{29})_2$, $C_1$–$C_5$ alkyl, and $C_2$–$C_4$ alkenyl;

$R^{29}$ is independently selected at each occurrence from the group: $R^{30}$, H, $C_1$–$C_6$ alkyl, phenyl, benzyl, and trifluoromethyl;

$R^{30}$ is a bond to $L_n$;

and a pharmaceutically acceptable salt thereof.

43. A compound according to claim 42, wherein the compound is of the formula:

wherein: Q is a compound of Formulae (Ia), (Ib), or (Ic):

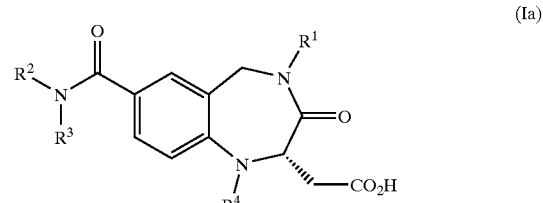

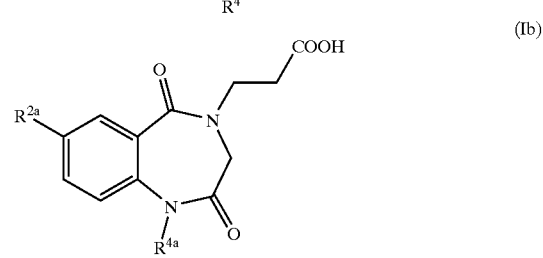

-continued (Ic)

R⁴ᵃ is benzyl substituted with a bond to $L_n$;

$R^{2b}$ is

Z is selected from the group: aryl substituted with 0–1 $R^{10}$, $C_{3-10}$ cycloalkyl substituted with 0–1 $R^{10}$, and a 5–10 membered heterocyclic ring system containing 1–4 heteroatoms independently selected from N, S, and O and substituted with 0–1 $R^{10}$;

$R^6$, $R^{6a}$, $R^7$, $R^{7a}$, and $R^8$ are independently selected at each occurrence from the group: H, =O, COOH, SO₃H, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O)NHR¹¹, NHC(=O)NHR¹¹, NHR¹¹, R¹¹, and a bond to $S_f$;

k is 0 or 1;

$S_f$ is a surfactant which is a lipid or a compound of the formula:

$$E^1\text{—}A^{10};$$
$$A^9$$

$A^9$ is $OR^{27}$;

$A^{10}$ is $OR^{27}$;

$R^{27}$ is C(=O)$C_{1-15}$ alkyl;

$E^1$ is $C_{1-4}$ alkylene substituted with 1–3 $R^{28}$;

$R^{28}$ is independently selected at each occurrence from the group: $R^{30}$, —PO₃H—$R^{30}$, =O, —CO₂$R^{29}$, —C(=O)$R^{29}$, —CH₂O$R^{29}$, —O$R^{29}$, and $C_1$–$C_5$ alkyl;

$R^{29}$ is independently selected at each occurrence from the group: $R^{30}$, H, $C_1$–$C_6$ alkyl, phenyl, and benzyl;

$R^{30}$ is a bond to $L_n$;

and a pharmaceutically acceptable salt thereof.

44. A compound according to claim 43, wherein the compound selected from the group:

Sodium 1,2-dipalmitoyl-sn-glycero-3-phosphatidylethanolamine-(S)-2-(2,5-diaza-9-(N-(benzimidazol-2-ylmethyl)-N-methylcarbamoyl)-5-(6-aminohexyl)-4-oxobicyclo[5.4.0]undeca-1(7),8,10-trien-3-yl)acetic acid-dodecoanoate conjugate;

DPPE-PEG₃₄₀₀-[(S)-2-(2,5-diaza-9-(N-(benzimidazol-2-ylmethyl)-N-methylcarbamoyl)-5-(6-aminohexyl)-4-oxobicyclo[5.4.0]updeca-1(7),8,10-trien-3-yl)acetic acid]-dodecoanoate conjugate; and

[(S)-2-(2-aza-(2-((5-(N-(1,3-bis-N-(6-(aminohexyl-4-oxobicyclo[5.4.0]undeca-1(7),8,10-trien-3-yl)acetic acid)(2-(2,5-diaza-9-(N-(benzimidazol-2-ylmethyl)carbamoyl)propyl)carbamoyl]-w-amino-PEG₃₄₀₀-dodecanoate-DPPE conjugate.

45. An ultrasound contrast agent composition, comprising:
(a) a compound of claim 41, comprising: a benzodiazepine, benzodiazepinedione, or dibenzotrihydroannulene that binds to the integrin $α_vβ_3$, or $α_vβ_5$, a surfactant and a linking group between the benzodiazepine and the surfactant;
(b) a parenterally acceptable carrier; and,
(c) an echogenic gas.

46. An ultrasound contrast agent composition of claim 45, further comprising: 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

47. An ultrasound contrast agent composition of claim 46, wherein the echogenic gas is a $C_{2-5}$ perfluorocarbon.

48. A method of imaging cancer in a patient comprising: (1) administering, by injection or infusion, an ultrasound contrast agent composition of claim 45 to a patient; and (2) imaging the patient using sonography.

49. A method of imaging therapeutic angiogenesis in a patient comprising: (1) administering, by injection or infusion, an ultrasound contrast agent composition of claim 45 to a patient; (2) imaging the area of the patient wherein the desired formation of new blood vessels is located.

50. A method of imaging atherosclerosis in a patient comprising: (1) administering, by injection or infusion, an ultrasound contrast agent composition of claim 45 to a patient; (2) imaging the area of the patient wherein the atherosclerosis is located.

51. A method of imaging restenosis in a patient comprising: (1) administering, by injection or infusion, an ultrasound contrast agent composition of claim 45 to a patient; (2) imaging the area of the patient wherein the restenosis is located.

52. A method of imaging cardiac ischemia in a patient comprising: (1) administering, by injection or infusion, an ultrasound contrast agent composition of claim 45 to a patient; (2) imaging the area of the myocardium wherein the ischemic region is located.

53. A method of imaging myocardial reperfusion injury in a patient comprising: (1) administering, by injection or infusion, an ultrasound contrast agent composition of claim 45 to a patient; (2) imaging the area of myocardium wherein the reperfusion injury is located.

54. A therapeutic radiopharmaceutical composition, comprising:
(a) a therapeutic radiopharmaceutical of claim 19; and,
(b) a parenterally acceptable carrier.

55. A diagnostic radiopharmaceutical composition, comprising:
(a) a diagnostic radiopharmaceutical, a MRI contrast agent, or a X-ray contrast agent of claim 10; and,
(b) a parenterally acceptable carrier.

* * * * *